United States Patent
Ferrara et al.

(10) Patent No.: US 9,284,369 B2
(45) Date of Patent: Mar. 15, 2016

(54) INHIBITION OF ANGIOGENESIS

(75) Inventors: Napoleon Ferrara, San Francisco, CA (US); Farbod Shojaei, San Diego, CA (US); Xiumin Wu, San Bruno, CA (US); Cuiling Zhong, Palo Alto, CA (US)

(73) Assignee: Genentech, Inc., South San Francisco, CA (US)

(*) Notice: Subject to any disclaimer, the term of this patent is extended or adjusted under 35 U.S.C. 154(b) by 1458 days.

(21) Appl. No.: 12/679,257

(22) PCT Filed: Sep. 19, 2008

(86) PCT No.: PCT/US2008/076954
§ 371 (c)(1),
(2), (4) Date: Aug. 30, 2010

(87) PCT Pub. No.: WO2009/039337
PCT Pub. Date: Mar. 26, 2009

(65) Prior Publication Data
US 2010/0316633 A1    Dec. 16, 2010

Related U.S. Application Data

(60) Provisional application No. 60/974,382, filed on Sep. 21, 2007, provisional application No. 61/083,071, filed on Jul. 23, 2008.

(51) Int. Cl.
*A61K 39/395* (2006.01)
*C07K 16/22* (2006.01)
*C07K 16/24* (2006.01)
*A61K 39/00* (2006.01)

(52) U.S. Cl.
CPC .............. *C07K 16/22* (2013.01); *C07K 16/243* (2013.01); *A61K 2039/505* (2013.01); *A61K 2039/507* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,060,278 B2 | 6/2006 | Ferrara et al. | |
| 7,622,115 B2* | 11/2009 | Fyfe et al. | 424/143.1 |
| 7,632,810 B2 | 12/2009 | Ferrara et al. | |
| 2005/0186208 A1 | 8/2005 | Fyfe et al. | |
| 2008/0219985 A1* | 9/2008 | Thompson et al. | 424/139.1 |

FOREIGN PATENT DOCUMENTS

| WO | WO 03/020892 A | | 3/2003 |
|---|---|---|---|
| WO | WO/2004/081229 | * | 9/2004 |
| WO | WO 2004/081229 A | | 9/2004 |
| WO | WO 2005/000900 | | 1/2005 |
| WO | WO 2008/120263 A | | 10/2008 |

OTHER PUBLICATIONS

Shojaei et al. (Nature. Dec. 6, 2007;450(7171):825-31.).*
Zimmerman et al (Drug Discovery Today, Jan. 2007, 12: 34-42).*
Miller et al. (Annals of Oncology, 2003, 14:20-28).*
Russian Federal Service for Intellectual Property, Office Action for Application No. 2010115755/15(022329), dated Nov. 16, 2011.
Casanovas, et al., "Drug resistance by evasion of antiangiogenic targeting of VEGF signaling in late-stage pancreatic islet tumors," Cancer Cell 8(4):299-309 (2005).
Kholodov, et al., "Clinical pharmacokinetics," Meditsina pp. 83-98, 134-138, 160, 378-380 (1985).
Lecouter, "Identification of an angiogenic mitogen selective for endocrine gland endothelium," Nature 412:877-884 (2001).
Sergeev "Short course in molecular pharmacology," p. 10 (1975).
Christopher et al., "Regulation of neutrophil homeostasis," Curr Opin Hematol 14:3-8(2007).
Ferrara et al., "EG-VEGF and Bv8: a novel family of tissue-restricted angiogenic factors," BBA—Reviews on Cancer 1654(1):69-78 (2004).
Ferrara et al., "Discovery and development of bevacizumab, an anti-VEGF antibody for treating cancer," Nature Reviews 3(5):391-400 (2004).
Ferrara et al., "Angiogenesis as a therapeutic target," Nature Publishing Group 438(7070):967-974 (2005).
Garcia-Sanz et al., "Three-Dimensional Microcomputed Tomography of Renal Vasculature in Rats," Hypertension 31:440-444(1998).
Gerber et al., "Pharmacology and pharmacodynamics of bevacizumab as monotherapy or in combination with cytotoxic therapy in preclinical studies," Cancer Research 65(3):671-680 (2005).
Kavgaci et al., "Endogenous Granulocyte Colony-Stimulating Factor )G-CSF) Levels in Chemotherapy-Induced Neutropenia and in Neutropenia Related with Primary Diseases," J Exp Clin Cancer Res 21:475-479(2002).
Kohchi et al., "Utilization of macrophages in anticancer therapy: the macrophage network theory," Anticancer Res 24:3311-3320(2004).
Kwon et al., "Enhanced Coronary Vasa Vasorum Neovascularization in Experimental Hypercholesterolemia," J Clin Invest 101(8):1551-1556(1998).
Lecouter et al., "The endocrine-gland-derived VEGF homologue Bv8 promotes angiogenesis in the testies: localization of Bv8 receptors to endothelial cells," Proceedings of the National Academy of Sciences of USA 100(5):2685-2690 (2003).
Maehara, N., "Experimental microcomputed tomography study of the 3D microangioarchitechture of tumors," Eur Radiol 13:1559-1565(2003).
Monnier et al., "Prokineticin 2/Bv8 is expressed in Kupffer cells in liver and is down regulated in human hepatocellular carcinoma," World Journal of Gastroenterology 14(8):1182-1191 (2008).

(Continued)

*Primary Examiner* — Laura B Goddard
*Assistant Examiner* — Meera Natarajan
(74) *Attorney, Agent, or Firm* — Jones Day

(57) ABSTRACT

The present invention relates generally to the inhibition of inflammatory cell-mediated angiogenesis. In particular, the invention concerns the prevention or treatment of tumor angiogenesis, and the inhibition of tumor development, using Bv8 antagonists, such as anti-Bv8 antibodies.

5 Claims, 72 Drawing Sheets

(56) References Cited

OTHER PUBLICATIONS

Mueller et al., "Tumor-stroma interactions directing phenotype and progression of epithelial skin tumor cells," *Differentiation* 70:486-497(2002).
Neben et al., "Mobilization of Hematopoietic Stem and Progenitor Cell Subpopulations From the Marrow to the Blood of Mice Following Cyclophosphamide and/or Granulocyte Colony-Stimulating Factor," *Blood* 81:1960-1971(1993).
Negri et al., "Bv8/Prokineticin proteins and their receptors," *Life Sciences* 81(14):1103-1116 (2007).
Shojaei et al., "Bv8 regulates myeloid-cell-dependent tumor angiogenesis," *Nature* 450(7171):825-831 (2007).
Shojaei et al., "Tumor refractoriness to anti-VEGF treatment is mediated by CD11b+Gr1+myeloid cells," *Nature Biotechnology* 25(8):911-920 (2007).
Shojaei et al., "Refractoriness to antivascular endothelial growth factor treatment: role of myeloid cells," *Cancer Research* 68(14):5501-5504-920 (2008).
Shojaei et al., "Role of Bv8 in neutrophil-dependent angiogenesis in a transgenic model fo cancer progression," *Proceedings of the National Academy of Sciences of the United States of America* 105(7):2640-2645 (2008).
Talmadge et al., "Pathways Mediating the Expansion and Immunosuppressive Activity of Myeloid-Derived Suppressor Cells and Their Relevance to Cancer Therapy," *Clin Cancer Res* 3:5243-5248(2007).
Yang et al., "Expansion of myeloid immune suppressor Cr+CD11b+ cells in tumor-bearing host directly promotes tumor angiogenesis." *Cancer Cell* 6:409-421(2004).
ISA/EP, International Search Report and Written Opinion dated Mar. 26, 2009 for application No. PCT/US2008/076954.
Le Couter et al., "Bv8 and endocrine gland-derived vascular endothelial growth factor simulate hematopoietic cell mobilization," PNAS 101(48):16813-16818 (2004).
International Preliminary Report on Patentability dated Mar. 24, 2010 of International application No. PCT/US2008/076954.
Taiwanese Search Report dated Jan. 7, 2014 of Taiwanese application No. 097136179.

* cited by examiner

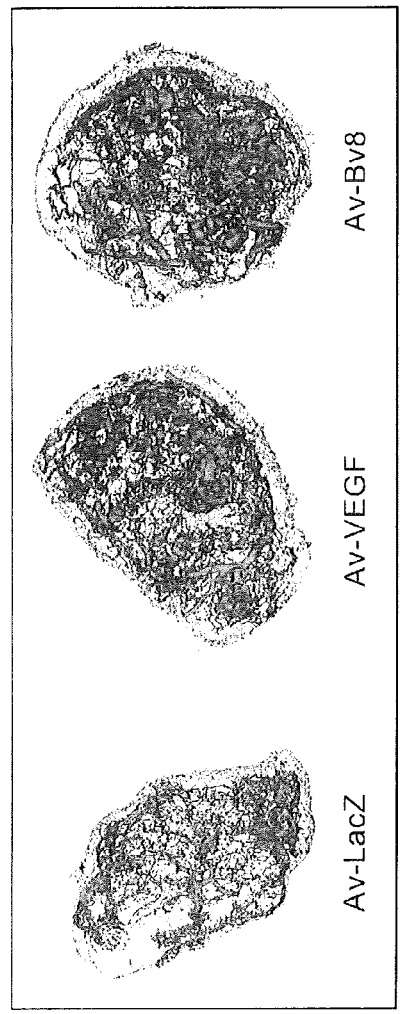
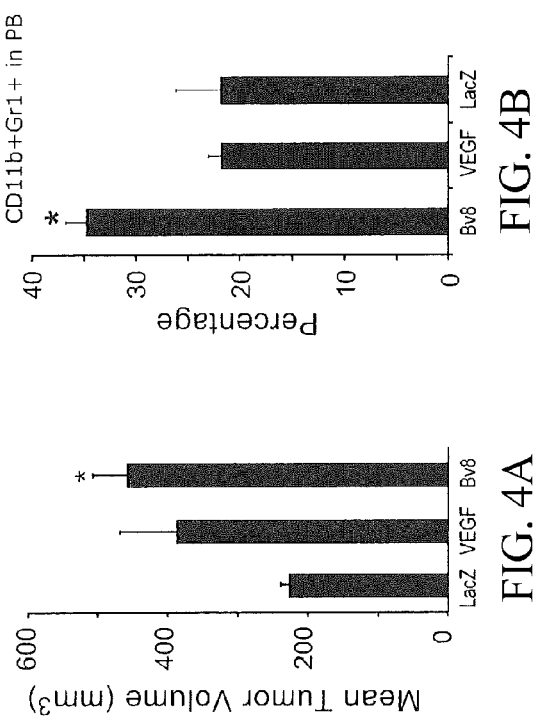
FIG. 4A  FIG. 4B  FIG. 4C  FIG. 4D
FIG. 4E

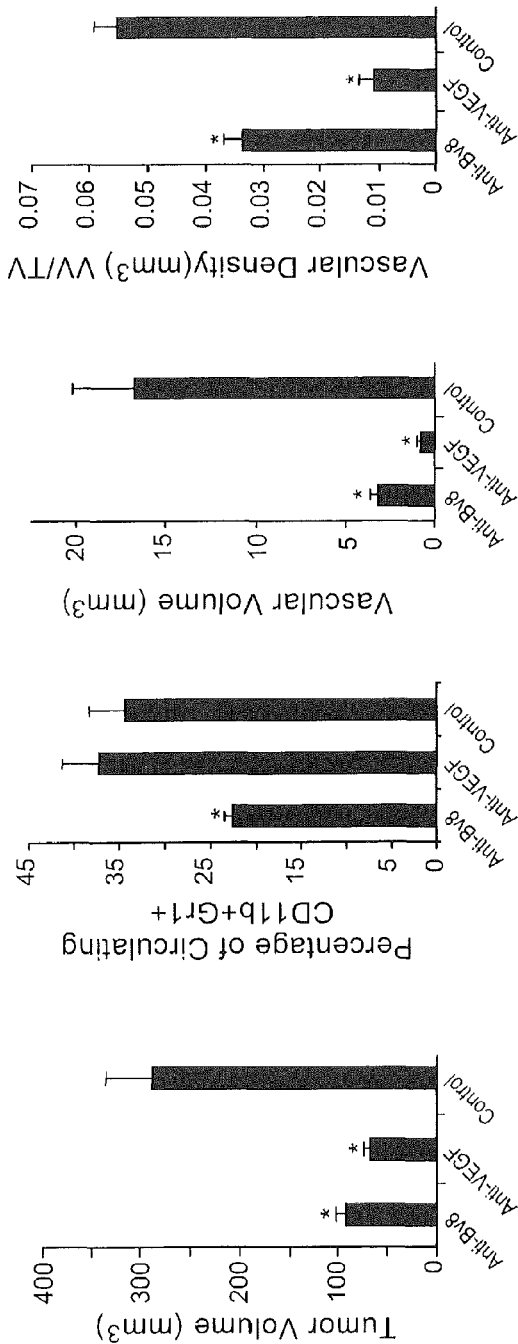
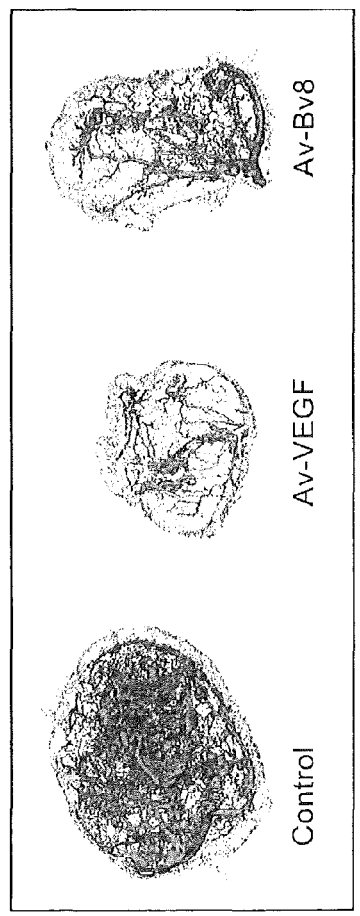
FIG. 4F FIG. 4G FIG. 4H FIG. 4I
FIG. 4J

```
TGAGGGCGCCATGAGGAGCCTGTGCTGCGCCCCACTCCTGCTCCTCTTGCTGCTGCCGCC
GCTGCTGCTCACGCCCCGCGCTGGGGACGCCGCCGTGATCACCGGGGCTTGTGACAAGGA
CTCCCAATGTGGTGGAGGCATGTGCTGTGCTGTCAGTATCTGGGTCAAGAGCATAAGGAT
TTGCACACCTATGGGCAAACTGGAGACAGCTGCCATCCACTGACTCGTAAAAACAATTT
TGGAAATGGAAGGCAGGAAAGAAGAAAGAGGAAGAGAAGCAAAAGGAAAAAGGAGGTTCC
ATTTTTTGGGCGGAGGATGCATCACACTTGCCCATGTCTGCCAGGCTTGGCCTGTTTACG
GACTTCATTTAACCGATTTATTTGTTTAGCCCAAAAGTAATCGCTCTGGAGTAGAAACCA
AATGTGA
```

FIG. 7

```
MRSLCCAPLLLLLLLPPLLLTPRAGDAAVITGACDKDSQCGGGMCCAVSIWVKSIRICT
PMGKLGDSCHPLTRKNNFGNGRQERRKRKRSKRKKRVPFFGRRMHHTCPCLPGLACLRT
SFNRFICLAQK
```

Important features of the protein:

Signal sequence:
1-21

Transmembrane domain:
none cAMP- and cGMP-dependent protein kinase phosphorylation site:
    87-90

N-myristoylation site:
    41-46
    42-47
    43-48

Amidation site:
    99-102

FIG. 8

```
GAGGGCGCCATGAGGAGCCTGTGCTGCGCCCCACTCCTGCTCCTCTTGCTGCTGCCGCCG
CTGCTGCTCACGCCCCGCGCTGGGGACGCCGCCGTGATCACCGGGGCTTGTGACAAGGAC
TCCCAATGTGGTGGAGGCATGTGCTGTGCTGTCAGTATCTGGGTCAAGAGCATAAGGATT
TGCACACCTATGGGCAAACTGGGAGACAGCTGCCATCCACTGACTCGTAAAGTTCCATTT
TTTGGGCGGAGGATGCATCACACTTGCCCATGTCTGCCAGGCTTGGCCTGTTTACGGACT
TCATTTAACCGATTTATTTGTTTAGCCCAAAAGTAATCGCTCTGGAGTAGAAACCAAATG
TGA
```

FIG. 9

```
MRSLCCAPLLLLLLLPPLLLTPRAGDAAVITGACDKDSQCGGGMCCAVSIWVKSIRIC
PMGKLGDSCHPLTRKVPFFGRRMHHTCPCLPGLACLRTSFNRFICLAQK

Important features of the protein:

Signal sequence:
1-21

Transmembrane domain:
none

N-myristoylation site:
    41-46
    42-47
    43-48

Amidation site:
    78-81
```

FIG. 10

```
CGGACGCGTGGGCGTCCCCTAACCGCCACCGCGTCCCCGGGACGCCATGGGGGACCCGCG
CTGTGCCCCGCTACTGCTACTTCTGCTGCTACCGCTGCTGTTCACACCGCCCGCCGGGGA
TGCCGCGGTCATCACCGGGGCTTGCGACAAGGACTCTCAGTGCGGAGGAGGCATGTGCTG
TGCTGTCAGTATCTGGGTTAAGAGCATAAGGATCTGCACACCTATGGGCCAAGTGGGCGA
CAGCTGCCACCCCCTGACTCGGAAAGTTCCATTTTGGGGCGGAGGATGCACCACACCTG
CCCCTGCCTGCCAGGCTTGGCGTGTTTAAGGACTTCTTTCAACCGGTTTATTTGCTTGGC
CCGGAAATGATCACTCTGAAGTAGGAACTTGAAATGCGACCCTCCGCTGCACAATGTCCG
TCGAGTCTCACTTGTAATTGTGGCAAACAAAGAATACTCCAGAAAGAAATGTTCTCCCCC
TTCCTTGACTTTCCAAGTAACGTTTCTATCTTTGATTTTTGAAGTGGCTTTTTTTTTTTT
TTTTTTTTCCTTTCCTTGAAGGAAAGTTTTGATTTTTGGAGAGATTTATAGAGGACTTTC
TGACATGGCTTCTCATTTCCCTGTTTATGTTTTGCCTTGACATTTTTGAATGCCAATAAC
AACTGTTTTCACAAATAGGAGAATAAGAGGGAACAATCTGTTGCAGAAACTTCCTTTTGC
CCTTTGCCCCACTCGCCCCGCCCCGCCCCGCCCCGCCCTGCCCATGCGCAGACAGACACA
CCCTTACTCTTCAAAGACTCTGATGATCCTCACCTTACTGTAGCATTGTGGGTTTCTACA
CTTCCCCGCCTTGCTGGTGGACCCACTGAGGAGGCTCAGAGAGCTAGCACTGTACAGGTT
TGAACCAGATCCCCCAAGCAGCTCATTTGGGGCAGACGTTGGGAGCGCTCCAGGAACTTT
CCTGCACCCATCTGGCCCACTGGCTTTCAGTTCTGCTGTTTAACTGGTGGGAGGACAAAA
TTAACGGGACCCTGAAGGAACCTGGCCCGTTTATCTAGATTTGTTTAAGTAAAAGACATT
TTCTCCTTGTTGTGGAATATTACATGTCTTTTTCTTTTTTATCTGAAGCTTTTTTTTTTT
TTCTTTAAGTCTTCTTGTTGGAGACATTTTAAAGAACGCCACTCGAGGAAGCATTGATTT
TCATYTGGCATGACAGGAGTCATCATTTTAAAAAATCGGTGTTAAGTTATAATTTAAACT
TTATTTGTAACCCAAAGGTYTAATGTAAATGGATTTCCTGATATCCTGCCATTTGTACTG
GTATCAATATTTYTATGT
```

FIG. 11

MGDPRCAPLLLLLLLPLLFTPPAGDAAVITGACDKDSQCGGGMCCAVSIWVKSIRICTP
MGQVGDSCHPLTRKVPFWGRRMHHTCPCLPGLACLRTSFNRFICLARK

Important features of the protein:

Signal sequence:
1-20

Transmembrane domain:
none

N-myristoylation site:
    40-45
    41-46
    42-47

Amidation site:
    77-80

FIG. 12

MRSLCCAPLLLLLLLPPLLLTPRAGDAAVITGACDKDSQCGGGMCCAVSI  50  human

MGDPRCAPLLLLLLLPPLLFTPRAGDAAVITGACDKDSQCGGGMCCAVSI  50  mouse

W VKSIRICTPMGKLGDSCHPLTRKNNFGNGRQERRKRKRSKRKKEVPFF-G

W VKSIRICTPMGQVGDSCHPLTRKSHVANGRQERRRAKRRKRKKEVVPFWG

RRMHHTCPCLPGLACLRTSFNRFICLAQK

RRMHHTCPCLPGLACLRTSFNRFICLARK

FIG. 13

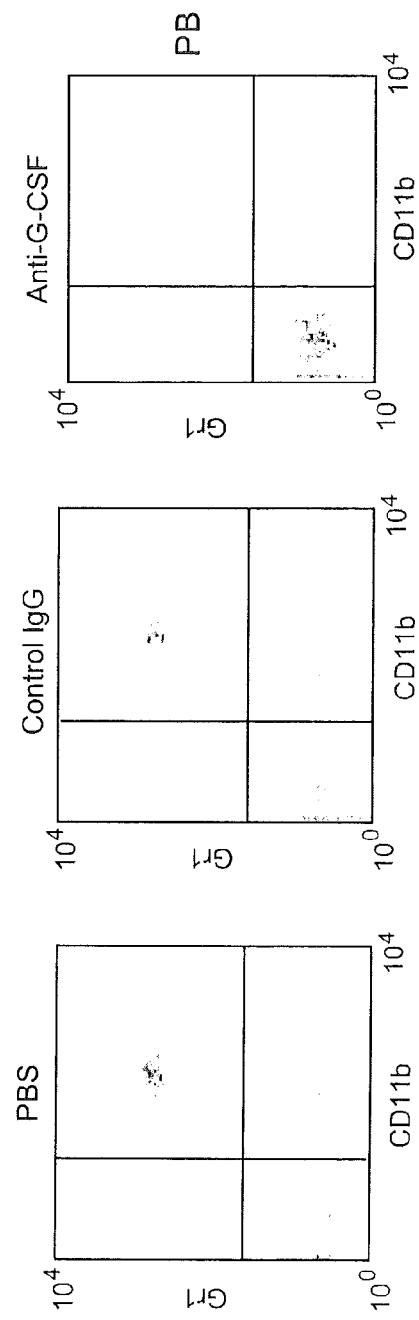
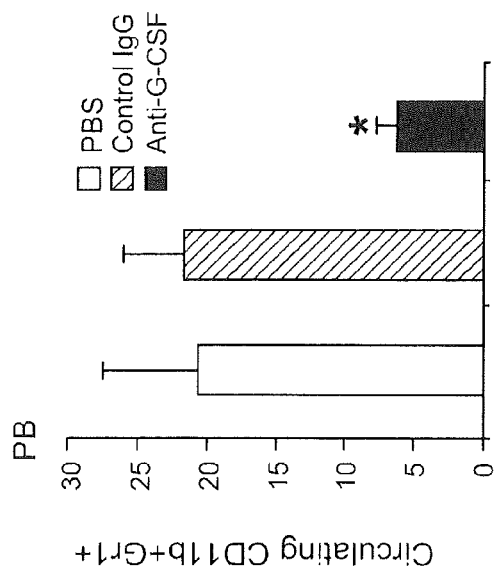
FIG. 20C
FIG. 20D
FIG. 20E
FIG. 20F

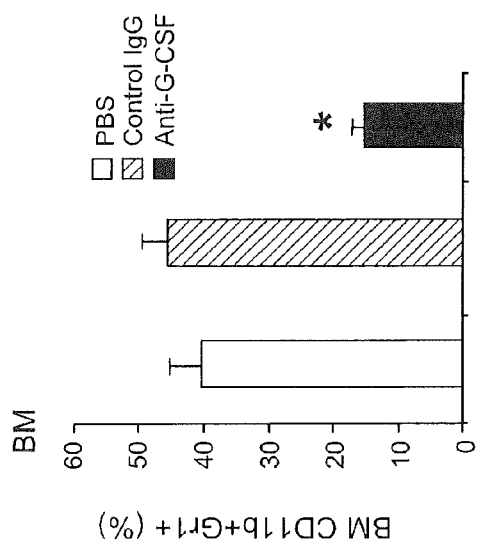
FIG. 20G
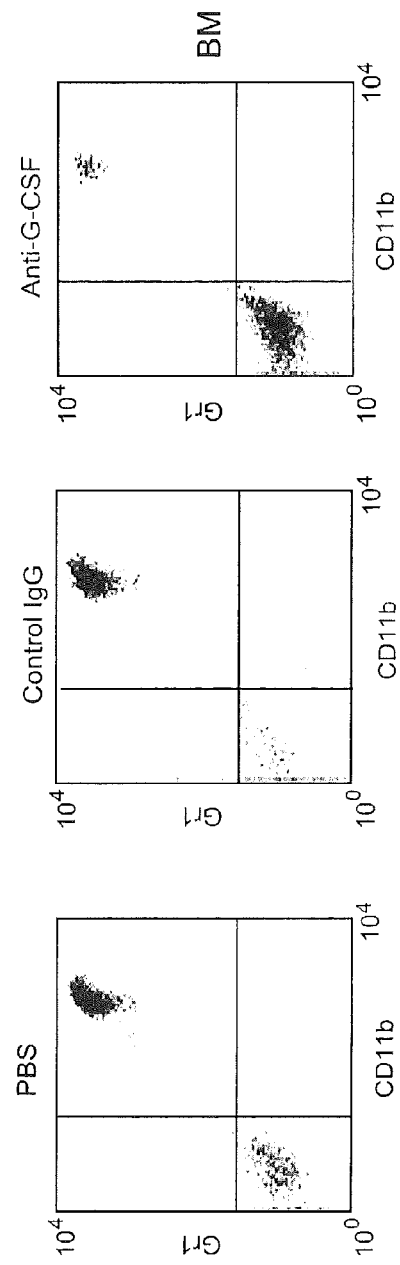
FIG. 20J
FIG. 20I
FIG. 20CH

Cytokine levels in conditioned media from human tumor cells or tumor-associated mouse fibroblasts isolated and cultured from xenografts.

| Source | IL-6 | G-CSF | SDF-1 |
|---|---|---|---|
| A673 | 138.7 | 20.6 | 15.6 |
| HM7 | 1.1 | 1.3 | 16.4 |
| HPAC | 398.2 | 11.1 | 30.4 |
| Calu-6 | 65 | 8.3 | 59.2 |
| HM7-derived fibroblasts | 892.1 | 60 | 27000 |
| HPAC-derived fibroblasts | 789.2 | 37.1 | 18000 |
| Calu-6-derived fibroblasts | 1487.7 | 163 | 17800 |

Values (pg/ $3 \times 10^5$ cells) are the average of duplicate determinations that varied <10%. The appropriate species-specific assays were performed for each cytokine.

FIG. 29

| Cell lines | Cell type | G-CSF | GM-CSF |
|---|---|---|---|
| HL-60 | promyeloblast | 1.1 | 0.8 |
| KG-1 | bone marrow myeloblast | 1.9*** | 0.5 |
| Hel 92.1.7 | bone marrow erythroblast | 3.3*** | 0.2 |
| U-937 | monocyte | 2.2*** | 1.5 |
| Jurkat | T lymphocyte | 0 | 0 |
| K562 | bone marro lymphoblast | 0 | 0 |

FIG. 30

SEQUENCE LISTING

```
<160> NUMBER OF SEQ ID NOS: 37

<210> SEQ ID NO 1
<211> LENGTH: 427
<212> TYPE: DNA
<213> ORGANISM: Homo sapiens

<400> SEQUENCE: 1
tgagggcgcc atgaggagcc tgtgctgcgc cccactcctg ctcctcttgc tgctgccgcc      60
gctgctgctc acgccccgcg ctggggacgc cgccgtgatc accggggctt gtgacaagga     120
ctcccaatgt ggtggaggca tgtgctgtgc tgtcagtatc tgggtcaaga gcataaggat     180
ttgcacacct atgggcaaac tgggagacag ctgccatcca ctgactcgta aaacaatttt     240
tggaaatgga aggcaggaaa gaagaaagag gaagagaagc aaaaggaaaa aggaggttcc     300
attttttggg cggaggatgc atcacacttg cccatgtctg ccaggcttgg cctgtttacg     360
gacttcattt aaccgattta tttgtttagc ccaaaagtaa tcgctctgga gtagaaacca     420
aatgtga                                                              427

<210> SEQ ID NO 2
<211> LENGTH: 129
<212> TYPE: PRT
<213> ORGANISM: Homo sapiens

<400> SEQUENCE: 2

Met Arg Ser Leu Cys Cys Ala Pro Leu Leu Leu Leu Leu Leu Leu Pro
1               5                   10                  15

Pro Leu Leu Leu Thr Pro Arg Ala Gly Asp Ala Ala Val Ile Thr Gly
            20                  25                  30

Ala Cys Asp Lys Asp Ser Gln Cys Gly Gly Gly Met Cys Cys Ala Val
        35                  40                  45
```

```
Ser Ile Trp Val Lys Ser Ile Arg Ile Cys Thr Pro Met Gly Lys Leu
         50                  55                  60

Gly Asp Ser Cys His Pro Leu Thr Arg Lys Asn Asn Phe Gly Asn Gly
 65                  70                  75                  80

Arg Gln Glu Arg Lys Arg Lys Ser Lys Arg Lys Glu Val
                 85                  90                  95

Pro Phe Phe Gly Arg Arg Met His His Thr Cys Pro Cys Leu Pro Gly
                100                 105                 110

Leu Ala Cys Leu Arg Thr Ser Phe Asn Arg Phe Ile Cys Leu Ala Gln
            115                 120                 125

Lys
```

<210> SEQ ID NO 3
<211> LENGTH: 363
<212> TYPE: DNA
<213> ORGANISM: Homo sapiens

<400> SEQUENCE: 3

```
gagggcgcca tgaggagcct gtgctgcgcc ccactcctgc tcctcttgct gctgccgccg      60
ctgctgctca cgccccgcgc tggggacgcc gccgtgatca ccggggcttg tgacaaggac     120
tcccaatgtg gtggaggcat gtgctgtgct gtcagtatct gggtcaagag cataaggatt     180
tgcacaccta tgggcaaact gggagacagc tgccatccac tgactcgtaa agttccattt     240
tttgggcgga ggatgcatca cacttgccca tgtctgccag gcttggcctg tttacggact     300
tcatttaacc gatttatttg tttagcccaa aagtaatcgc tctggagtag aaaccaaatg     360
tga                                                                  363
```

<210> SEQ ID NO 4
<211> LENGTH: 108
<212> TYPE: PRT
<213> ORGANISM: Homo sapiens

<400> SEQUENCE: 4

```
Met Arg Ser Leu Cys Cys Ala Pro Leu Leu Leu Leu Leu Leu Leu Pro
 1               5                  10                  15

Pro Leu Leu Leu Thr Pro Arg Ala Gly Asp Ala Ala Val Ile Thr Gly
                 20                  25                  30

Ala Cys Asp Lys Asp Ser Gln Cys Gly Gly Gly Met Cys Cys Ala Val
             35                  40                  45

Ser Ile Trp Val Lys Ser Ile Arg Ile Cys Thr Pro Met Gly Lys Leu
         50                  55                  60

Gly Asp Ser Cys His Pro Leu Thr Arg Lys Val Pro Phe Phe Gly Arg
 65                  70                  75                  80

Arg Met His His Thr Cys Pro Cys Leu Pro Gly Leu Ala Cys Leu Arg
                 85                  90                  95

Thr Ser Phe Asn Arg Phe Ile Cys Leu Ala Gln Lys
            100                 105
```

<210> SEQ ID NO 5
<211> LENGTH: 1338
<212> TYPE: DNA
<213> ORGANISM: Mus sp.

<400> SEQUENCE: 5

```
cggacgcgtg ggcgtcccct aaccgccacc gcgtccccgg gacgccatgg gggacccgcg      60
```

```
ctgtgccccg ctactgctac ttctgctgct accgctgctg ttcacaccgc cgccggggga    120
tgccgcggtc atcaccgggg cttgcgacaa ggactctcag tgcggaggag gcatgtgctg    180
tgctgtcagt atctgggtta agagcataag gatctgcaca cctatgggcc aagtgggcga    240
cagctgccac cccctgactc ggaaagttcc attttggggg cggaggatgc accacacctg    300
cccctgcctg ccaggcttgg cgtgtttaag gacttctttc aaccggttta tttgcttggc    360
ccggaaatga tcactctgaa gtaggaactt gaaatgcgac cctccgctgc acaatgtccg    420
tcgagtctca cttgtaattg tggcaaacaa agaatactcc agaaagaaat gttctccccc    480
ttccttgact ttccaagtaa cgtttctatc tttgattttt gaagtggctt ttttttttt    540 tttttttcc tttccttgaa ggaaagtttt gattttgga gagatttata gaggactttc    600
tgacatggct tctcatttcc ctgtttatgt tttgccttga cattttgaa tgccaataac    660 aactgtttc acaaatagga gaataagagg gaacaatctg ttgcagaaac ttccttttgc    720
cctttgcccc actcgccccg ccccgccccg ccccgccctg ccatgcgca gacagacaca    780 cccttactct tcaaagactc tgatgatcct caccttactg tagcattgtg ggtttctaca    840
cttccccgcc ttgctggtgg acccactgag gaggctcaga gagctagcac tgtacaggtt    900
tgaaccagat cccccaagca gctcatttgg ggcagacgtt gggagcgctc caggaacttt    960
cctgcaccca tctggcccac tggctttcag ttctgctgtt taactggtgg gaggacaaaa   1020
ttaacgggac cctgaaggaa cctggcccgt ttatctagat ttgtttaagt aaaagacatt   1080
ttctccttgt tgtggaatat tacatgtctt tttctttttt atctgaagct ttttttttt   1140 ttctttaagt cttcttgttg gagacatttt aaagaacgcc actcgaggaa gcattgattt   1200
tcatytggca tgacaggagt catcattta aaaaatcggt gttaagttat aatttaaact   1260
ttatttgtaa cccaaaggty taatgtaaat ggatttcctg atatcctgcc atttgtactg   1320
gtatcaatat ttytatgt                                                 1338
```

<210> SEQ ID NO 6
<211> LENGTH: 107
<212> TYPE: PRT
<213> ORGANISM: Mus sp.

<400> SEQUENCE: 6

Met Gly Asp Pro Arg Cys Ala Pro Leu Leu Leu Leu Leu Leu Leu Pro
1               5                   10                  15

Leu Leu Phe Thr Pro Pro Ala Gly Asp Ala Ala Val Ile Thr Gly Ala
            20                  25                  30

Cys Asp Lys Asp Ser Gln Cys Gly Gly Gly Met Cys Cys Ala Val Ser
        35                  40                  45

Ile Trp Val Lys Ser Ile Arg Ile Cys Thr Pro Met Gly Gln Val Gly
    50                  55                  60

Asp Ser Cys His Pro Leu Thr Arg Lys Val Pro Phe Trp Gly Arg Arg
65                  70                  75                  80

Met His His Thr Cys Pro Cys Leu Pro Gly Leu Ala Cys Leu Arg Thr
                85                  90                  95

Ser Phe Asn Arg Phe Ile Cys Leu Ala Arg Lys
            100                 105

<210> SEQ ID NO 7
<211> LENGTH: 22
<212> TYPE: DNA
<213> ORGANISM: Artificial Sequence
<220> FEATURE:

-continued

```
<223> OTHER INFORMATION: /note="Description of Artificial Sequence:
      Synthetic primer"

<400> SEQUENCE: 7
gcatgacagg agtcatcatt tt                                              22

<210> SEQ ID NO 8
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 8
aaatggcagg atatcaggaa a                                               21

<210> SEQ ID NO 9
<211> LENGTH: 38
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 9
aaactttatt tgtaacccaa aggtctaatg taaatgga                             38

<210> SEQ ID NO 10
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 10
atggcacgga agctagga                                                   18

<210> SEQ ID NO 11
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 11
gcagagctga agtcctcttg a                                               21

<210> SEQ ID NO 12
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 12
tgctgctgga cccttcctaa acct                                            24

<210> SEQ ID NO 13
<211> LENGTH: 19
<212> TYPE: DNA
<213> ORGANISM: Artificial Sequence
<220> FEATURE:
<223> OTHER INFORMATION: /note="Description of Artificial Sequence:
```

Synthetic primer"

<400> SEQUENCE: 13
cagcgcacat gaagacttg                          19

<210> SEQ ID NO 14
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 14
gtcatcttcg gtttcctgag t                       21

<210> SEQ ID NO 15
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 15
tccaggcagc acccctgatg                         20

<210> SEQ ID NO 16
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 16
gaactccacg tgagcgca                           18

<210> SEQ ID NO 17
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 17
gggtcccatg ttgatgatgc                         20

<210> SEQ ID NO 18
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 18
ctccctgata cacaccagcc cacctg                  26

<210> SEQ ID NO 19
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

```
<400> SEQUENCE: 19
ctggaaggct tcttacaatg g                                          21

<210> SEQ ID NO 20
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 20
ggcatcccaa ttgtcttga                                             19

<210> SEQ ID NO 21
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 21
tccaggtctg cactggactt accg                                       24

<210> SEQ ID NO 22
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 22
tcaccatcgt tcgtgacttc                                            20

<210> SEQ ID NO 23
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 23
agaaggcagt gaggtagtgc tt                                         22

<210> SEQ ID NO 24
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 24
tccttcacga acacagtggg gaa                                        23

<210> SEQ ID NO 25
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"
```

<400> SEQUENCE: 25
aggtcaaagg gaatgtgttc aaa                                          23

<210> SEQ ID NO 26
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 26
ccttgtctgc cttcagcttg t                                            21

<210> SEQ ID NO 27
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 27
acaagcgcat cctcatggag cacatc                                       26

<210> SEQ ID NO 28
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 28
cgcaagcgcc gtgaa                                                   15

<210> SEQ ID NO 29
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 29
ggtctcttcc tccttggata aagtc                                        25

<210> SEQ ID NO 30
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 30
ccaggccaag aaggaggaga tcatca                                       26

<210> SEQ ID NO 31
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 31

```
aatgacgagg gcctggagt                                                    19
```

<210> SEQ ID NO 32
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 32

```
ttgatccgca taatctgcat g                                                 21
```

<210> SEQ ID NO 33
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic probe"

<400> SEQUENCE: 33

```
tgtgcccact gaggagtcca acatca                                            26
```

<210> SEQ ID NO 34
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 34

Gly Ser Gly Ser
1

<210> SEQ ID NO 35
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 35

Gly Gly Gly Ser
1

<210> SEQ ID NO 36
<211> LENGTH: 6
<212> TYPE: PRT
<213> ORGANISM: Artificial Sequence
<220> FEATURE:
<223> OTHER INFORMATION: /note="Description of Artificial Sequence:
      Synthetic 6x His tag"

<400> SEQUENCE: 36

His His His His His His
1               5

<210> SEQ ID NO 37
<211> LENGTH: 130
<212> TYPE: PRT
<213> ORGANISM: Mus sp.

<400> SEQUENCE: 37

-continued

```
Met Gly Asp Pro Arg Cys Ala Pro Leu Leu Leu Leu Leu Leu Pro
1               5               10                  15

Pro Leu Leu Phe Thr Pro Arg Ala Gly Asp Ala Ala Val Ile Thr Gly
            20              25              30

Ala Cys Asp Lys Asp Ser Gln Cys Gly Gly Gly Met Cys Cys Ala Val
            35              40              45

Ser Ile Trp Val Lys Ser Ile Arg Ile Cys Thr Pro Met Gly Gln Val
    50              55              60

Gly Asp Ser Cys His Pro Leu Thr Arg Lys Ser His Val Ala Asn Gly
65              70              75              80

Arg Gln Glu Arg Arg Arg Ala Lys Arg Arg Lys Arg Lys Lys Glu Val
            85              90              95

Val Pro Phe Trp Gly Arg Arg Met His His Thr Cys Pro Cys Leu Pro
            100             105             110

Gly Leu Ala Cys Leu Arg Thr Ser Phe Asn Arg Phe Ile Cys Leu Ala
        115             120             125

Arg Lys
    130
```

INHIBITION OF ANGIOGENESIS

CROSS REFERENCE TO RELATED APPLICATIONS

This application is a U.S. National Stage application of International Application No. PCT/US2008/076954, filed 19 Sep. 2008, which claims the benefit of U.S. Patent Application No. 60/974,382, filed 21 Sep. 2007, and U.S. Patent Application No. 61/083,071, filed 23 Jul. 2008, the contents of which are incorporated herein by reference in their entirety.

FIELD OF THE INVENTION

The present invention relates generally to the inhibition of inflammatory cell-mediated angiogenesis. In particular, the invention concerns the prevention or treatment of tumor angiogenesis, and the inhibition of tumor development, using Bv8 antagonists, such as anti-Bv8 antibodies.

BACKGROUND OF THE INVENTION

It is well established that angiogenesis plays an important role in tumor progression and metastasis and anti-angiogenesis represents a clinically validated anti-cancer strategy (Folkman, J., *Nat Med* 1, 27-31 (1995); Ferrara, N. and Kerbel, R. S., *Nature* 438, 967-974 (2005); Carmeliet, P. *Nat Med* 9, 653-660 (2003)). Angiogenesis also plays a key pathogenic role in a variety of other disorders, including age-related macular degeneration (AMD). Choroidal neovascularization has been reported to be dependent, at least in part, on neutrophil infiltration (Zhou et al., *Mol Vis* 11:414-424 (2005)). Tumor cells have been traditionally considered the main source of mediators of angiogenesis (Folkman, J., *N Engl J Med* 385, 1182-1186 (1971)). Indeed, much research has shown that cancer cells may produce a variety of angiogenic factors, including vascular endothelial growth factor-A (VEGF-A), angiopoietins, hepatocyte growth factor (HGF) and basic fibroblast growth factor (bFGF), and various mutations in oncogenes or tumor suppressor genes may result in increased production of at least some of these factors (Rak, J., et al., *Cancer Res* 55, 4575-4580 (1995); Wizigmann, et al., *Cancer Res* 55, 1358-1364 (1995)). However, compelling evidence now supports the notion that the stroma, consisting of fibroblasts, pericytes, mesenchymal stem cells and inflammatory-immune cells, and endothelial progenitors also contribute to tumor growth not only through secretion of angiogenic factors but also by modulation of the immune system (Hanahan, D. and Weinberg, R. A., *Cell* 100, 57-70 (2000); Coussens, L. M. and Werb, Z., *Nature* 420, 860-867 (2002); Blankenstein T., *Curr Opin Immunol* 17:180-186 (2005); Karnoub et al., *Nature* 449:557-563 (2005); Orimo et al., *Cell Cycle* 5:1497-1601 (2006); and Rafii, S. et al., *Nat Rev Cancer* 2, 826-835 (2002)). Potentially, some of these cells may inhibit tumor growth by immune surveillance mechanisms, but much of the evidence indicates that a marked infiltration by leukocytes and other inflammatory cells in tumors carries a poor prognosis (Coussens, et al., supra).

Recent studies have directly implicated different populations of myeloid cells in the regulation of tumor angiogenesis (Da Palma, M., et al., *Nat Med* 9, 789-795 (2003); Yang, L. et al., *Cancer Cell* 6, 409-421 (2004); De Palma M., et al., *Cancer Cell* 8, 211-226 (2005)) and VEGF-induced neovascularization in the adult (Grunewald, M. et al., *Cell* 124, 175-189 (2006)). Very recent studies have provided evidence for a role of CD11b+Gr1+ myeloid cells in mediating refractoriness to anti-VEGF therapy in some tumor models (Shojaei, F. et al., *Cell* 124, 175-189 (2006)). The role of neutrophils in initiating the angiogenic switch in a transgenic model of multi-stage carcinogenesis has been described (Nozawa, H. et al., *Proc Natl Acad Sci USA* 103, 12493-12498 (2006)). Myeloid cells may locally secrete angiogenic factors or produce proteases such as matrix metalloproteinase-9 (Yang, L., et al., supra; Nozawa et al., supra; van Kempen, L. C. et al., *Eur J Cancer* 42, 728-734 (2006)), which may in turn promote angiogenesis by increasing the bioavailability and activity of VEGF-A in the tumor microenvironment (Bergers G., et al., *Nat Cell Biol* 2, 737-744 (2000)). Nevertheless, our understandings of the mechanisms by which myeloid cells are mobilized from the BM and promote tumorigenesis remains incomplete.

Bv8 and EG-VEGF are two highly related secreted proteins, also referred to as prokineticin-1 and -2, which structurally belong to a larger class of peptides defined by a five disulphide bridge motif called a colipase fold (DeCouter, J. et al., *Nature* 420, 860-867 (2002); LeCouter. J. et al., *Proc Natl Acad Sci USA* 100, 2685-2690 (2003); Li, M. et al., *Mol Pharmacol* 59, 692-698 (2001)). Bv8 was initially identified as a secreted protein from the skin of the frog *Bombina variegate* (Mollay, C. et al., *Eur J Pharmacol* 374, 189-196 (1999)). The cloning and expression of Bv8 are described in WO 03/020892 published on Mar. 13, 2003. Bv8 and EG-VEGF bind two highly related G-protein coupled receptors (GPCR), EG-VEGF/PKR-1 (R1) and EG-VEGF/PKR-2 (R2) (Masuda, Y et al., *Biochem Biophys Res Commun* 293, 496-402 (2002); Lin, D. C. et al., *J Biol Chem* 277, 19276-19280 (2002)). EG-VEGF and Bv8 were characterized as mitogens selective for specific endothelial cell types (LeCouter, J. et al., (2001) and (2003), supra). Other activities have been ascribed to this family, including nociception (Mollay, C. et al., supra), gastrointestinal tract motility (Li, M. et al., supra), regulation of circadian locomotor rhythm (Cheng, M. Y., et al., *Nature* 417, 405-410 (2002)) and olfactory bulb neurogenesis (Matsumoto, S., et al., *Proc Natl Acad Sci USA* 103, 4140-4145 (2006)). Furthermore, Bv8 or EG-VEGF stimulated production of granulocytic and monocytic colonies in vitro (LeCouter, J. et al., (2003), supra; Dorsch, M. et al., *J. Leukoc Biol* 78(2), 426-34 (2005)). Bv8 has been characterized as a chemoattractact for macrophages (LeCouter et al., *Proc Natl Acad Sci USA* 101, 16813-16919 (2004)).

Recognition of vascular endothelial growth factor (VEGF) as a primary regulator of angiogenesis in pathological conditions has led to numerous attempts to block VEGF activities. VEGF is one of the best characterized and most potent positive regulators of angiogenesis. See, e.g., Ferrara, N. & Kerbel, R. S. *Angiogenesis as a therapeutic target. Nature* 438: 967-74 (2005). In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997) *Endocrine Rev.* 18:4-25. Moreover, studies have reported mitogenic effects of VEGF on a few non-endothelial cell types, such as retinal pigment epithelial cells, pancreatic duct cells and Schwann cells. See, e.g., Guerrin et al. *J. Cell Physiol.* 164: 385-394 (1995); Oberg-Welsh et al. *Mol. Cell. Endocrinol.* 126:125-132 (1997); and, Sondell et al. *J. Neurosci.* 19:5731-5740 (1999).

Recognition of vascular endothelial growth factor (VEGF) as a primary regulator of angiogenesis in pathological conditions has led to numerous attempts to block VEGF activities. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling. See, e.g., Siemeister et al. *Cancer Metastasis Rev.* 17:241-248 (1998). Anti-VEGF neutralizing antibodies have been shown to suppress the growth of a variety of human tumor cell lines in nude mice (Kim et al. *Nature* 362:841-844 (1993); Warren et al. *J. Clin. Invest.* 95:1789-1797 (1995); Borgström et al. *Cancer Res.* 56:4032-4039 (1996); and Melnyk et al. *Cancer Res.* 56:921-924 (1996)) and also inhibit intraocular angiogenesis in models of ischemic retinal disorders (Adamis et al. *Arch. Opthalmol.* 114:66-71 (1996)). Indeed, a humanized anti-VEGF antibody, bevacizumab (AVASTIN®, Genentech, South San Francisco, Calif.) has been approved by the US FDA in combination with intravenous 5-fluorouracil-based (5-FU) chemotherapy, for first- or second-line treatment of patients with metastatic carcinoma of the colon or rectum and in combination with carboplatin and paclitaxel for the first-line treatment of patients with unresectable, locally advanced, recurrent or metastatic non-squamous non-small cell lung cancer (NSCLC). See, e.g., Ferrara et al., *Nature Reviews Drug Discovery*, 3:391-400 (2004).

However, the long-term ability of therapeutic compounds to interfere with tumor growth is frequently limited by the development of drug resistance. Several mechanisms of resistance to various cytotoxic compounds have been identified and functionally characterized, primarily in unicellular tumor models. See, e.g., Longley, D. B. & Johnston, P. G. *Molecular mechanisms of drug resistance. J Pathol* 205:275-92 (2005). In addition, host stromal-tumor cell interactions may be involved in drug-resistant phenotypes. Stromal cells secrete a variety of pro-angiogenic factors and are not prone to the same genetic instability and increases in mutation rate as tumor cells (Kerbel, R. S. *Inhibition of tumor angiogenesis as a strategy to circumvent acquired resistance to anti-cancer therapeutic agents. Bioessays* 13:31-6 (1991). Reviewed by Ferrara & Kerbel and Hazlehurst et al. in Ferrara, N. & Kerbel, R. S. *Angiogenesis as a therapeutic target. Nature* 438: 967-74 (2005); and, Hazlehurst, L. A., Landowski, T. H. & Dalton, W. S. *Role of the tumor microenvironment in mediating de novo resistance to drugs and physiological mediators of cell death. Oncogene* 22:7396-402 (2003).

In preclinical models, VEGF signaling blockade with the humanized monoclonal antibody bevacizumab (AVASTIN®, Genentech, South San Francisco, Calif.) or the murine precursor to bevacizumab (A4.6.1 (hybridoma cell line producing A4.6.1 deposited on Mar. 29, 1991, ATCC HB-10709)) significantly inhibited tumor growth and reduced tumor angiogenesis in most xenograft models tested (reviewed by Gerber & Ferrara in Gerber, H. P. & Ferrara, N. *Pharmacology and pharmacodynamics of bevacizumab as monotherapy or in combination with cytotoxic therapy in preclinical studies. Cancer Res* 65:671-80 (2005)). The pharmacologic effects of single-agent anti-VEGF treatment were most pronounced when treatment was started in the early stages of tumor growth. If treatment was delayed until tumors were well established, the inhibitory effects were typically transient, and tumors eventually developed resistance. See, e.g., Klement, G. et al. *Differences in therapeutic indexes of combination metronomic chemotherapy and an anti-VEGFR-2 antibody in multidrug-resistant human breast cancer xenografts. Clin Cancer Res* 8:221-32 (2002). The cellular and molecular events underlying such resistance to anti-VEGF treatment are complex. See, e.g., Casanovas, O., Hicklin, D. J., Bergers, G. & Hanahan, D. *Drug resistance by evasion of antiangiogenic targeting of VEGF signaling in late-stage pancreatic islet tumors. Cancer Cell* 8:299-309 (2005); and, Kerbel, R. S. et al. *Possible mechanisms of acquired resistance to anti-angiogenic drugs: implications for the use of combination therapy approaches. Cancer Metastasis Rev* 20:79-86 (2001). A variety of factors may be involved. For example, combination treatment with compounds targeting VEGF and fibroblast growth factor (FGF) signaling improved efficacy and delayed onset of resistance in late-stage tumors in a genetic model of pancreatic islet carcinogenesis. See, Casanovas, O., Hicklin, D. J., Bergers, G. & Hanahan, D. *Drug resistance by evasion of antiangiogenic targeting of VEGF signaling in late-stage pancreatic islet tumors. Cancer Cell* 8, 299-309 (2005). Other investigators have identified tumor-infiltrating stromal fibroblasts as a potent source of alternative pro-angiogenic factors. See, e.g., Dong, J. et al. *VEGF-null cells require PDGFR alpha signaling-mediated stromal fibroblast recruitment for tumorigenesis. Embo J* 23:2800-10 (2004); and, Orimo, A. et al. *Stromal fibroblasts present in invasive human breast carcinomas promote tumor growth and angiogenesis through elevated SDF-1/CXCL12 secretion. Cell* 121:335-48 (2005).

Inflammatory cells can participate in angiogenesis by secreting inflammatory cytokines, which can affect endothelial cell activation, proliferation, migration, and survival (reviewed in Albini et al. and Balkwill et al. in Albini, A., Tosetti, F., Benelli, R. & Noonan, D. M. *Tumor inflammatory angiogenesis and its chemoprevention. Cancer Res* 65:10637-41 (2005); and, Balkwill, F., Charles, K. A. & Mantovani, A. *Smoldering and polarized inflammation in the initiation and promotion of malignant disease. Cancer Cell* 7:211-7 (2005). Several tumor-infiltrating inflammatory cells secrete pro-angiogenic factors, including monocytes/macrophages (see, e.g., De Palma, M. et al. *Tie2 identities a hematopoietic lineage of proangiogenic monocytes required for tumor vessel formation and a mesenchymal population of pericyte progenitors. Cancer Cell* 8:211-26 (2005); and, Yang, L. et al. *Expansion of myeloid immune suppressor Gr+CD11b+ cells in tumor-bearing host directly promotes tumor angiogenesis. Cancer Cell* 6:409-21 (2004)), T- and B-lymphocytes (see, e.g., Freeman, M. R. et al. *Peripheral blood T lymphocytes and lymphocytes infiltrating human cancers express vascular endothelial growth factor: a potential role for T cells in angiogenesis. Cancer Res* 55:4140-5 (1995)), vascular leukocytes (see, e.g., Conejo-Garcia, J. R. et al. *Vascular leukocytes contribute to tumor vascularization. Blood* 105:679-81 (2005)), dendritic cells (see, e.g., Conejo-Garcia, J. R. et al. *Tumor-infiltrating dendritic cell precursors recruited by a beta-defensin contribute to vasculogenesis under the influence of Vegf-A. Nat Med* 10:950-8 (2004)), neutrophils (see, e.g., Coussens, L. M., Tinkle, C. L., Hanahan, D. & Werb, Z. *MMP-9 supplied by bone marrow-derived cells contributes to skin carcinogenesis. Cell* 103:481-90 (2000)), and mast cells (see, e.g., Coussens, L. M. et al. *Inflammatory mast cells up-regulate angiogenesis during squamous epithelial carcinogenesis. Genes Dev* 13:382-97 (1999); and (reviewed in de Visser and Coussens in de Visser, K. E., Eichten, A. & Coussens, L. M. *Paradoxical roles of the immune system during cancer development. Nat Rev Cancer* 6:24-37 (2006)).

It was suggested that bone marrow-derived endothelial progenitor cells (EPCs (see, e.g., Lyden, D. et al. *Impaired recruitment of bone-marrow-derived endothelial and hematopoietic precursor cells blocks tumor angiogenesis and growth. Nat Med* 7, 1194-201 (2001)) and perivascular progenitor cells (see, e.g., Song, S., Ewald, A. J., Stallcup, W., Werb, Z. & Bergers, G. *PDGFRbeta+ progenitor cells in tumors regulate pericyte differentiation and vascular survival. Nat Cell Biol* 7:870-9 (2005)) contribute to vessel formation in some experimental models of tumor growth (reviewed in Rafii et al. in Rafii, S. Lyden, D., Benezra, R., Hattori, K. & Heissig, B. *Vascular and haematopoietic stem cells: novel tar sets for anti-angiogenesis therapy? Nat Rev Cancer* 2:826-35 (2002)). Myeloid lineage hematopoietic cells, including tumor-associated macrophages (TAMS), were shown to stimulate angiogenesis either directly by secreting angiogenic factors or indirectly by producing extracellular matrix-degrading proteases, which in turn release sequestered angiogenic factors (reviewed in Lewis, C. E. & Pollard, J. W. *Distinct role of macrophages in different tumor microenvironments. Cancer Research* 66:605-612 (2006); and, Naldini, A. & Carraro, F. *Role of inflammatory mediators in angiogenesis. Curr Drug Targets Inflamm Allergy* 4:3-8 (2005)). Among the myeloid cell lineages, CD11b+Gr1+ progenitor cells isolated from the spleens of tumor-bearing mice promoted angiogenesis when co-injected with tumor cells (see, e.g., Yang, L. et al. *Expansion of myeloid immune suppressor Gr+CD11b+ cells in tumor-bearing host directly promotes tumor angiogenesis. Cancer Cell* 6:409-21 (2004)) and tumor-infiltrating macrophage numbers correlated with poor prognosis in some human tumors (reviewed in Balkwill et al. in Balkwill, F., Charles, K. A. & Mantovani, A. *Smoldering and polarized inflammation in the initiation and promotion of malignant disease. Cancer Cell* 7:211-7 (2005)). However, in another study, macrophages inhibited growth of experimental tumors in mice, suggesting their potential as anticancer therapy. See, e.g., Kohchi, C. et al. *Utilization of macrophages in anticancer therapy: the macrophage network theory. Anticancer Res* 24:3311-20 (2004). Shojaei, F. Wu, et al. *Tumor refractoriness to anti-VEGF treatment is mediated by CD11b(+)Gr1(+) myeloid cells. Nat Biotechnology* 2007 25(8):911-20, reported on the role of CD11b(+)Gr1(+) myeloid cells in the resistance of tumors to treatment with anti-VEGF antibodies. Similar findings are disclosed in co-pending U.S. application Ser. No. 11/692,681, filed on Mar. 28, 2007.

Despite the relative abundance of myeloid cells and their potential to produce pro-angiogenic factors, their role in tumor resistance to anti-VEGF treatment remains unknown. There is a need to discover and understand the biological functions of myeloid cells, resistant tumors, and the factors that they produce. The present invention addresses these and other needs, as will be apparent upon review of the following disclosure.

SUMMARY OF THE INVENTION

The present invention is based, at least in part, on experimental data indicating that Bv8 regulates mobilization of CD11b+Gr1+ cells from the bone marrow (BM) during tumor development and promotes tumor angiogenesis. Thus, the present invention provides methods and compositions for diagnosing and treating tumors resistant to treatment with VEGF antagonists.

In one aspect, the invention concerns a method of tumor treatment, comprising administering to a mammalian subject, such as a human subject, having a tumor previously treated with a vascular endothelial growth factor (VEGF) antagonist, an effective amount of a Bv8 antagonist. The human subject may be, but does not need to be, refractory to treatment with a VEGF antagonist.

In one embodiment, the VEGF antagonist is an anti-VEGF antibody or a fragment thereof, where the anti-VEGF antibody may, for example, be bevacizumab or a fragment or variant thereof.

In another embodiment, the Bv8 antagonist is an anti-Bv8 or an anti-Bv8 receptor monoclonal antibody or a fragment thereof, where the Bv8 receptor may be PKR-1/EG-VEGFR1 or PKR-2/EG-VEGFR2. The Bv8 to which the antibody binds, is a native-sequence Bv8 polypeptide of the mammal treated. Similarly the Bv8 receptor to which the antibody binds is a native sequence Bv8 receptor of the mammal treated.

The antibodies or antibody fragments can be chimeric, humanized or human.

In a further embodiment, the subject is further administered an anti-VEGF antibody, where VEGF can be any VEGF molecule, specifically including, without limitation, the 165-amino acid vascular endothelial cell growth factor, and related 121-, 145-, 189-, and 206-amino acid vascular endothelial cell growth factors, together with the naturally occurring allelic and processed forms thereof.

In a particular embodiment, the anti-VEGF antibody is bevacizumab or a fragment or variant thereof.

In another embodiment, in addition to the administration of a Bv8 antagonist and optionally a VEGF antagonist, the mammalian subject, such as a human patient, is treated with one or more additional myeloid cell reduction agents, such as a Gr1 antagonist, an elastase inhibitor, a MCP-1 antagonist, and/or a MIP-1 alpha antagonist.

In yet another embodiment, the mammalian subject treated, such as a human subject, is subjected to chemotherapy and/or radiation therapy, where the chemotherapy may, for example, comprise the administration of a cytotoxic agent. Preferably, the additional treatment is a treatment known as "standard of care" for the treatment of the particular tumor targeted.

The tumor may be any kind of benign or cancerous tumor, including, without limitation, carcinoma including adenocarcinoma, lymphoma, blastoma, melanoma, sarcoma, and leukemia. The preferred cancer herein is colon cancer, rectal cancer, lung cancer, and breast cancer, in particular, metastatic carcinoma of the colon or rectum, or non-squamous non-small cell lung cancer (NSCLC).

In a particular embodiment, the above method further comprises the step of monitoring the efficacy of treatment by determining the number and/or frequency of circulating and/or bone marrow CD11b+Gr1+ cells in a biological sample obtained from the mammalian subject, such as human, relative to pre-treatment number or frequency.

In another aspect, the invention concerns a method of tumor treatment, comprising
(a) administering to a tumor-bearing mammalian subject, such as human, an effective amount of a Bv8 antagonist, and
(b) monitoring the efficacy of said treatment by determining the number and/or frequency of circulating and/or bone marrow CD11b+Gr1+ cells in a biological sample obtained from the mammalian subject, such as human, relative to pre-treatment number or frequency, wherein a reduced number or frequency indicates that the treatment is effective.

In a further aspect, the invention concerns a method for the inhibition of inflammatory-cell mediated angiogenesis in a mammalian, such as human subject, comprising administering to the subject an effective amount of a Bv8 antagonist.

The antagonist can, for example, be an anti-Bv8 or anti-Bv8 receptor monoclonal antibody or a fragment thereof, which may be chimeric, humanized or human. The Bv8 to which the antibody binds, is a native-sequence Bv8 polypetide of the mammal treated. Similarly the Bv8 receptor to which the antibody binds is a native sequence Bv8 receptor of the mammal treated.

The method may further comprise the step of monitoring the efficacy of treatment by determining the number and/or frequency of circulating and/or bone marrow CD11b+Gr1+ cells in a biological sample obtained from the mammalian subject, such as human, relative to pre-treatment number or frequency.

In another embodiment, the method may further comprise the administration of an additional inhibitor of angiogenesis, such as, for example, an antibody to an angiogenic factor.

Examples of angiogenic factors include, without limitation, vascular endothelial growth factor (VEGF), angiopoietins, hepatocyte growth factor (HGF) and basic fibroblast growth factor (bFGF).

In yet another aspect, the invention concerns a method for identifying a tumor-bearing human subject for treatment with a Bv8 antagonist, comprising determining that the subject is refractory to treatment with a VEGF antagonist.

In a still further aspect, the invention concerns the inhibition of neutrophil mobilization stimulated by G-CSF by administering a Bv8 antagonist alone, or in combination with a G-CSF antagonist.

The invention further concerns the inhibition of Bv8-mediated migration of cells of myeloid lineage by Bv8 antagonists.

The invention further concerns the depletion of CD11b+ Gr1+ myeloid cells to inhibit tumor development and/or growth, by administering a Bv8 atagonist.

In another aspect, the invention concerns a method of tumor treatment comprising administering to a tumor-bearing human subject an effective amount of a G-CSF antagonist.

In a particular embodiment, the G-CSF antagonist is an anti-G-CSF antibody or antibody fragment. The antibody or antibody fragment may be chimeric, humanized or human. Optionally, the G-CSF antagonist is administered in combination with a Bv8 antagonist and/or a VEGF antagonist, such as, for example, an anti-Bv8 antibody and/or an anti-VEGF antibody.

In another embodiment, the G-CSF antagonist is administered in combination with a different anti-tumor agent and/or treatment regiment, such as chemotherapy and/or radiation therapy.

In yet another aspect, the invention concerns a method for the inhibition of neutrophil migration in a human subject, comprising administering to the subject an effective amount of a Bv8 antagonist.

In a further aspect, the invention concerns a method for the treatment of a non-neoplastic condition benefiting from anti-angiogenic therapy, comprising administering to a human subject previously diagnosed with such non-neoplastic condition and treated with a vascular endothelial growth factor (VEGF) antagonist, an effective amount of a Bv8 antagonist.

In one embodiment, the non-neoplastic condition is refractory to treatment with a VEGF antagonist.

The non-neoplastic condition may, for example, be selected from the group consisting of undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion, and pleural effusion.

In a still further aspect, the invention concerns a neutralizing anti-Bv8 antibody, and compositions comprising such antibody.

In a particular embodiment, the neutralizing antibody binds essentially to the same epitope, or to the same epitope, as the murine anti-Bv8 antibody 3F1 or 2B9. Just as before, the antibody may be an antibody fragment, and may be chimeric, humanized or human.

BRIEF DESCRIPTION OF THE DRAWINGS

Throughout the description, BM=bone marrow, and PB=peripheral blood.

FIG. 4. Bv8 regulates tumor angiogenesis. Immunodeficient mice were implanted with $5\times10^6$ HM7 cells as described. Five days after implantation, mice were injected with $10^7$ pfu of Av-Bv8, Av-VEGF or Av-LacZ. a. Terminal tumor volume measurement in all treatments indicated a significant difference in tumor volume in Av-Bv8 and Av-VEGF compared to Av-LacZ tumors. b. The frequency of CD11b+ Gr1+ cells in the (peripheral blood (PB) was greater in Av-Bv8 treated mice compared to Av-VEGF and Av-LaczZ animals. c&d. Micro-CT analysis revealed increased vascular volume (c) in mice that were injected by Bv8- and VEGF-adenoviruses compared to LacZ-injected mice. e. A representative image of tumors injected with Av-LacZ, Av-VEGF and Av-Bv8 is shown. The vascular networks and the tumors are shown in red and gray, respectively. f. Anti-Bv8 Mab treatment inhibits tumor growth by affecting the tumor vasculature. Nude mice were implanted with HM7 cells and were treated with anti-Bv8, anti-VEGF or control antibodies. Consistent with data in FIG. 2b, both anti-Bv8 and anti-VEGF treatments result in significant tumor growth inhibition compared to control. g. Anti-Bv8 treatment reduces the frequency of circulating CD11b+Gr1+ in the PB compared to anti-VEGF and control. h&i. The Micro-CT approach, described above, showed a significant decrease in vascular volume (h) and vascular density (i) in anti-Bv8 versus control treated mice. The degree of inhibition is similar to that provided by anti-VEGF treatment. j. Representative micro-CT angiographic data are shown for anti-Bv8, anti-VEGF and control treatments. The vascular networks and the tumors are shown in red and gray, respectively.

FIG. 7. Nucleotide sequence (SEQ ID NO: 1) of a cDNA encoding a human Bv8 homologue. Also presented in bold font and underlined are positions of the respective start and stop codons.

FIG. 8. Amino acid sequence (SEQ ID NO: 2) of a human Bv8 homologue polypeptide as derived from the encoding sequence of SEQ ID NO: 1. A putative signal sequence is comprised of amino acids 1 through 21.

FIG. 9. Nucleotide sequence (SEQ ID NO: 3) of a cDNA encoding an alternatively spliced version of the human Bv8 homologue. Also presented in bold font and underlined are the positions of the respective start and stop codons.

FIG. 10. Amino acid sequence (SEQ ID NO: 4) of a human Bv8 homologue polypeptide as derived from the coding sequence of SEQ ID NO: 3.

FIG. 11. Nucleotide sequence (SEQ ID NO: 5) of a mouse Bv8 homologue. Also presented in bold font and underlined are the positions of the respective start and stop codons.

FIG. 12. Amino acid sequence (SEQ ID NO: 6) of a mouse Bv8 homologue polypeptide as derived from the coding sequence of SEQ ID NO: 5.

FIG. 13. Alignment of the mouse (SEQ ID NO: 37) and human (SEQ ID NO: 2) Bv8 homologues. A potential heparin-binding domain is boxed. As indicated, this domain is not present in an alternatively spliced transcript. The mouse and human Bv8 homologues are approximately 96% identical.

Figure 1A:
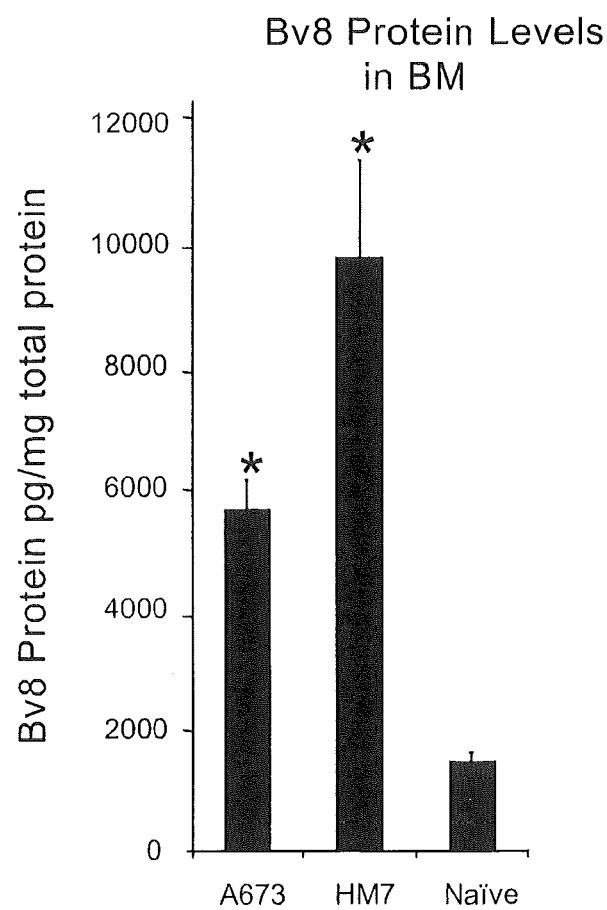
FIG. 1. Regulation of Bv8 expression and activity on BM cells. a. Tumors induce expression of Bv8 protein in the BM. Beige nude mice were implanted with A673 or HM7 tumor cells. A specific ELISA showed higher (p<0.05) levels of Bv8 in BMMNCs of tumor-implanted relative to Matrigel™-implanted mice after six days. b. Bv8 expression is specifically upregulated in the CD11b+Gr1+ subset of BM cells. Beige nude mice were implanted with A673, HM7, HPAC, Calu-6 and Jurkat cells. After 10 days, CD11b+Gr1+ myeloid cells were isolated from the BM of mice and TM analysis determined Bv8 expression in myeloid and non-myeloid (CD11b– Gr1–) subsets. Asterisks indicate significant differences (p<0.05) when comparing CD11b+Gr1+ in each tumor versus the corresponding CD11b–Gr1– population. c. G-CSF is a major inducer of Bv8 expression. BMMNCs were isolated from naïve mouse and were incubated with a series of cytokines and chemokines and Bv8 expression was evaluated by Taqman™, as described in Methods. d. G-CSF is the major inducer of Bv8 is in CD11b+Gr1+ cells. BMMNCs were isolated from Balb-c mice and were sorted to CD11b+Gr1+ and CD11b–Gr1– subsets by FACS. Whole BM, CD11b+ Gr1+ and CD11b–Gr1– populations were treated with SDF1α, G-CSF and GM-CSF, as described in Methods. e. Hypoxia enhances Bv8 up-regulation by G-CSF in myeloid cells. BM CD11b+Gr1+ were incubated with G-CSF at 20 or 2500 pg/ml in either normoxic or hypoxic (1% $O_2$) conditions for 4 hrs. f. Bv8 levels are significantly increased in the BM following injection of G-CSF. Balb-c mice were injected s.c. with G-CSF on day 0 and then daily for 8 days. BM Samples were taken at day 1, 3, 6 and 8 and the levels of Bv8 protein was measured as described. g. Treatment with anti-G-CSF inhibits G-CSF induced upregulation of Bv8. Freshly isolated BMMNCs were incubated with HM7 tumor lysate and various concentrations of anti-G-CSF, as indicated. Expression of Bv8 was monitored in BMMNCs by Taqman™. h. Anti-G-CSF reduces the level of Bv8 in the BM of non-tumor bearing mice. Balb/c nude mice were treated with PBS, control IgG and anti-G-CSF and levels of Bv8 in BMMNCs were measured by ELISA as described in Methods. i. Anti-G-CSF reduces the level of Bv8 in the BM of HM7 tumor bearing mice. See Methods for details. Forty-eight hours after tumor or Matrigel™ implantation, levels of Bv8 protein were measured in BMMNCs as described. j. Bv8 plays a role in neutrophils mobilization induced by G-CSF. Balb/c nude mice were treated i.p. with several agents including anti-G-CSF, anti-Bv8, control Mab and control IgG antibody twice in 12 hrs, as described in Methods. All mice were bled 6 hrs after final injection and the frequency of CD11b+Gr1+ cells was determined in a FACSCalibur flow cytometer (Becton Dickinson) as described.

Supplemental FIG. 1. Characterization of the Bv8 protein produced by BMMNCs. a. Mouse bone marrow-derived mononuclear cells (BMMNCs) were isolated and lysed as described in the Materials and Methods section of Example 1. The lysate was applied to a heparin-Sepharose™ column pre-equilibrated in 20 mM Tris pH7.2, 50 mM NaCl. The column was eluted with a NaCl gradient as described in the Materials and Methods. Bv8 concentrations in each fraction were measured by ELISA. Fractions 13 and 14, eluted in the presence of about 0.4M NaCl, had the highest Bv8 levels. b. In agreement with ELISA data, Western blot analysis shows that Bv8 is highly enriched in fractions 13 and 14.

Supplemental FIG. 2. G-CSF is a key regulator of Bv8 expression in normal mice and in tumor bearing mice. a. Bv8 levels are significantly increased in the serum following injection of G-CSF. Balb-c nude mice were injected i.p. with G-CSF on day 0 and then daily for 8 days. Samples were taken at days 1, 3, 6 and 8. b. Neutrophil count from the above experiment showed an increased in the number of circulating neutrophils in G-CSF treated mice. c.&d. Balb/c nude mice were treated with PBS, control IgG and anti-G-CSF for 8 consecutive days and the frequency of CD11b+Gr1+ cells in the peripheral blood (PB) (c) and BM (d) was determined using FACS staining as described. e.&f. Balb/c nude mice were pre-treated with anti-G-CSF or control IgG antibodies 12 hrs before tumor-Matrigel™ implantation. Matrigel™- and tumor-bearing mice were treated with anti-G-CSF or control IgG for two consecutive days. At terminal analysis, the frequency of CD11b+Gr1+ in the PB (e) and BM (f) was investigated using FACS.

Supplemental FIG. 3. a. Bv8 induces trans-well migration of CD11b+Gr1+ myeloid cells. Controls were PBS or media alone. b&c. Expression of Bv8 receptors in BMMNCs. Beige nude mice were implanted with A673, HM7, HPAC or Calu-06 cells as described. After 10 days, CD11b+Gr1+ myeloid cells were isolated from the BM and Taqman™ analysis was performed to investigate EG-VEGFRs expression in myeloid and non-myeloid (CD11b−Gr1−) subsets of tumor versus Matrigel™-implanted mice. Such analysis reveals higher expression of EG-VEGF/PK-R2 (c) than EG-VEGF/PK-R1, (b) in BMMNCs. d. Bv8 alters the fate of the progenitor population to myeloid cells (CD11b+Gr1+) and also inhibitors cell death in the Lin-population. The Lin-fraction, isolated from the BMMNCs of beige nude mice, was incubated with Bv8 for 5 days and the frequency of CD11b+Gr1+ cells was evaluated in a FACSCalibur machine. In addition, 7AAD staining was employed to measure the number of dead cells in each treatment. e. Bv8 induces clonogenic capacity of progenitor cells. Lin-population were treated with Bv8 or PBS for 5 days and were plated on methylcellulose (7500 cells per well) and were incubated in 5% $CO_2$ and 37° C. for 15 days. Differential and total colony counts revealed a greater clonogenic capacity of Bv8 treated cells. L Bv8 is a survival factor for myloid populations. The CD11b+Gr1+ cells, isolated from the BMMNCs of beige/nude mice, were cultured in media and were treated with Bv8 (300 ng/ml) for 5 days. Cell death was measured in a FACSCalibur machine using 7AAD staining. g&h. Discontinuing anti-Bv8 treatment results in rapid tumor growth. Mice were implanted with A673 (e) or HM7 (f) tumors and were treated with anti-Bv8 or control antibodies as described. Treatment was stopped at day 7 after implantation, as indicated by arrow in the figure. i&j. Discontinued treatment of anti-Bv8 results in rebound of CD11b+ Gr1+ cells to A673 (i) and HM7 (j) tumors.

Supplemental FIG. 4. Effects of anti-Bv8 antibodies on hematopoiesis in non-tumor bearing mice. Balb/c nude mice were treated with PBS, control antibody or anti-Bv8 antibodies at therapeutic dose for 3 weeks. Body weights (a), organ weights (b), and also lineages of myeloid and lymphoid cells were analyzed in the BM (c), spleen (d) and PB (e).

Supplemental FIG. 5. Treatment with anti-Bv8 antibodies reduces the number of CD11b+Gr1+ cells in the PB and in tumors in the A673 model. Beige/nude mice were implanted with $5 \times 10^6$ A673 cells and received anti-Bv8 treatment, starting 48 hours after implantation ad twice weekly thereafter. Kinetics of CD11b+ (data not shown), Gr1+ (data not shown) and CD11b+Gr1+ cells were monitored at different time points (i.e. days 5, 10, 19 and 29 after implantation) in anti-Bv8 and control treated mice. a. BMMNCs were isolated from each treatment group and underwent the staining procedure as described in the Materials and Methods section of Example 1. b. Mice were bled at each time point and the frequency of CD11b+Gr1+ was measured using a FACSCalibur. c. Tumor cells were counted individually and numbers of CD11b+Gr1+ cells were calculated by multiplying the frequency of these cells by the total number of tumor cells. Asterisks indicate significant difference ($p<0.05$) at each time point when comparing anti-Bv8 treated mice versus the corresponding control treated population.

Supplemental FIG. 6. Representative FACS profiles of populations of CD11b, Gr1 and CD11b+Gr1+ cells in tumor bearing mice. Beige nude mice (n=5) were implanted with $5 \times 10^6$ A673, Calu6, HM7, HPAC or Jurkat cells. Mice were treated with anti-Bv8 or control Mabs as described in the Materials and Methods section of Example 1. Mice were analyzed at day 10 after tumor implantation and the frequency of CD11b+, Gr1+, and CDb11+Gr1+ cells was measured in BM, PB, tumors and spleens as described.

Supplemental FIG. 7. Tumor implantation increases the frequency of CD11b+Gr1+ in the BM and spleen. Beige nude mice (n=5) were implanted with $5 \times 10^6$ A673, Calu6, HM7, HPAC or Jurkat cells. Mice were treated with anti-Bv8 control Mabs as described in the Materials and Methods, and BM or splenic cells were then isolated from tumor-bearing mice and were stained with anti-G11 and anti-CD11b. Graphs represent the percentage of CD11b+, Gr1+, and CD11b+Gr1+ cells in the BM (a) and spleen (b). The inset on the top right shows the frequency of CD11b+, Gr1+, and CD11b+Gr1+ cells in Matrigel™-implanted mice. c. Anti-Bv8 treatment reduces the clonogenic capacity of BMMNCs and splenocytes. Nude mice were implanted with A673 and HM7 cells and were then treated with anti-Bv8 or control antibodies as described. BMMNCs and splenocytes were harvested from tumor bearing mice 10 days after tumor implantation and were seeded for CFU assay.

Supplemental FIG. 8. Bv8 promotes tube formation in TAEC and fails to stimulate the growth of tumor cells. a. Bv8 induces in vitro tube formation in endothelial cells. TEACS were seeded on plates coated with Matrigel™ and then incubated with either basal media (control, Bv8 or VEGF-A, with or without anti-Bv8, as described in the Materials and Methods section of Example 1). Pictures (phase contrast; original magnification 20×) show the appearance of the endothelial tubes after incubation for 36 hours. b. TAECs express markers of conventional endothelial cells. The identity of TAECs used in these experiments was confirmed by flow cytometry (data not shown) and RT-PCR using CD31, VEGFR2, TIE2, VE-CADH, CK8 and E-CDH in TAECs, skin endothelial cells (SkECs), epithelial cells and fibroblasts. GAPDH was used as internal control. c. TAECs activate MAPK signaling in response to Bv8 stimulation. Cells were treated with Bv8 (200 ng/ml), VEGF (positive control; 40 ng/ml), Complete Media (CM) or mock (0.5% DSA) for 5, 10 and 20 minutes at 37° C. Western blot analysis, described in the Materials and Methods section of Example 1, detected phosphorylated MAPK (P-MAPK) in Bv8 treated wells, whereas mock (PBS) treatment did not induce P-MAPK activation. d. Bv8 does not induce proliferation of tumor cells. A673, Calu-6, HM7 and HPAC cells were treated with different concentrations of recombinant Bv8 and were then pulsed with BrdU. Proliferation was qualtified by BrdU incorporation.

Supplemental FIG. 9. a. Bv8 promotes tumor angiogenesis. HM7-tumor bearing mice received a single intratumoral dose of Ad-LacZ, Av-Bv8 low titer, Av-Bv8 high titer, and Av-VEGF 5 days after tumor implantation. Vescular surface areas were measured 4 days after adenovirus delivery using MECA-32 staining of tumor sections. b. Anti-Bv8 treatment results in inhibition of tumor angiogenesis. Beige nude mice were implanted with Jurkat cells and were treated with control (Panels a-c), anti-Bv8 (Panels d-f) and anti-VEGF (Panels g-i) antibodies. Note the marked suppression of tumor angiogenesis by anti-Bv8 or anti-VEGF treatment. Panels 1, b, s, e, g, h and H&E staining and Panels c, f, t are MECA-32 staining (tumor areas are indicated by asterisk).

Supplemental FIG. 10. The role of Bv8 in tumor growth. Tumor cells and tumor-associated stroma signal up-regulation of Bv8 in the BM via release of chemokines and cytokines such as G-CSF, IL-6 and SDF-1. Bv8 may amplify myeloid cell mobilization elicited by G-CSF by autorine and paracrine mechanisms. Tumor necrosis is known to promote myeloid cells infiltration. Myeloid cells homing in the tumor by a variety of mechanisms may locally produce Bv8, which is turn directly stimulated endothelial cell proliferation and angiogenesis. Cytokines, hypoxia and anti-VEGF therapy may also result in increased expression of Bv8 by myeloid cells within the tumor microenvironment. Bv8 produced by tumor-infiltrative myeloid cells may also signal to the BM to further promote mobilization, transendothelial migration and homing of myeloid cells to the tumor.

Supplemental Table 1. Cytokine levels in conditioned media from human tumor cells or tumor-associated mouse fibroblasts isolated and cultured from xenografts.

Supplemental Table 2. Various cell lines treated with either G-CSF or GM-CSF at 10 ng/ml for 4 hr. RNA was subsequently extracted and subjected to Taqman analysis using RPL19 as the housekeeping gene for normalization. Fold change was shown with un-treated being 1. *** $p<0.01$ vs. un-treated control. Three independent studies were conducted.

DETAILED DESCRIPTION OF THE INVENTION

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

A. Definitions

The terms "Bv8," "Bv8 homologue," "prokineticin-2," (also known as "PK2," "KAL4," and "MIT1") are used herein interchangeably, and refer to a native-sequence, Bv8 polypeptide, Bv8 variants, and chimeric Bv8, each of which is defined herein.

Bv8 nucleic acid is RNA or DNA that encodes a Bv8 polypeptide, as defined above, or which hybridizes to such DNA or RNA and remains stably bound to it under stringent hybridization conditions and is greater than about 10 nucleotides in length. Stringent conditions are those which (1) employ low ionic strength and high temperature for washing, for example, 0.15 M NaCl/0.015 M sodium citrate/0.1% NaDodSO$_4$ at 50° C., or (2) use during hybridization a denaturing agent such as formamide, for example, 50% (vol/vol) formamide with 0.1% bovine serum albumin/0.1% Ficoll/ 0.1% polyvinlypyrrolidone/50 mM sodium phosphate buffer at pH 6.5 with 750 mM NaCl, 75 mM sodium citrate at 42° C.

Nucleic acid is operably linked when it is placed into a functional relationship with another nucleic acid sequence. Bv8 nucleic acid may be operably linked with another nucleic acid sequence in a vector such that it may be expressed in a particular host organism. This may be done by methods well known in the art. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adapters or linkers are used in accord with conventional practice.

"Native sequence Bv8" comprises a polypeptide having the same amino acid sequence as Bv8 derived from nature, regardless of its mode of preparation. Thus, native sequence Bv8 can have the amino acid sequence of naturally occurring human Bv8, murine Bv8, or Bv8 from any other mammalian species. For example a full-length native sequence human Bv8 amino acid sequence is shown in FIG. 8 (SEQ ID NO: 2). A second full-length native sequence human Bv8 is shown in FIG. 10 (SEQ ID NO: 4). These two sequences are the result of the alternative splicing of an exon that encodes a canonical heparin binding domain. Thus the native sequence human Bv8 whose amino acid sequence is shown in FIG. 8 (SEQ ID NO: 2) comprises a heparin binding domain, while the native sequence Bv8 depicted in FIG. 10 (SEQ ID NO: 4) does not. A native sequence mouse Bv8 amino acid sequence is shown in FIG. 12 (SEQ ID NO: 6). Human and murine Bv8 sequences are also disclosed, for example, in Wechselberger et al. (FEBS Lett. 462:177-181 (1999)) and Li et al. (Mol. Pharm. 59:692-698 (2001)). Such native sequence Bv8 can be isolated from nature or can be produced by recombinant and/or synthetic means. The term "native sequence Bv8" specifically encompasses naturally occurring prepro, pro and mature forms and truncated forms of Bv8, naturally occurring variant forms (e.g. alternatively spliced forms, such as that shown in FIG. 10 (SEQ ID NO: 4)), and naturally occurring allelic variants. A preferred native sequence Bv8 is a full-length native sequence human Bv8 as shown in FIG. 8 (SEQ ID NO: 2).

"Bv8 variants" are biologically active Bv8 polypeptides having an amino acid sequence which differs from the sequence of a native sequence Bv8 polypeptide, such as those shown in FIGS. 8, 10 and 12 (SEQ ID NOs: 2, 4 and 6) for human and murine Bv8, by virtue of an insertion, deletion, modification and/or substitution of one or more amino acid residues within the native sequence. Bv8 variants generally have less than 100% sequence identity with a native sequence Bv8, such as the human Bv8 of FIG. 8 (SEQ ID NO: 2). Ordinarily, however, a biologically active Bv8 variant will have an amino acid sequence with at least about 70% amino acid sequence identity with the amino acid sequence of a naturally occurring Bv8 such as the human Bv8 of FIG. 8 (SEQ ID NO: 2), preferably at least about 75%, more preferably at least about 80%, even more preferably at least about 85%, even more preferably at least about 90%, with increasing preference of at least about 95% to at least about 99% amino acid sequence identity, in 1% increments. The Bv8 variants include peptide fragments of at least 5 amino acids that retain a biological activity of the corresponding native sequence Bv8 polypeptide. Bv8 variants also include Bv8 polypeptides wherein one or more amino acid residues are added at the N- or C-terminus of or within, a native Bv8 sequence. Bv8 variants also include Bv8 polypeptides where a number of amino acid residues are deleted and optionally substituted by one or more amino acid residues. Bv8 variants also may be covalently modified, for example by substitution with a moiety other than a naturally occurring amino acid or by modifying an amino acid residue to produce a non-naturally occurring amino acid. Bv8 variants may comprise a heparin binding domain.

In general, a polypeptide "variant" (i.e. a variant of any polypeptide disclosed herein) means a biologically active polypeptide having at least about 80% amino acid sequence identity with the corresponding native sequence polypeptide. Such variants include, for instance, polypeptides wherein one or more amino acid (naturally occurring amino acid and/or a non-naturally occurring amino acid) residues are added, or deleted, at the N- and/or C-terminus of the polypeptide. Ordinarily, a variant will have at least about 80% amino acid sequence identity, or at least about 90% amino acid sequence identity, or at least about 95% or more amino acid sequence identity with the native sequence polypeptide. Variants also include polypeptide fragments (e.g., subsequences, truncations, etc.), typically biologically active, of the native sequence.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, e.g., digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

A "chimeric Bv8" molecule is a polypeptide comprising full-length Bv8 or one or more domains thereof fused or bonded to heterologous polypeptide. The chimeric Bv8 molecule will generally share at least one biological property in common with naturally occurring Bv8. An example of a chimeric Bv8 molecule is one that is epitope tagged for purification purposes. Another chimeric Bv8 molecule is a Bv8 immunoadhesin.

The term "epitope-tagged" when used herein refers to a chimeric polypeptide comprising Bv8 fused to a "tag polypeptide". The tag polypeptide has enough residues to provide an epitope against which an antibody can be made, yet is short enough such that it does not interfere with biological activity of the Bv8. The tag polypeptide preferably is fairly unique so that the antibody against it does not substantially cross-react with other epitopes. Suitable tag polypeptides generally have at least six amino acid residues and usually between about 8-50 amino acid residues (preferably between about 9-30 residues). Preferred are poly-histidine sequences, which bind nickle, allowing isolation of the tagged protein by Ni-NTA chromatography as described (See, e.g., Lindsay et al. Neuron 17:571-574 (1996)).

"Isolated Bv8" means Bv8 that has been purified from a Bv8 source or has been prepared by recombinant or synthetic methods and purified. Purified Bv8 is substantially free of other polypeptides or peptides. "Substantially free" here means less than about 5%, preferably less than about 2%. more preferably less than about 1%, even more preferably less than about 0.5%, most preferably less than about 0.1% contamination with other source proteins.

"Essentially pure" protein means a composition comprising at least about 90% by weight of the protein, based on total weight of the composition, preferably at least about 95% by weight, more preferably at least about 90% by weight, even more preferably at least about 95% by weight. "Essentially homogeneous" protein means a composition comprising at least about 99% by weight of protein, based on total weight of the composition.

The term "antagonist" when used herein refers to a molecule capable of neutralizing, blocking, inhibiting, abrogating, reducing or interfering with the activities of a protein of the invention including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of a protein of the invention, and fusions proteins, receptor molecules and derivatives which bind specifically to protein thereby sequestering its binding to its target, antagonist variants of the protein, antisense molecules directed to a protein of the invention, RNA aptamers, and ribozymes against a protein of the invention.

A "blocking" antibody or an "antagonist" antibody is one which inhibits or reduces biological activity of the antigen it binds. Certain blocking antibodies or antagonist antibodies substantially or completely inhibit the biological activity of the antigen.

The term "Bv8 antagonist," as used herein, refers to any molecule that partially or fully blocks, inhibits, or neutralizes the ability of a native sequence Bv8 to modulate myeloid mobilization and/or to promote angiogenesis during tumor development. Suitable antagonist molecules specifically include antagonist antibodies or antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of Bv8, and fusions proteins, receptor molecules and derivatives which bind specifically to Bv8 thereby sequestering its binding to its target, antagonist variants of Bv8, antisense molecules directed to Bv8, RNA aptamers, and ribozymes against Bv8.

In particular, Bv8 antagonists include, without limitation, antibodies and antibody fragments specifically binding to a native sequence Bv8 polypeptide, or a native sequence Bv8 receptor (PKR-1/EG-VEGFR1 or PKR-2/EG-VEGFR2) polypeptide. Methods for identifying antagonists of a Bv8 polypeptide may comprise contacting a Bv8 polypeptide with a candidate antagonist molecule and measuring a detectable change in the ability of Bv8 to modulate myeloid cell mobilization and/or promote tumor angiogenesis.

"Active" or "activity," in connection with Bv8 or G-CSF, for the purposes herein refers to form(s) of Bv8 or G0CSF which retain a biological and/or an immunological activity of native or naturally-occurring Bv8 or G-CSF, wherein "biological" activity refers to a biological function (either inhibitory or stimulatory) caused by a native or naturally-occurring Bv8 or G-CSF, other than the ability to induce the production of an antibody against an antigenic epitope, possessed by a native or naturally-occurring Bv8 or G-CSF, and an "immunological" activity refers to the ability to induce the production of an antibody against an antigenic epitope possessed by a native or naturally-occurring Bv8 or G-CSF. A preferred Bv8 biological activity is the ability to modulate myeloid cell mobilization and/or promote tumor angiogenesis.

"Bv8 receptor" is a molecule to which Bv8 binds and which mediates the biological properties of Bv8. Therefore, the term "Bv8 receptor" includes within its meaning PKR1/EG-VEGF receptor-1 and PKR2/EG-VEGF receptor-2 (LeCouter et al., 2003, *Proc. Natl. Acad. Sci. USA*, 100:2685-

2690: Lin et al., 2002, *J. Biol. Chem.*, 277:19276-19280; Masuda et al. 2002, *Biochem. Biophys. Res. Commun.*, 293: 396-402).

The term "VEGF" as used herein refers to a native sequence vascular endothelial growth factor and varians thereof.

The terms "VEGF" and "VEGF-A" are used interchangeably to refer to the native sequence 165-amino acid vascular endothelial cell growth factor and related 121-, 145-, 183-, 189-, and 206-amino acid vascular endothelial cell growth factors, as described by Leung et al. *Science,* 246:1306 (1989), Houck et al. *Mol. Endocrin.,* 5:1806 (1991), and, Robinson & Stringer, *Journal of Cell Science,* 144(5):853-865 (2001), together with the naturally occurring allelic and processed forms thereof, as well as variants thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native sequence VEGF.

A "VEGF antagonist" refers to a molecule (peptidyl or non-peptidyl) capable of neutralizing, blocking, inhibiting, abrogating, reducing or interfering with activities of a native sequence VEGF including its binding to one or more VEGF receptors. VEGF antagonists include anti-VEGF antibodies and antigen-binding fragments thereof, receptor molecules and derivatives which bind specifically to VEGF thereby sequestering its binding to one or more receptors (e.g., soluble VEGF receptor proteins, or VEGF binding fragments thereof, or chimeric VEGF receptor proteins), anti-VEGF receptor antibodies and VEGF receptor antagonists such as small molecule inhibitors of the VEGFR tyrosine kinases, and fusions proteins, e.g., VEGF-Trap (Regeneron), VEGF$_{121}$-gelonin (Peregine). VEGF antagonists also include antagonist variants of VEGF, antisense molecules directed to VEGF, RNA aptamers, and ribozymes against VEGF or VEGF receptors. VEGF antagonists useful in the methods of the invention further include peptidyl or non-peptidyl compounds that specifically bind VEGF, such as anti-VEGF antibodies and antigen-binding fragments thereof, polypeptides, or fragments thereof that specifically bind to VEGF; antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. In one embodiment, the VEGF antagonist reduces or inhibits, by at least 10%, 20%, 30%, 40%, 50%, 60%, 70%, 80%, 90% or more, the expression level or biological activity of VEGF. In another embodiment, the VEGF inhibited by the VEGF antagonist is VEGF (8-109), VEGF (1-109), or VEGF$_{165}$.

The term "anti-VEGF antibody" or an antibody that binds to VEGF" refers to an antibody that is capable of binding to VEGF with sufficient affinity and specificity that the antibody is useful as a diagnostic and/or therapeutic agent in targeting VEGF. For example, the anti-VEGF antibody of the invention can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al., *Journal of Immunological Methods* 288:149-164 (2004); and WO2005012359. The antibody selected will normally have a sufficiently strong binding affinity for VEGF, for example, the antibody may bind hVEGF with a K$_d$ value of between 100 nM-1 pM. Antibody affinities may be determined by a surface plasmon resonance based assay (such as the BIAcore™ assay as described in PCT Application Publication No. WO2005/012359); enzyme-linked immunoabsorbent assay (ELISA); and competition assays (e.g. RIA's), for example. The antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B, VEGF-C, VEGF-D or VEGF-E, nor other growth factors such as PlGF, PDGF or bFGF. In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599, including but not limited to the antibody known as "bevacizumab (BV)," also known as "rhuMAb VEGF" or "AVASTIN®." Bevacizumab comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005. Additional preferred antibodies include the G6 or B20 series antibodies (e.g., G6-23, G6-31, B20-4.1), as described in PCT Application Publication No. WO2005/012359. For additional preferred antibodies see U.S. Pat. Nos. 7,060,269, 6,582,959, 6,703, 020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004).

A "G6 series antibody" according to this invention, is an anti-VEGF antibody that is derived from a sequence of a G6 antibody or G6-derived antibody according to any one of FIGS. 7, 24-26, and 34-35 of PCT Application Publication No. WO2005/012359.

A "hematopoietic stem/progenitor cell" or "primitive hematopoietic cell" is one which is able to differentiate to form a more committed or mature blood cell type. "Lymphoid blood cell lineages" are those hematopoietic precursor cells which are able to differentiate to form lymphocytes (B-cells or T-cells). Likewise, "lymphopoeisis" is the formation of lymphocytes. "Erythroid blood cell lineages" are those hematopoietic precursor cells which are able to differentiate to form erythrocytes (red blood cells) and "erythropoeisis" is the formation of erythrocytes.

The phrase "myeloid blood cell lineages", for the purposes herein, encompasses all hematopoietic progenitor cells, other than lymphoid and erythroid blood cell lineages as defined above, and "myelopoiesis" involves the formation of blood cells (other than lymphocytes and erythrocytes).

A myeloid cell population can be enriched in myeloid immune cells that are Gr1+/CD11b+ (or CD11b+Gr1+) or Gr1+/Mac-1+. These cells express a marker for myeloid cells of the macrophage lineage, CD11b, and a marker for granulocytes, Gr1. A Gr1+/CD11b+ can be selected by immunoadherent panning, for example, with an antibody to Gr1+.

A "myeloid cell reduction agent" or "myeloid cell reducing agent" refers to an agent that reduces or ablates a myeloid cell population. Typically, the myeloid cell reducing agent will reduce or ablate myeloid cells, CD11b+Gr1+, monocytes, macrophages, etc. Examples of myeloid cell reducing agents include, but are not limited to, Gr1+ antagonist, CD11b antagonist, CD18 antagonist, elastase inhibitor, MCP-1 antagonist, MIP-1 alpha antagonist, etc.

The term "Gr1 antagonist" when used herein refers to a molecule which binds to Gr1 and inhibits or substantially reduces a biological activity of Gr1. Non-limiting examples of Gr1 antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. In one embodiment of the invention, the Gr1 antagonist is an antibody, especially an anti-Gr1 antibody which binds human Gr1.

The term "CD11b antagonist" when used herein refers to a molecule which binds to CD11b and inhibits or substantially reduces a biological activity of CD11b. Normally, the antagonist will block (partially or completely) the ability of a cell (e.g. immature myeloid cell) expressing the CD11b subunit at its cell surface to bind to endothelium. Non-limiting examples of CD11b antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. In one embodiment of the invention, the CD11b antagonist is an antibody, especially an anti-CD11b antibody which binds human CD11b. Exemplary CD11b antibodies include MY904 (U.S. Pat. No. 4,840,793); 1B6c (see Zhang et al., Brain Research 698:79-85 (1995)); CBRN1/5 and CBRM1/19 (WO94/08620).

The term "CD18 antagonist" when used herein refers to a molecule which binds to CD18 (preferably human CD18) and inhibits or substantially reduces a biological activity of CD18. Normally, the antagonist will block (partially or completely) the ability of a cell (e.g. a neutrophil) expressing the CD18 subunit at its cell surface to bind to endothelium. Non-limiting examples of CD18 antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. In one embodiment of the invention, the CD18 antagonist is an antibody.

Examples of anti-CD18 antibodies include MHM23 (Hildreth et al., *Eur. J. Immunol.* 13:202-208 (1983)); M18/2 (IgG$_{2a}$; Sanches-Madrid et al., *J. Exp. Med.* 158:586-602 (1983)); H52 (American Type Culture Collection (ATCC) Deposit HB 10160); Mas191c and 1OT18 (Vermot Desroches et al., *Scand. J. Immunol.* 33:277-286 (1991)); and NA-8 (WO 94/12214). In one embodiment, the antibody is one which binds to the CD18 epitope to which either MHM23 or 1152 binds. In one embodiment of the invention, the antibody has a high affinity for the CD18 polypeptide. In certain embodiments, the antibody may bind to a region in the extracellular domain of CD18 which associates with CD11b and the antibody may also dissociate a and P chains (e.g. the antibody may dissociate the CD11b and CD18 complex as is the case for the MHM23 antibody).

Monocyte chemotactic protein (MCP-1) is a chemokine involved in innate immunity and Th2 effector response, and CD4+ T cell differentiation. See, e.g., Paul, W. E., *Fundamental Immunology*, 5$^{th}$ *Edition*, Lippincott Williams & Wilkins, (Philadelphia, 2003) at pages 801-840.

The term "MCP-1 antagonist" when used herein refers to a molecule which binds to MCP-1 and inhibits or substantially reduces a biological activity of MCP-1. Non-limiting examples of MCP-1 antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. In one embodiment of the invention, the MCP-1 antagonist is an antibody, especially an anti-MCP-1 antibody which binds human MCP-1.

Macrophage inflammatory proteins alpha and beta (MIP-1 alpha and beta) are known chemokines. MIP-1 alpha is involved in innate immunity and Th1 effector response, and CD4+ T cell differentiation. See, e.g., Paul, W. E., *Fundamental Immunology*, 5$^{th}$ *Edition*, Lippincott Williams & Wilkins, (Philadelphia, 2003) at pages 801-840.

The term "MIP-1 alpha antagonist" when used herein refers to a molecule which binds to MIP-1 alpha and inhibits or substantially reduces a biological activity of MIP-1 alpha. Non-limiting examples of MIP-1 alpha antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. In one embodiment of the invention, the MIP-1 alpha antagonist is an antibody, especially an anti-MIP-1 alpha antibody which binds human MIP-1 alpha.

A "URCGP" refers to a protein that is upregulated in CD11b+Gr+1 cells from anti-VEGF resistant tumors. URCGPs include, but are not limited to, neutropil elastase, CD14, expi, Il-13R, LDLR, TLR-1, RLF, Endo-Lip, SOCS13, FGF13, IL-4R, IL-11R, IL-1RII, IFN TM1, TNFRSF18, WNT5A, Secretory carrier membrane 1, HSP86, EGFR, EphRB2, GPCR25, HGF, Angiopoietin Like-6, Eph-RA7, Semaphorin V1b, Neurotrophin 5, Claudin-18, MDC15, ECM and ADAMTS7B. In certain embodiment, the URCGPs refer to IL-13R, TLR-1, Endo-Lip, FGF13 and/or IL-4R.

A "DRCGP" refers to a protein that is downregulated in CD11b+Gr1+ cells from anti-VEGF resistant tumors. DRCGPs include, but are not limited to, THBS1, Crea7, Aquaporin-1, solute carrier family protein (SCF38), apolipoprotein E (APOE), fatty acid binding protein (FABP), NCAM-140, Fibronectin type III, WIP, CD74, ICAM-2, Jagged1, ltga4, ITGB7, TGF-BII-R, TGFb IEP, Smad4, BMPR1A, CD83, Dectin-1, CD48, E-selectin, IL-15, Suppressor of cytokine signaling 4, Cytor4 and CX3CR1. In certain embodiment, the DRCGPs refer to THBS1 and/or Crea7.

A "URRTP" refers to a protein that is upregulated in anti-VEGF resistant tumors. URRTPs include, but are not limited to, Notch2, DMD8, MCP-1, ITGB7, G-CSF, IL-8R, MIP2, MSCA, GM-CSF, IL-1R, Meg-SF, HSP1A, IL-1R, G-CSFR, IGF2, HSP9A, FGF18, ELM1, Ledgfa, scavenger receptor type A, Macrophage C-type lectin, Pigr3, Macrophage SRT-1, G protein-coupled receptor, ScyA7, IL-1R2, IL-1 inducible protein, IL-1beta and ILIX Precuror. In certain embodiment, the URRTPs refer to. MSCA, MIP2, IL-8R and/or G-CSF.

A "DRRTP" refers to a protein that is downregulated in anti-VEGF resistant tumors. URRTPs include, but are not limited to, IL10-R2, Erb-2.1, Caveolin3, Semcap3, INTG4, THBSP-4, ErbB3, JAM, Eng, JAM, Eng, JAM-2, Pecam1, Tlr3, TGF-B, FIZZ1, Wfs1, TP 14A, EMAP, SULF-2, Extracellular matrix 2, CTFG, TFPI, XCP2, Ramp2, ROR-alpha, Ephrin B1, SPARC-like 1, and Semaphorin A. In certain embodiments, the DRRTP refer to IL10-R2, THBSP-4, and/or JAM-2.

The term "detecting" is used in the broadest sense to include both qualitative and quantitative measurements of a target molecule.

The term "biological sample" refers to a body sample from any animal, but preferably is from a mammal, more preferably from a human. Such samples include biological fluids such as blood, serum, plasma, bone marrow, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts. The preferred biological sample herein is serum, plasma, urine or a bone marrow sample.

The term "antibody" is used in the broadest sense and specifically covers monoclonal antibodies (including full length or intact monoclonal antibodies), polyclonal antibodies, multivalent antibodies, multispecific antibodies (e.g., bispecific antibodies) formed from at least two intact antibodies, and antibody fragments (see below) so long as they exhibit the desired biological activity.

Unless indicated otherwise, the expression "multivalent antibody" is used throughout this specification to denote an antibody comprising three or more antigen binding sites. The multivalent antibody is typically engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VII domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057 1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. Monoclonal antibodies are highly specific, being directed against a single antigen. In certain embodiments, a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations that typically include different antibodies directed against different determinants (epitopes), each monoclonal antibody is directed against a single determinant on the antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1991); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al. J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/

10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321: 522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409. See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *PNAS (USA)* 95:6157-6162 (1998)); Hoogenboom and Winter, *J. Mol. Biol.,* 227:381 (1991); Marks et al., *J. Mol. Biol.,* 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy, Alan R. Liss,* p. 77 (1985); Boerner et al., *J. Immunol.,* 147 (1):86-95 (1991); and U.S. Pat. No. 5,750,373.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of *Proteins of Immunological Interest, 5th Ed.* Public Health Service, National Institutes of Health, Bethesda, Md. (1991)). The constant domains are not involved directly in binding an antibody to an antigen, but exhibit various effector functions, such as participation of the antibody in antibody-dependent cellular toxicity.

The term "hypervariable region," "HVR," or "HV," when used herein refers to the amino acid residues of an antibody which are responsible for antigen-binding. For example, the term hypervariable region refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1) 50-65 or 49-65 (H12) and 93-102, 94-102, or 95-102 (H3) in the VII. The variable domain residues are numbered according to Kabat et al., supra, for each of these definitions.

"Framework Region" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

Throughout the present specification and claims, the Kabat numbering system is generally used when referring to a residue in the variable domain (approximately, residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., *Sequences of Proteins of Immunological Interest*, 5th Ed. Public Health Service, National Institutes of Health, Bethesda, Md. (1991) expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$ (including non-A and A allotypes), $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The "light chains" of antibodies (immunoglobulins) from any vertebrate species can be assigned to one of two clearly distinct types, called kappa (κ) and lambda (γ), based on the amino acid sequences of their constant domains.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. The Fc region of an immunoglobulin generally comprises two constant domains, a CH2 domain and a CH3 domain, and optionally comprises a CH4 domain.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

By "Fc region chain" herein is meant one of the two polypeptide chains of an Fc region.

The "CH12 domain" of a human IgG Fc region (also referred to as "Cg2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immuno* 1.22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

A "parent antibody" or "wild-type" antibody is an antibody comprising an amino acid sequence which lacks one or more amino acid sequence alterations compared to an antibody variant as herein disclosed. Thus, the parent antibody generally has at least one hypervariable region which differs in amino acid sequence from the amino acid sequence of the corresponding hypervariable region of an antibody variant as herein disclosed. The parent polypeptide may comprise a native sequence (i.e. a naturally occurring) antibody (including a naturally occurring allelic variant), or an antibody with pre-existing amino acid sequence modifications (such as insertions, deletions and/or other alterations) of a naturally occurring sequence. Throughout the disclosure, "wild type," "WT,", and "parent" or "parental" antibody are used interchangeably.

As used herein, "antibody variant" or "variant antibody" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. The antibody variant is generally one which comprises one or more amino acid alterations in or adjacent to one or more hypervariable regions thereof.

A "variant Fc region" comprises an amino acid sequence which differs from that of a native sequence Fc region by virtue of at least one amino acid modification. In certain embodiments, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide, e.g. from about one to about ten amino acid substitutions, and preferably from about one to about five amino acid substitutions in a native sequence Fc region or in the Fc region of the parent polypeptide. The variant Fc region herein will typically possess, e.g., at least about 80% sequence identity with a native sequence Fc region and/or with an Fc region of a parent polypeptide, or at least about 90% sequence identity therewith, or at least about 95% sequence or more identity therewith.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils; with PBMCs and NK cells being generally preferred. The effector cells may be isolated from a native source thereof, e.g. from blood or PBMCs as described herein.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

An "affinity matured" antibody is one with one or more alterations in one or more CDRs thereof which result an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "flexible linker" herein refers to a peptide comprising two or more amino acid residues joined by peptide bond(s), and provides more rotational freedom for two polypeptides (such as two Fd regions) linked thereby. Such rotational freedom allows two or more antigen binding sites joined by the flexible linker to each access target antigen(s) more efficiently. Examples of suitable flexible linker peptide sequences include gly-ser, gly-ser-gly-ser (SEQ ID NO: 34), ala-ser, and gly-gly-gly-ser (SEQ ID NO: 35).

A "dimerization domain" is formed by the association of at least two amino acid residues (generally cysteine residues) or of at least two peptides or polypeptides (which may have the same, or different, amino acid sequences). The peptides or polypeptides may interact with each other through covalent and/or non-covalent association(s). Examples of dimerization domains herein include an Fc region; a hinge region; a CH3 domain; a CH4 domain; a CH1-CL pair; an "interface" with an engineered "knob" and/or "protruberance" as described in U.S. Pat. No. 5,821,333, expressly incorporated herein by reference; a leucine zipper (e.g. a jun/fos leucine zipper, see Kostelney et al., *J. Immunol.,* 148: 1547-1553 (1992); or a yeast GCN4 leucine zipper); an isoleucine zipper; a receptor dimer pair (e.g., interleukin-8 receptor (IL-8R); and integrin heterodimers such as LFA-1 and GPIIIb/IIIa), or the dimerization region(s) thereof; dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF); see Arakawa et al. *J. Biol. Chem.* 269(45): 27833-27839 (1994) and Radziejewski et al. *Biochem.* 32(48): 1350 (1993)), or the dimerization region(s) thereof; a pair of cysteine residues able to form a disulfide bond; a pair of peptides or polypeptides, each comprising at least one cysteine residue (e.g. from about one, two or three to about ten cysteine residues) such that disulfide bond(s) can form between the peptides or polypeptides (hereinafter "a synthetic hinge"); and antibody variable domains. The most preferred dimerization domain herein is an Fc region or a hinge region.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

The term "epitope" is used to refer to binding sites for (monoclonal or polyclonal) antibodies on protein antigens.

By "Bv8 antagonist antibody" is meant an antibody that is a Bv8 antagonist, as hereinabove defined, and thus partially or fully blocks, inhibits, or neutralizes the ability of Bv8 to modulate myeloid mobilization and/or to promote angiogenesis during tumor development.

The term "Bv8 immunoadhesin" is used interchangeably with the term "Bv8-immunoglobulin chimera", and refers to a chimeric molecule that combines at least a portion of a Bv8 molecule (native or variant) with an immunoglobulin sequence. The immunoglobulin sequence preferably, but not necessarily, is an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

Examples of homomultimeric immunoadhesins which have been described for therapeutic use include the CD4-IgG immunoadhesin for blocking the binding of HIV to cell-surface CD4. Data obtained from Phase I clinical trials, in which CD4-IgG was administered to pregnant women just before delivery, suggests that this immunoadhesin may be useful in the prevention of maternal-fetal transfer of HIV (Ashkenazi et al., Intern. Rev. Immunol. 10:219-227 (1993)). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi, A. et al. (1991) *PNAS USA* 88:10535-10539). ENBREL® (etanercept), an immunoadhesin comprising a TNF receptor sequence fused to an IgG Fc region, was approved by the U.S. Food and Drug Administration (FDA), on Nov. 2, 1998, for the treatment of rheumatoid arthritis. The new expanded use of ENBREL® in the treatment of rheumatoid arthritis was approved by FDA on Jun. 6, 2000. For recent information on TNF blockers, including ENBREL®, see Lovell et al., N. Engl. J. Med. 342: 763-169 (2000), and accompanying editorial on p810-811; and Weinblatt et al., N. Engl. J. Med. 340: 253-259 (1999); reviewed in Maini and Taylor, Annu. Rev. Med. 51: 207-229 (2000).

If the two arms of the immunoadhesin structure have different specificities, the immunoadhesin is called a "bispecific immunoadhesin" by analogy to bispecific antibodies. Dietsch et al., J. Immunol. Methods 162:123 (1993) describe such a bispecific immunoadhesin combining the extracellular domains of the adhesion molecules, E-selectin and P-selectin, each of which selectins is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol that forms an intermolecular disulfide bond between the chimeric molecules of the chimeric heteromultimer. The multimerization domain may comprise an immunoglobulin constant region. In addition a multimerization region may be engineered such that steric interactions not only promote stable interaction, but further promote the formation of heterodimers over homodimers from a mixture of monomers. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from IgG1, IgG.2, IgG3 or IgG4 subtypes, IgA, IgE, IgD or IgM, but preferably IgG1 or IgG3.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration or damage, such as the pathology of a disease or conditions associated with the mobilization of myeloid cells and/or with tumor angiogenesis.

The term "effective amount" or "therapeutically effective amount" refers to an amount of a drug effective to treat a disease or disorder in a mammal. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth; allow for treatment of the resistant tumor, and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, other higher primates, rodents, domestic and farm animals, and zoo, sports, or pet animals, such as mice, rats, dogs, cats, cattle, horses, sheep, pigs, goats, rabbits, etc. Preferably, the mammal is human.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

The term "resistant tumor" refers to cancer, cancerous cells, or a tumor that does not respond completely, or loses or shows a reduced response over the course of cancer therapy to a cancer therapy comprising at least a VEGF antagonist. A resistant tumor also refers to a tumor diagnosed as resistant herein (also referred to herein as "anti-VEGF resistant tumor"). In certain embodiments, there is an increase in CD11b+Gr1+ cells in a resistant tumor compared to a tumor that is sensitive to therapy that includes at least a VEGF antagonist.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, toxins, and other-agents to treat cancer, e.g., anti-VEGF neutralizing antibody, VEGF antagonist, anti-HER-2, anti-CD20, an epidermal growth factor receptor (EGFR) antagonist (e.g., a tyrosine kinase inhibitor), HER1/EGFR inhibitor, erlotinib, a COX-2 inhibitor (e.g., celecoxib), interferons, cytokines, antagonists (e.g., neutralizing antibodies) that bind to one or more of the ErbB2, ErbB3, ErbB4, or VEGF receptor(s), inhibitors for receptor tyrosine kinases for platet-derived growth factor (PDGF) and/or stem cell factor (SCF) (e.g., imatinib mesylate (Gleevec® Novartis)), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu), chemotherapeutic agents, and toxins such as small molecule toxins or enzymatically active toxins of bacterial, fungal, plant or animal origin, including fragments and/or variants thereof.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 44544-methylphenyl)-3-(trifluoromethyl)-1H-pyrazol-1-yl)benzenesulfonamide; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factors (e.g., VEGF, VEGF-B, VEGF-C, VEGF-D, VEGF-E); placental derived growth factor (PlGF); platelet derived growth factors (PDGF, e.g., PDGFA, PDGFB, PDGFC, PDGFD); integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20-IL-30; secretoglobin/uteroglobin; oncostatin M (OSM); a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "angiogenic factor or agent" is a growth factor which stimulates the development of blood vessels, e.g., promotes angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, ANGPTL3, ANGPTL4, etc. It would also include factors that accelerate wound healing, such as growth hormone, insulin-like growth factor-I (IGF-I), VIGF, epidermal growth factor (EGF), CTGF and members of its family, and TGF-α and TGF-β. See, e.g., Klagsbrun and D'Amore, *Annu. Rev. Physiol.,* 53:217-39 (1991); Streit and Detmar, *Oncogene,* 22:3172-3179 (2003); Ferrara & Alitalo, *Nature Medicine* 5(12):1359-1364 (1999); Tonini et al., *Oncogene,* 22:6549-6556 (2003) (e.g., Table 1 listing angiogenic factors); and, Sato *Int. J. Clin. Oncol.,* 8:200-206 (2003).

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, to antibodies to VEGF receptors, small molecules that block VEGF receptor signaling (e.g., PTK787/ZK2284, SU6668, SUTENT/SU11248 (sunitinib malate), AMG706). Anti-angiogensis agents also include native angiogenesis inhibitors, e.g., angiostatin, endostatin, etc. See, e.g., Klagsbrun and D'Amore, *Annu. Rev. Physiol.,* 53:217-39 (1991); Streit and Detmar, *Oncogene,* 22:3172-3179 (2003) (e.g., Table 3 listing anti-angiogenic therapy in malignant melanoma); Ferrara & Alitalo, *Nature Medicine* 5(12):1359-1364 (1999); Tonini et al., *Oncogene,* 22:6549-6556 (2003) (e.g., Table 2 listing antiangiogenic factors); and, Sato *Int. J. Clin. Oncol.,* 8:200-206 (2003) (e.g., Table 1 lists Anti-angiogenic agents used in clinical trials).

The term "immunosuppressive agent" as used herein refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal antiinflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, and dexamethasone; dihydrofolate reductase inhibitors such as methotrexate (oral or subcutaneous); hydroxycloroquine; sulfasalazine; leflunomide; cytokine or cytokine receptor antibodies including anti-interferon-alpha, -beta, or -gamma antibodies, anti-tumor necrosis factor-alpha antibodies (infliximab or adalimumab), anti-TNF-alpha immunoahesin (etanercept), anti-tumor necrosis factor-beta antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 1990/08187 published Jul. 26, 1990); streptokinase; TGF-beta; streptodornase; RNA or DNA from the host; FK506; RS-61443; deoxyspergualin; rapamycin; T-cell receptor (Cohen et al., U.S. Pat. No. 5,114,721); T-cell-receptor fragments (Offner et al., *Science,* 251: 430-432 (1991); WO 1990/11294; Ianeway, Nature, 341: 482 (1989); and WO 1991/01133); and T-cell-receptor antibodies (EP 340,109) such as T10B9.

Examples of "nonsteroidal anti-inflammatory drugs" or "NSAIDs" are acetylsalicylic acid, ibuprofen, naproxen, indomethacin, sulindac, tolmetin, including salts and derivatives thereof, etc.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order "Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

A "liposome" is a small vesicle composed of various types of lipids, phospholipids and/or surfactant which is useful for delivery of a drug (such as a Bv8 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "amino acid alteration" refers to a change in the amino acid sequence of a predetermined amino acid sequence. Exemplary alterations include insertions, substitutions and deletions. An "amino acid substitution" refers to the replacement of an existing amino acid residue in a predetermined amino acid sequence; with another different amino acid residue.

A "replacement" amino acid residue refers to an amino acid residue that replaces or substitutes another amino acid residue in an amino acid sequence. The replacement residue may be a naturally occurring or non-naturally occurring amino acid residue.

An "amino acid insertion" refers to the introduction of one or more amino acid residues into a predetermined amino acid sequence. The amino acid insertion may comprise a "peptide insertion" in which case a peptide comprising two or more amino acid residues joined by peptide bond(s) is introduced into the predetermined amino acid sequence. Where the amino acid insertion involves insertion of a peptide, the inserted peptide may be generated by random mutagenesis such that it has an amino acid sequence which does not exist in nature. An amino acid alteration "adjacent a hypervariable region" refers to the introduction or substitution of one or more amino acid residues at the N-terminal and/or C-terminal end of a hypervariable region, such that at least one of the inserted or replacement amino acid residue(s) form a peptide bond with the N-terminal or C-terminal amino acid residue of the hypervariable region in question.

A "naturally occurring amino acid residue" is one encoded by the genetic code, generally selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro): serine (Ser); threonine (Thr); tryptophan (Trp); tyrosine (Tyr); and valine (Val).

A "non-naturally occurring amino acid residue" herein is an amino acid residue other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

As used herein, an antibody with a "high-affinity" is an antibody having a $K_D$, or dissociation constant, in the nanomolar (nM) range or better. A $K_D$ in the "nanomolar range or better" may be denoted by X nM, where X is a number less than about 10.

The term "filamentous phage" refers to a viral particle capable of displaying a heterogenous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al. Gene 9: 127-140 (1980), Smith et al. Science 228: 1315-1317 (1985); and Parmley and Smith Gene 73: 305-318 (1988)).

The term "panning" is used to refer to the multiple rounds of screening process in identification and isolation of phages carrying compounds, such as antibodies, with high affinity and specificity to a target.

The term "short-interfering RNA (siRNA)" refers to small double-stranded RNAs that interfere with gene expression. siRNAs are an intermediate of RNA interference, the process double-stranded RNA silences homologous genes. siRNAs typically are comprised of two single-stranded RNAs of about 15-25 nucleotides in length that form a duplex, which may include single-stranded overhang(s). Processing of the double-stranded RNA by an enzymatic complex, for example by polymerases, results in the cleavage of the double-stranded RNA to produce siRNAs. The antisense strand of the siRNA is used by an RNA interference (RNAi) silencing complex to guide mRNA cleavage, thereby promoting mRNA degradation. To silence a specific gene using siRNAs, for example in a mammalian cell, the base pairing region is selected to avoid chance complementarity to an unrelated mRNA. RNAi silencing complexes have been identified in the art, such as, for example, by Fire et al., Nature 391:806-811 (1998) and McManus et al., Nat. Rev. Genet. 3(10):737-47 (2002).

The term "interfering RNA (RNAi)" is used herein to refer to a double-stranded RNA that results in catalytic degradation of specific mRNAs, and thus can be used to inhibit/lower expression of a particular gene.

An "effective amount" is an amount sufficient to effect beneficial or desired therapeutic (including preventative) results. An effective amount can be administered in one or more administrations.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. The term "progeny" refers to any and all offspring of every generation subsequent to an originally transformed cell or cell line. Mutant progeny that have the same function or biological activity as screened for in the originally transformed cell are included. Where distinct designations are intended, it will be clear from the context.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"High stringency conditions", as defined herein, are identified by those that: (1) employ low ionic strength and high temperature for washing; 0.015 M sodium chloride/0.0015 M sodium citrate/0.1% sodium dodecyl sulfate at 50° C.; (2) employ during hybridization a denaturing agent; 50% (v/v) formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

B. Detailed Description

The present invention is based, at least in part, on the recognition that Bv8 plays an important role in the cellular and molecular events leading to resistance of tumors to treatment including the administration of at least one VEGF antagonists, such as an anti-VEGF antibody. The invention is further based on the recognition that Bv8 expression is exquisitely responsive to G-CSF, and thus is linked to a major homeostatic mechanism involved in the regulation of neutrophils differentiation and production.

Copending application Ser. No. 11/692,681 filed on Mar. 28, 2007, the entire disclosure of which is expressly incorporated by reference herein, describes a correlation between recruitment of hematopoietic bone marrow-derived cells and the development of tumor resistance to anti-VEGF treatment. The immune system includes hematopoietic cells, which include erythrocytes, lymphocytes, and cells of myeloid lineage. These cell types all arise from the same pluripotent stem cells. In an adult, hematopoiesis occurs in the bone marrow where stem cells divide infrequently to produce more stem cells (self-renewal) and various committed progenitor cells. It is the committed progenitor cells that will in response to specific regulator factors produce a hematopoietic cell. These regulatory factors are primarily produced by the surrounding stromal cells and in other tissues and include, for example, colony-stimulating factors (CSFs), erythropoietin (EPO), interleukin 3 (IL3), granulocyte/macrophage CSF (GM-CSF), granulocyte CSF (G-CSF), macrophage CSF (M-CSF), and STEEL factor. Alterations in the immune systems in cancer patients has been suggested to contribute to the inability or reduced ability of the immune system to mount a successful attack against the cancer, thus allowing progression of tumor growth. See, e.g., Gabrilovich et al., *Antibodies to Vascular Endothelial Growth Factor Enhances the Efficacy of Cancer Immunotherapy by Improving Endogenous Dendritic Cell Function, Clinical Cancer Research* 5:2963-2970 (1999). Factors produced by tumors may lead to abnormal myelopoiesis and may lead to the suppression of the immune response to the tumor. See, e.g., Kusmartsev and Gabrilovich, *Immature myeloid cells and cancer-associated immune suppression. Caner Immunol Immunothera.* 51:293-298 (2002).

Recent studies have directly implicated CD11b+Gr1+ myeloid cells in mediating refractoriness to anti-VEGF therapy. (Shojaei, F., et al., *Nature Biotechnol* 25:911-20 (2007)), and co-pending application Ser. No. 11/692,681. The CD11/CD18 family is related structurally and genetically to the larger integrin family of receptors that modulate cell adhesive interactions, which include; embryogenesis, adhesion to extracellular substrates, and cell differentiation (Hynes, R. O., *Cell* 48: 549-554 (1987); Kishimoto et al., *Adv. Immunol.* 46: 149-182 (1989); Kishimoto et al., *Cell* 48: 681-690 (1987); and, Ruoslahti et al., *Science* 238: 491-497 (1987)). Integrins are a class of membrane-spanning heterodimers comprising an α subunit in noncovalent association with a β subunit. The β subunits are generally capable of association with more than one α subunit and the heterodimers sharing a common β subunit have been classified as subfamilies within the integrin population (Larson and Springer, *Structure and function of leukocyte integrins, Immunol. Rev.* 114: 181-217 (1990)).

The integrin molecules of the CD11/CD18 family, and their cellular ligands, have been found to mediate a variety of cell-cell interactions, especially in inflammation. These proteins have been demonstrated to be critical for adhesive functions in the immune system (Kishimoto et al., *Adv. Immunol.* 46: 149-182 (1989)). Monoclonal antibodies to LFA-1 have been shown to block leukocyte adhesion to endothelial cells (Dustin et al., *J. Cell. Biol.* 107: 321-331 (1988); Smith et al., *J. Clin. Invest* 83: 2008-2017 (1989)) and to inhibit T-cell activation (Kuypers et al., *Res. Immunol.,* 140: 461 (1989)), conjugate formation required for antigen-specific CTL killing (Kishimoto et al., *Adv. Immunol.* 46: 149-182 (1989)), T. cell proliferation (Davignon et al., *J. Immunol.* 127: 590-595 (1981)) and NK cell killing (Krensky et al., *J. Immunol.* 131: 611-616 (1983)).

The CD11/CD18 family of adhesion receptor molecules comprises four highly related cell surface glycoproteins; LFA-1 (CD11a/CD18), Mac-1 (CD11b/CD18), p150.95 (CD11c/CD18) and (CD11d/CD18). Each of these heterodimers has a unique α-chain (CD11a, b, c or d) and the invariant (β-chain (CD18). CD18 integrins located on leukocytes may bind to intercellular adhesion molecule-1 (ICAM-1) which is expressed on vascular endothelium and other cells, thereby mediating leukocyte adhesion and transendothelial migration. LFA-1 is present on the surface of all mature leukocytes except a subset of macrophages and is considered the major lymphoid integrin. The expression of Mac-1, p150.95 and CD11d/CD18 is predominantly confined to cells of the myeloid lineage (which include neutrophils, monocytes, macrophage and mast cells). CD11b+Gr1+ are markers also found on myeloid cells. It has been suggested that the balance between mature and immature myeloid cells is an indication for cancer and in progressive tumor growth the balance shifts toward immature myeloid cells with a decrease and function of dendritic cells. See, e.g., Kusmartsev and Gabrilovich, *Immature myeloid cells and cancer-associated immune suppression. Caner Immunol Immunothera.* 51:293-298 (2002). Shifting the balance, e.g., by differentiating the immature myeloid cells in tumor bearing mice improved the effect of cancer vaccines. See, Kusmartsev et al., *All-trans-*

*Retinoic Acid Eliminates Immature Myeloid Cells from Tumor-bearing Mice and Improves the Effect of Vaccination.* Cancer Research 63:4441-4449 (2003). It was also observed that in cancer patients, the level of VEGF in the circulation correlated with an increase number of immature myeloid cells. See, Almand et al., *Clinical significance of defective dendritic cells differentiation in cancer.* Clin. Cancer Res. 6:1755 (2000).

It has been shown that the mobilization and activation of CD11b+Gr1+ myeloid cells can result in the resistance to anti-VEGF treatment. It has also been shown that bone marrow-derived CD11b+Gr1+ myeloid cells isolated from tumor-bearing mice can confer resistance in tumors to anti-VEGF treatment and conditioned media from anti-VEGF-resistant (but not anti-VEGF-sensitive tumors) stimulated migration of CD11b+Gr1+ cells.

The experimental data disclosed herein demonstrate that Bv8 regulates mobilization of CD11b+Gr1+ cells from the bone marros ruding tumor development, and also locally promotes tumor angiogenesis. Accordingly, Bv8 is a promising target for the treatment of tumors resistant to treatment with VEGF antagonists.

The data disclosed herein also indicate that Bv8 expression is exquisitely responsive to G-CSF, and thus is linked to a major homeostatic mechanism involved in the regulation of neutrophils differentiation and production. Due to this broader role plays by Bv8 in the pathology of non-tumoral types of inflammatory-cell mediated angiogenesis, Bv8 is also a promising target for the inhibition of undesired, inflammatory cell mediated angiogenesis in general.

C. Making Anti-Bv8 Antibodies Acting as Inhibitors of Tumor Angiogenesis

The antibodies identified by the binding and activity assays of the present invention can be produced by methods known in the art, including techniques of recombinant DNA technology.

i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCI_2$, or $R_1N=C=NR$, where R and $R_1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al, Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subloned by limiting dilution procedures and grown by standard methods (coding, MonoclonalAntibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., Nature, 348: 552-554 (1990).

Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (J.sub.H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992). Human antibodies can also be derived from phage-display libraries (Hoogenboom et al, J. Mol. Biol., 227:381 (1991); Marks et al, J. Mol. Biol., 222:581-597 (1991); Vaughan et al. Nature Biotech 14:309 (1996)). Generation of human antibodies from antibody phage display libraries is further described below.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10:163-167 (1992)). In another embodiment as described in the example below, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Examples of BsAbs include those with one arm directed against Bv8 and another arm directed against VEGF or EG-VEGF.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991). According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments can also be directly recovered from *E. coli*, and can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al. *J. Immunol.* 147: 60 (1991).

(vii) Effector Function Engineering

It may be desirable to modify the antibody of the invention with respect to effector function, so as to enhance the effectiveness of the antibody. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al Anti-Cancer Drug Design 3:219-230 (1989).

(viii) Antibody-Salvage Receptor Binding Epitope Fusions.

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or V.sub.H region, or more than one such region, of the antibody. Alternatively, the epitope is taken from the CH2 domain of the Fc region and transferred to the CL region or VL region, or both, of the antibody fragment.

(ix) Other Covalent Modifications of Antibodies

Covalent modifications of antibodies are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Examples of covalent modifications are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate). A variety of radionuclides are available for the production of radioconjugate antibodies. Examples include, but are not limited to, e.g., $^{212}$Bi, $^{131}$I, $^{131}$In, $^{90}$Y and $^{186}$Re.

Chemotherapeutic agents useful in the generation of such immunoconjugates have been described above. For example, BCNU, streptozoicin, vincristine, 5-fluorouracil, the family of agents known collectively LL-E33288 complex described in U.S. Pat. Nos. 5,053,394, 5,770,710, esperamicins (U.S. Pat. No. 5,877,296), etc. (see also the definition of chemotherapeutic agents herein) can be conjugated to antibodies of the invention or fragments thereof.

For selective destruction of the tumor, the antibody may comprise a highly radioactive atom. A variety of radioactive isotopes are available for the production of radioconjugated antibodies or fragments thereof. Examples include, but are not limited to, e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb, $^{111}$In, radioactive isotopes of Lu, etc. When the conjugate is used for diagnosis, it may comprise a radioactive atom for scintigraphic studies, for example $^{99m}$tc or $^{123}$I, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $^{99m}$tc or $^{123}$I, $^{186}$Re and $^{111}$In can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. See, e.g., *Monoclonal Antibodies in Immunoscintigraphy* (Chatal, CRC Press 1989) which describes other methods in detail.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, neomycin, and the tricothecenes. See, e.g., WO 93/21232 published Oct. 28, 1993.

Conjugates of the antibody and cytotoxic agent are made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

Alternatively, a fusion protein comprising the anti-VEGF, and/or the anti-protein of the invention antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In certain embodiments, the antibody is conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In certain embodiments, an immunoconjugate is formed between an antibody and a compound with nucleolytic activity (e.g., a ribonuclease or a DNA endonuclease such as a deoxyribonuclease; Dnase).

The invention provides an antibody of the invention, which is conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

An antibody of the invention can be conjugated to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. In one embodiment, maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., Cancer Research 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Typical coupling agents include N-succinimidyl-3-(2-pyridyldithio) propionate (SPDP) (Carlsson et al., Biochem. J. 173:723-737 [1978]) and N-succinimidyl-4-(2-pyridylthio) pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. The linkage is formed at the C-3 position of maytansinol or a maytansinol analogue.

Another immunoconjugate of interest comprises an antibody of the invention conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$, (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

(x) Generation of Antibodies From Synthetic Antibody Phage Libraries

In a preferred embodiment, the invention provides a method for generating and selecting novel antibodies using a unique phage display approach. The approach involves generation of synthetic antibody phage libraries based on single framework template, design of sufficient diversities within variable domains, display of polypeptides having the diversified variable domains, selection of candidate antibodies with high affinity to target the antigen, and isolation of the selected antibodies.

Details of the phage display methods can be found, for example, WO03/102157 published Dec. 11, 2003, the entire disclosure of which is expressly incorporated herein by reference.

In one aspect, the antibody libraries used in the invention can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence $(DVK)_7$. In some embodiments, a library is created by substitution of residues 95-100a with amino acids encoded by both DVK and NNK codon sets. An example of an oligonucleotide set that is useful for creating these substitutions comprises the sequence $(DVK)_6 (NNK)$. In another embodiment, a library is created by substitution of at least residues 95-100a with amino acids encoded by both DVK and NNK codon sets. An example of an oligonucleotide set that is useful for creating these substitutions comprises the sequence $(DVK)_5 (NNK)$. Another example of an oligonucleotide set that is useful for creating these substitutions comprises the sequence $(NNK)_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (eg. utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANW; amino acid position 32 is encoded by THT; optionally, amino acid position 33 is encoded by CTG; in CDRL2: amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized $41)_5$ antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

(xi) Antibody Variants

The novel antibodies generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-Bv8 antibody mutant preferably has a binding affinity for Bv8 which is at least about 10 fold stronger, preferably at least about 20 fold stronger, more preferably at least about 50 fold stronger, and sometimes at least about 100 fold or 200 fold stronger, than the binding affinity of the parent antibody.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) *Science* 233:747-753); interact with/effect the conformation of a CDR (Chothia et al. (1987) *J. Mol. Biol.* 196:901-917); and/or participate in the V$_L$-V$_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened.

Preferred Substitutions:

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies' biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) *Proc. Natl. Acad. Sci. USA* 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336: 1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

(xii) Recombinant Production of Antibodies

For recombinant production of an antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, *Enterobacteriaceae* such as *Escherichia*, e.g., *E. coli, Enterobacter, Erwinia, Klebsiella, Proteus, Salmonella*, e.g., *Salmonella typhimurium, Serrafia*, e.g., *Serratia marcescans*, and *Shigeila*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), and *E coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of Autographa californica NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subloned for growth in suspension culture, Graham et al, J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed cells, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma$, $\gamma 2$, or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipiation are also available depending on the antibody to be recovered.

D. Uses of Bv8 Antagonists

The Bv8 antagonists of the present invention can be used, alone or in combination with other therapeutic agent(s) for the inhibition of angiogenesis, in particular inflammatory-cell dependent angiogenesis and/or tumorigenesis.

Primary targets for the treatment methods of the present invention are tumors that have shown or are known to be resistant to treatment with VEGF antagonists, in particular anti-VEGF antibodies.

Examples of diseases and disorders to be treated by the methods of the present invention include neoplastic disorders, such as those described herein under the terms "cancer" and "cancerous." Non-neoplastic conditions that are amenable to treatment with antagonists of the invention include, but are not limited to, e.g., undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The invention provides combined therapies in which a Bv8 antagonist of the present invention is administered in combination with another therapy. Combination treatment specifically includes the administration of a Bv8 antagonist herein in combination with a VEGF antagonist, such as an anti-VEGF antibody. In addition, or alternatively, the Bv8 antagonists herein can be administered in combination with one or more further agents, e.g., myeloid cell reduction agent, anti-cancer agents or therapeutics, anti-angiogenesis agents, or an anti-neovascularization therapeutics to treat various neoplastic or non-neoplastic conditions, such as inflammatory cell-dependent angiogenesis or tumorigenesis.

In one embodiment, the neoplastic or non-neoplastic condition is characterized by pathological disorder associated with aberrant or undesired angiogenesis that is resistant to VEGF antagonist treatment. The antagonists of the invention can be administered serially or in combination with another agent that is effective for those purposes, either in the same composition or as separate compositions. Alternatively, or additionally, multiple antagonists, agents and/or agonists of the invention can be administered.

The administration of the antagonist and/or agents can be done simultaneously, e.g., as a single composition or as two or more distinct compositions using the same or different administration routes. Alternatively, or additionally, the administration can be done sequentially, in any order. In certain embodiments, intervals ranging from minutes to days, to weeks to months, can be present between the administrations of the two or more compositions. For example, the VEGF antagonist may be administered first, followed by a different antagonist or agent, e.g., myeloid cell reduction agent, of the invention (other than a VEGF antagonist). However, simultaneous administration or administration of the different antagonist or agent of the invention first is also contemplated.

The effective amounts of therapeutic agents administered will be at the physician's or veterinarian's discretion. Dosage administration and adjustment is done to achieve maximal management of the conditions to be treated. The dose will additionally depend on such factors as the type of therapeutic agent to be used and the specific patient being treated. Suitable dosages for the VEGF antagonist are those presently used and can be lowered due to the combined action (synergy) of the VEGF antagonist and the different antagonist of the invention. In certain embodiments, the combination of the inhibitors potentiates the efficacy of a single inhibitor. The term "potentiate" refers to an improvement in the efficacy of a therapeutic agent at its common or approved dose. See also the section entitled Pharmaceutical Compositions herein.

Anti-angiogenic therapy in relationship to cancer is a cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics. In one embodiment of the invention, anti-cancer agent or therapeutic is an anti-angiogenic agent. In another embodiment, anti-cancer agent is a chemotherapeutic agent.

Many anti-angiogenic agents have been identified and are known in the arts, including those listed herein, e.g., listed under Definitions, and by, e.g., Carmeliet and Jain, *Nature* 407:249-257 (2000); Ferrara et al., *Nature Reviews: Drug Discovery*, 3:391-400 (2004); and Sato *Int. J. Clin. Oncol.*, 8:200-206 (2003). See also, US Patent Application US20030055006. In one embodiment, an antagonist of the invention is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent of the invention. In certain embodiment, one or more additional therapeutic agents, e.g., anti-cancer agents, can be administered in combination with agent of the invention, the VEGF antagonist, and/or an anti-angiogenesis agent.

In certain aspects of the invention, other therapeutic agents useful for combination tumor therapy with the Bv8 antagonists of the invention include other cancer therapies, (e.g., surgery, radiological treatments (e.g., involving irradiation or administration of radioactive substances), chemotherapy, treatment with anti-cancer agents listed herein and known in the art, or combinations thereof). Alternatively, or additionally, two or more antibodies binding the same or two or more different antigens disclosed herein can be co-administered to the patient. Sometimes, it may be beneficial to also administer one or more cytokines to the patient.

In certain aspects, the invention provides a method of blocking or reducing resistant tumor growth or growth of a cancer cell, by administering effective amounts of an antagonist of VEGF and an antagonist of the invention and one or more chemotherapeutic agents to a patient susceptible to, or diagnosed with, cancer. A variety of chemotherapeutic agents may be used in the combined treatment methods of the invention. An exemplary and non-limiting list of chemotherapeutic agents contemplated is provided herein under "Definition."

As will be understood by those of ordinary skill in the art, the appropriate doses of chemotherapeutic agents will be generally around those already employed in clinical therapies wherein the chemotherapeutics are administered alone or in combination with other chemotherapeutics. Variation in dosage will likely occur depending on the condition being treated. The physician administering treatment will be able to determine the appropriate dose for the individual subject.

The invention also provides methods and compositions for inhibiting or preventing relapse tumor growth or relapse cancer cell growth. Relapse tumor growth or relapse cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients or the patients are no longer receiving any beneficial effect from the therapy such that these patients need additional effective therapy. As used herein, the phrase can also refer to a condition of the "non-responsive/refractory" patient, e.g., which describe patients who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context. A tumor resistant to anti-VEGF treatment is an example of a relapse tumor growth.

The invention provides methods of blocking or reducing relapse tumor growth or relapse cancer cell growth in a subject by administering one or more antagonists of the invention to block or reduce the relapse tumor growth or relapse cancer cell growth in subject. In certain embodiments, the antagonist can be administered subsequent to the cancer therapeutic. In certain embodiments, the antagonists of the invention are administered simultaneously with cancer therapy, e.g., chemotherapy. Alternatively, or additionally, the antagonist therapy alternates with another cancer therapy, which can be performed in any order. The invention also encompasses methods for administering one or more inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenesis agent, e.g., a VEGF antagonist. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN®(Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., *Journal of Immunological Methods* 288:149-164 (2004); and, WO2005012359. Additional agents can be administered in combination with VEGF antagonist and an antagonist of the invention for blocking or reducing relapse tumor growth or relapse cancer cell growth, e.g., see section entitled Combination Therapies herein.

In one embodiment, the Bv8 antagonists of the invention, can be administered in combination with one or more myeloid cell reduction agents, including, but not limited to therapeutics that reduce expression of Gr1, neutrophil elastase, MCP-1, MIP-1 alpha, URCGPs or URRTPs. Myeloid cell reduction agents for use in combination with the Bv8 antagonists of the present invention specifically include Gr1 antagonists, Cd11B antagonists, CD18 antagonists, elastase inhibitors, MCP-1 antagonists, MIP-1 alpha antagonist, clodronate, alone or in any combination.

In addition, the Bv8 antagonists of the present invention can be administered in combination with hormonal, radiation and chemotherapeutic agents thereby resensitizing the cancer cells to one or more of these agents, which can then be administered (or continue to be administered) to treat or manage cancer, including to prevent metastasis.

Tumor sensitivity to treatment with a VEGF antagonist can be assessed by providing one or more test cell populations from the subject that includes cells capable of expressing one or more nucleic acid sequences homologous to nucleic acid encoding a URCGP, DRCGP, URRTP or DRRTP. Expression of the sequences is compared to a reference cell population. Any reference cell population can be used, as long as the VEGF antagonist sensitivity status of the cells in the reference cell population is known. Comparison can be performed on test and reference samples measured concurrently or at temporally distinct times. An example of the latter is the use of compiled expression information, e.g., a sequence database, which assembles information about expression levels of known sequences in cells whose sensitivity status is known. In certain embodiments of the invention, the reference cell population is enriched for CD11b+Gr1+ myeloid cells. In certain embodiments of the invention, the reference cell population is enriched for tumor cells.

Tumors resistant to treatment with VEGF antagonists can also be identified using the diagnostic marker sets provided in copending application Ser. No. 11/692,682 filed on Mar. 28, 2007. For example, a marker set can include two or more, three or more, four or more, five or more, six or more, seven or more, eight or more, nine or more, ten or more, twelve or more, thirteen or more, fourteen or more, fifteen or more, twenty or more, or the entire set, of molecules. The molecule is a nucleic acid encoding a protein or a protein with an altered expression and/or activity, and is selected from the following: Notch2, DMD8, MCP-1, ITGB7, G-CSF, IL-8R, MIP2, MSCA, GM-CSF, IL-1R, Meg-SF, HSP1A, IL-1R, G-CSFR, IL10-R1, Erb-2.1, Caveolin3, Semcap3, INTG4, THBSP-4, ErbB3, JAM, Eng, JAM, Eng, JAM-2, Pecam1, Tlr3, neutropil elastase, CD14, expi, Il-13R, LDLR, TLR-1, RLF, Endo-Lip, SOCS13, FGF13, IL-4R, THBS1, Crea7, Aquaporin-1, SCF38, APOE, FABP, IL-11R, IFN TM1. TNFRSF18, WNT5A, Secretory carrier membrane 1, HSP86, EGFR, EphRB2, GPCR25, HGF, Angiopoietin Like-6, Eph-RA7, Semaphorin V1b, Neurotrophin 5, Claudin-18, MDC15, ECM, ADAMTS7B, NCAM-140, Fibronectin type III, WIP, CD74, ICAM-2, Jagged1, Itga4, ITGB7, TGF-BII-R, TGFb IEP, Smad4, BMPR1A, CD83, Dectin-1, CD48, E-selectin, IL-15, Suppressor of cytokine signaling 4, Cytor4, CX3CR1, IGF2, HSP9A, FGF 18, ELM1, Ledgfa, scavenger receptor type A, Macrophage C-type lectin, Pigr3, Macrophage SRT-1, G protein-coupled receptor, ScyA7, IL-1R2, IL-1 inducible protein, IL-1beta, ILIX Precuror, TGF-B, FIZZ1, Wfs1, TP 14A, EMAP, SULF-2, Extracellular matrix 2, CTFG, TFPI, XCP2, Ramp2, ROR-alpha, Ephrin B1, SPARC-like 1 and Semaphorin A. In one embodiment of the invention, an antibody is provided that detects the protein. In one embodiment, the molecules are derived from CD11b+Gr1+ cells and include, e.g., IL-13R, TLR-1, Endo-Lip, FGF13, IL-4R, THBS1 and Crea7. In another embodiment, the molecules are derived from resistant tumors and include, e.g., MSCA, MIP2, IL-8R, G-CSF, IL10-R2, THBSP-4, and JAM-2.

E. Pharmaceutical Compositions and Administration

The Bv8 antagonists, such as anti-Bv8 antibodies, of the present invention, clone or in combination with other therapeutic agents, are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes, and/or subcutaneous administration.

In certain embodiments, the treatment of the invention involves the combined administration of a Bv8 antagonist and a VEGF antagonist and/or one or more myeloid cell reduction agent or chermotherapeutic agent. In one embodiment, additional anti-cancer agents are present, e.g., one or more different anti-angiogenesis agents, one or more chemotherapeutic agents, etc. The invention also contemplates administration of multiple inhibitors, e.g., multiple antibodies to the same antigen or multiple antibodies to different proteins of the invention. In one embodiment, a cocktail of different chemotherapeutic agents is administered with the Bv8 antagonist herein. The combined administration includes coadministration, using separate formulations or a single pharmaceutical formulation, and/or consecutive administration in either order. For example, a VEGF antagonist may precede, follow, alternate with administration of the Bv8 antagonist, or may be given simultaneously therewith. In one embodiment, there is a time period while both (or all) active agents simultaneously exert their biological activities.

For the prevention or treatment of disease, the appropriate dosage of the agent of the invention will depend on the type of disease to be treated, as defined above, the severity and course of the disease, whether the inhibitor is administered for preventive or therapeutic purposes, previous therapy, the patient's clinical history and response to the inhibitor, and the discretion of the attending physician. The inhibitor is suitably administered to the patient at one time or over a series of treatments. In a combination therapy regimen, the compositions of the invention are administered in a therapeutically effective amount or a therapeutically synergistic amount. As used herein, a therapeutically effective amount is such that administration of a composition of the invention and/or co-administration of VEGF antagonist and one or more other therapeutic agents, results in reduction or inhibition of the targeting disease or condition. The effect of the administration of a combination of agents can be additive. In one embodiment, the result of the administration is a synergistic effect. A therapeutically synergistic amount is that amount of VEGF antagonist and one or more other therapeutic agents, e.g., a Bv8 antagonist and optionally a myeloid cell reduction agent, a chemotherapeutic agent and/or an anti-cancer agent, necessary to synergistically or significantly reduce or eliminate conditions or symptoms associated with a particular disease.

Depending on the type and severity of the disease, about 1 µg/kg to 50 mg/kg (e.g. 0.1-20 mg/kg) of Bv8 antagonist, VEGF antagonist, myeloid cell reduction agent, a chemotherapeutic agent, or an anti-cancer agent is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. Typically, the clinician will administered a molecule(s) of the invention until a dosage(s) is reached that provides the required biological effect. The progress of the therapy of the invention is easily monitored by conventional techniques and assays.

For example, preparation and dosing schedules for angiogenesis inhibitors, e.g., anti-VEGF antibodies, such as AVASTIN® (Genentech), may be used according to manufacturers' instructions or determined empirically by the skilled practitioner. In another example, preparation and dosing schedules for such chemotherapeutic agents may be used according to manufacturers' instructions or as determined empirically by the skilled practitioner. Preparation and dosing schedules for chemotherapy are also described in *Chemotherapy Service Ed.*, M. C. Perry, Williams & Wilkins, Baltimore, Md. (1992).

The efficacy of the treatment of the invention can be measured by various endpoints commonly used in evaluating neoplastic or non-neoplastic disorders. For example, cancer treatments can be evaluated by, e.g., but not limited to, tumor regression, tumor weight or size shrinkage, time to progression, duration of survival, progression free survival, overall response rate, duration of response, quality of life, protein expression and/or activity. Because the anti-angiogenic agents described herein target the tumor vasculature and not necessarily the neoplastic cells themselves, they represent a unique class of anticancer drugs, and therefore can require unique measures and definitions of clinical responses to drugs. For example, tumor shrinkage of greater than 50% in a 2-dimensional analysis is the standard cut-off for declaring a response. However, the inhibitors of the invention may cause inhibition of metastatic spread without shrinkage of the primary tumor, or may simply exert a tumouristatic effect. Accordingly, approaches to determining efficacy of the therapy can be employed, including for example, measurement of plasma or urinary markers of angiogenesis and measurement of response through radiological imaging.

In another embodiment of the invention, an article of manufacture containing materials useful for the treatment of the disorders or diagnosing the disorders described above is provided. The article of manufacture comprises a container, a label and a package insert. Suitable containers include, for example, bottles, vials, syringes, etc. The containers may be formed from a variety of materials such as glass or plastic. In one embodiment, the container holds a composition which is effective for treating the condition and may have a sterile access port (for example the container may be an intravenous solution bag or a vial having a stopper pierceable by a hypodermic injection needle). At least one active agent in the composition is VEGF modulator and at least a second active agent is a myeloid cell reduction agent and/or a chemotherapeutic agent. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution.

Further details of the invention are illustrated by the following non-limiting examples.

EXAMPLE 1

Materials and Methods

Gene Expression Analysis by Taqman™

RNA from tissues or cells was prepared using the RNeasy Mini Kit® (Qiagen). 50 ng total RNA per reaction was used for the real time PCR (Taqman™) analysis. For mouse/human Bv8 and EG-VEGF/Bv8 receptor 1 (PKR-1/EG-VEGFR1, R-1), testis RNA (BD Biosciences) served as control. For mouse/human EG-VEGF/Bv8 receptor 2 (PKR-2/EG-VEGFR2, R2), hypothalamus or whole brain (BD Biosciences) served as the control tissues. Reactions were run on 9600 Emulation mode of 7500 Real (Perkin Elmer) time PCR system (Applied Biosystems) and the absolute quantification with standard curve was used with Sequence Detection System (SDS) software. The expression level of each gene was further quantified against the house-keeping gene RPL19 in the same sample. To confirm the expression of VEGFR-1, VEGFR-2, EG-VEGF/Bv8 R1 and EG-VEGF/Bv8 R2 in the tumor-associated endothelial cells, standard RT-PCR was conducted using the Titan One Tube™ RT-PCR system (Roche) and the end products were checked on 2% agarose gel (Invitrogen) for the correct size. The sequence of Taqman™ primers are as follows:

Mouse Bv8 forward:
(SEQ ID NO: 7)
GCA TGA CAG GAG TCA TCA TTT T, reverse:
(SEQ ID NO: 8)
AAA TGG CAG GAT ATC AGG AAA, probe:
(SEQ ID NO: 9)
AAA CTT TAT TTG TAA CCC AAA GGT CTA ATG TAA ATG GA;

Human Bv8 forward:
(SEQ ID NO: 10)
ATG GCA CGG AAG CTA GGA, reverse:
(SEQ ID NO: 11)
GCA GAG CTG AAG TCC TCT TGA, probe:
(SEQ ID NO: 12)
TGC TGC TGG ACC CTT CCT AAA CCT;

Mouse Bv8 R1 forward:
(SEQ ID NO: 13)
CAG CGC ACA TGA AGA CTT G, reverse:
(SEQ ID NO: 14)
GTC ATC TTC GGT TTC CTG AGT, probe:
(SEQ ID NO: 15)
TCC AGG CAG CAC CCC TGA TG;

Mouse Bv8 R2 forward:
(SEQ ID NO: 16)
GAA CTC CAC GTG AGC GCA, reverse:
(SEQ ID NO: 17)
GGG TCC CAT GTT GAT GAT GC, probe:
(SEQ ID NO: 18)
CTC CCT GAT ACA CAC CAG CCC ACC TG;

Human Bv8 R1 forward:
(SEQ ID NO: 19)
CTG GAA GGC TTC TTA CAA TGG, reverse:
(SEQ ID NO: 20)
GGC ATC CCA ATT GTC TTG A, probe:
(SEQ ID NO: 21)
TCC AGG TCT GCA CTG GAC TTA CCG;

Human Bv8 R2 forward:
(SEQ ID NO: 22)
TCA CCA TCG TTC GTG ACT TC, reverse:
(SEQ ID NO: 23)
AGA AGG CAG TGA GGT AGT GCT T, probe:
(SEQ ID NO: 24)
TCC TTC ACG AAC ACA GTG GGG AA;

Mouse RPL19 forward:
(SEQ ID NO: 25)
AGG TCA AAG GGA ATG TGT TCA AA, reverse:
(SEQ ID NO: 26)
CCT TGT CTG CCT TCA GCT TGT, probe:
(SEQ ID NO: 27)
ACA AGC GCA TCC TCA TGG AGC ACA TC;

Human RPL19 forward:
(SEQ ID NO: 28)
CGC AAG CGC CGT GAA, reverse:
(SEQ ID NO: 29)
GGT CTC TTC CTC CTT GGA TAA AGT C, probe:
(SEQ ID NO: 30)
CCA GGC AAA GAA GGA GGA GAT CAT CA;

Flow Cytometry

BM mononuclear cells (BMMNCs), PB and tumor cells were harvested from mice implanted with several tumor types. Red blood cells were lysed using Ack (Cambrax, MA) lysis buffer, followed by staining with rat anti-mouse CD11b (Myletnyi Biotech, CA) conjugated to APC and rat anti-mouse Gr1 (BD Biosciences, CA) conjugated to PE. To exclude dead cells, 7AAD (aminoactiomycin D; BD Biosciences CA) was added to all samples prior to data acquisition in the FACSCalibur instrument Migration Assays BMMNCs were isolated from naïve Beige nude mice and the CD11b+Gr1+ population was sorted using CD11b microbeads (Miltenyi Biotech, CA) according to protocols provided by the manufacturer. An aliquot of the sorted cells were stained with anti-CD11bAPC and antiGr1-PE to ensure the purity (100%) of CD11b+Gr1+ cells. For migration assay, $2.0 \times 10^5$ cells were plated on the top chamber of transwells (Corning Incorporated, NY). The bottom chambers contained 600 µL of media (IMDM (Gibco BRL, CA) supplemented with BIT (Stem Cell Technologies, BC, Canada) containing human Bv8, control antibody, and murine recombinant VEGF in separate wells. Cells were incubated at 37° C. and 5% CO2 for 9 hrs and migration of CD11+b+Gr1+ cells was evaluated by counting the cells in the bottom chamber.

Regulation of Bv8 Gene Expression in Cultured BMMN Cells

Recombinant mouse MCP-1, MIP-1α, MIP-1β, MIP-2, bFGF, VEGF, GM-CSF, G-CSF, SDF-1 and TNFα were purchased from R&D Systems (Minneapolis, Minn.). Recombinant mouse KC, IFNγ, Bv8 (Prokineticin-2), IL-4, IL-10, IL-13, TGF-β were from PeproTech Inc. (Rocky Hill, N.J.). All cytokines were used at 10 ng/ml except for VEGF and Bv8, which were tested at 50 ng/ml. Conditioned media at 1:3 dilution were used (final FBS concentration was 0.17%). Data were normalized against total cell number. BM cells were flushed from mouse leg bones with DMEM containing 10% FBS. Cells were centrifuged at 1200 rpm for 5 min and resuspended in HBSS media containing 0.2% BSA (low endotoxin, Serologicals Corp. Norcross, Ga.). Two million cells were incubated in 24-well plates with various cytokines for 4 hr at 37° C. in a 5% CO2 incubator. Cells were then transferred in eppendorf tubes, centrifuged and lysed by RNA lysis buffer (Qiagen, Valencia, Calif.). Bv8 expression was assessed by Taqman™ with RPL19 (Ribosomal Protein L19) as the internal control gene. In some cases, CD11b+Gr1+ or CD11b–Gr1– BM cells were obtained using FACS sorting.

To test the effects of anti-G-CSF antibodies on Bv8 gene expression induced by the tumor environment, BMMNCs isolated from Balb c/nude mice were treated for 4 hrs with either lysates of HM7 tumors which had been implanted in mice for 24-36 hours or with control buffer. Tumor lysates were pre-incubated with a goat anti-G-CSF neutralizing polyclonal IgG (AF-414-NA, R&D Systems) or control goat IgG (R&D Systems) at various concentrations for 45 min before adding to the BMMNCs. The ability of the anti-G-CSF IgG to block mouse and human G-CSF was verified. Expression of Bv8 in BMMNCs was subsequently evaluated using Taqman™ analysis. 9 animals were used for the study and data were analyzed from 3 independent studies.

Collection of Media Conditioned by Tumor Cells

A673, HM7, HPAC and Calu6 cells were cultured in growth media until they reached ~90% confluency. Growth media was then changed to 0.5% FBS-containing DMEM:F12 (50:50) media. Exponentially growing TIB42 cells at density of $5 \times 10^5$/ml were switched to 0.5% FBS-containing DMEM:F12 media. After a three days incubation, the conditioned media were collected. Cell viability and total cell number were measured using Vi-Cell™XR cell viability analyzer (Beckman Coulter).

Tumor Cell Proliferation Assays

A673, HM7, HPAC and Calu6 cells were trypsinized and washed in media containing 0.5% FBS before seeding into 96-well black Viewplate (Packard Bioscience Company, Meriden, Conn.). Cells were incubated with various amounts of Bv8 (PeproTech Inc., Rocky Hill, N.J.) for 3 days. 10% FBS-containing media served as a positive control. Cell proliferation was assessed by BrdU incorporation using the Cell Proliferation ELISA kit (Roche).

In Vivo G-CSF and Anti-G-CSF Studies

Eight weeks old Balb/c mice were subcutaneously injected with 10 µg recombinant human G-CSF (Neupogen, Amgen) daily for eight consecutive days. Control animals were given PBS. At the end of study, BM, whole blood and spleen samples were taken for analysis. One group of animals was maintained for two days after G-CSF discontinuation. Neutrophil count was done using an automated, high-resolution, flow cytometry-based hematology analyzer (CellDyn 3000). Serum and BM Bv8 levels were measured by ELISA.

To determine the role of Bv8 in G-CSF-induced mobilization of CD11b+Gr1+ cells, Balb/c nude mice received two doses of anti-Bv8 antibodies (5+5 mg/kg), 12 hours apart, followed by mouse G-CSF (R&D Systems; 2 µg/mouse) fours hours after the second dose of Mab. As a positive control, we used a rat anti-mouse G-CSF Mab (Mab414, R&D Systems; 10 µg/mouse) given at the same interval as anti-Bv8, followed by mouse G-CSF. After six hours, mice were bled and the frequency of CD11b+Gr1+ cells was determined as described. To determine the role of G-CSF in regulating Bv8 expression in the absence of tumor, Balb/c nude mice were given daily i.p. injections of control rat IgG (Genentech) or rat anti-G-CSF Mab (Mab414, R&D Systems, 10 µg/mouse) for eight consecutive days. Animals were euthanized and total proteins were extracted from BMMNCs. Bv8 levels were measured by ELISA, as described. To assess the significance of G-CSF in regulating Bv8 expression in tumors, Balb/c nude mice were pretreated with 10 µg of rat anti-G-CSF Mab or rat IgG as above described, followed after 12 hours by implantation with HM7 cells ($5 \times 10^6$ per mouse). Controls were implanted with empty Matrigel™. Animals then received daily administration of antibodies for two days. Forty-eight hours after Matrigel™ or tumor implantation, mice were euthanized and Bv8 levels in BMMNCs were measured as described above.

Generation and Screening of Anti-Bv8 Neutralizing Antibodies

Mouse monoclonal antibodies directed against recombinant human Bv8 protein were generated. Antibodies were screened using two independent assays. One assay was based on the ability of Bv8 protein to induce proliferation of bovine adrenal cortex-derived endothelial cells, as described (LeCouter et al., 2003, supra). The second assay relayed on the ability of Bv8 to induce a signaling cascade in Chinese hamster ovary (CHO) cells stably expressing each of its receptors. Briefly, CHO cells stably expressing the beta lactamase gene under the NFAT promoter (Invitrogen) were grown in DMEM supplemented with 10% fetal bovine serum. Human PKR1 or PKR2 cDNA (Masuda, Y., et al., supra and Lin, D. C. et al., supra in pMSCV-Hygromycin were transduced. Cells expressing the transgene were selected in 500 mg/ml Hygromycin for 2 weeks. Responders cells were subsequently isolated by FACS sorting for their ability to cleave the FRET-based fluorescent substrate CCF4 following 16 h stimulation with hBv8, as suggested by the manufacturer. Neutralizing antibodies were identified for their ability to block Bv8-induced beta-lactamase expression. CHO—NFAT beta-lactamase PKR1 or PKR2 were stimulated by hBv8 at 100-200 ng/ml for 16 h in presence or absence of purified mouse monoclonal anti-Bv8 antibodies at various concentrations. After stimulation, cells were incubated with CCF4 for 1 hour and the fluorescence was measured with a 96 well plate reader Envision™ (Perkin Helmer).

To directly establish the role of Bv8 during tumorigenesis, we made use of neutralizing anti-Bv8 monoclonal antibodies (Mabs). Murine Mabs 3F1 and 2B9, which cross-react with mouse and human Bv8, were employed. These Mabs were selected on the basis of their ability to inhibit Bv8-stimulated adrenal cortex endothelial cell proliferation (LeCouter et al., Nature 412:877-884 (2001)) and inhibit signaling in CHO cells transfected with Bv8 GPCRs. Mab 2B9 maximally inhibited ~70% of the mitogenic effect of human or mouse Bv8 proteins, while Mab 3F1 inhibited as much as 50%. However, the combination of the two Mabs, each at the concentration of 5-10 µg/ml, completely blocked the mitogenic effects elicited by 100 ng/ml human or mouse Bv8. The antibodies, tested alone or in combination, had no effect on endothelial cell proliferation under basal conditions or following stimulation with the structurally unrelated VEGF-A or the related EG-VEGF. Also, neither the anti-Bv8 Mabs nor Bv8 itself had any detectable effects on the proliferation of the tumor cells lines tested in this study, over a wide range of concentrations (data not shown).

To determine the most effective therapeutic regimen in vivo, in initial experiments we performed dose-response studies with Mabs 3F1 and 2B9, individually and in combination, in the A673 model. As predicted by the in vitro data, a combination of the two Mabs was more effective than a single Mab. Administration of 5 mg/kg of each Mab twice weekly achieved a maximal inhibitory effect on tumor growth. Therefore, this regimen was used in all subsequent proof-of-concept experiments. In addition to the A673 rhabdomyosarcoma, we tested additional models including the human HM-7, Jurkat, HPAC and Calu-6 cell lines and the mouse EL-4 and TIB42 lymphomas.

In Vivo Tumor Studies

The human tumor cell line Calu-6, A-673, JURKAT, HPAC and HM7 as well as the mouse lymphoma lines EL4 and TIB42, were grown in Ham's F12, low glucose DMEM 1:1 supplemented with 10% v/v FBS, 1% v/v penicillin/streptomycin, 2 mM L-Gln and 1 µg/ml Fungizone™ (Invitrogen™, CA). Cells were incubated at 37° C. in an atmosphere of 95% air/5% $CO_2$. For mouse xenograft experiments, tumor cells were suspended at a concentration of $1 \times 10^8$ cells/ml and injected (100 µl/mouse) subcutaneously into the dorsal flank of either Balb-c or beige nude XID immunodeficient mice (Harlan Sprague Dawley, IN). 24 or 48 hours points after tumor cell inoculation, i.p. administration of anti-Bv8 mAbs 2B9 and 3F1 was initiated, at a total dose of 10 mg/kg (5 mg/kg of each Mab) (n=10). As controls, we employed anti-Ragweed Mab and anti-VEGF Mab G6.31 or B20 (Liang, W. C., et al., *J Biol Chem* 281, 951-961 (2006)). Thereafter the mice were treated twice weekly. Tumor volumes were calculated every second day using the ellipsoid volume formulas (6×L×W×H, where L=length, W=width, and H=height) (Tomayko, M. M. and Reynolds, C. P., *Cancer Chemother Pharmacol* 24, 148-154 (1989)). For statistical analysis of differences between groups, a one-way ANOVA followed by a Tukey HSD pair wise analysis was performed using JMP software (SAS Institute Inc.). A p value <0.005 was considered significant.

Histological Analysis and Immunohistochemistry

Tumors were fixed in neutral-buffered formalin for 24 hours prior to paraffin embedding. H & E staining and immunohistochemistry were performed as described previously (ref). Briefly, immunohistochemical staining with rat anti-mouse PLVAP monoclonal MECA-32 (BD-Pharmingen) was performed using Target antigen retrieval solution (DAKO) at 99 degrees C. then at room temperature, for 20 minutes each. Primary antibody was detected sequentially using a biotinylated secondary antibody (Vector), and Vectastain ABC Elite™ reagents. Reaction product was generated using metal-enhanced DAB (Pierce Chemical, IL). Sections were lightly counterstained with hematoxylin, dehydrated, and coverslipped.

Construction of Adenovirus Vectors

Adenovirus vectors encoding LacZ and $mVEGF_{164}$ were described previously (LeCouter et al., 2001, supra). Adenoviral mBv8 was generated using the AdEasy XL™ adenoviral vector system (Stratagene). Adenoviral mBv8 was generated using the AdEasy XL™ adenoviral vector system (Stratagene). The cDNA of mBV8 with a 6×His tag (SEQ ID NO: 36) at its C-terminus was cloned between the XhoI and Hind III sites of the pShuttle-CMV vector. The resultant pShuttle-CMV-mBV8 plasmid was recombined with pAdEasy-1™ in BJ5183-AD-1, an electroporation-competent strain pre-transformed with the adenoviral backbone. The recombinant adenoviral Bv8 plasmid was then transfected into AD-293 cells for packaging virus particles. Adenovirus stocks were purified by CsCl gradient. Adenovirus was titered using Adeno-X Rapid™ titer kit (Clontech).

Isolation and Characterization of Tumor-Associated Endothelial Cells

Tumor associated endothelial cells (TAECs) were isolated using a magnetic beads sorting system (Miltenyi Biotech), essentially as previously described (Hida et al., *Cancer Res* 64:8249-8255 (2004)). Briefly, TIB42 mouse lymphoma cells were injected into the dorsal lateral flanks of female beige nude mice. When tumors reached a diameter of ~1000 $mm^3$, they were excised, minced and then digested with collagenase II (Worthington Biochemical Corporation). Cell suspensions were than filtered using 100 µm to 40 µm meshes. $CD31^+$ cells were finally sorted using a FITC-CD31 antibody (BD Biosciences) according to the manufacturer's instructions. CD31+ cells were seeded in gelatin coated plates in the presence of EGM-2MV media (Cambrex). After 24 hs in culture CD31+ non-adherent cells were removed by washing several times with PBS.

For RT-PCR, RNA was extracted from cultured cells using the RNeasy™ minikit (QIAGEN). For the experiments shown, 80 ng of RNA were used for each 50 ul reaction and the cDNA was amplified for 28 cycles. Primer sequences are available upon request.

TIB42-TAEC cells were starved for 6 hr in basal media supplemented with 0.5% BSA. Cells were then stimulated with human recombinant Bv8 (200 ng/ml; PeproTech), Complete Media (CM), VEGF (100 ng/ml; PeproTech) or BSA (0.5%). Cell extracts were collected at the indicated timepoints. Western blot analysis of the extracts from TIB42-TAEC cells was performed using PhosphoPlus p44/42 MAPK™ antibody kit (Cell signaling). To evaluate the consistency and reproducibility of this result each condition was tested in duplicated and the experiments were performed three times, with similar results.

For in vitro tube formation, TIB42-TAEC cells (passages 6-8) were starved for 5 hs in serum free medium. After this, cells were collected and resuspended in serum free medium supplemented with 5% BSA and treated with VEGF-A (100 ng/ml), Bv8 (200 ng/ml) or no addition (control). For specificity tests, Bv8, was incubated in the presence of anti-Bv8 Mabs (10 µg/ml). $5 \times 10^5$ cells were seeded in each well of a 24 well pre-coated with Matrigel™ (BD Biosciences) and tube formation was evaluated after 36 hours.

Micro-Computed Tomographic Angiography

HM7-tumor bearing animals received a 50 ul i.p. injection of heparin 10 minutes before euthanization by inhalation of carbon dioxide. The thoracic cavity was opened, an incision was made in the apex of the heart, and a polyethylene cannula (id 0.58 mm, od 0.96 mm) was passed through the left ventricle and secured in the ascending aorta with 5-0 silk suture. A 17 ml solution of 0.1 mM sodium nitroprusside in 0.9% saline was perfused at a rate of 6 ml/min to provide a state of maximum vasodilatation and remove blood. MICROFIL® (Carver, Mass.), a commercially available lead chromate latex, was prepared as recommended by the manufacturer and perfuse at a rate of 2 ml/min for 17 ml. The infused latex mixture was allowed to polymerize at room temperature for sixty minutes before dissection of tissues of interest. Dissected tumors were immersed in 10% neutral buffered formalin.

The tumors were then imaged with a µCT40™ (SCANCO Medical, Basserdorf, Switzerland) x-ray micro-computed tomography (micro-CT) system. The tumors were imaged with soybean oil as the background media. The micro-CT images were generated by operating the x-ray tube at an energy level of 45 kV, a current of 177 μA and an integration time of 300 milliseconds. Axial images were obtained at an isotropic resolution of 16 μm.

The vascular network and tumor were extracted by a series of image processing steps. An intensity threshold of 1195 Houndsfield Units (HU) and morphological filtering (erosion and dilation) were applied to the volumetric micro-CT image data to extract the vascular volume (VV). The tumor volume (TV) was extracted from the background in similar fashion with an intensity threshold of −8 HU. Vessel density (VV/TV) was determined from the ratio of VV to TV. The vascular and tumor intensity thresholds were determined by visual inspection of the segmentation results from a subset of samples. Computations were performed by an in-house image analysis algorithm written in C++ and Python that employed the AVW image processing software library (AnalyzeDirect Inc., Lenexa, Kans.). Three-dimensional (3D) surface renderings were created from the micro-CT data with the use of Analyze 6.0 (AnalyzeDirect Inc., Lenexa, Kans.), an image analysis software package. Statistical analysis was performed with JMP statistical software package (SAS Institute Inc., Cary, N.C., USA). Group comparisons for Micro-CT metrics (VV, TV, VV/TV) were evaluated with Dunnett's test for multiple comparisons. P-values less than 0.05 were considered significant.

Partial Purification of Bv8 Protein and Western Blot Analysis of BMMNC Lysate.

Balb/c mice (n=20) were subcutaneously injected with human G-CSF (10 μg/day, Amgen) and intraperitoneally injected with mGM-CSF (0.5 μg/day, PeproTech) daily for 4 days, to expand the CD11b+gr1+ population. On day 5, the BM cells were isolated and the cell pellet was resuspended in 2 ml of 0.5% Triton X-100™. The cell lysate was then forced through a 25 gauge needle for four times, and the salt concentration was adjusted to 50 mM NaCl. The crude extract was applied to a heparin-Sepharose® column (Hi-Trap, 1 ml) pre-equilibrated with 20 mM Tris pH17.2, 50 mM NaCl. The column was eluted using a two-step linear gradient: 50 mM to 1M NaCl, and then 1M to 2M NaCl in 20 mM Iris, pH 7.2. The flow rate was 1 ml/min. Absorbance was monitored at 280 nm. Fractions of 1 ml were collected and assayed for mBv8 using ELISA and Western blot. For Western blot analysis, 100 μl of fractions were concentrated 4 fold using Microcon YM-3® spin column (MILLIPORE), and then loaded on a 4-20% SDS-PAGE (Invitrogen). The blot was stained overnight using a combination of three hamster antibodies against mBv8 (2D3, 3B8 and 4E10) at a total concentration of 10 μg/ml in blocking buffer (PBST, 0.1% Tween 20 in PBS and 5% skim milk). Following three washes, the blot was incubated with a horseradish peroxidase-conjugated goat anti-hamster IgG (ImmunoResearch Laboratories), and was then developed using the enhanced chemiluminescence plus Western blotting Detection System™ (GE Healthcare Bio-Science).

Mouse Bv8 ELISA

MaxiSorp® 96-well microwell plates (Nalge Nunc International, Rochester, N.Y.) were coated with 1.0 mg/ml 3F1 antibody (a mouse anti-human BV8 antibody, which also binds to mouse Bv8 in 50 mM carbonate buffer, pH 9.6, at 4° C. overnight. Plates were washed with PBS containing 0.05% polysorbate 20 and blocked with 0.5% bovine serum albumin, 10 ppm Proclin 300™ (Supelco, Bellefonte, Pa.) in PBS at room temperature for 1 h. After plates were washed, mouse BV8 standards (0.039-2.50 ng/ml in 2-fold serial dilution, Genentech) and samples (minimum 1:10 dilution) in PBS containing 0.5% bovine serum albumin, 0.05% polysorbate 20, 10 ppm Proclin 300® (Supelco, Bellefonte, Pa.) and 0.35N NaCl (sample buffer) were added to the plates. The plates were incubated for 2 h at room temperature. Unbound antibody was removed by a wash step. Antibody bound to the plates was detected by adding biotinylated 4E10 antibody (a hamster anti-mouse BV8 antibody, Genentech) followed by streptavidin-HRP (GE Healthcare, Buckinghamshire, United Kingdom) and 3,3',5,5'-tetramethyl benzidine (Kirkegaard & Perry Laboratories, Gaithersburg, Md.) as the substrate. The reaction was stopped by adding 1 M phosphoric acid. Absorbance was read at 450 nm on a Titertek™ stacker reader (ICN, Costa Mesa, Calif.). The titration curves of the standards were fit using a four-parameter regression curve-fitting program (Genentech). Data points which fell in the range of the standard curve were used for calculating the mouse BV8 concentrations in samples.

This assay can tolerated 10% mouse serum and 10% lysis buffer and has a sensitivity of 0.39 ng/ml for serum and tissue lysate samples. It is specific to BV8. Anti-VEGF G6-31 human IgG1, human G-CSF and human VEGF up to 30 mg/ml, or human EG-VEGF up to 5 mg/ml only gave a background signal. This ELISA also detects human BV8 but with 26% or less efficiency. The presence of anti-BV8 3F1 up to 14 ng/ml and anti-BV8 2B9 up to 124 ng/ml did not affect detection of 0.5 ng/ml BV8 in sample buffer significantly.

Results

To determine whether Bv8 expression in the BM is affected by tumor growth at a distant site, A673 and HM7 tumor cells were transplanted in immunodeficient mice. As illustrated in FIG. 1a, implantation of both tumors resulted in significant increases in Bv8 levels in the BM by ELISA compared to empty Matrigel™ implantation.

To characterize the Bv8 protein produced in the BM and validate our ELISA, mouse bone marrow mononuclear cells (BMMNCs) lysate was subjected to heparin-sepharose affinity chromatography. As illustrated in Supplemental (hereinafter S) FIG. 1a, Bv8 strongly bound to the column and was eluted as a single peak in the presence of ~0.4 M NaCl. This was confirmed by Western blot analysis, which demonstrated the presence of the expected ~9 kDa band in the immunoreactive fractions (S FIG. 1b).

Figure 1B:
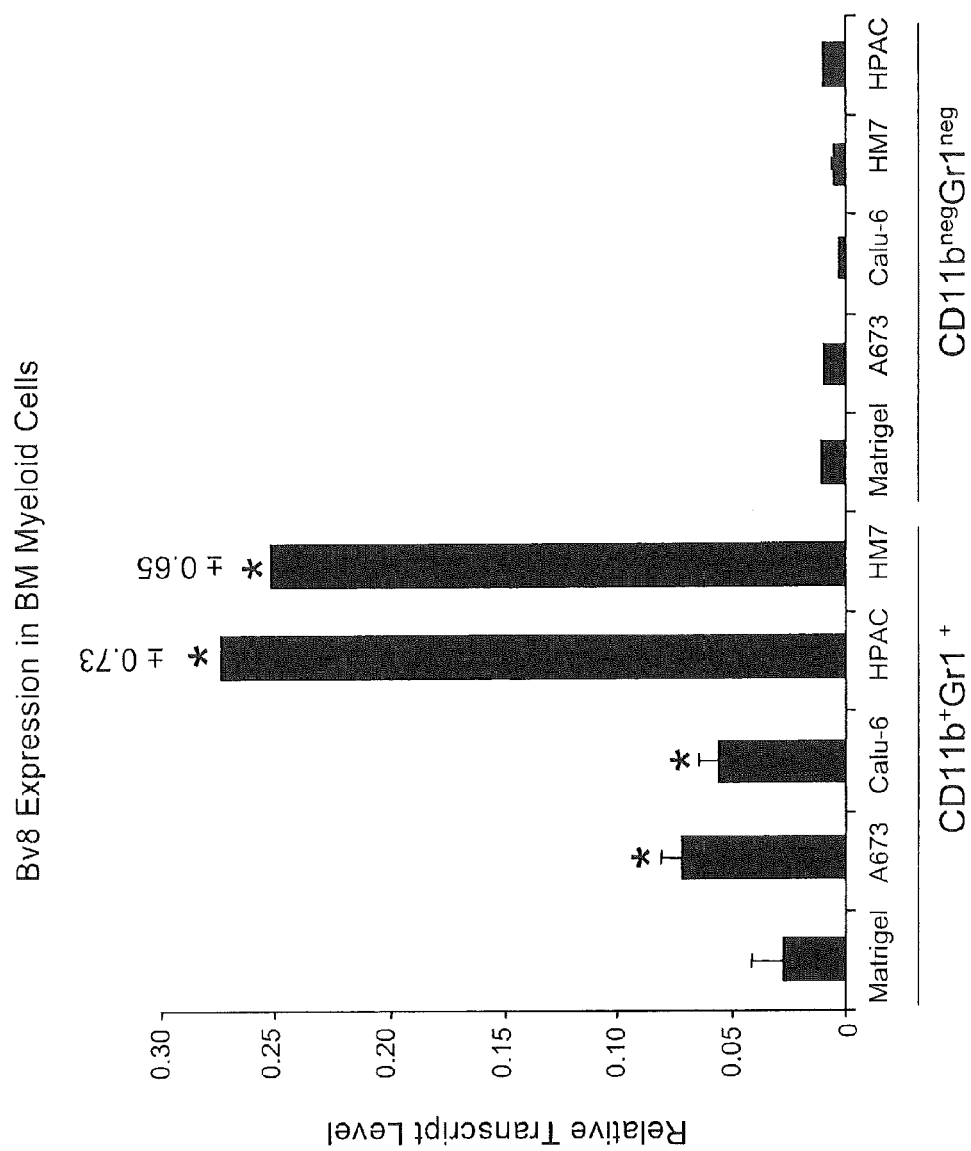

BMMNCs comprise of several subsets of cells, mainly of myeloid and lymphoid lineages. To elucidate what subset of BMMNCs is enriched in Bv8, several tumor cell lines, including A673, Calu-6, HM7, HPAC and Jurkat were implanted in mice. Taqman™ analysis indicated that Bv8 was highly expressed in CD11b+Gr1+ myeloid cells (consists primarily of neutrophils but also includes cells of the macrophage lineage (Yang et al., *Cancer Cell* 6:409-421 (2004); Dahl et al., *Nat Immunol* 4:1029-1036 (2003); Lagasse and Weissman, *J Immunol Methods* 197:139-150 (1996)) compared to CD11b−Gr1− cells (mostly non-myeloid subset) (FIG. 1b).

Figure 1C:
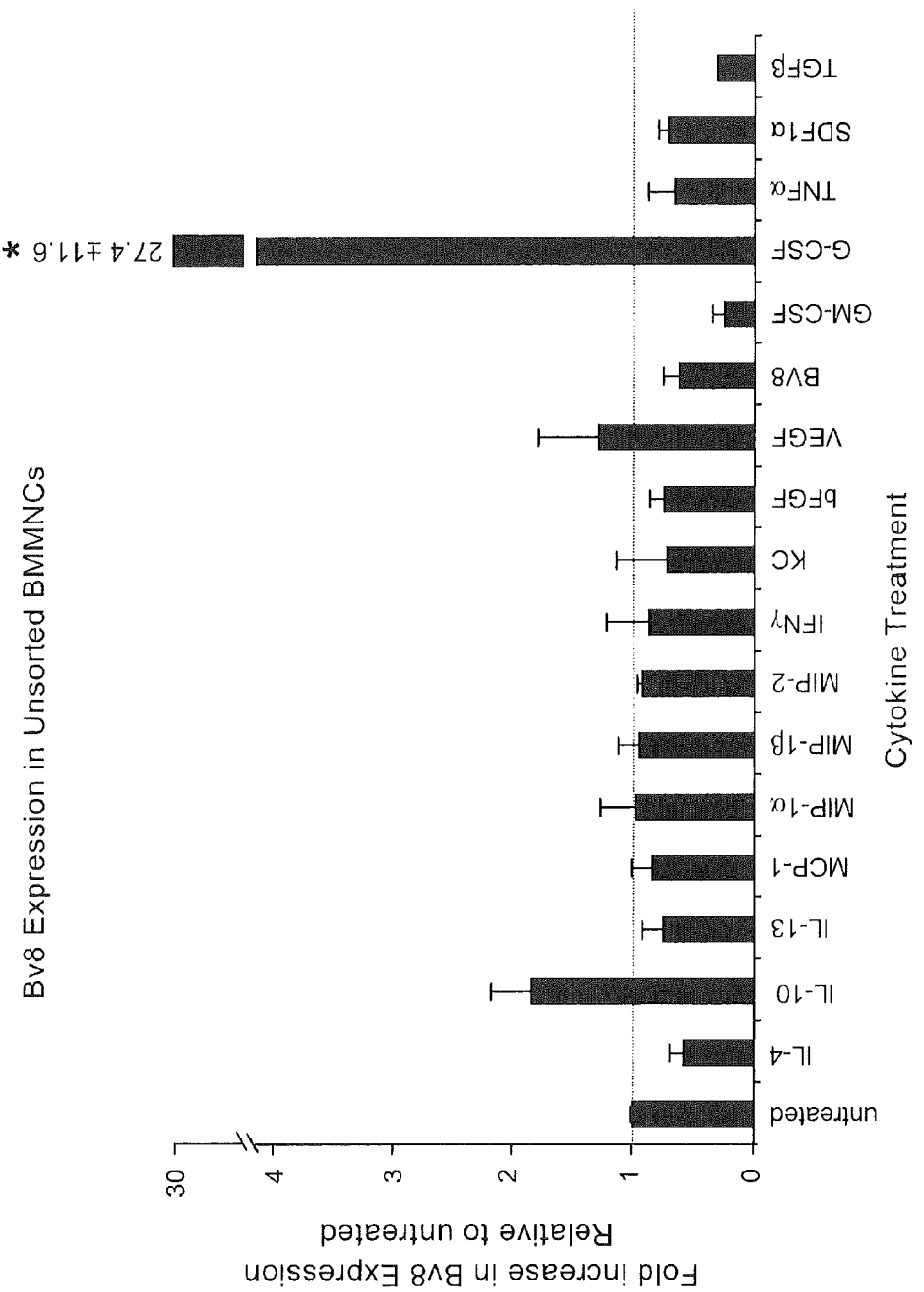

To identify molecules potentially involved in regulating Bv8 expression, the ability of a panel of cytokines/chemokines to induce Bv8 expression in unsorted BMMNCs by Taqman™ was examined. Most of cytokines did not elicit any significant up-regulation of Bv8 in BMMNCs (FIG. 1c). However, G-CSF (10 ng/ml) resulted in a dramatic up-regulation of Bv8 (>27 fold, FIG. 1c). None of the cytokines tested resulted in a marked up-regulation of VEGF-A (data not shown).

Figure 1D:
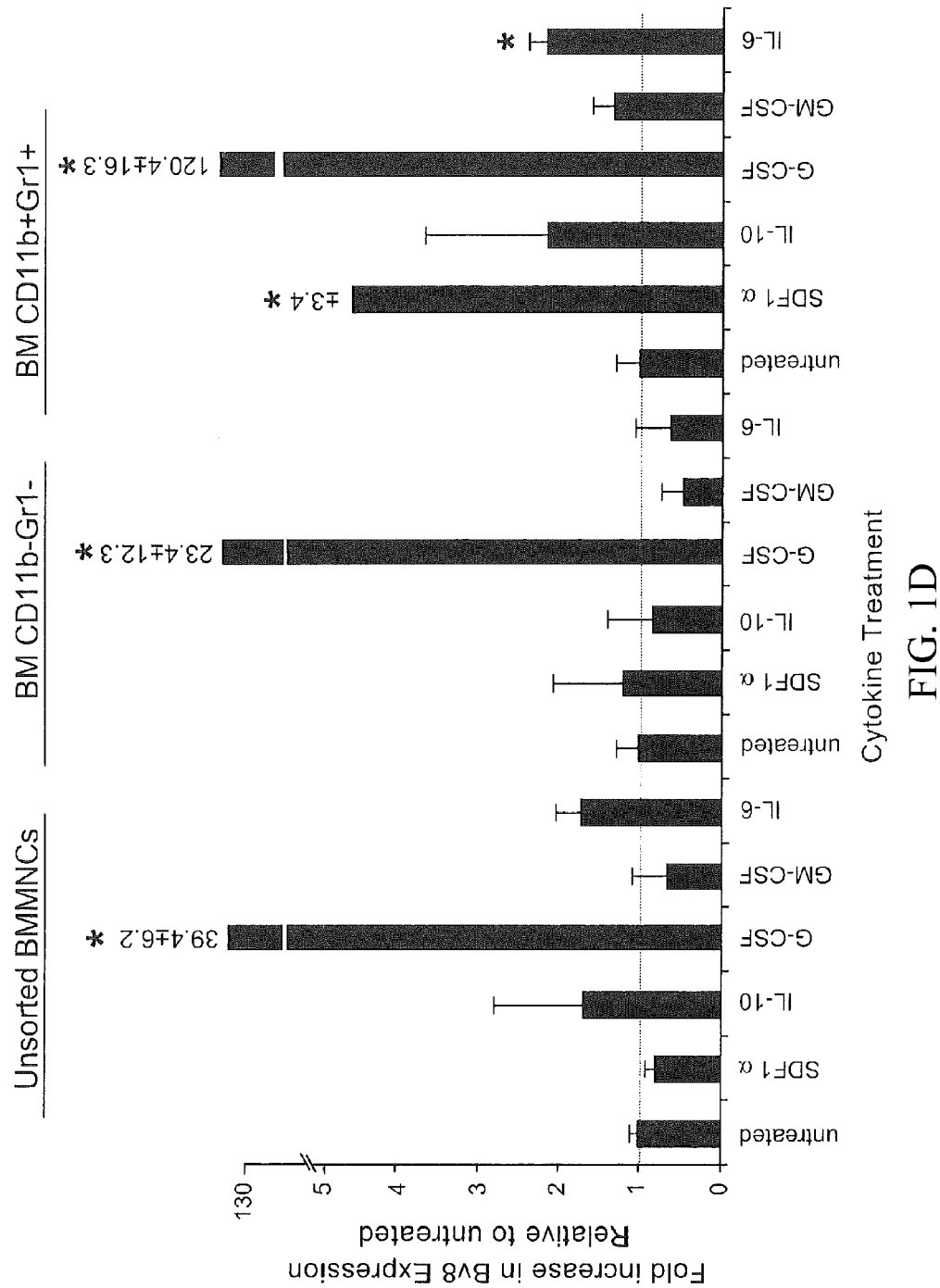

Analysis of different subsets of BMMNCs revealed that G-CSF results in Bv8 up-regulation over 100 fold above background in purified CD11b+Gr1+ cells (FIG. 1d). A substantially lower G-CSF mediated up-regulation of Bv8 was detected in whole BM or in the CD11b−Gr1− fraction. Surprisingly, GM-CSF had no effect on Bv8 expression (FIG. 1 c&d), thus emphasizing the highly selective nature of the regulation of this factor. Interestingly, IL-6 and SDF-1, which did not show any significant stimulation when tested on unsorted BM cells, resulted in a significant 2-3 fold up-regulation of Bv8 when tested on purified CD11b+Gr1+ cells (FIG. 1c&d).

Figure 1E:
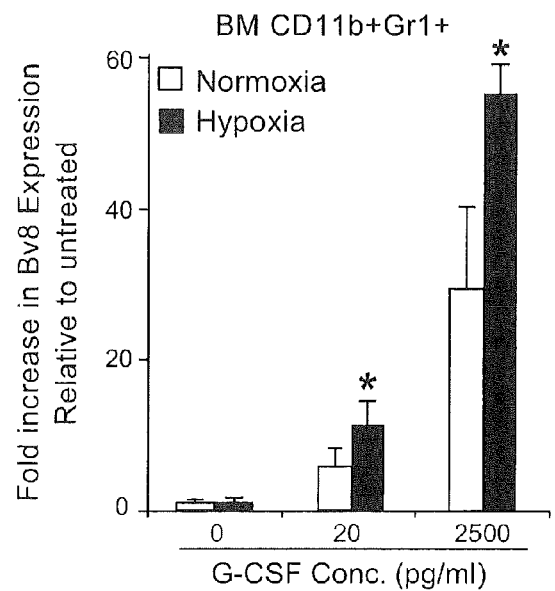
Figure 1F:
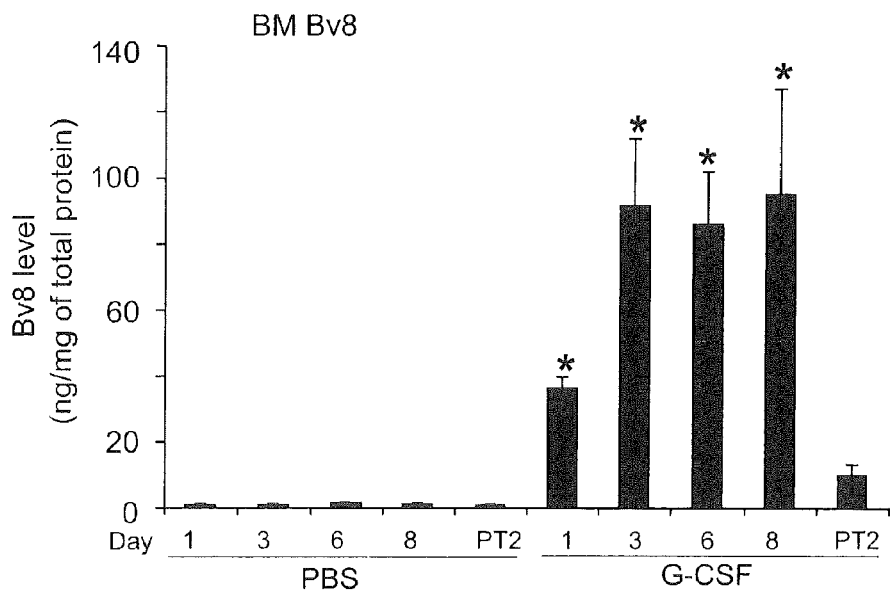
Figure 2A:
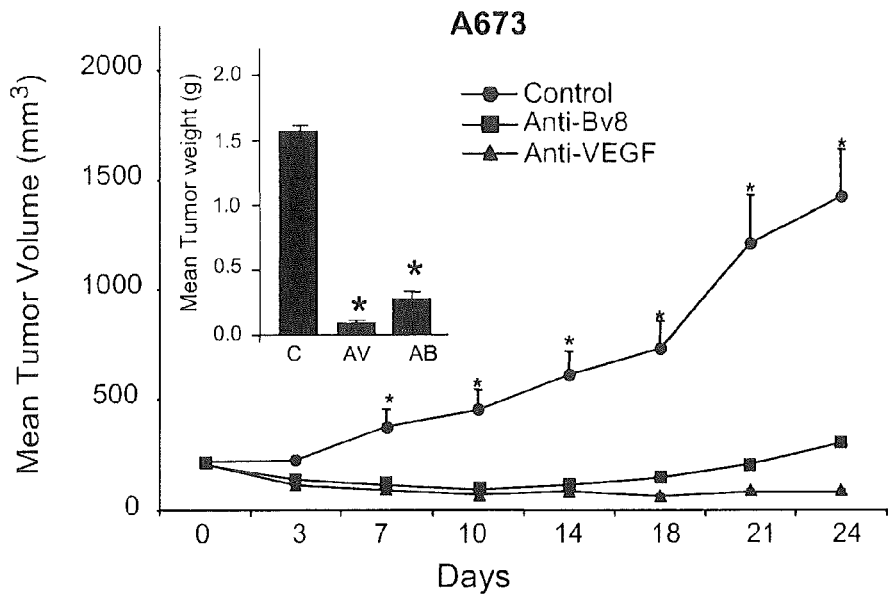
FIG. 2. Effects of anti-Bv8 antibodies on the growth of tumor cell lines transplanted in nude mice. A673 (a), HM7 (b), HPAC (c) and Jurkat (d) tumor cells were implanted in Balb-c nude mice as described in the text. Treatment with control (anti-Ragweed), anti-Bv8 or anti-VEGF-A Mabs (n=10) was initiated 24-48 hours after tumor cell inoculation. Tumor volumes were measured twice weekly. Tumor weight was determined at the end of the experiment. Data shown are means±SEM. Asterisks indicate significant difference in anti-Bv8 or anti-VEGF compared to control treated groups ($p<0.05$). e. Anti-Bv8 and anti-VEGF have additive effects to inhibit tumor growth in anti-VEGF resistant tumors. Beige nude mice were implanted with TIB42 cells and were treated with control, anti-Bv8, anti-VEGF and anti-Bv8 plus anti-VEGF antibodies. Inset shows the terminal tumor weights in all four treatments. C: Control, AV: Anti-VEGF, AB: Anti-Bv8.
Figure 2B:
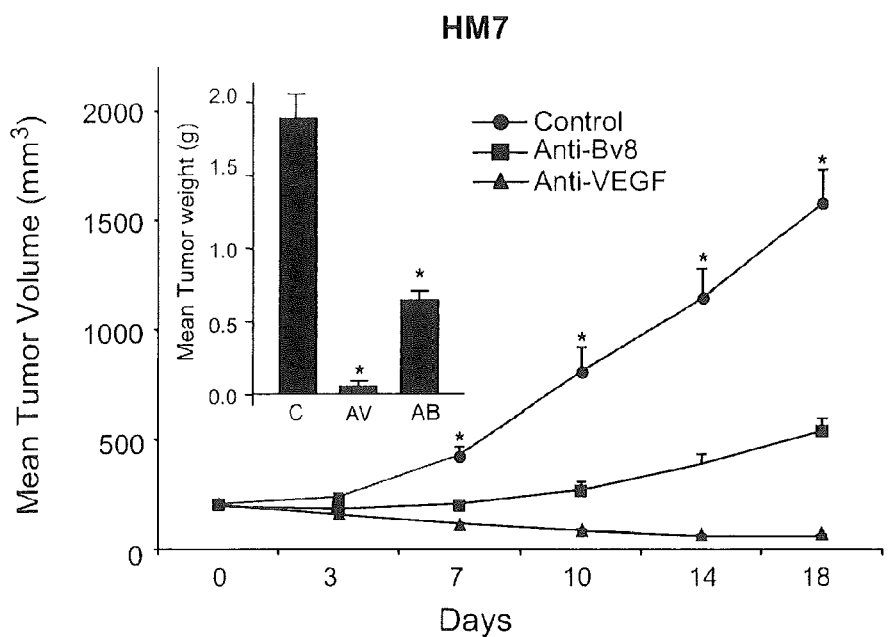
Figure 2C:
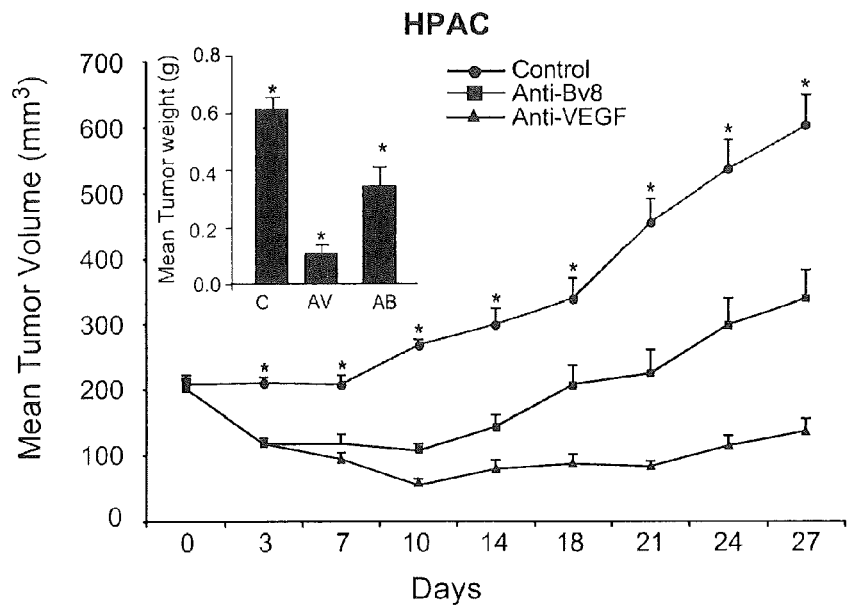
Figure 2D:
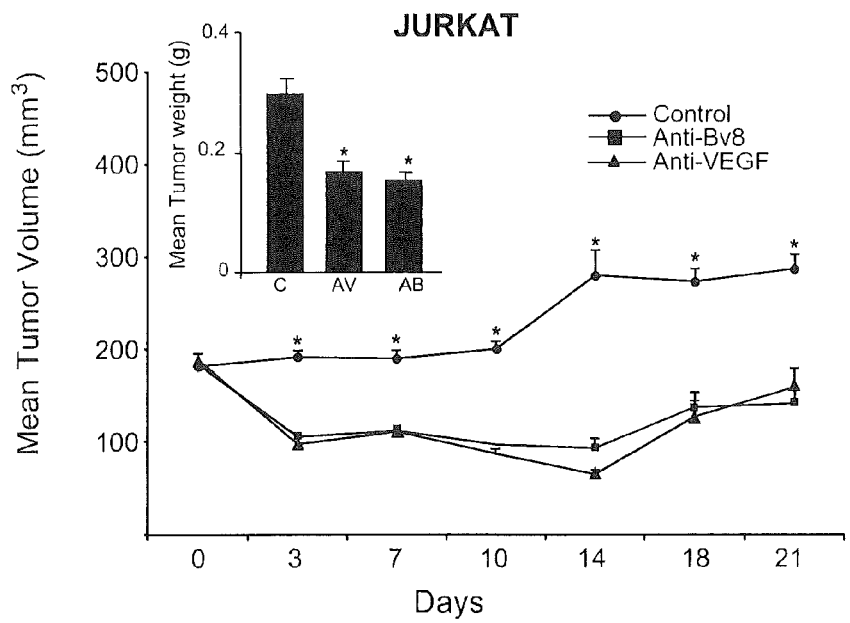
Figure 2E:
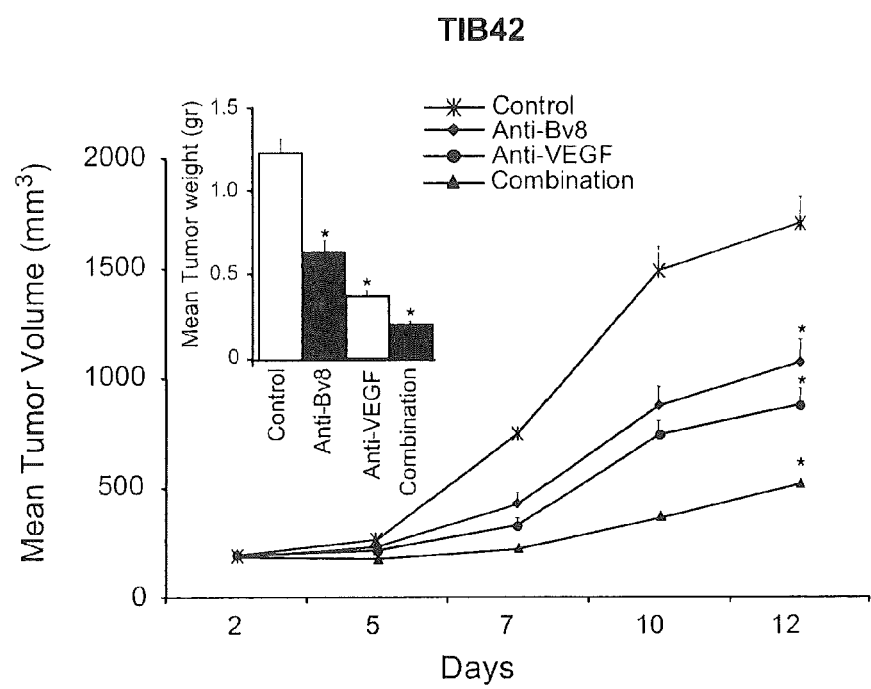

To further characterize the response to G-CSF in CD11b+ Gr1+ cells, we tested whether lower, more physiologically relevant, concentrations of the cytokine may induce Bv8 expression. Also, previous studies have shown that Bv8 gene expression can be increased by hypoxia (LeCouter et al., 2003, supra) and thus we wished to test whether hypoxia may modulate Bv8 response to G-CSF. As shown in FIG. 1e, as little as 20 pg/ml G-CSF resulted in ~10 fold stimulation of Bv8 expression under hypoxic conditions. This stimulation was significantly higher than that detected under normoxic conditions (~5 fold). In addition to the in vitro studies, up-regulation of Bv8 by G-CSF was verified in vivo. Administration of recombinant G-CSF to Balb/c mice resulted in a time- and dose-dependent increase in the levels of Bv8 protein in the BM (FIG. 1f) and in the serum (FIG. 2a), coincident with an increase in peripheral blood (PB) neutrophils (FIG. 2b). Similar results were obtained in Balb-c nude mice (data not shown). Remarkably, as early as 24 hours after G-CSF administration, the Bv8 levels in the BM increased ~30-fold above background. Serum levels were also dramatically increased. BM and serum Bv8 returned to near baseline levels within 48 hours after discontinuing G-CSF, indicating that Bv8 is tightly regulated by G-CSF in the BM. However, G-CSF administration had no effect on Bv8 levels in kidney, brain and liver (data not shown).

G-CSF is a principal regulator of granulopoiesis, causing myeloid/granulocytic progenitors to differentiate into neutrophils G-CSF also plays a key in the mobilization of neutrophils from the BM in response to a variety to environmental stresses and is secreted by several cell types, including endothelial cells and fibroblasts (Christopher, M. J. & Link, D.C., *Curr Opin Hematol* 14, 3-8 (2007)). Furthermore, G-CSF, together with other hematopoietic cytokines, including IL-6 and SDF-1, is constitutively expressed by tumor and/or stromal cells in malignant tumors (reviewed in Mueller, M. M. & Fusenig, N. E., *Differentiation* 70, 486-497 (2002)). To test whether G-CSF. IL-6 or SDF-1 are expressed in our tumor models, the levels of these cytokines were measured in the media conditioned by tumor cells or tumor-associated fibroblasts. As shown in S Table 1, they were detectable, albeit at different concentrations, in both compartments. Thus, G-CSF (and/or other cytokine) mediated up-regulation of Bv8 in the BM may contribute to mobilization of myeloid cells. Subsequent homing of these cells in the tumor may be regulated by additional cytokines and also potentially by Bv8 secreted by tumor-associated myeloid cells.

Figure 1G:
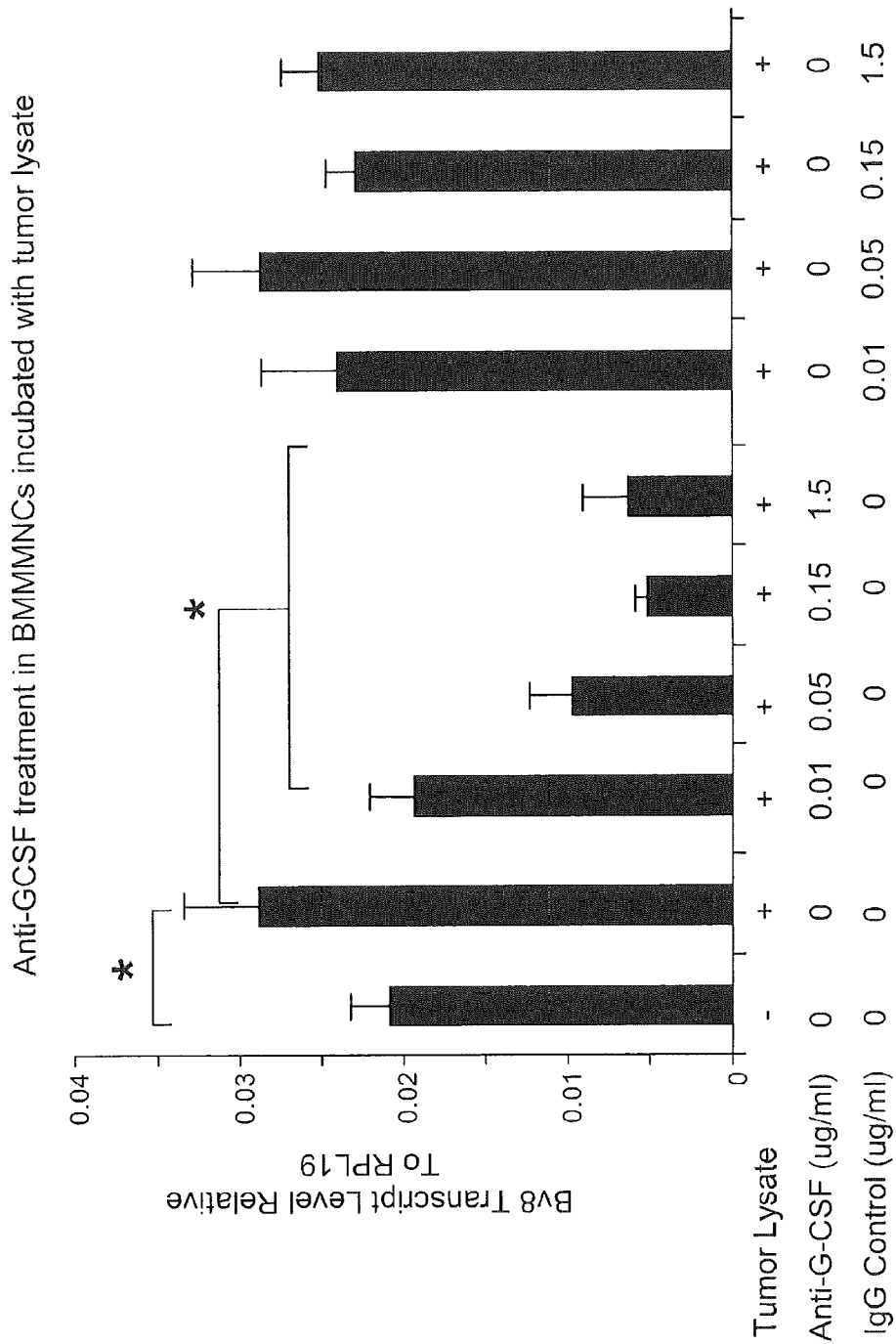
Figures 1H, 1I:
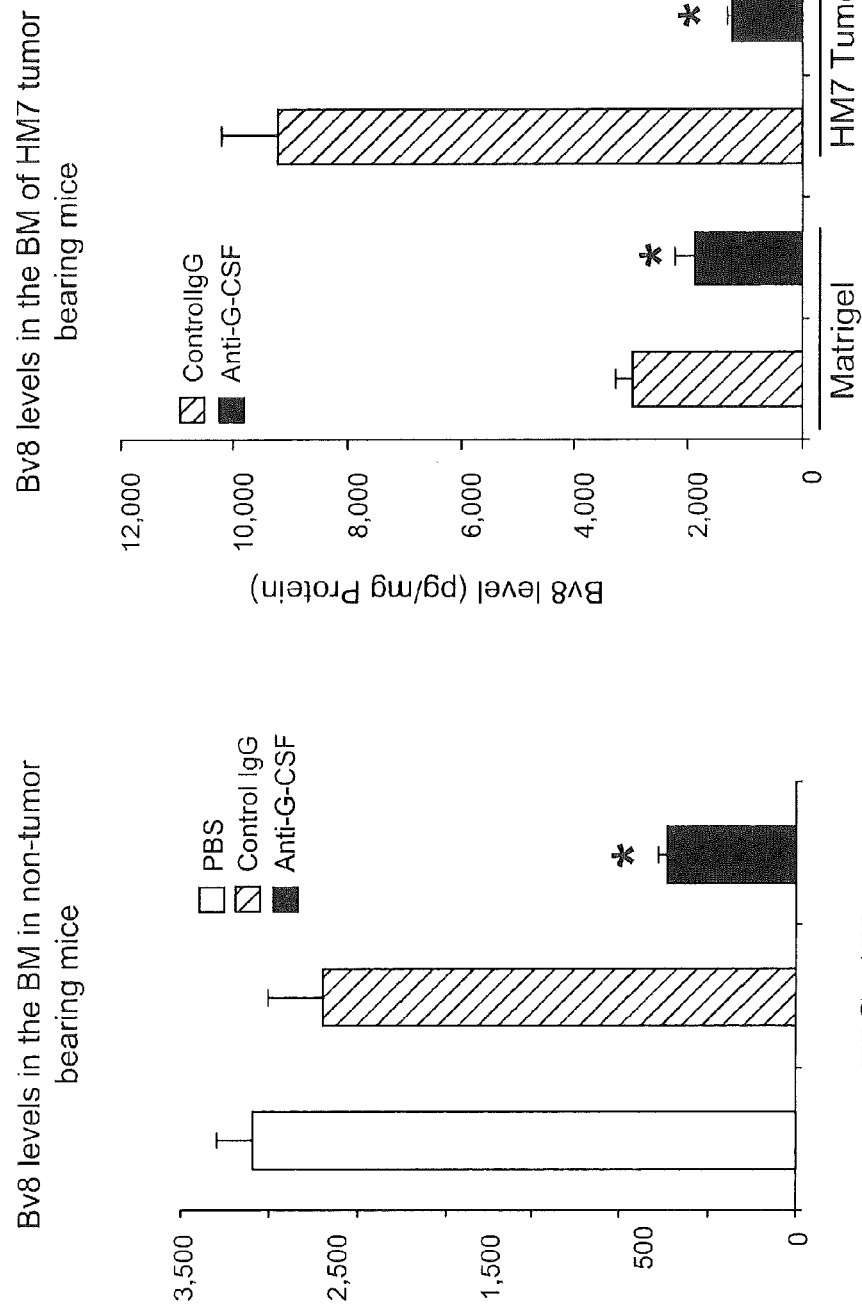

To define the potential role of G-CSF in regulating Bv8 expression within the tumor microenvironment, cultured BMMNCs were incubated with aliquots of lysates from HM7 tumors in the presence of anti-G-CSF or control antibodies (FIG. 1g). Analysis of Bv8 transcript demonstrated a significant dose-dependent reduction in Bv8 expression in BMMNCs treated with anti-G-CSF compared to the control IgG treated wells. Interestingly, in the presence of anti-G-CSF the expression level of Bv8 went below non-stimulated levels, suggesting the unopposed action of inhibitors of Bv8 expression present in the tumor homogenate. In vivo studies confirmed a key role for G-CSF in regulating Bv8 expression. Bv8 protein was significantly reduced in non-tumor bearing mice treated with anti-G-CSF compared controls (FIG. 1h).

Next, it was tested whether G-CSF plays a role in mediating Bv8 up-regulation in the BM of tumor-bearing mice. As illustrated in FIG. 1i, a monoclonal anti-G-CSF antibody, but not a control IgG, virtually abolished the peak in Bv8 protein occurring in the BM shortly after tumor implantation. Very similar results were obtained with a polyclonal goat anti-G-CSF IgG (data not shown). Anti-G-CSF treatment also resulted in a significant reduction in the frequency of circulating—as well as BM-CD11b+Gr1+ cells in non-tumor- and tumor-bearing mice (S FIG. 2c-f). Therefore, while we do not rule out the involvement of additional factors, our findings indicate that Bv8 expression is dependent on G-CSF, both in vitro and in vivo.

Figure 1J:
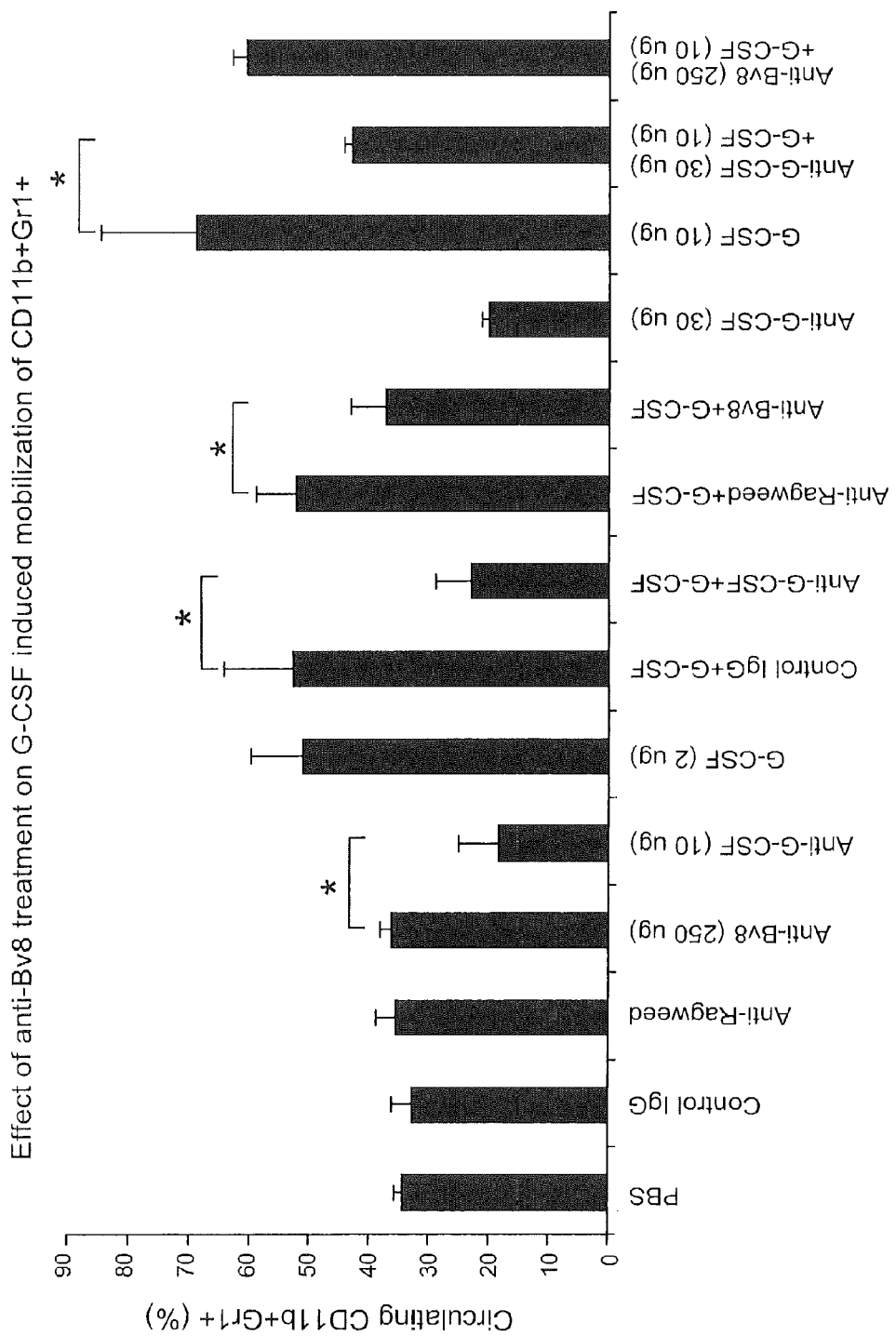

Given the strong up-regulation of Bv8 by G-CSF, we wished to determine whether Bv8 may contribute to mobilization of neutrophils induced by recombinant G-CSF (FIG. 1j). A sub-maximal dose of G-CSF (2 µg) induced within six hours a significant mobilization of CD11b+Gr1+ to the peripheral blood of mice. The effect of G-CSF was completely blocked by an anti-G-CSF antibody. Anti-Bv8 antibodies (hereafter anti-Bv8) also inhibited G-CSF-mediated mobilization of CD11b+Gr1+ cells (FIG. 1j). However, anti-Bv8 had little effect on the mobilization induced by a maximal dose of G-CSF (10 µg). Therefore, Bv8 may function to modulate or augment neutrophil mobilization stimulated by G-CSF.

Figure 3A:
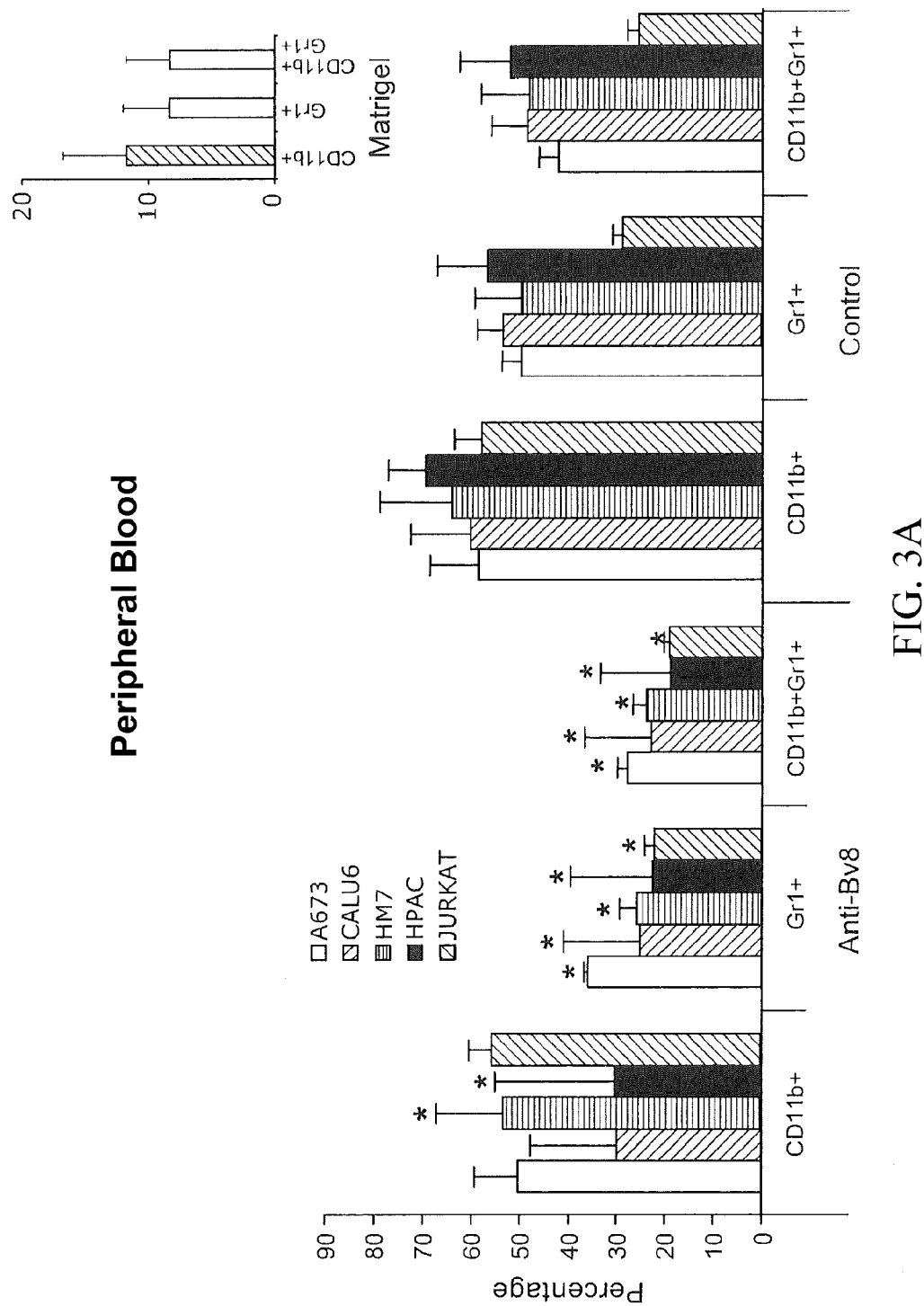
FIG. 3. Anti-Bv8 treatment reduces CD11b+Gr1+ cells in the PB and in tumors in several models. a & b. Nude mice (n=5) were implanted with A673, Calu6, HM7, HPAC and Jurkat cells. Mice were then treated with anti-Bv8 or control Mabs as described in Methods. Analysis was performed ten days after tumor implantation and the frequency of CD11b+, Gr1+ and CD11b+Gr1+ cells was measured in PB (a), and tumors (b) as described. Inset in part a shows the frequency of CD11b+Gr1+ and CD11b+Gr1+ cells in Matrigel™ mice. c & d. Intra-tumor injection of BM CD11b+Gr1+ can override the tumor growth inhibition by anti-Bv8 treatment. Nude mice were implanted with A673 (c) and HM7 (d) tumors and were treated with anti-Bv8 or control Mabs. At day 7 (denoted by arrows), CD11b+Gr1+ cells were isolated from the BM of mice primed with A673 and HM7 tumors using CD11b+ beads. The purified population was directly injected in the tumor bearing mice and the treatment was continued as described.

In vitro, Bv8 promoted migration of BM CD11b+Gr1+ cells in a trans-well assay, to a degree comparable to SDF-1 (S FIG. 3a). Anti-Bv8 completely inhibited Bv8-stimulated migration of myeloid cells but did not have any effect on SDF-1 induced migration, thus confirming the specificity of the effects. Taqman™ analysis of Bv8 receptors, R1 and R2 (S FIG. 3b&c) in the BM revealed higher expression of R2 compared to R1. However, the precise contribution of R1 vs. R2 in mediating Bv8 signaling in BMMNCs remains to be determined. These findings suggest that cell-type specific up-regulation of Bv8 and its receptors is part of the program of bone-marrow gene activation following tumor implantation. To further characterize the effects of Bv8 on the cells of the hematopoietic system, both lineage depleted (Lin— that is devoid of CD11b+Gr1+ cells) and CD11b+Gr1+ cells were isolated from the BM of naïve mice and were treated with recombinant Bv8. Analysis of Lin-population indicated higher expression of CD11b+Gr1+ cells in Bv8-treated cells compared to controls, suggesting that Bv8 alters the fate of progenitor population to cells of myeloid lineage (S FIG. 3d). Moreover, analysis of cellular viability showed that the number of dead cells in Bv8-treated wells was significantly lower than controls, indicating that Bv8 is a potential survival factor for primitive hematopoietic cells (S FIG. 3d). To functionally assess the effects of Bv8 on Lin-cells, we performed a CFU analysis of Bv8-treated cells, which showed greater number of colonies ($p<0.05$) compared to control-treated cells (S FIG. 3e). Analysis of CD11b+Gr1+ cells further supported a role for Bv8 as a survival factor, since Bv8 treated cells contained fewer dead cells compared to controls (S FIG. 3f). Finally, treatment of CD11b+Gr1+ cells with Bv8 resulted in the activation of MAPK pathway in a time dependent manner (data not shown).

To elucidate the role of Bv8 in normal hematopoiesis, anti-Bv8 or anti-Ragweed (hereafter control) antibodies were tested in non-tumor bearing mice. Neither anti-Bv8 nor control showed any significant effects on normal hematopoiesis and hematological parameters in Balb/c nude mice (S FIG. 4). These data suggest that under steady-state, physiological conditions, Bv8 plays a very limited role in the regulation of hematopoiesis.

To investigate the significance of Bv8 in tumor growth in vivo, we tested whether administration of anti-Bv8 or control antibodies may affect the growth of several tumor cell lines transplanted into immuno-deficient mice. As illustrated in FIG. 2, administration of anti-Bv8 resulted in a significant decrease in tumor volume and terminal tumor weight compared to control-treated animals in all tumor models examined. In the A673 model, the growth inhibition was ~80% and approached that achieved with anti-VEGF Mab G6.31 (hereafter anti-VEGF) or B20 (data not shown), which block mouse and human VEGF-A (Liang et al., *J Biol Chem* 281: 951-961 (2006)) (FIG. 2a). The HM7 tumor model also demonstrated a marked growth inhibition by anti-Bv8 treatment (FIG. 2b). A significant inhibition was observed also in tumors derived from the human HPAC (FIG. 2c) and the Jurkat (FIG. 2d) cell lines. The tumor implantation experiments shown were performed in Balb/c nude mice. Similar results were obtained also in Beige nude mice (data not shown). In addition to human xenografts, anti-Bv8 alone or in combination with anti-VEGF antibodies were shown to be efficient in reducing tumor volume in TIB-42 anti-VEGF refractory tumors (FIG. 2f). Discontinuation of the treatment resulted in the rapid tumor growth in mice bearing A673 (S FIG. 3g) and HM7 tumors (S FIG. 3h). In addition, tumors analyses revealed an increase in the number of infiltrating CD11b+Gr1+ cells (S FIG. 3i&j).

Figure 3B:
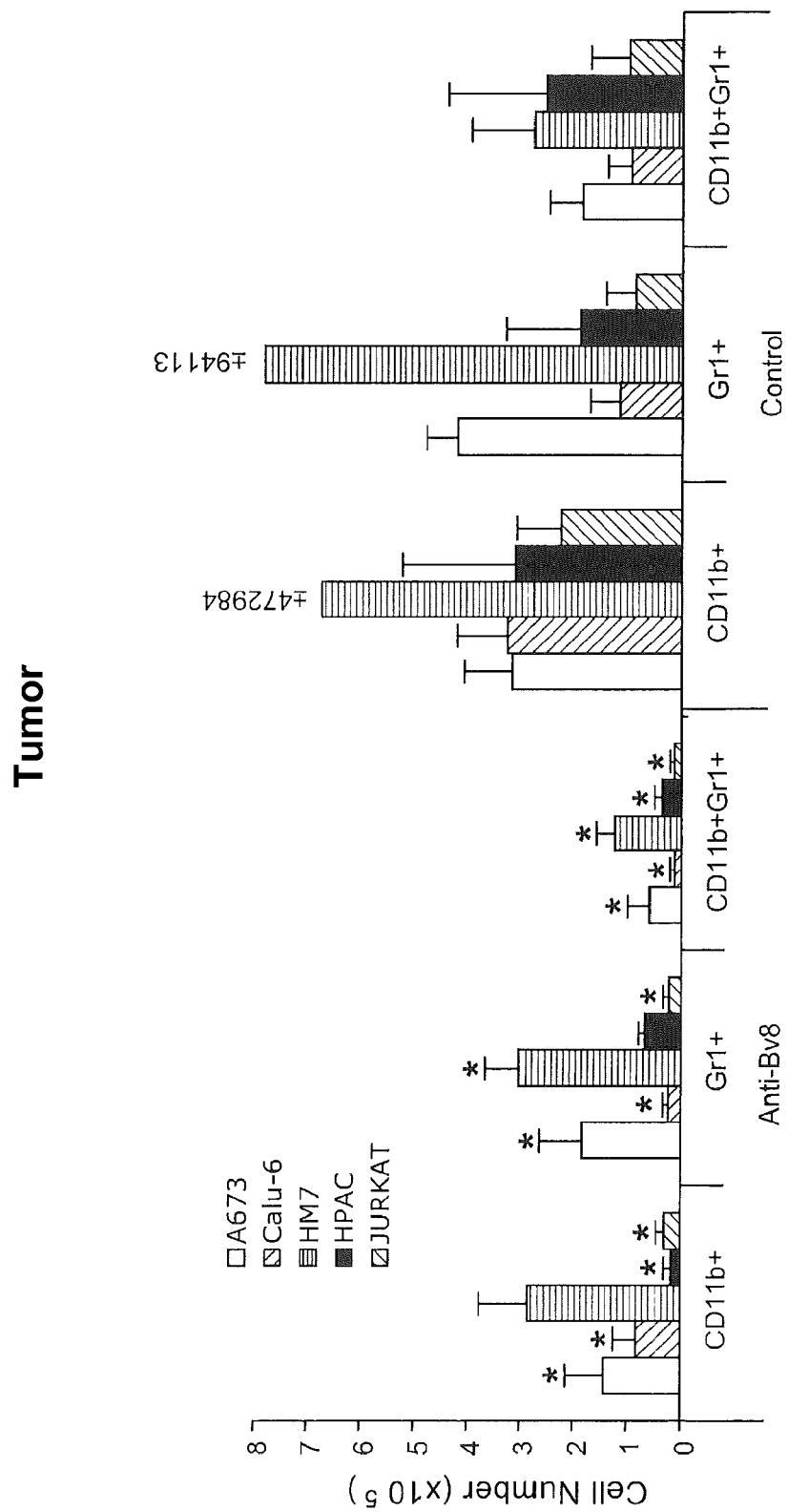

To monitor myeloid cells at different stages of tumorigenesis, we investigated the kinetics of CD11b+Gr1+ cells in the BM, PB and tumors in the A673 model at different time points (S FIG. 5). BM analysis did not reveal any significant difference in the frequency of CD11b+Gr1+ cells (S FIG. 5a) between anti-Bv8 and control treated mice. However, there was a significant reduction in the numbers (data not shown) and frequency of CD11b+Gr1+ cells in the PB in anti-Bv8 compared to control treated mice at all time point tested (S FIG. 5b). In addition, we found a significant reduction in the number of CD11b+Gr1+ cells in A673 tumors at several time points in anti-Bv8 treated tumors compared to controls (S FIG. 5c). Using flow cytometry (representative FACS profiles are shown in S FIG. 6), the kinetics of CD11b+Gr1+ populations were also investigated in the PB, tumors, BM and spleen of mice implanted with Calu-6, HM7, HPAC and Jurkat cells (FIG. 3a&b and also S FIG. 7d&e). Consistent with the time-course study in A673 tumors, treatment with anti-Bv8 resulted in a significant decrease in the frequency of CD11b+Gr1+ cells in the PB also in all tumor models mentioned above (FIG. 3a). A significant reduction in the number of CD11b+Gr1+ in the tumors in anti-Bv8 treated animals was also observed (FIG. 3b). These findings indicate that Bv8 regulates mobilization and potentially homing of CD11b+Gr1+ cells to the tumors. In addition, neutrophils (mainly identified by the expression of Gr1 (Okazaki, T. et al., *Int Immunol* 18, 1-9 (2006)) appear to be the main population affected by anti-Bv8 treatment.

Figure 3C:
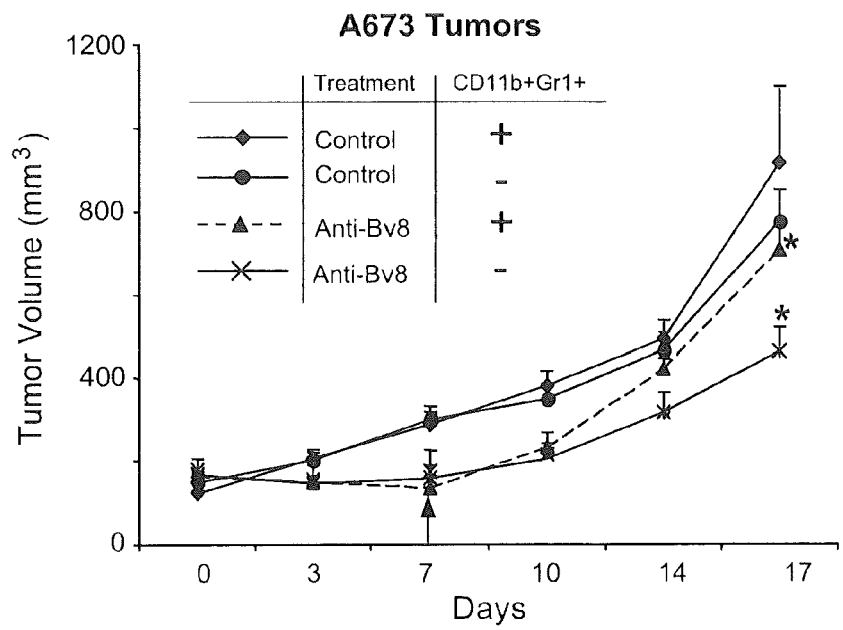
Figure 3D:
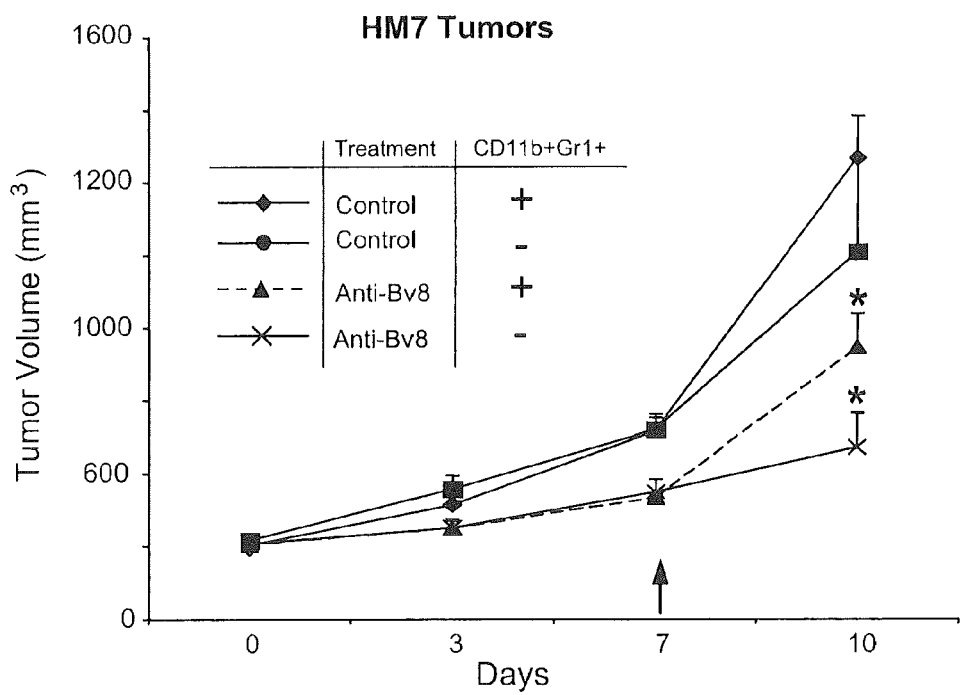

Previous studies have shown that transplantation of myeloid cells, including CD11b+Gr1+ cells, enhances tumor growth, whereas their depletion may reduce it. To directly assess the role of the myeloid subset in Bv8-regulated tumor growth, we isolated BM CD11b+Gr1+ cells from mice bearing A673 or HM7 tumors 7 days after tumor implantation and injected them into the tumors. This resulted in a more rapid tumor growth in anti-Bv8 treated animals (FIG. 3c&d). Therefore, an excess of CD11b+Gr1+ cells may override the tumor growth inhibition elicited by anti-Bv8 treatment. To further characterize the myeloid subset in the bone marrow and tumors, we used F480 as a marker for infiltrating macrophages in CD11b subset. We found that treatment with anti-Bv8 results in a small reduction in the number of macrophages (CD11b+F480+), both in the bone marrow and within tumors in A673 implanted mice (data not shown). Therefore, anti-Bv8 appears to affect primarily granulocytic, and to a more modest degree, macrophage subsets in tumors.

A significant increase in the frequency of CD11b+Gr1+ was observed in the BM and spleen of tumor-bearing mice compared to Matrigel™-implanted mice (S FIG. 7 a&b), However, in contrast to the reduction observed in the PB and tumor, anti-Bv8 treatment did not affect markedly the frequency of CD11b+Gr1+ cells in the BM and spleen. CFU analysis of BM and splenocytes isolated from mice bearing A673 and HM7 tumors (S FIG. 7c) showed that the number of colonies in anti-Bv8 treated mice was significantly reduced compared to control treated mice. These findings suggest that Bv8 neutralization in vivo impairs the ability of splenocytes and BM cells to differentiate and form colonies in vitro.

The magnitude of the anti-tumor effects of anti-Bv8 antibodies is unlikely to be accounted for solely by decreases in the numbers of CD11b+Gr1+ cells in the tumors, which is expected to result in reduced levels of MMP-9 and VEGF-A (Yan et al., *Cancer Cell* 6:409-421 (2004); Nozawa et al., *Proc. Natl. Acad. Sci. USA* 103:12493-12498 (2006)). It is likely that local neutralization of Bv8 activities is a major mechanism of anti-tumor effects of anti-Bv8. Bv8 and the related EG-VEGF have been characterized as mitogens selective for specific endothelial cell types Bergers, G. et al., *Nat Cell Biol* 2, 737-744 (2000); Lin, R. et al., *J Biol Chem* 277, 8724-8729 (2002)). We therefore sought to determine whether Bv8 affects the tumor vasculature. We established and characterized cultures of tumor-associated endothelial cells (TAECs) from xenografted tumors. TAECs formed tubes in Matrigel™ in response to VEGF-A, while control wells showed little or no evidence of tube formation (S FIG. 8a). The addition of Bv8 protein promoted tube formation to a degree comparable to that induced by VEGF-A (S FIG. 8a). Anti-Bv8 antibodies blocked Bv8-induced tube formation but did not inhibit tube formation induced by VEGF. These findings confirm the specificity of the effects and also suggest that Bv8 and VEGF employ different pathways to induce tube formation in TAECs. PCR analysis confirmed the expression of markers of endothelial cells, but not epithelial cells, such as CD31, VEGFR2 and Tie2 in TAECs verifying the endothelial nature of TAECs (S FIG. 8b). In agreement with these findings Bv8 or VEGF-A resulted in strong induction of MAP kinase phosphorylation in TAECs (S FIG. 8c). Taqman™ analysis showed expression of both EG-VEGF/PKR-1 and -2 in TAECs (data not shown). However, recombinant Bv8 failed to stimulate the proliferation of several tumor cell lines in vitro (S FIG. 8d), further supporting the hypothesis that Bv8 mainly targets endothelial cells in the tumor environment.

To corroborate the hypothesis that Bv8 may locally promote tumor angiogenesis, recombinant adenovirus encoding mBv8 (Av-Bv8) was intra-tumorally delivered into HM7 tumor-bearing mice. Av-LacZ and Av-VEGF served as negative and positive controls, respectively. To minimize any systemic effects of the recombinant proteins, we administered low titers of virus ($10^7$ pfu). Compared to control Av-LacZ, Av-Bv8 resulted in an increase in tumor volumes, comparable to that induced by Av-VEGF (FIG. 4a). Consistent with the in vitro observations, administration of Av-Bv8 resulted in enhanced mobilization of CD11b+Gr1+ compared to Av-LacZ and Av-VEGF (FIG. 4b). Higher titers ($10^9$ pfu) of Av-Bv8 also enhanced tumor growth and resulted in higher mobilization of CD11b+Gr1+ cells in the PB and in the tumor (data not shown).

To assess the tumor vasculature, X-ray micro-computed tomography (micro-CT) was employed (Garcia-Sanz, A., et al., *Hypertension* 31, 440-444 (1998); Maehara, N., *Eur radiol* 13, 1559-1565 (2003); Kwon, H. M. et al., *J Clin Invest* 101, 1551-1556 (1998)). Micro-CT provides an overall analysis of tumor vasculature in the entire tumor and thus may overcome some limitations inherent in some other approaches such as immunohistochemistry (IHC). Such analysis demonstrated that Av-Bv8 and Av-VEGF had almost indistinguishable effects, since both resulted in increases ($p<0.05$) in vascular volume (FIG. 4c) compared to the Av-LacZ group. Representative images of the whole tumor mass from each treatment group are shown in FIG. 45e. The surface renderings of the extracted vascular network (red) and tumor (gray) are generated by the image-processing algorithm that defines the volumetric regions employed in the analysis. IHC for MECA-32 confirmed a significant increase in vascular surface areas in HM7 tumors following Av-Bv8 administration, relative to control Av-LacZ (S FIG. 9a).

To further investigate the role of Bv8 in tumor angiogenesis, using a loss of function approach, we analyzed the tumor vasculature in HM7 tumors treated with anti-Bv8, anti-VEGF or control antibodies. In agreement with the experiments illustrated in FIG. 2, anti-Bv8 treatment resulted in a significant reduction in tumor volume (FIG. 4f) and circulating CD11b+Gr1+ cells (FIG. 4g) compared to control treated mice. Using the same micro-CT angiographic approach described above, analysis of tumor vasculature revealed significant reductions in vascular volume in both the anti-Bv8 and anti-VEGF groups relative to control treated tumors (FIG. 4h). Blood vessel density (VV/TV) was also significantly reduced in anti-Bv8 and anti-VEGF groups relative to control (FIG. 4i). Micro-CT data support the hypothesis that inhibition of tumor growth in anti-Bv8 treated mice is a result of inhibition of the tumor vascular development. A representative image of the entire tumor mass is shown in FIG. 4j. Therefore, using gain- and loss-of-function approaches, our data indicate that Bv8 promotes tumor growth primarily through induction of tumor angiogenesis. Histological examinations were also consistent with a role of Bv8 in promoting tumor angiogenesis (S FIG. 9b). Analysis of endothelial cells in Jurkat tumors indicated that, similar to anti-VEGF, administration of anti-Bv8 antibodies markedly inhibited tumor vascularization.

Figure 5A:
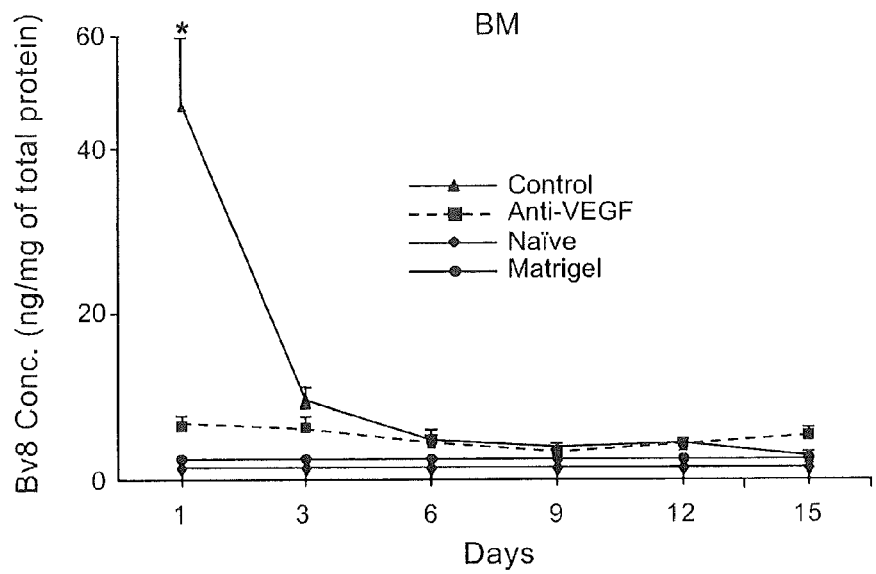
FIG. 5. Anti-VEGF treatment induces Bv8 expression. a-d. Nude mice were implanted with HM7 cells and were treated with anti-VEGF or control Mabs as described. Bv8 protein concentrations were measured in the BM (a), PB (b), spleen (c) and tumors (d) at days 1, 3, 6, 9, 12 and 15 after tumor implantation. All the experiments were performed in parallel with Matrigel™-implanted and naïve mice. e. IHC data to further confirm infiltration of neutrophils in A673 and HM7 implanted animals. Formalin fixed sections provided from mice bearing A673 or HM7 and treated with control, anti-Bv8 or anti-VEGF antibodies for 15 days. Sections were stained with anti-Gr1 antibody as described in the "methods". f. CD11b+ cells are the main source of Bv8 in the tumors. Beige nude mice were implanted with A673, Calu-6, HM7, HPAC and Jurkat cells and were euthanized at they 10 after tumor cell transplantation. Populations of cells enriched for CD11b+ were isolated using CD11b microbeads as described. Expression of Bv8 was analyzed using Taqman™ primers specific for mouse Bv8 transcripts. Data were normalized using mouse GAPDH.
Figure 5B:
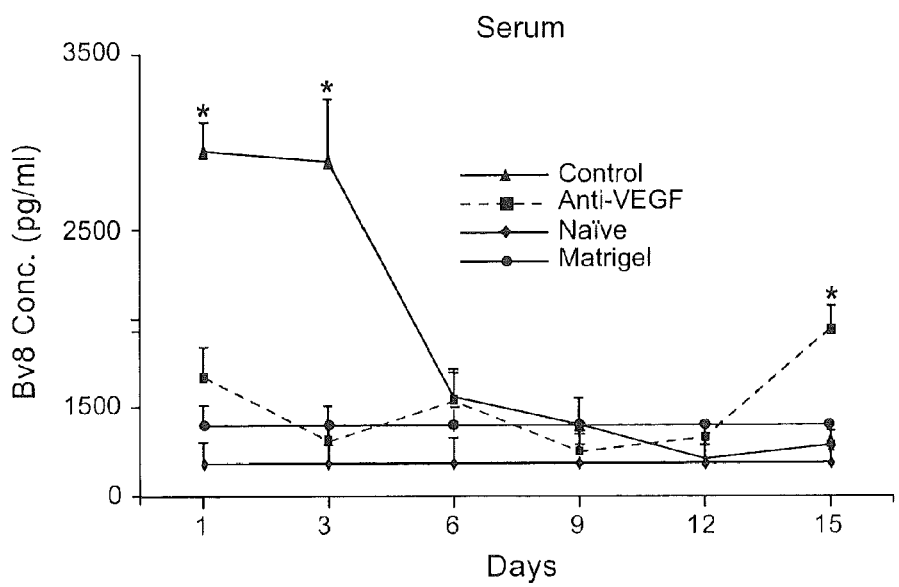
Figure 5C:
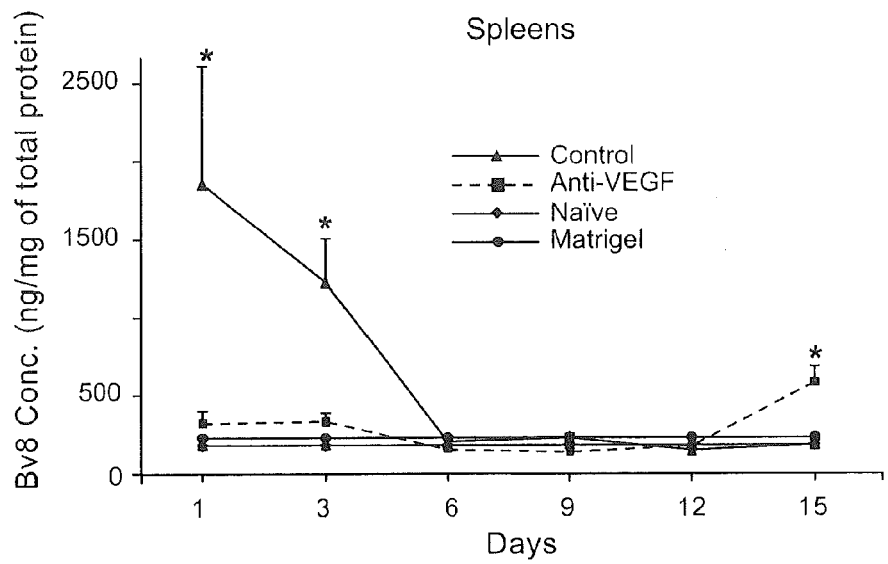
Figure 5D:
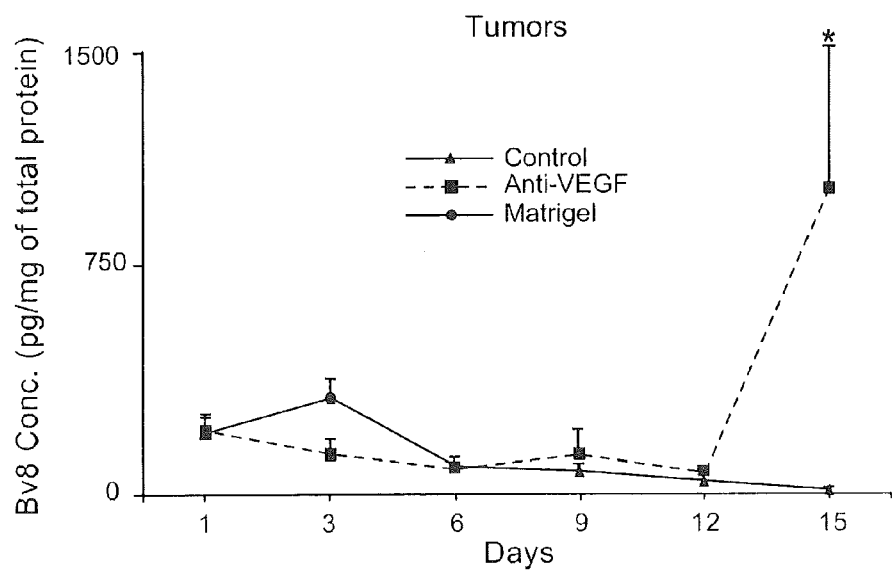
Figure 5E:
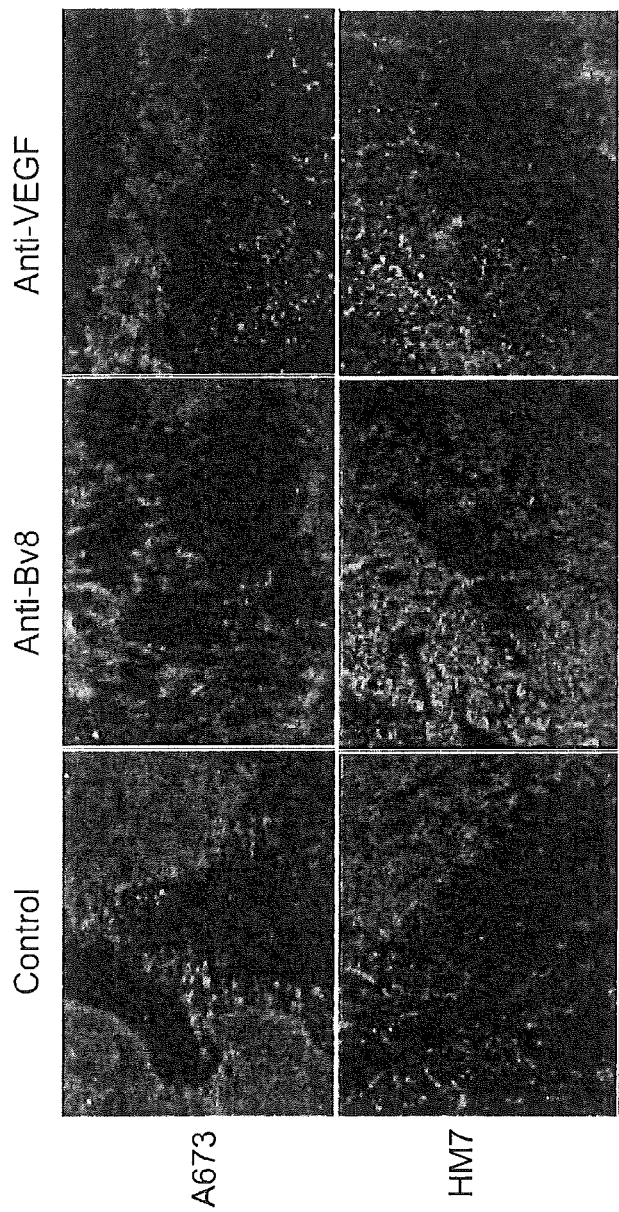
Figure 5F:
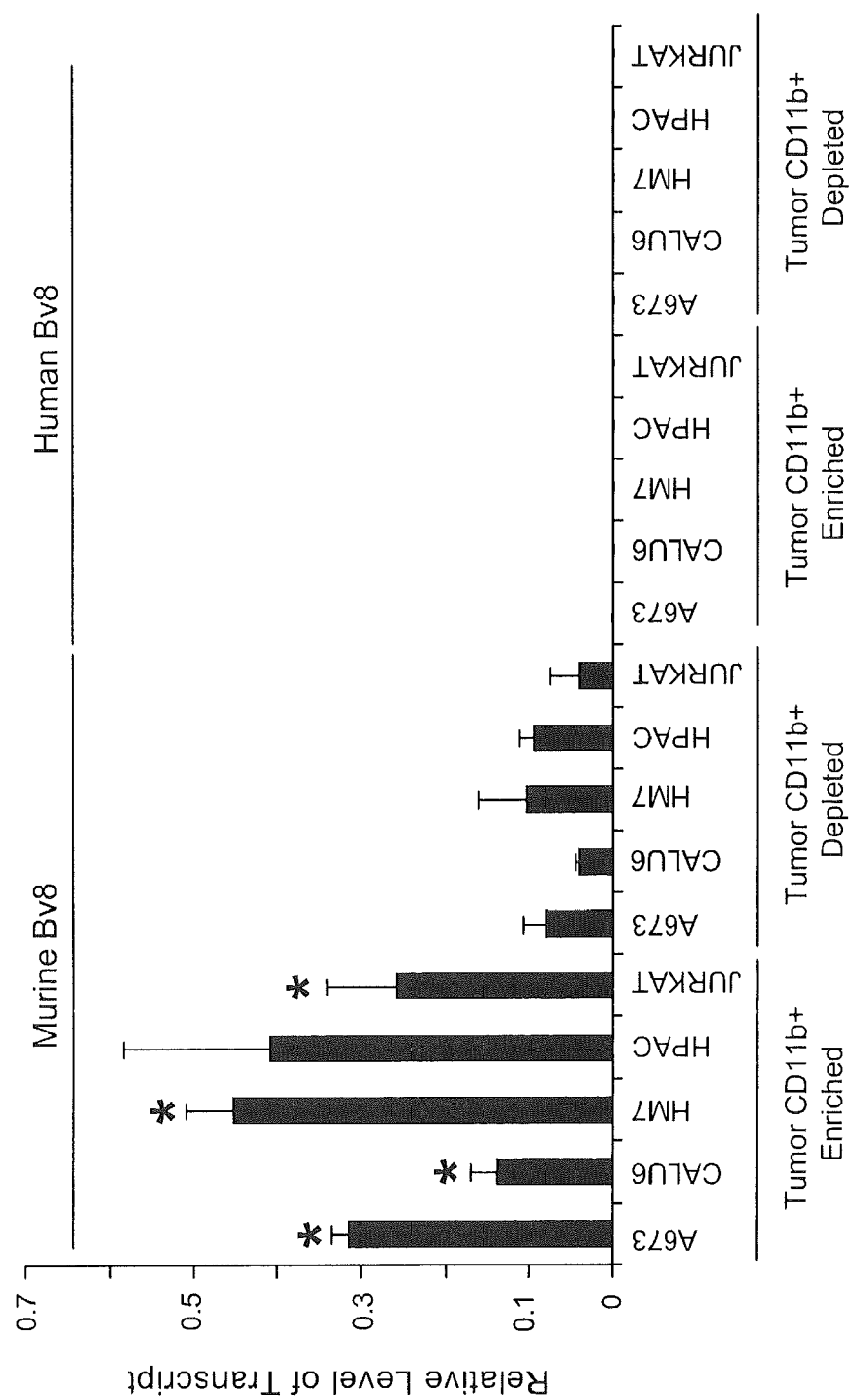

To characterize Bv8 expression in various tissues in a time-dependent manner (FIG. 5), we measured Bv8 protein levels in BM (FIG. 5a), PB (FIG. 5b), spleen (FIG. 5c) and tumors (FIG. 5d), in mice bearing HM7 tumors and treated with control or anti-VEGF. Analysis of Bv8 protein levels in control treated mice revealed a peak shortly after tumor implantation in BM, PB and spleen. However, anti-VEGF treated mice showed minimal Bv8 expression at such early stages, possibly due to efficient tumor suppression elicited by the treatment. However, at later time points, coincident with the beginning of VEGF-independent tumor growth, Bv8 levels were significantly increased in anti-VEGF treated mice, especially in PB, spleen and tumors (FIG. 5b-d). In agreement with these findings, a large infiltration of Gr1+ cells in necrotic areas of A673- and HM7-tumors treated with anti-VEGF for 15 or 21 days was observed (FIG. 5e). A possible explanation is that long-term hypoxia and/or tumor necrosis elicited by anti-VEGF trigger BM activation and neutrophil recruitment. These findings agree with early experiments showing that, in several murine tumor models, anti-VEGF treatment results in up-regulation of Bv8 mRNA, suggesting that Bv8 might contribute to resistance to anti-VEGF therapy (data not shown). To further define the sources of Bv8 in the tumors, we sub-fractionated the cell populations in A673, Calu-6, HM7, HPAC and Jurkat tumors into CD11b+ and CD11b− fractions. Taqman™ analysis showed a significant up-regulation of mBv8 transcript in the CD11b+ compartment compared to the negative fraction (FIG. 50). However, using human Bv8 primers, PCR did not identify any human Bv8 in either population (FIG. 51), i.e. tumor associated CD11b+ and CD11b−, suggesting that the tumor stroma, particularly myeloid cells, is the major source of Bv8 in all the tumors tested. In agreement with these findings, none of the tumor cell lines tested produced detectable levels of Bv8 protein in vitro by ELISA (data not shown).

Therefore, anti-Bv8 treatment might be most effective when combined with anti-VEGF. To test this hypothesis, we implanted mice with HM7 (FIG. 6a) or A673 cells (FIG. 6b) and initiated treatments after the tumors had reached ~400 mm³ volumes. Consistent with the presence of lower intratumoral Bv8 levels, anti-Bv8 treatment had a smaller effect on tumor growth inhibition in both HM7 and A673 tumors compared to early-stage treatment (FIG. 2). Anti-VEGF provided a more complete inhibition, but tumors eventually escaped. However, combination of anti-VEGF and anti-Bv8 treatments significantly ($p<0.05$) inhibited tumor growth compared to each monotherapy. Likewise, the combination therapy resulted in a significant reduction in tumor volumes and weight in TIB42 (FIG. 2e) and EL4 murine lymphomas (FIG. 6c), both of which are refractory to anti-VEGF treatment. Therefore our data suggest that anti-Bv8 treatment has a potential for combination therapy in tumors that are refractory to anti-VEGF treatment.

To verify that the effects of anti-Bv8 are not limited to immunodeficient mice, we implanted the murine anti-VEGF resistant EL4 cell line into both immunodeficient and immunocompetent mice and tested the effects of anti-Bv8 or anti-VEGF monotherapy, as well as the combination. As illustrated in FIG. 6, c & d, the effects of such treatments were almost indistinguishable in the two strains. These findings indicate that anti-Bv8 may suppress tumor growth even in the presence of an intact immune system. In further support of this conclusion, anti-Bv8 treatment inhibits the angiogenic switch in the Rip-Tag multi-stage carcinogenesis model in immunocompetent mice (unpublished observations).

Figure 6A:
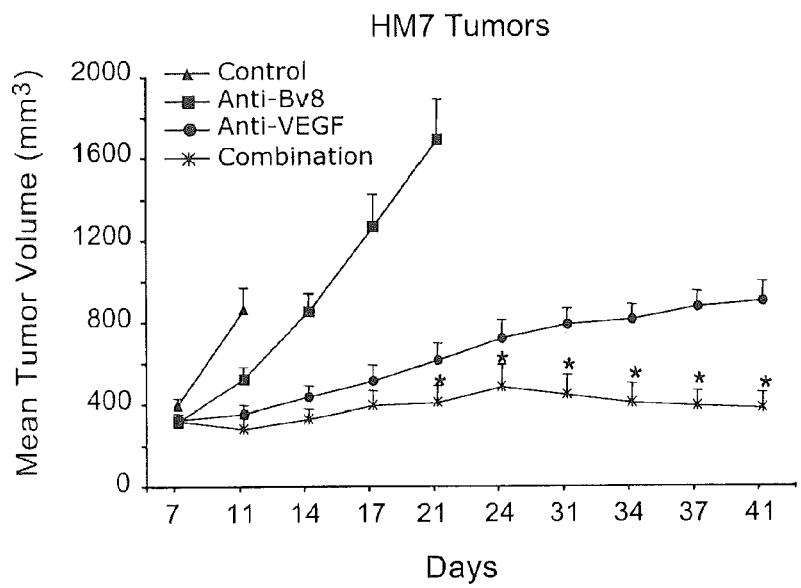
FIG. 6. Anti-Bv8 has additive effects with anti-VEGF or cytotoxic chemotherapy. a&b. Anti-Bv8 treatment is mostly effective when treatment is initiated early in tumor development. Nude mice were implanted with HM7 (a) and A673 (b) tumors and did not receive any treatments until tumors reached ~400 mm$^3$. Mice were then treated with control, anti-Bv8, anti-VEGF or combination (anti-VEGF plus anti-Bv8) of antibodies. Tumor volume was measured as described. * indicates significant difference ($p<0.05$) in tumor volume between combination therapy vs. anti-VEGF monotherapy. c&d. Anti-Bv8 has an additive effect in anti-VEGF resistant tumors when used in combination with anti-VEGF. Nude mice (c) and C57B1/6 (d) mice were implanted with EL4 cells and underwent treatment with control, anti-Bv8, anti-VEGF or the combination. Tumor volume and terminal tumor weight were measured as described. * indicates significant difference ($p<0.5$) in tumor volume in control vs. each monotherapy or the combination therapy. Differences in tumor volume are also significant when comparing combination vs. each monotherapy. e. Cisplatin and anti-VEGF treatment increase Bv8 concentration in the serum. Beige nude mice were implanted with A673 cells and were treated with PBS, cisplatin (5 mg/kg) plus control antibody, cisplatin plus anti-Bv8, or cisplatin plus anti-VEGF or the combination cisplatin, anti-Bv8 and anti-VEGF. Serum Bv8 protein concentrations were measured by ELISA. f. Chemotherapy plus anti-VEGF and anti-Bv8 can effectively suppress tumor growth in established A673 tumors. Beige nude mice were injected with A673 cells and received treatments, as mentioned above, 13 days after tumor cell implantation. * indicates significant difference ($p<0.05$) between combination therapies vs. cisplatin plus control.
Figure 6B:
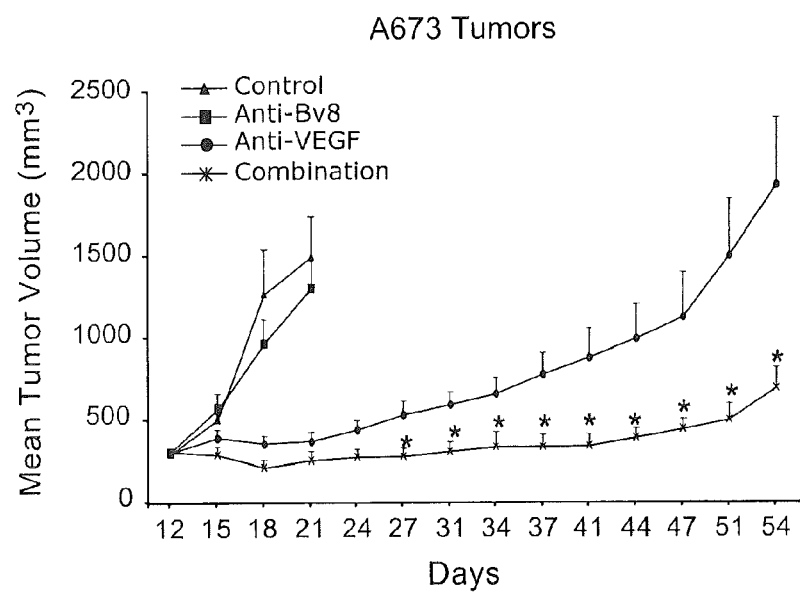
Figure 6C:
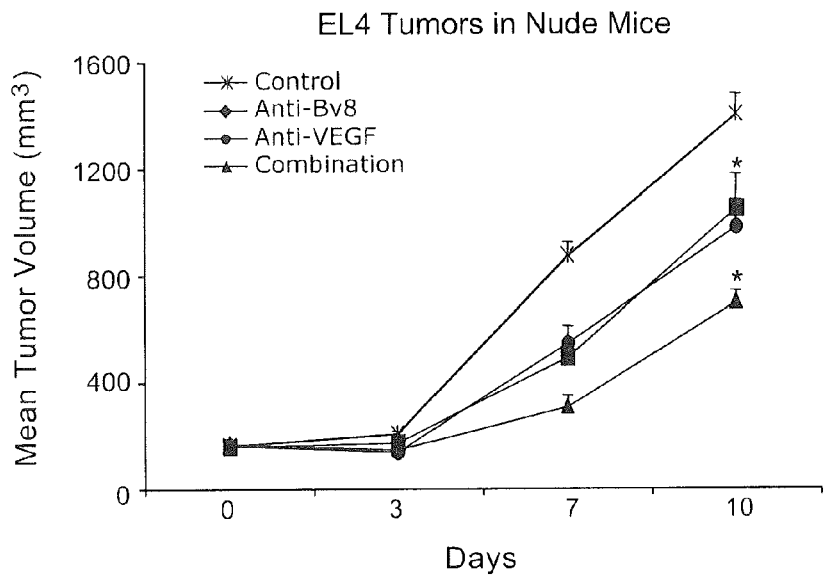
Figure 6D:
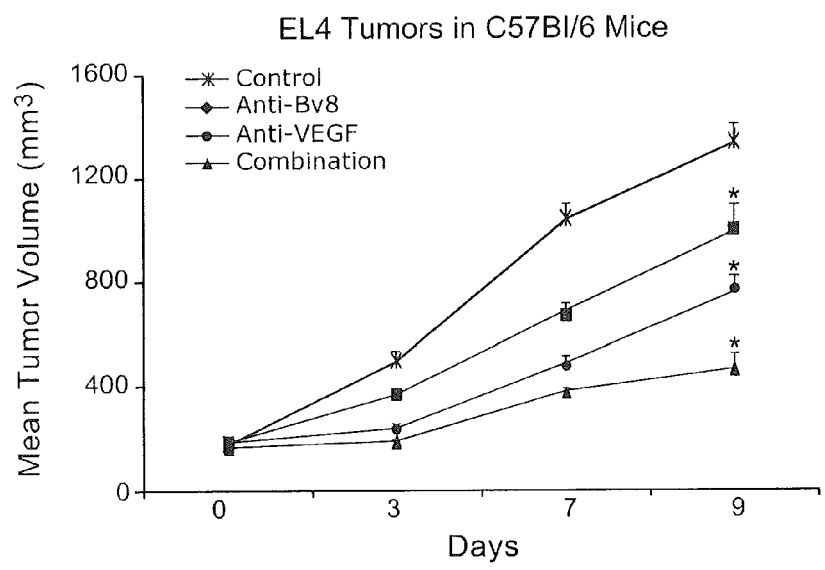
Figure 6E:
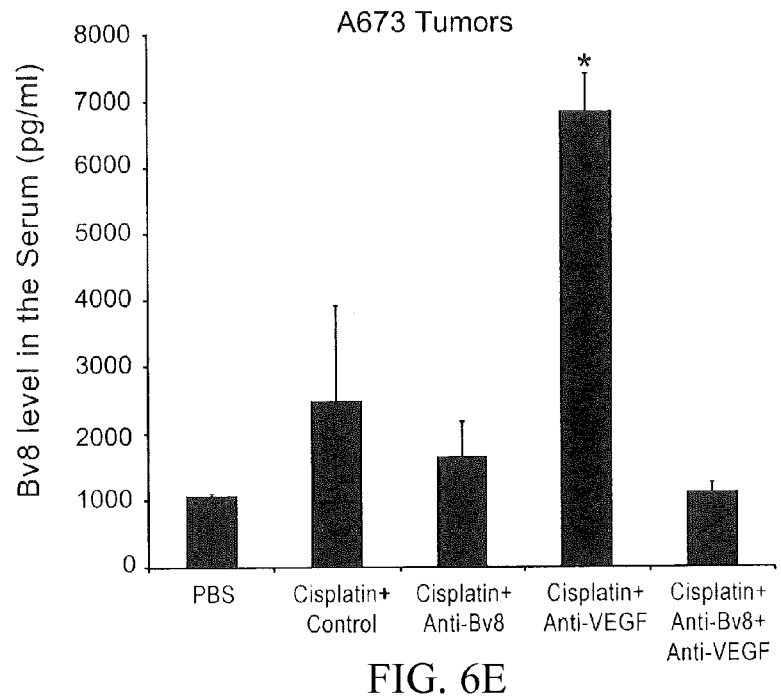
Figure 6F:
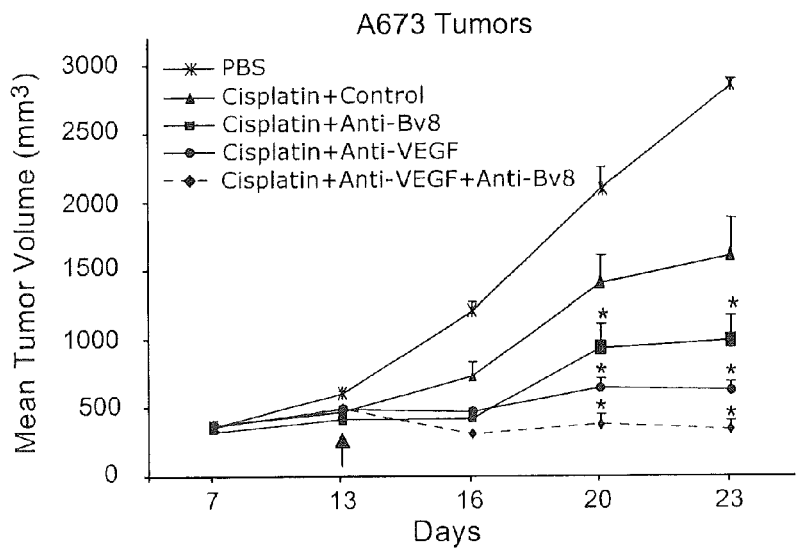

Cytotoxic agents are known to result in mobilization of hematopoietic cells from the BM (Neben, S. et al., *Blood* 81, 1960-1967 (1993)). Furthermore, chemotherapy-induced tumor necrosis may results in release of chemokines such as G-CSF, followed by a compensatory increase in neutrophil production (Kavgaci, H. et al., *J Exp Clin Cancer Res* 21, 475-479 (2002)). Therefore, we sought to investigate whether treatment with cytotoxic agents, alone or in combination with anti-VEGF, may affect the efficacy of anti-Bv8 treatment. For this purpose, mice were implanted with A673 cells and were treated with cisplatin, alone or in combination with anti-Bv8, anti-VEGF or combination of the two treatments. Bv8 level in the serum was significantly ($p<0.05$) increased in mice treated with cisplatin, alone or in combination with anti-VEGF (FIG. 6e). Both anti-Bv8 and anti-VEGF enhanced the anti-tumor activity of cisplatin. However, the combination of cisplatin plus anti-VEGF and anti-Bv8 resulted in almost complete inhibition of tumor growth in A673 ($p<0.05$; FIG. 6f). Therefore, anti-Bv8 treatment might be used as an additive agent in combination with anti-VEGF or cytotoxic agents. S FIG. 8 illustrates a model for role of Bv8 in tumorigenesis.

Growing evidences suggest that affecting either tumor recruitment or the angiogenic properties of myeloid cells may represent a novel anti-cancer strategy (Shojaei, F., et al., *Nature Biotechnol* 25:911-20 (2007)). However, progress in achieving this goal has been hampered by the complexity and potential redundancy of mediators. Our findings indicate that, in spite of such complexity, blocking the action of a single cytokine, Bv8, has a significant impact on the growth of multiple tumor types. Thus, these data raise the possibility that Bv8 or its receptors represent therapeutic targets for future anti-angiogenic therapy. Additional studies are required to further define the role of this signaling system in different tumor types and at different stages of tumor progression. Interestingly, recent studies have shown that administration of G-CSF may accelerate tumor growth (Okazaki, T., et al., supra; Hirbe, A. C., et al., Blood 109, 3424-3431 (2007)). Whether Bv8 up-regulation contributes to such effects is an interesting possibility that deserves further investigation. Conversely, anti-G-CSF antibodies, by reducing Bv8 expression, might inhibit tumor growth. Our laboratory is investigating this possibility.

Finally, the finding that Bv8 expression is so exquisitely responsive to G-CSF links Bv8 to a major homeostatic mechanism involved in the regulation of neutrophil differentiation and production. Therefore, it is possible that Bv8 plays a broader pathophysiological role, including non-tumoral types of inflammatory-cell mediated angiogenesis.

EXAMPLE 2

Materials and Methods

Isolation of Whole Human Bone Marrow Cells from Fresh Bone Marrow Collections

Fresh bone marrow samples were obtained from ALL-CELLS (Emeryville, Calif.). The bone marrow was first diluted with 10% FBS-containing DMEM and then passed through a 40 μm cell strainer (BD Biosciences, Bedford, Mass.) to remove tissue debris. Cells were centrifuged at 1200 rpm for 5 min and red blood cells were lysed in the presence of ice cold 0.2% NaCl for 30 sec, followed by addition of ice cold 1.6% NaCl.

Isolation of Neutrophils, Monocytes and Lymphocytes from Peripheral Blood

Isolation procedures were as previously described (Kulczycki A, Jr. J Immunol 133:849-854 (1984)), with minor modifications. Briefly, fresh heparinized healthy human blood (Health Services, Genentech Inc.) was applied on CAPPEL LSM Lymphocyte Separation Medium (MP Biomedicals, Solon, Ohio). After centrifugation at 3000 rpm for 15 min without brake, the plasma was removed and monocytes were collected at the interphase. Monocytes were further purified using Monocyte isolation kit II (Miltenyi Biotec, Auburn, Calif.) and FACS sorting. The purity of the cell population was evaluated by FACS by $CD14^+CD16^-$ expression. Lymphocytes were harvested by collecting the cells binding to the column and their purity was examined by CD3 expression for T lymphocytes and CD19 expression for B lymphocytes. Neutrophils were collected by carefully removing the layer immediately above the red blood cells, followed by addition of HBSS (without $Ca^{2+}$ and $Mg^{2+}$) and 6% Dextran 500 (GE Healthcare Bio-sciences AB, Sweden) prepared in 0.9% NaCl. After allowing red blood cells to settle for 30-60 min at RT, neutrophils in the supernatant were removed. Any residual red blood cells were further removed until >90% of them were eliminated. The purity of the cells was evaluated by FACS analysis as $CD15^+CD16^+$ populations. All three populations from peripheral blood (neutrophils, monocytes and lymphocytes) were >95% pure by FACS and morphology analysis. Cells were then washed once with HBSS containing 0.2% BSA (low in endotoxin, Serologicals, Corp. Norcross, Ga.) before use.

Gene Expression Analysis by Taqman

RNA was prepared using the RNeasy™ Mini Kit (Qiagen). 50 ng total RNA per reaction was used for the real time PCR (Taqman) analysis. For human Bv8, testis RNA (BD Biosciences) served as control. Reactions were run on 9600 Emulation mode of 7500 Real time PCR system (Applied Biosystems, Foster City, Calif.) and the absolute quantification with standard curve was used with Sequence Detection System (SDS) software. The expression level of each gene was further quantified relative to the housekeeping gene RPL19 in the same sample. The sequences of Taqman primers are as follows: Human Bv8 forward: ATG GCA CGG AAG CTA GGA (SEQ ID NO: 10), reverse: GCA GAG CTG AAG TCC TCT TGA (SEQ ID NO: 11), probe: TGC TGC TGG ACC CTT CCT AAA CCT (SEQ ID NO: 12); Human RPL19 forward: CGC AAG CGC CGT GAA (SEQ ID NO: 28), reverse: GGT CTC TTC CTC CTT GGA TAA AGT C (SEQ ID NO: 29), probe: CCA GGC CAA GAA GGA GGA GAT CAT CA (SEQ ID NO: 30). Human specific VEGF forward: AAT GAC GAG GGC CTG GAG T (SEQ ID NO: 31), reverse: TTG ATC CGC ATA ATC TGC ATG (SEQ ID NO: 32), probe: TGT GCC CAC TGA GGA GTC CAA CAT CA (SEQ ID NO: 33).

Taqman reagents for human PKR1/EG-VEGFR1 and PKR2/EG-VEGFR2 were obtained from Applied Biosystems.

Regulation of Bv8 Gene Expression in Cultured Blood Cells

Recombinant human MCP-1, MIP-1α, MIP-1β, MIP-2, bFGF, VEGF, GM-CSF, G-CSF, SDF-1α, M-CSF, Erythropoietin (EPO) and TNFα were purchased from R&D Systems (Minneapolis, Minn.). Recombinant human IL-8, IFNγ, Bv8 (Prokineticin-2), IL-4, IL-10, IL-13, TGF-β were from PeproTech Inc. (Rocky Hill, N.J.). SCF (Stem Cell factor) was from Invitrogen Biosource (Carlsbad, Calif.). In some cases, G-CSF from Amgen (Neupogen/Filgrastim) was used. All cytokines were used at 10 ng/ml. Freshly purified cells were washed and re-suspended in HBSS media containing 0.2% BSA (low endotoxin, Serologicals Corp. Norcross, Ga.). Two million cells were incubated in 24-well plates with various cytokines and chemokines for 4 hr at 37° C. in a 5% $CO_2$ incubator. Cells were then transferred into eppendorf tubes, centrifuged and lysed with RNA lysis buffer (Qiagen, Valencia, Calif.). Bv8 expression was assessed by Taqman with RPL19 (Ribosomal Protein L19) as the internal control gene.

Partial Purification of Bv8 Protein from Peripheral Blood Neutrophils

Neutrophils from 500 ml of fresh human blood were isolated as described above. Cell pellets were suspended in 10 ml of 0.5% Triton X-100 with proteinase inhibitors (Roche) and lysed at 4° C. for 10 min on a shaker. Cell lysates were then forced through a 25 gauge needle twice, and the salt concentration was adjusted to 50 mM NaCl, 20 mM Tris HCl (pH 7.3). The crude extract was applied to a heparin-Sepharose column (Amersham Biosciences, Sweden) pre-equilibrated with 20 mM Tris pH 7.2, 50 mM NaCl and 0.5% Triton X-100. The column was eluted using a linear gradient: 50 mM to 2M NaCl in 20 mM Tris, pH 7.3, in the presence of 0.5% Triton X-100. The flow rate was 1 ml/min. Absorbance was monitored at 280 nm. Fractions of 1 ml were collected and assayed for human Bv8 by ELISA. Peak Bv8 fractions and several off-peak fractions were then pooled and concentrated up to 10 fold using Microcon Centrifugal Filter Devices, Ultracel YM-3 (Millipore, Bedford, Mass.) and tested for its biological activity.

Human Bv8 ELISA

MaxiSorp® 96-well microwell plates (Nalge Nunc International, Rochester, N.Y.) were coated with 1.0 μg/ml 3F1 mouse monoclonal antibody (Genentech Inc.) in 50 mM carbonate buffer, pH 9.6, at 4° C. overnight. Plates were washed with PBS containing 0.05% polysorbate 20 and blocked with 0.5% bovine serum albumin, 15 p.p.m. (parts per million) Proclin 300 (Supelco, Bellefonte, Pa.) in PBS at room temperature for 1 h. After plates were washed, human Bv8 standards (0.020-2.5 ng/ml in 2-fold serial dilution, PeproTech, Rocky Hill, N.J.) and samples (minimum 1:10 dilution) in PBS containing 0.5% bovine serum albumin, 0.05% polysorbate 20, 15 p.p.m. Proclin 300 (Supelco, Bellefonte, Pa.) and 0.35N NaCl (sample buffer) were serially diluted and were added to each well. The plates were incubated for 2 hr at room temperature followed by a washing step. The bound Bv8 was detected by adding the secondary antibody, a biotinylated hamster anti-Bv8 antibody clone 3B8 (Genentech Inc.) followed by adding streptavidin-HRP (GE Healthcare, Buckinghamshire, United Kingdom) and 3,3',5,5'-tetramethyl benzidine (Kirkegaard & Perry Laboratories, Gaithersburg, Md.) as the substrate. The reaction was stopped by adding 1 M phosphoric acid. Absorbance was read at 450 nm on a ThermoMax microplate reader (Molecular Devices, Menlo Park, Calif.). The titration curves of the standards were calculated using a four-parameter regression curve-fitting program (Genentech Inc). Human Bv8 concentration was calculated by extrapolating the optical density values of samples to the data range in the standard curve. The Bv8 ELISA was capable of measuring up to 10% lysis buffer and had the sensitivity to detect Bv8 as low as 0.20 ng/ml in tissue lysates. The ELISA was specifically developed and optimized for Bv8 because human EG-VEGF, VEGF-A, VEGF-C and G-CSF (R&D Systems, Minneapolis, Minn.) up to 30 □g/ml only gave a background signal; the presence of these molecules and anti-VEGF (Genentech Inc.) up to 30 □g/ml did not affect detection of 100 pg/ml human Bv8 in sample buffer. This ELISA could also detect mouse Bv8 but with less than 7% sensitivity.

Bv8 Bioactivity Assay

The GeneBLAzer® NFAT-CHO cells were obtained from Invitrogen Corporation (Carlsbad, Calif.). Cells were stably transfected with PKR1/EG-VEGFR1 and grown in DMEM (high glucose) containing 10% dialysed serum, 0.1 mM NEAA, 2 mM GlutaMax™ (Gibco), 1 mM sodium pyruvate, 10 μg/ml Zeocin, 500 μg/ml hygromycin. Cells were plated into 96-well Viewplate (Packard) with $2.5\times10^4$ in 80 ml/well in 1% DMEM overnight at 5% $CO_2$, 37° C. On the following day, cells were treated with various column fractions that were concentrated with Microcon Centrifugal Filter Devices (Ultracel YM-3) from Millipore. 0.2-0.02 ng/ml hBv8 (Peprotech Inc.) prepared in 1% DMEM was used as a positive control. One hour later, media was removed and replaced with 80 ml Hank's solution containing 0.1% BSA and 6× loading buffer containing 1 mM CCF4 (Invitrogen Corporation). Plates were incubated for 1.5 hr at room temperature in the dark and read on Wallac plate reader at excitation wavelength of 410 nm and emission wavelength of 450/520 nm. Negative controls were cells with no ligand added and control media alone. CHO cells were stimulated with recombinant human Bv8 or pooled fractions for 1 hr before adding the β-lactamase substrate CCF4. To assess the specificity of the column fractions, anti-Bv8 antibodies 2B9 and 3F1 were added at 20 mg/ml.

Analysis of while Blood Cells from G-CSF Treated Donors

Peripheral white blood cells were obtained from normal donors after 4-5 days of G-CSF treatment by apheresis collections (Cellular Therapy and Cell Processing Facilities, Fred Hutchinson Cancer Research Center, Seattle, Wash.). White blood cells from untreated individuals were collected by the same procedure and served as un-paired controls. Cells were then concentrated and re-suspended in cryoprotective media with Human Serum Albumin plus 10% DMSO. After thawing in a 37° C. water bath, cell viability was >95% by trypan blue exclusion test. Cells were briefly washed with HBSS buffer containing 0.2% BSA and lysed either in RNA lysis buffer (Qiagen) or RIPA buffer containing proteinase inhibitors (Roche) for RNA extraction or protein measurements.

Chemotaxis of Peripheral Blood Neutrophils $10^6$ cells were washed with HBSS containing 0.2% BSA before putting into transwell insert with 5 μm pore size (Corning Incorporated, Lowell, Mass.). In the lower chamber, media alone or media with various cytokines at various concentrations (maximum at 200 ng/ml) was added. After 3 hr at 37° C., cells in the lower chamber were transferred, mixed with 9 ml ZPAK solution and counted on Z2 Coulter Particle Count and Size Analyzer (Beckman Coulter, Fullerton, Calif.).

Culture of Human Leukemia Cells

U937, HL-60, THP-1, Hel 92.1.7, KG-1, K562, Jurkat cells were obtained from the ATCC® (Manassas, Va.). Most cells were grown in 10% FBS-containing RPMI. KG-1 cells were grown in 20% FBS-containing Iscove's modified Dulbecco's medium. For THP-1 cells, 10% FBS-containing RPMI was used with Sodium Pyruvate, HEPES and β-mercaptoethanol. For regulation studies, 1 million cells with viability higher than 95% were used. Regulation studies were performed under both normoxia and hypoxia conditions for 4 hr in 1 ml HBSS media containing 0.2% BSA.

Statistical Analysis

Student t-test was used to calculate statistical significance.

Results

Regulation of Bv8 in Human Bone Marrow and Various Blood Cells

It has been previously reported that G-CSF results in a dramatic up-regulation (>30 fold) of Bv8 expression in mouse bone marrow cells and peripheral neutrophils (Shojaei et al. *Nature* 450:825-831 (2007) and Example 1).

In the present study, it was evaluated whether G-CSF is also an inducer of Bv8 expression in isolated human peripheral neutrophils and whole bone marrow cells. 10 ng/ml G-CSF resulted in an average of 7 fold (range 6-12) induction of Bv8 expression within 4 hr. The lower fold increase compared to mouse neutrophils may be due, at least in part, to a higher basal Bv8 expression in human cells (data not shown). Time-course studies indicated that G-CSF induces Bv8 mRNA within 4 hr, and the effect was sustained for up to 24 hr (data not shown). We identified GM-CSF as an additional positive regulator of Bv8 expression in human bone marrow cells and neutrophils (FIGS. 14 A and B). A significant ~2.5-fold increase in Bv8 expression was observed with 10 ng/ml GM-CSF. This is unlike mouse neutrophils that show no Bv8 induction by GM-CSF. Other cytokines tested including IL-6, IL-1β, and EPO (Erythropoietin) had no stimulatory effect on human Bv8 expression in neutrophils or bone marrow cells.

Unlike neutrophils, monocytes and lymphocytes did not show any change in Bv8 expression in response to G-CSF (FIGS. 14 C and D). Surprisingly, GM-CSF decreased Bv8 expression in human monocytes, with about 75% inhibition upon 4 hr treatment. IL-10 up-regulated Bv8 expression in monocytes and lymphocytes, whereas SDF-1α showed a significant stimulatory effect only on monocytes (FIGS. 14 C and D). A lower basal level of Bv8 expression was found in monocytes and lymphocytes compared to that in neutrophils or bone marrow cells (data not shown).

In conclusion, the effects of G-CSF and GM-CSF on Bv8 gene expression in neutrophils were quite unique, since two related cytokines, M-CSF and SCF, had no effect.

Regulation of Bv8 Receptors in Human Bone Marrow Cells and Neutrophils

Figure 15A:
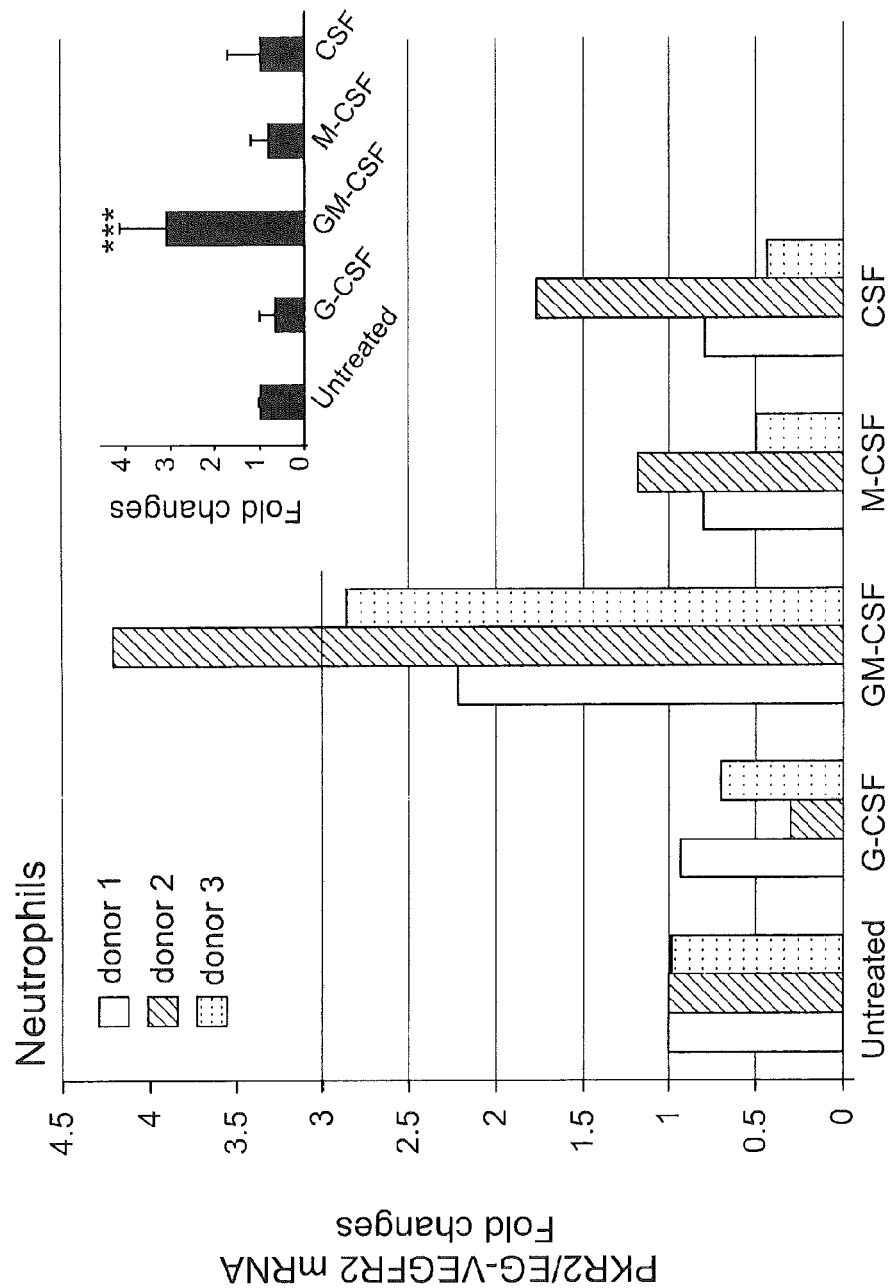
FIG. 15. Regulation of Bv8 receptor PKR2/EG-VEGFR2 expression by various G-CSF-related cytokines in human bone marrow cells and neutrophils. (A) Fresh isolated neutrophils or (B) bone marrow cells were treated with various G-CSF-related cytokines. After 4 hr incubation in vitro, cells were collected and RNA was extracted for PKR2/EG-VEGFR2 expression by Taqman. RPL19 was used as the internal control gene for normalization. Experiments were done using 3 independent healthy donors. Response to cytokines from each individual donor was shown and the average expression level from all 3 donors was then plotted in the inserted panels. *** $p<0.01$ vs. un-treated control.
Figure 15B:
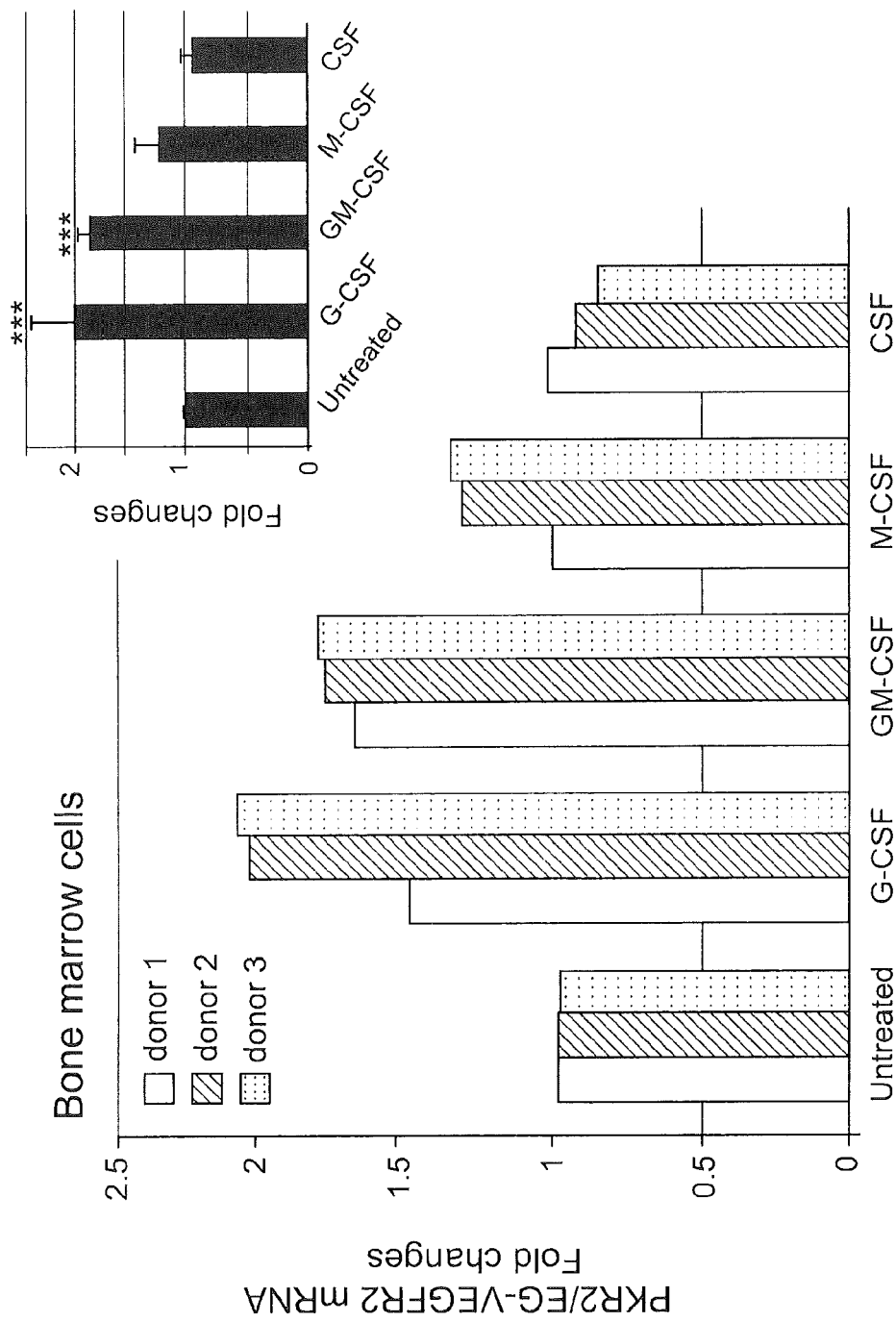

Unlike mouse neutrophils, which express both PKR1/EG-VEGFR1 and PKR2/EG-VEGFR2, isolated human neutrophils express at detectable level only PKR2/EG-VEGFR2. After 4 hr incubation in vitro, GM-CSF, but not G-CSF, elicited a significant up-regulation of PKR2/EG-VEGFR2 expression (with an average of 4-fold induction) (FIG. 15A). In human bone marrow, both G-CSF and GM-CSF seemed to regulate PKR2/EG-VEGFR2 to a significant level (FIG. 15 B).

Figure 16A:
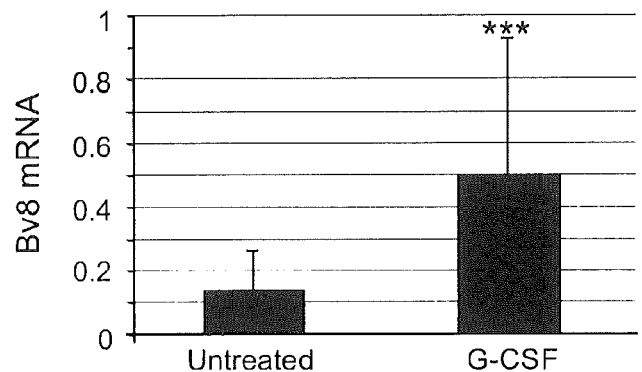
FIG. 16. Bv8 and PKR2/EG-VEGFR2 are upregulated in mononuclear cells from G-CSF treated donors. White blood cells from G-CSF treated (n=12) and un-treated individuals from (n=11) (un-paired) were briefly washed and pelleted before RNA extraction or lysing into RIPA buffer containing proteinase inhibitors. Taqman analysis on Bv8 (A), PKR2/EG-VEGFR2 expression (C) and specific human Bv8 ELISA (B) was performed. Data was normalized against RPL19 expression for Taqman and total protein concentration for ELISA. ***$p<0.01$ vs. un-treated control.
Figure 16B:
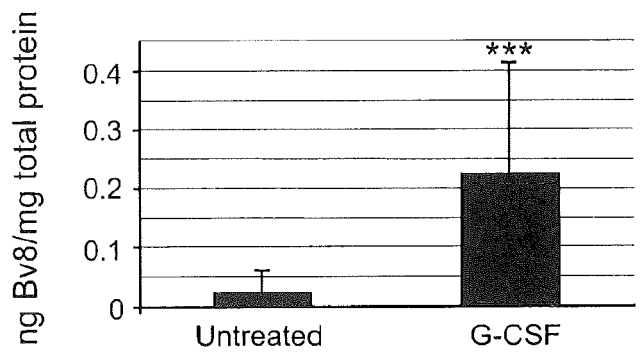
Figure 16C:
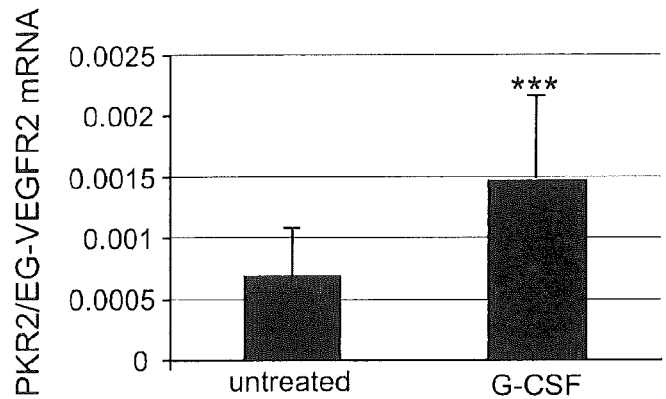

Upregulation of Bv8 and PKR2/EG-VEGFR2 in Mobilized Peripheral Mononuclear Cells from Donors Treated with G-CSF Peripheral blood mononuclear cells from 11 untreated and 12 G-CSF-treated individuals were obtained via apheresis collections. We examined Bv8 gene expression by Taqman and also measured the Bv8 protein level by ELISA. About 4.5-fold increase in Bv8 expression and a 10-fold increase in protein level were detected in G-CSF mobilized mononuclear cells compared to mononuclear cells from untreated donors (FIG. 16). Similarly, PKR2/EG-VEGFR2, but not PKR1/EG-VEGFR1 was detectable in clinical collected white blood cells when patients were treated with G-CSF for 4-5 days. Mononuclear cells from G-CSF-treated individuals showed a significant induction of PKR2/EG-VEGFR2 expression (~2-fold) compared to un-treated control samples (FIG. 16B).

Bv8 Produced by Human Neutrophils is Biologically Active

Figure 14A:
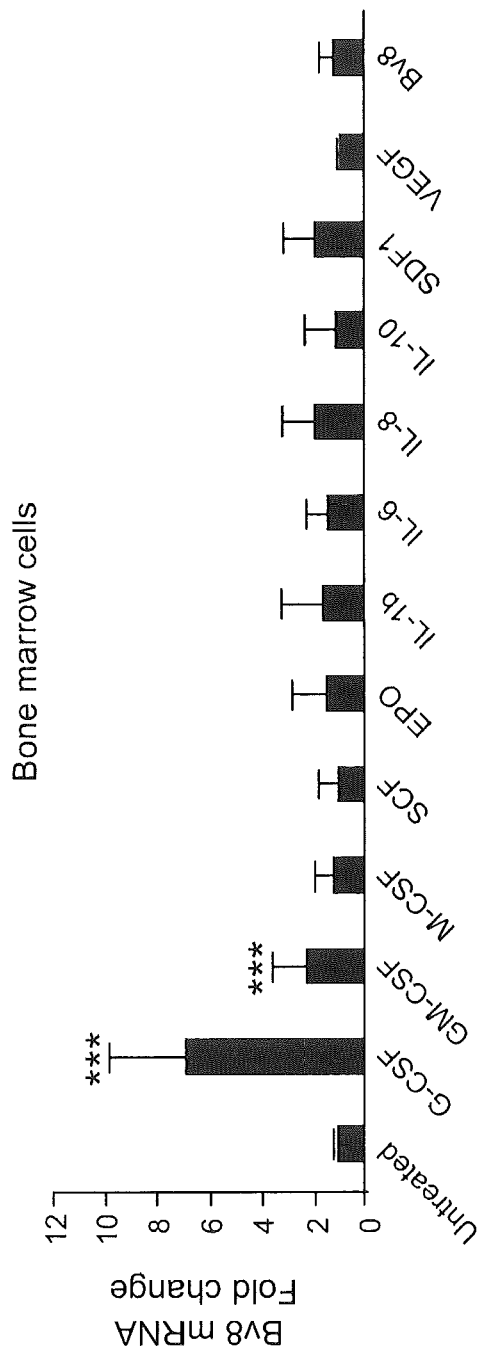
FIG. 14. Regulation of Bv8 expression in vitro using purified human blood cells and fresh bone marrow cells. Cells were treated with various cytokines or chemokines at 10 ng/ml for 4 hr before subjected to RNA extraction and Taqman analysis for Bv8 expression. All data were further normalized against internal control gene RPL19 as fold change, with un-treated sample as 1. 20 different human donors without medication were used for the study as described in Materials and Methods. A representative image of purified cells and their marker expressions by FACS were shown at right. (A) Fresh bone marrow cells, (B) neutrophils, (C) monocytes, (D) lymphocytes. *** $p<0.01$ vs. un-treated control.
Figure 14B:
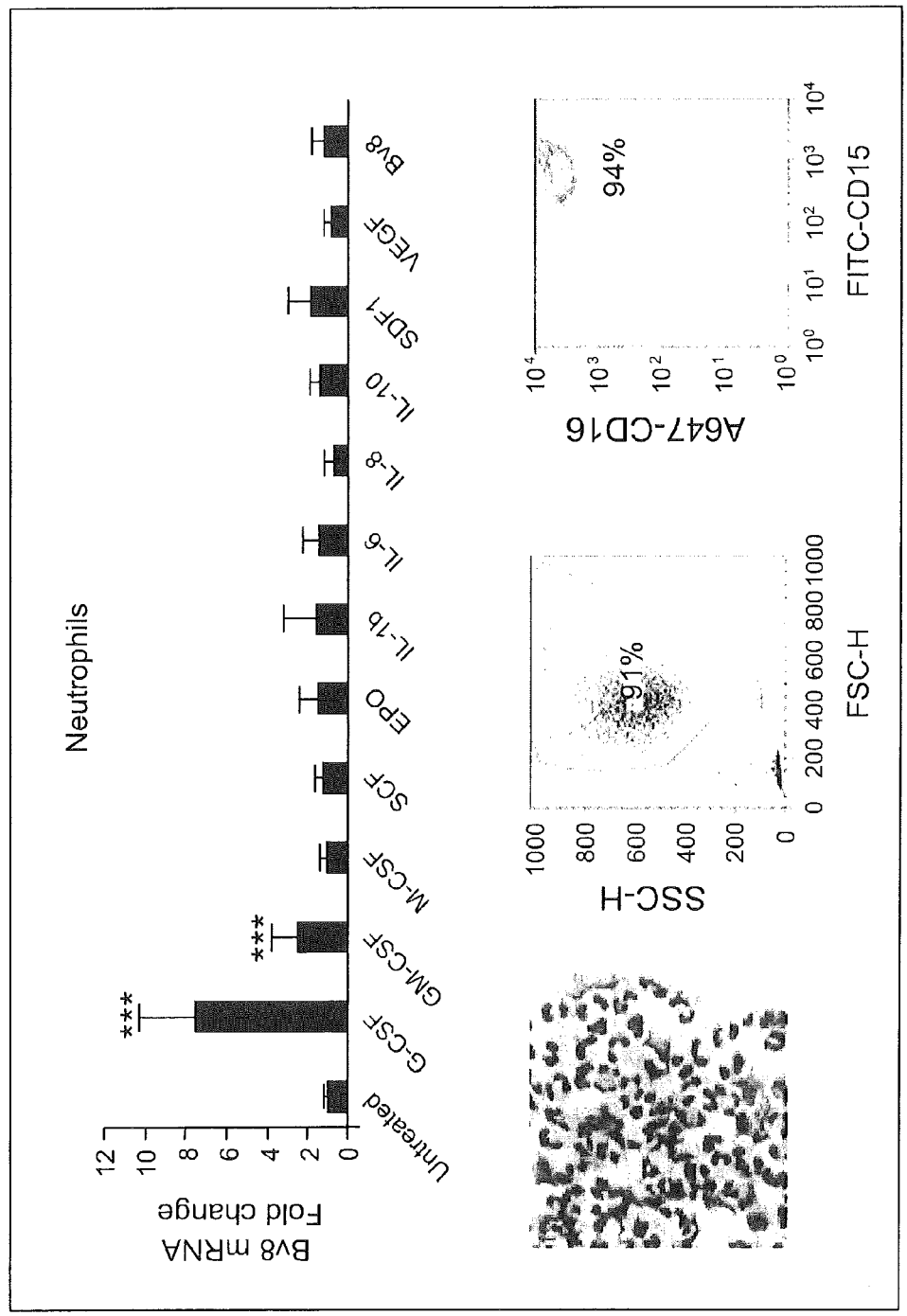
Figure 14C:
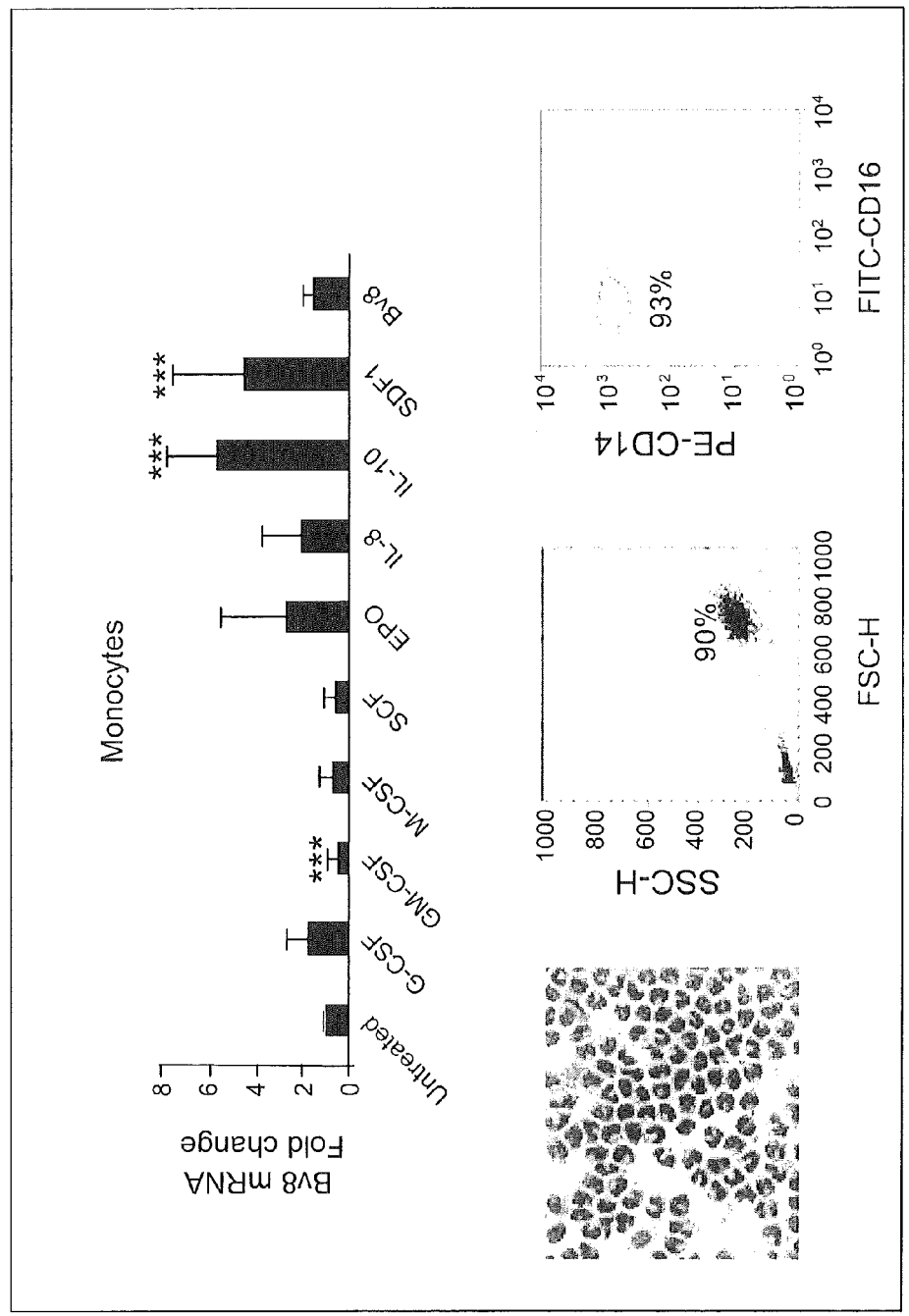
Figure 14D:
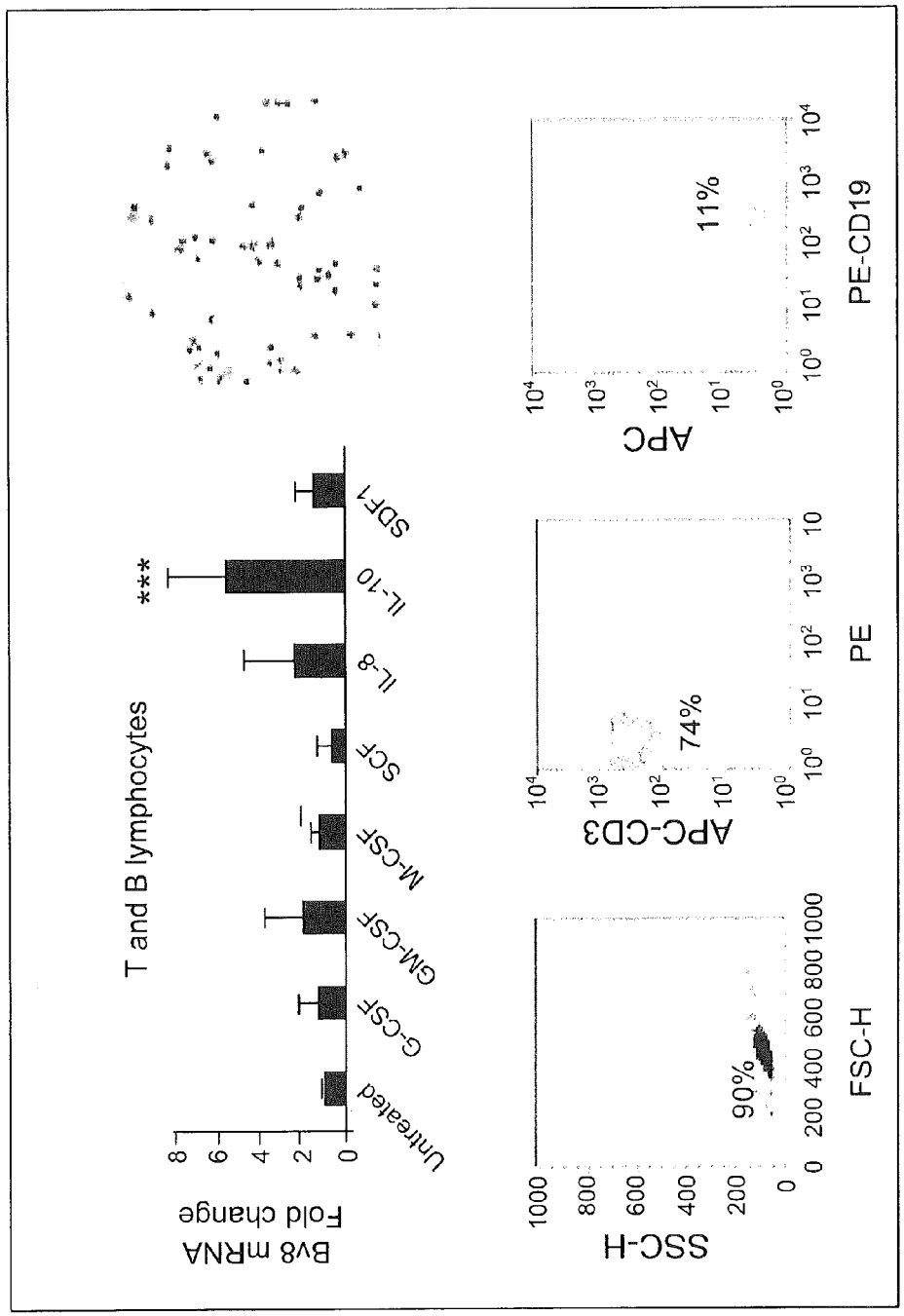
Figure 17A:
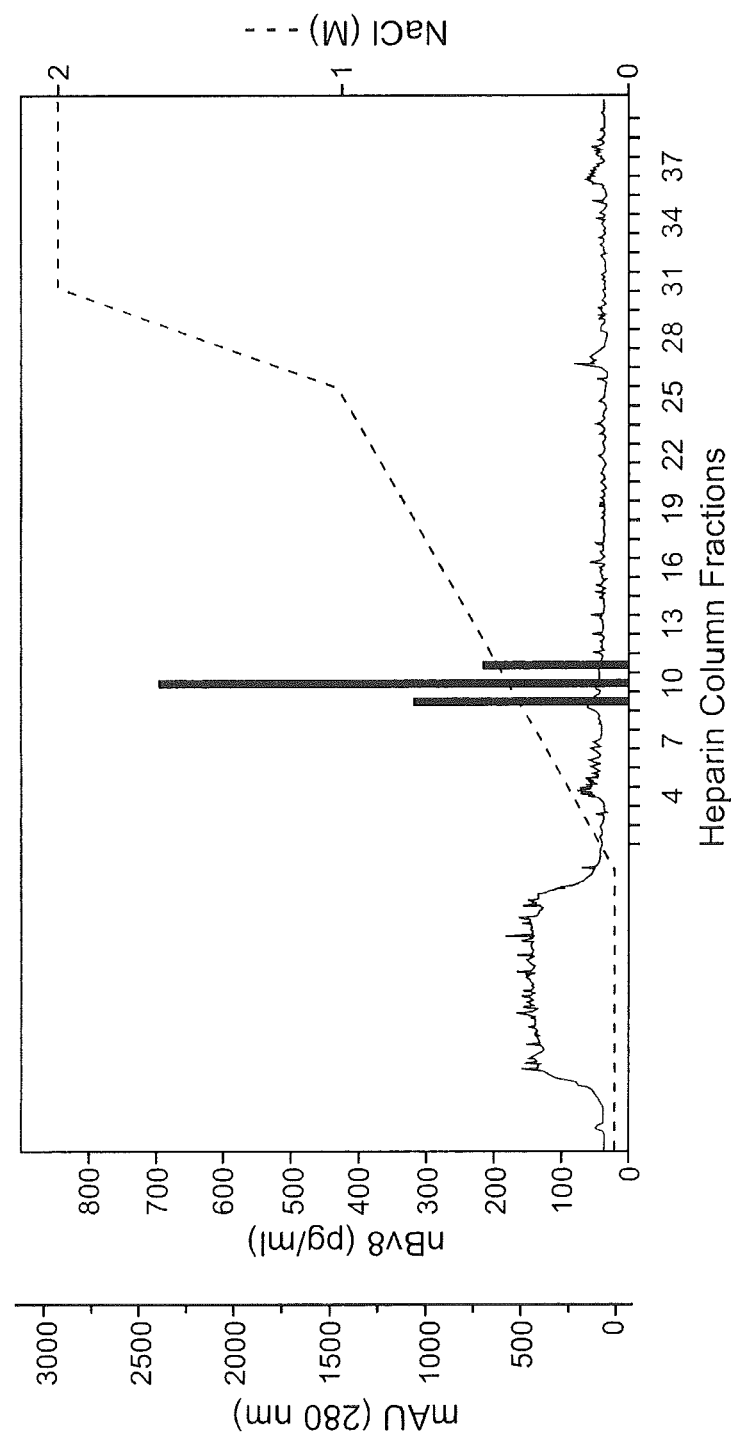
FIG. 17. Characterization of the Bv8 protein produced by human neutrophils. (A) Human neutrophils were isolated and lysed as described in Materials and Methods. The lysate was applied to a heparin-Sepharose as described. Fraction 9, 10 and 11, eluted in the presence of ~0.4 M NaCl, had the highest Bv8 levels. Data shown here was representative of 3 independent isolations. (B) Biological activity of purified human Bv8 from human neutrophils. The GeneBLAzer NFAT-CHO cells transfected with PKR1/EG-VEGFR1 were used to detect Bv8-induced activation of downstream G-protein-coupled receptor signaling pathway. Recombinant human Bv8 was used at 20 ng/ml to serve as a positive control and human VEGF at 200 ng/ml was used as a negative control. Data were further normalized as fold change, with untreated wells being 1. *** $p<0.01$ vs. un-treated or buffer control. Three independent studies were conducted.

To characterize the Bv8 protein, we solubilized peripheral human neutrophil pellets in 0.5% Triton® X-100. Neutrophil lysates were then subjected to heparin-Sepharose affinity chromatography as described in Materials and Methods. As illustrated in FIG. 14A, Bv8 bound to the column and was eluted in the presence of ~0.4M NaCl, similar to the mouse Bv8 protein. ELISA further confirmed the presence of Bv8 in fractions 9, 10 and 11 (FIG. 17A).

Figure 17B:
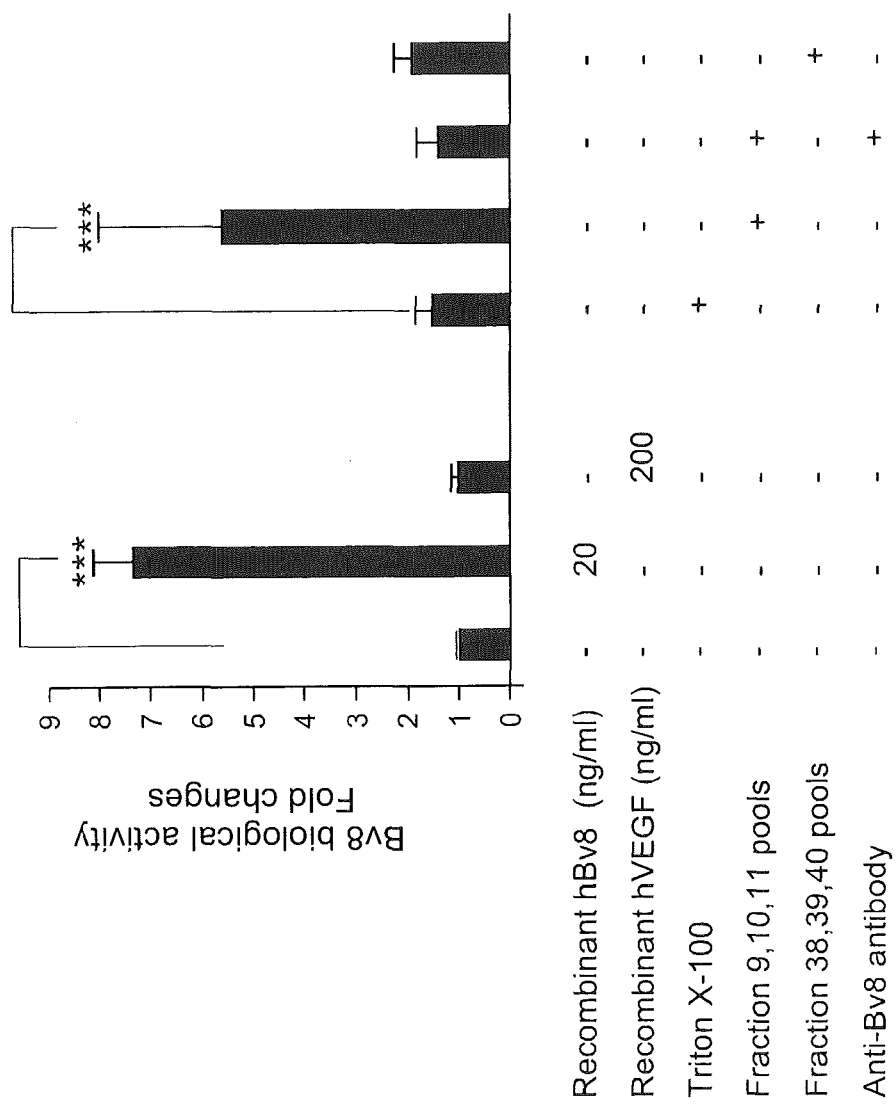
Figure 18A:
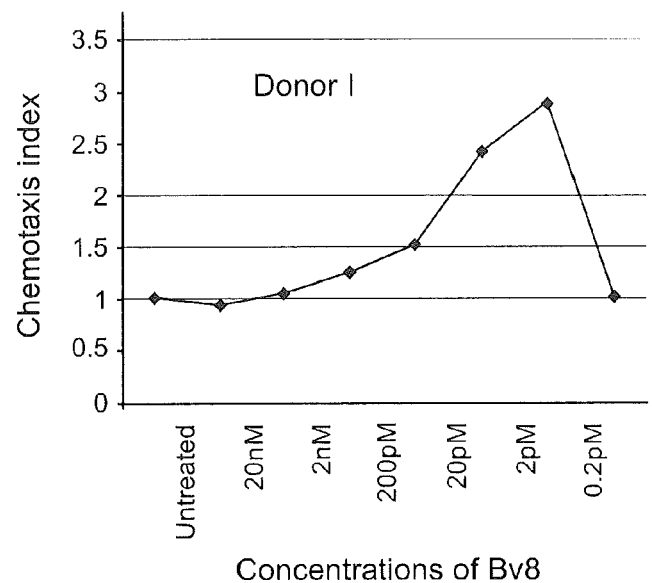
FIG. 18. Migration of neutrophils in response to Bv8. $10^6$ neutrophils suspended in HBSS containing 0.2% BSA were put into transwell insert with 5 μm pore size. To the lower chamber, media alone or media with purified recombinant human Bv8 (0.2 pM-20 nM) or other known chemotactic factors, such as SDR-1α, at various concentrations (up to 20 nM) was added. After 3 hr at 37° C., cells in the lower chamber were counted and data was further normalized as fold increase, with untreated samples being 1. Experiments were performed on 6 healthy donors.
Figure 18B:
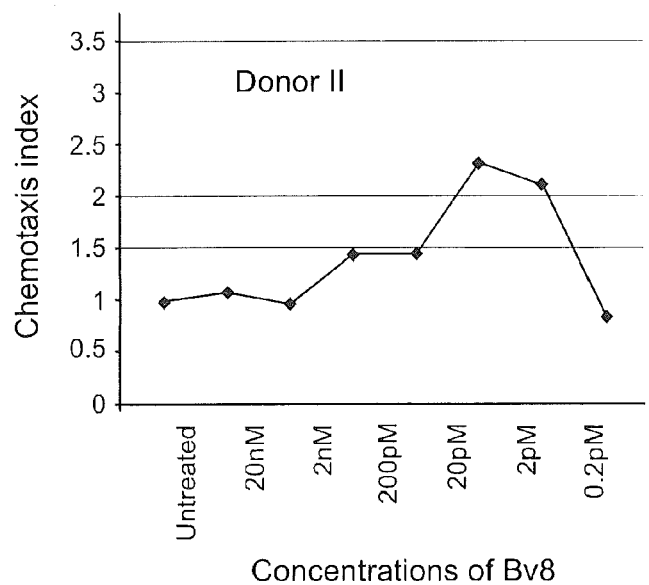
Figure 18C:
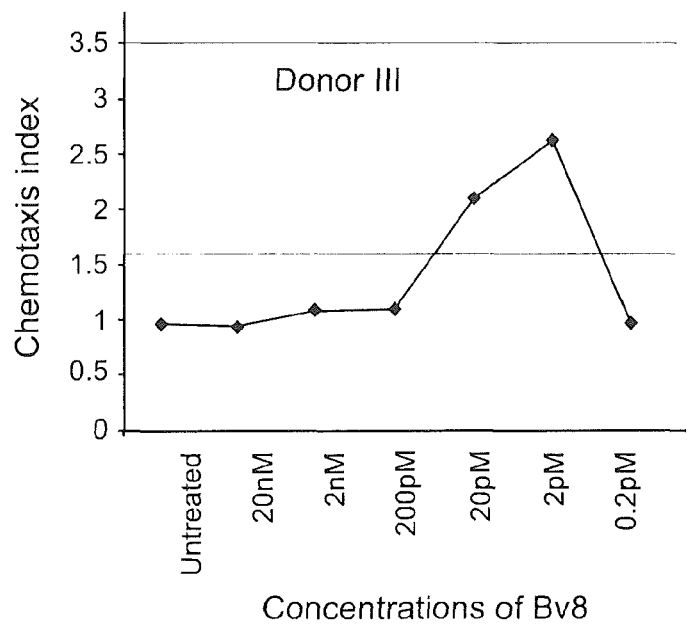
Figure 18D:
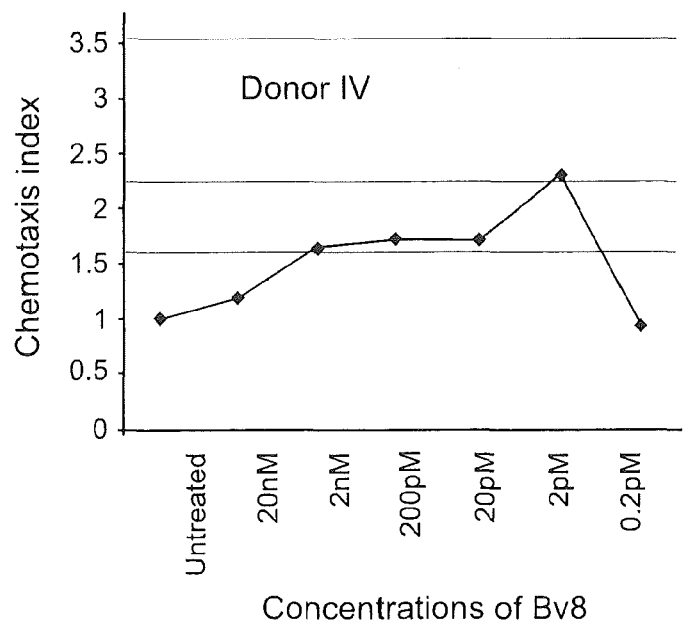
Figure 18E:
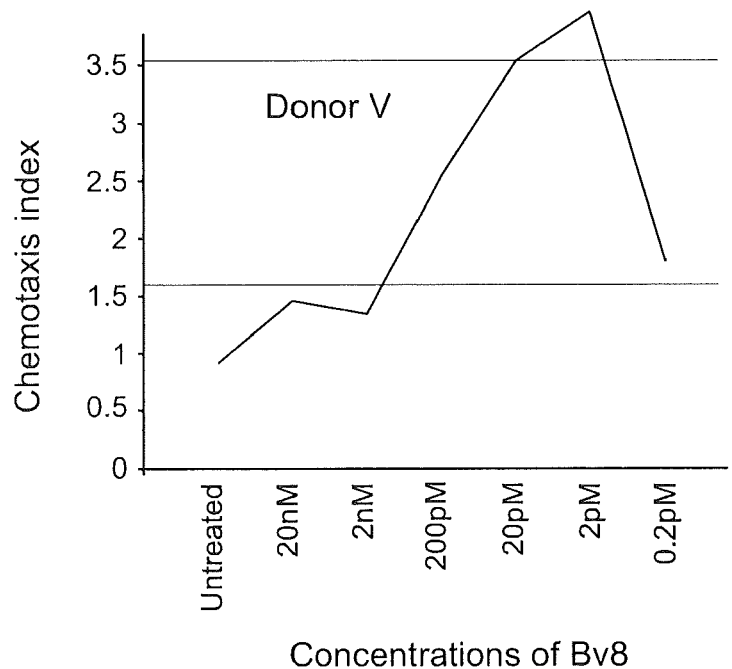
Figure 18F:
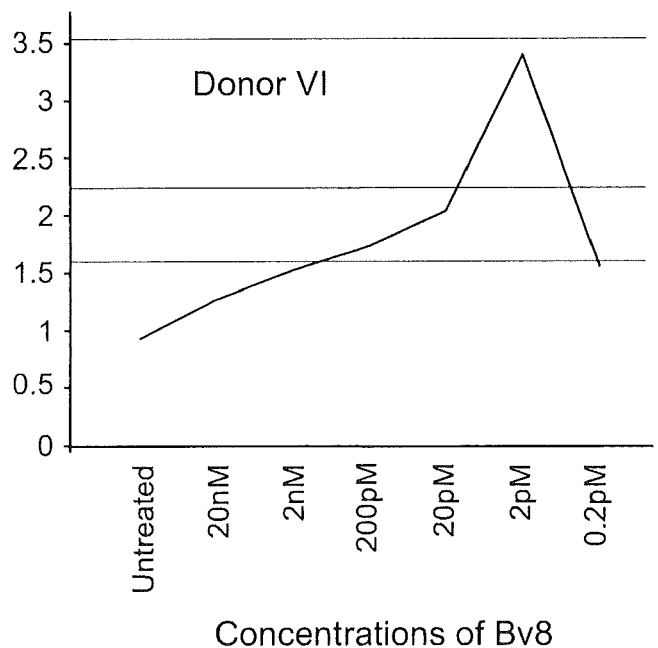
Figure 19A:
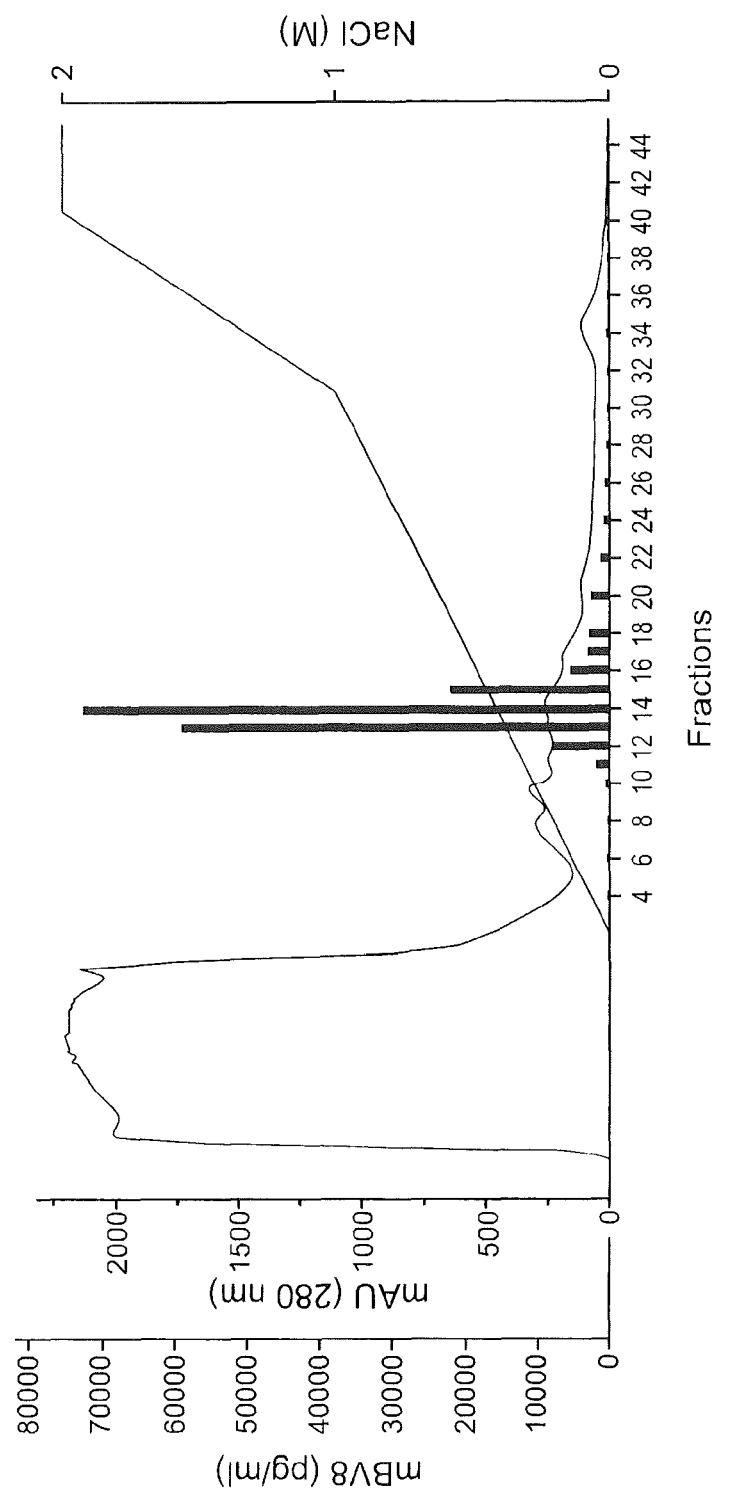
Figure 19B:
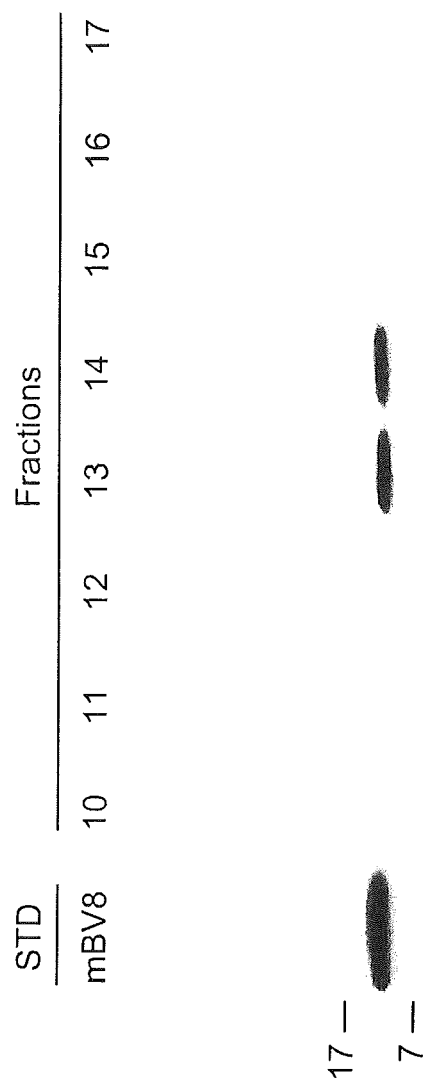
Figure 20A:
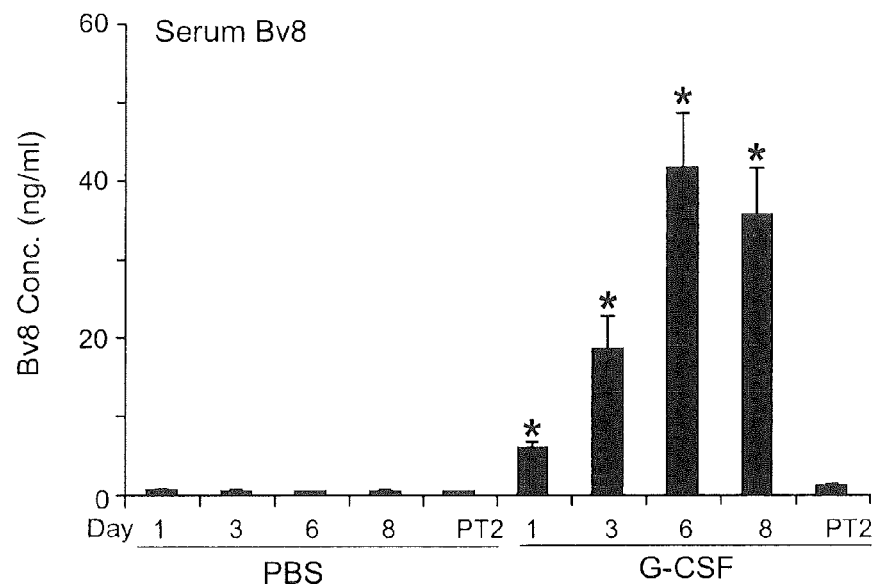
Figure 20B:
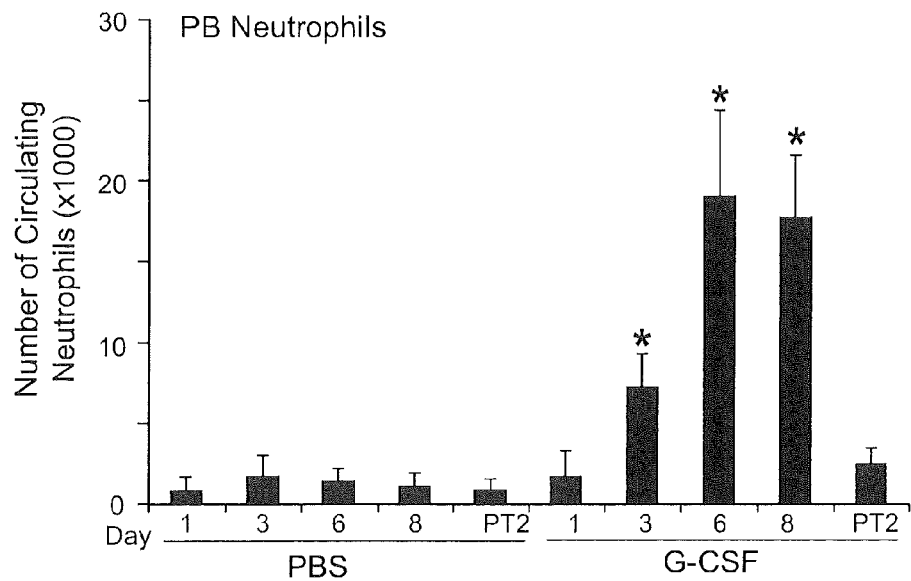
Figure 20L:
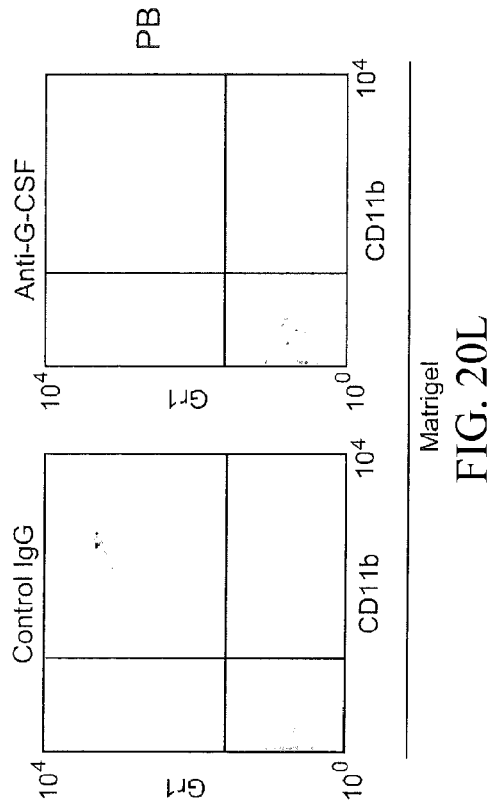
Figure 20M:
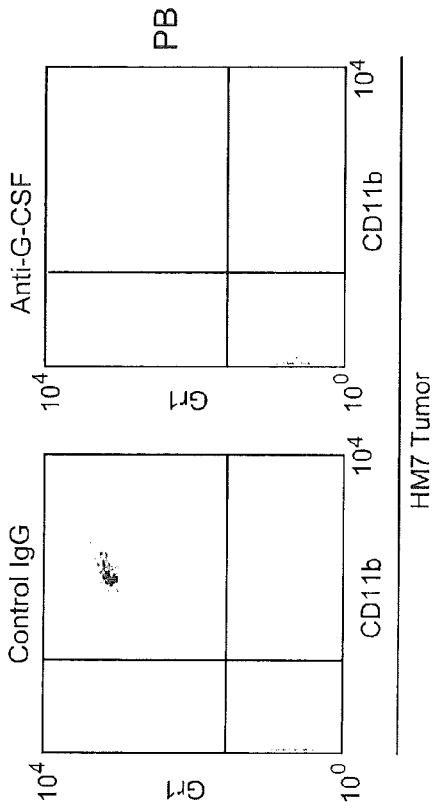
Figure 20K:
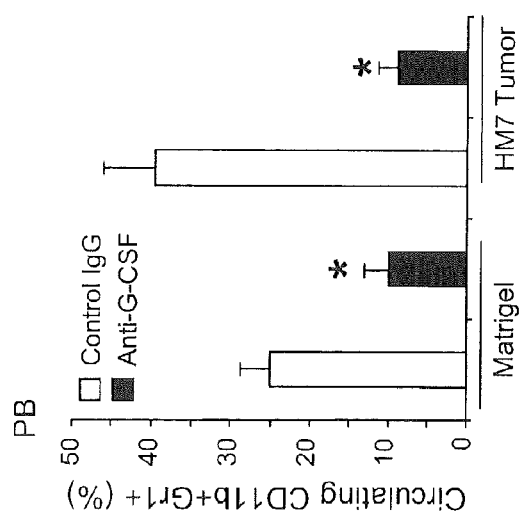
Figure 20O:
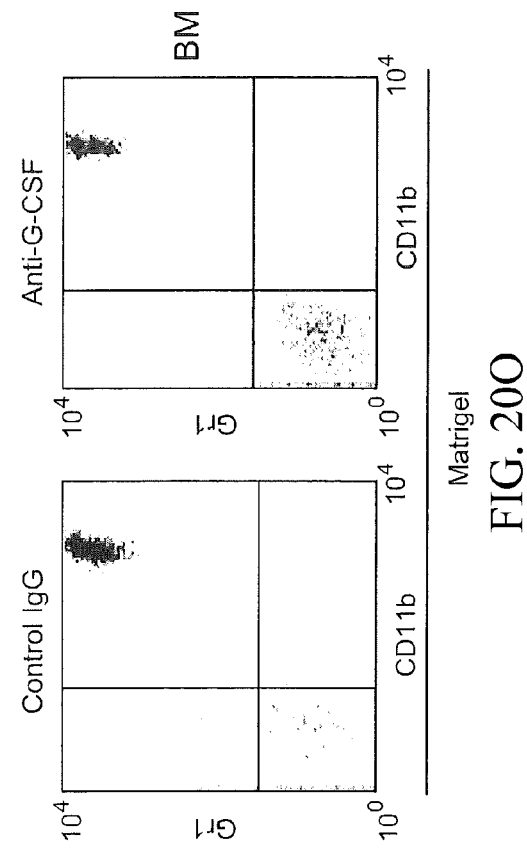
Figure 20P:
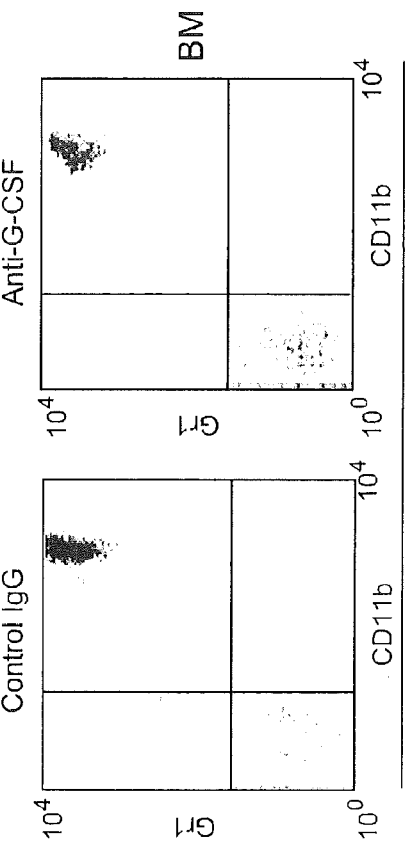
Figure 20N:
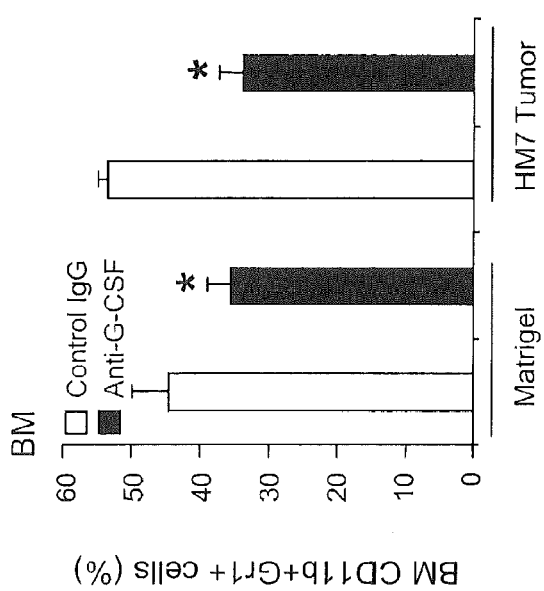
Figure 21A:
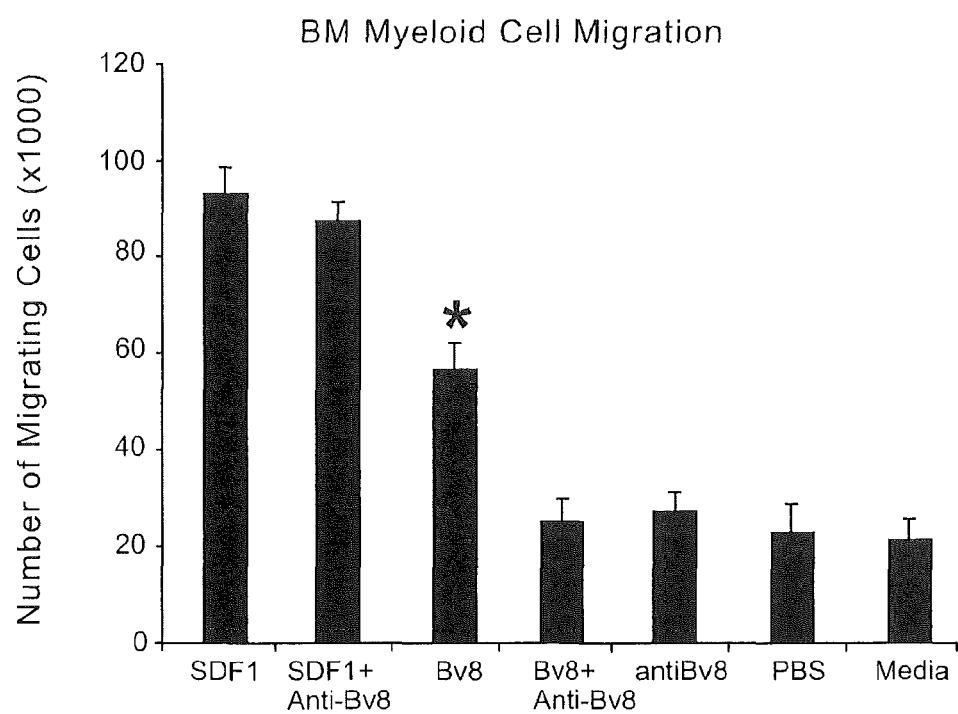
Figure 21B:
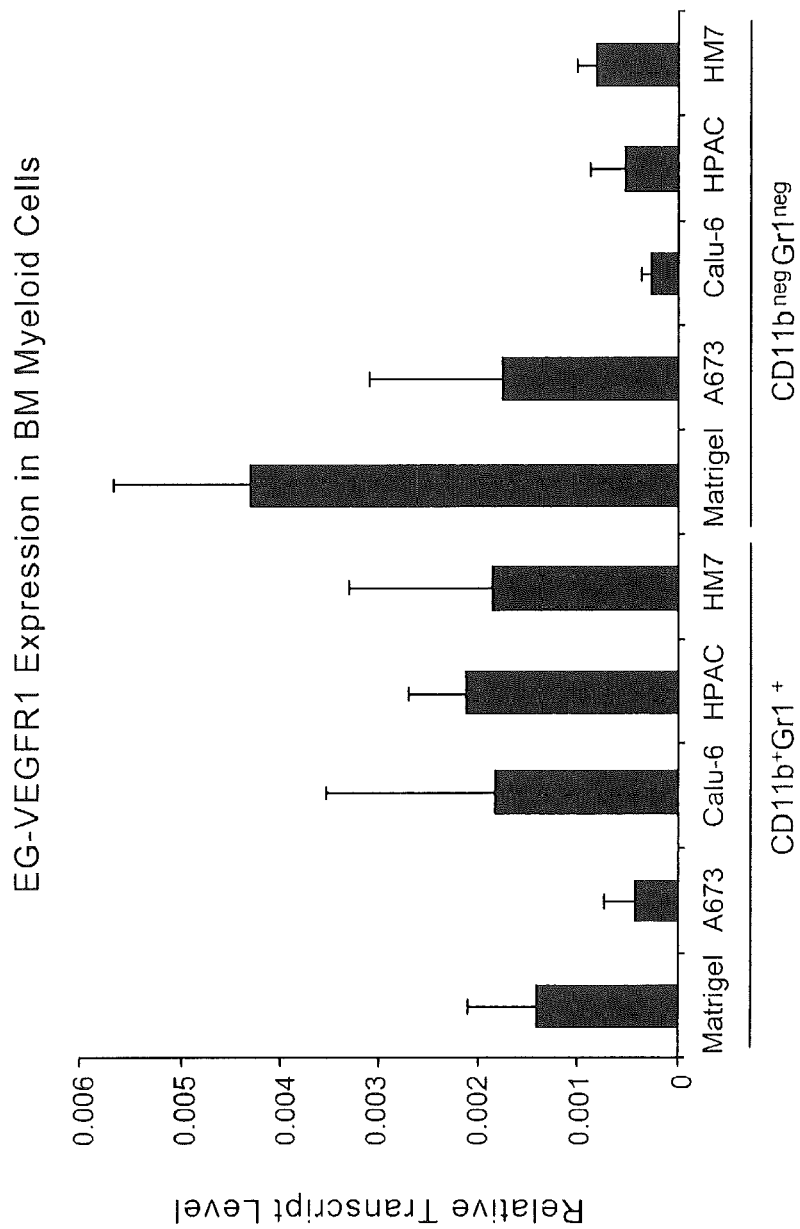
Figure 21C:
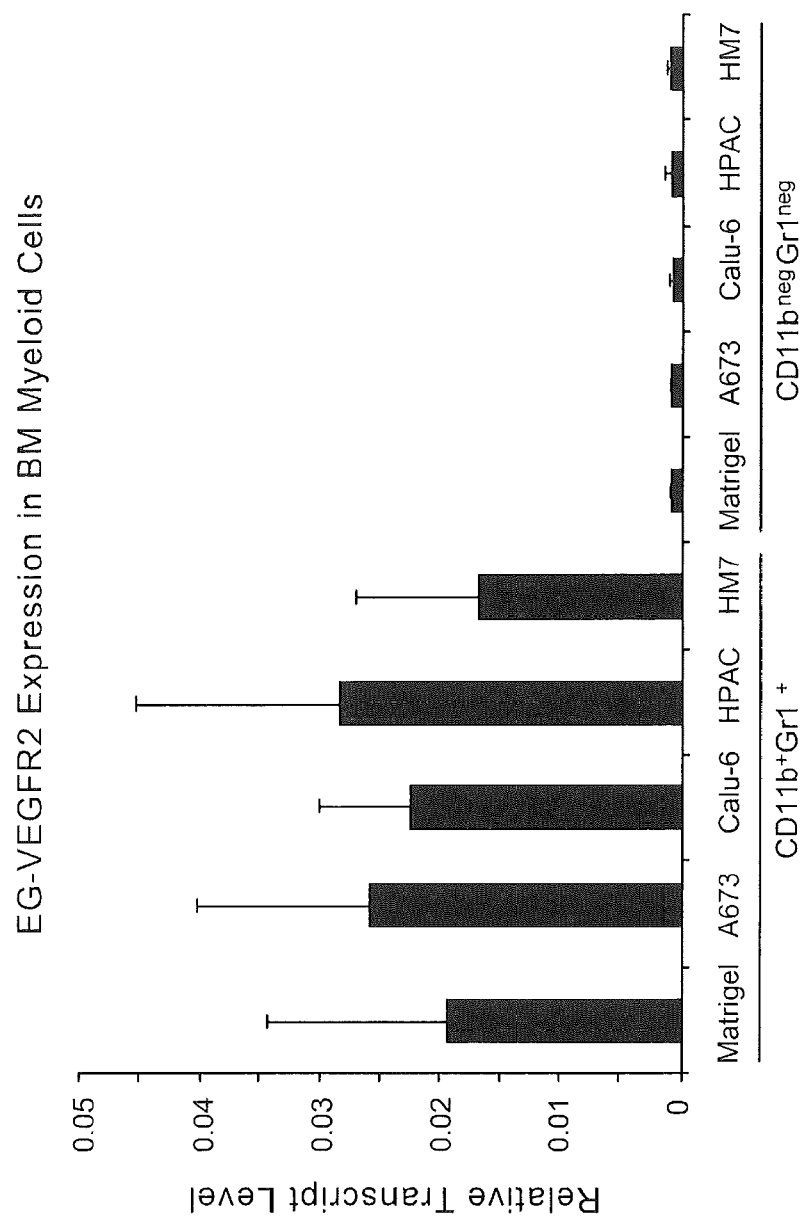
Figures 21D, 21E, 21F:
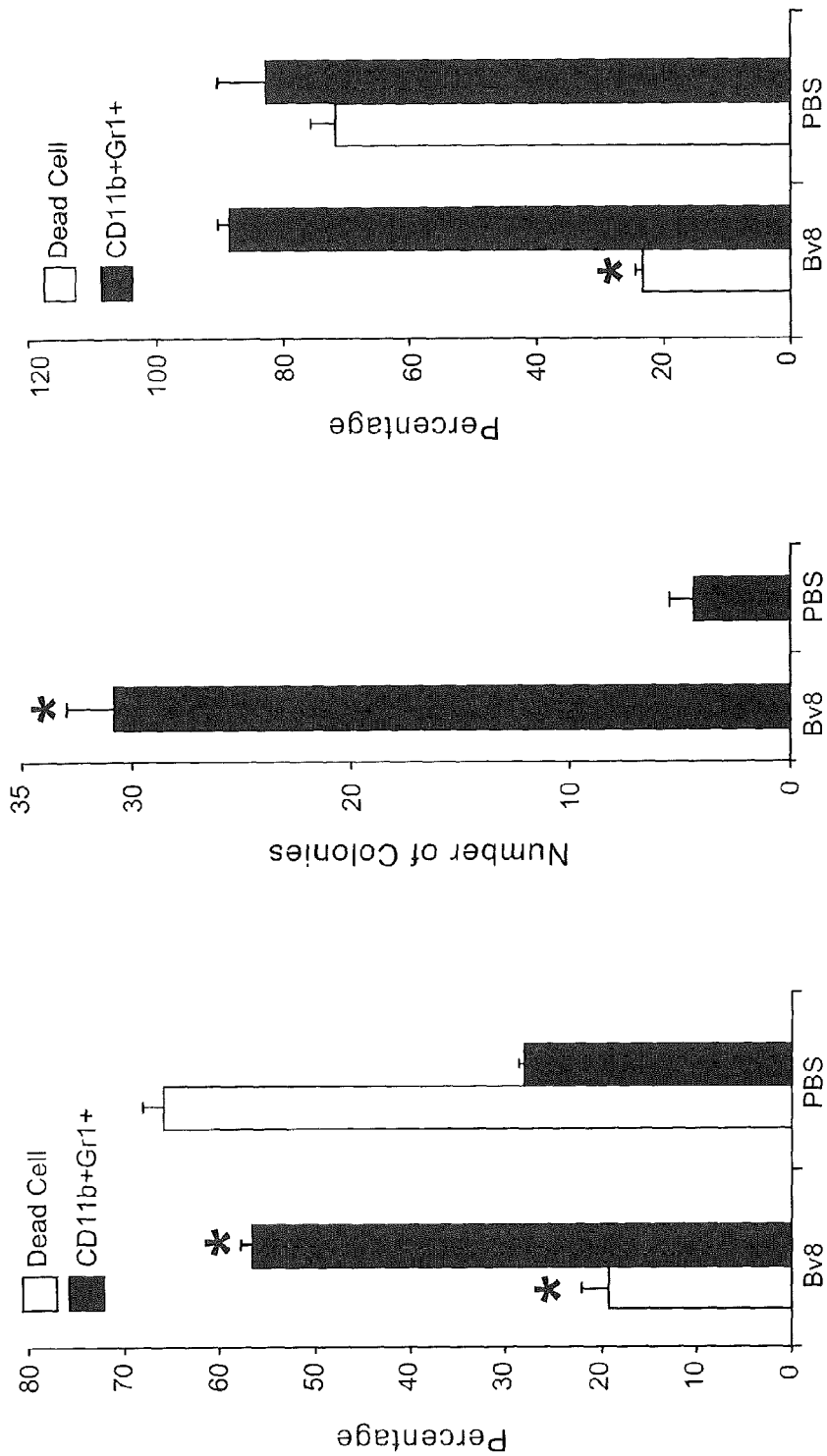
Figure 21G:
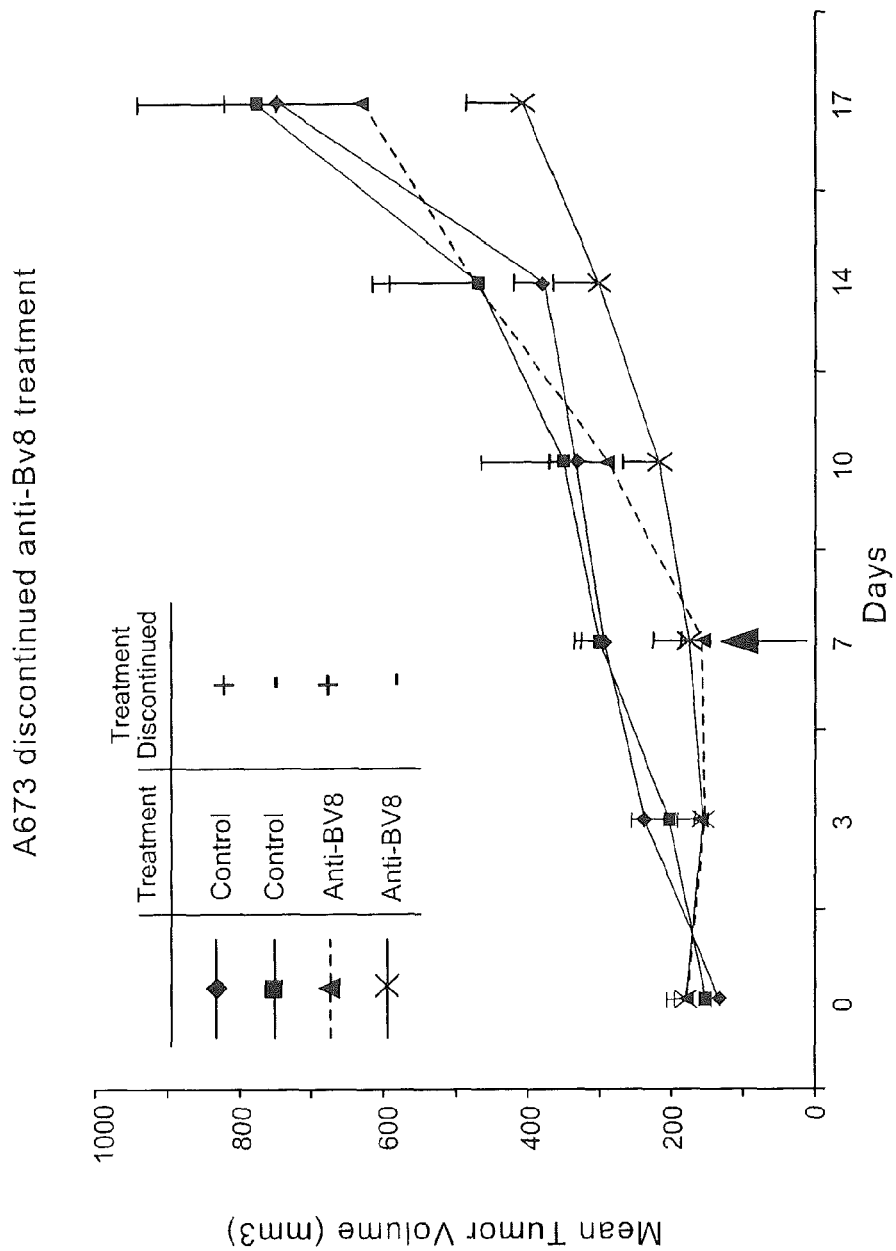
Figure 21H:
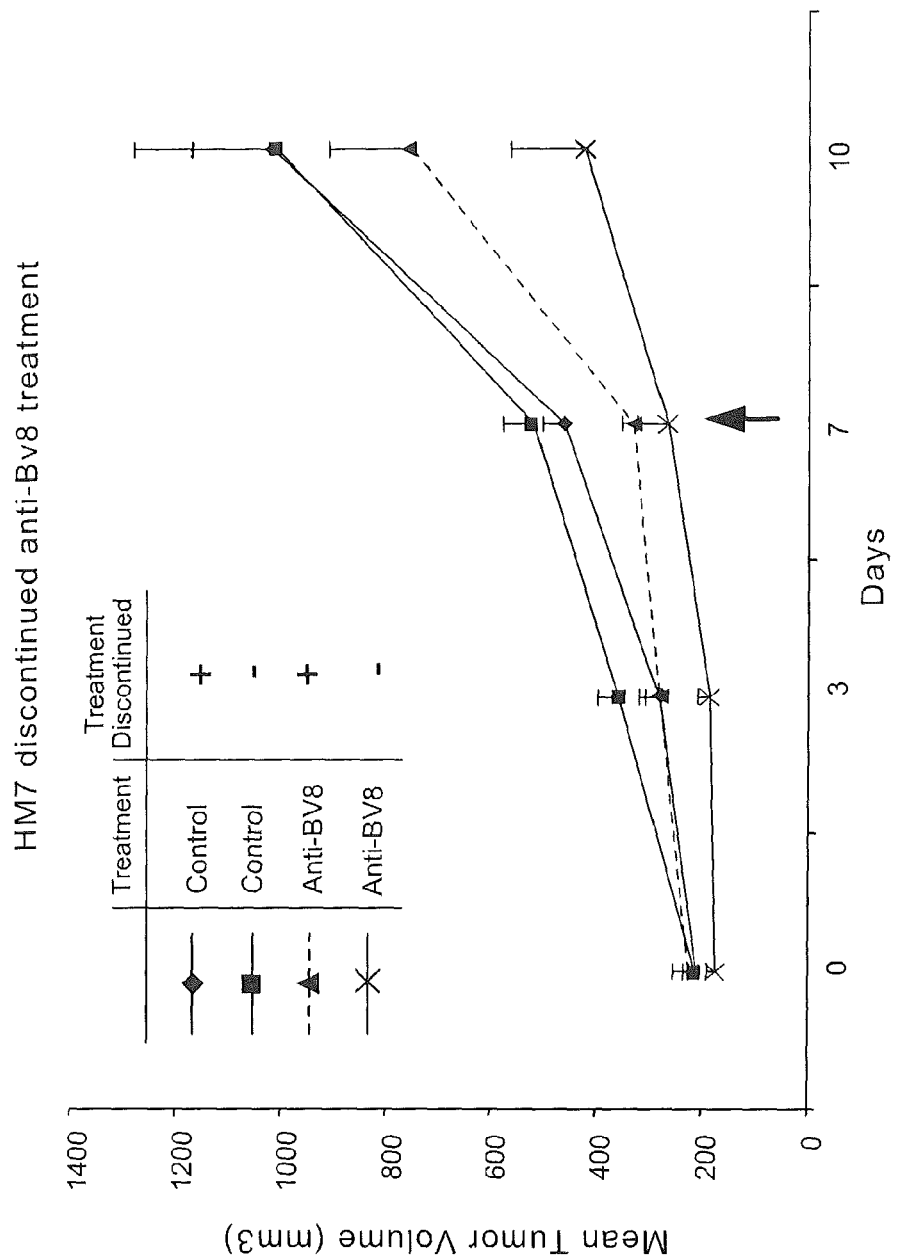
Figures 21I, 21J:
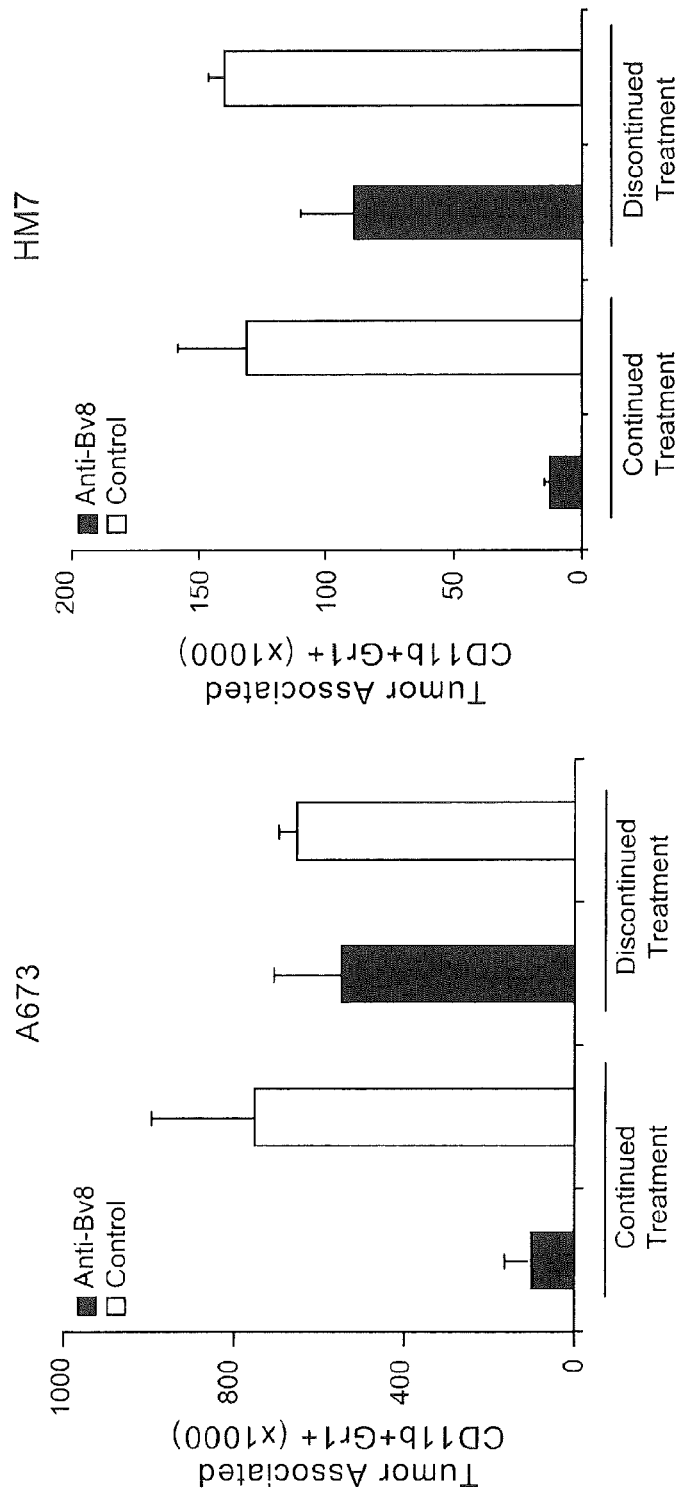
Figure 22B:
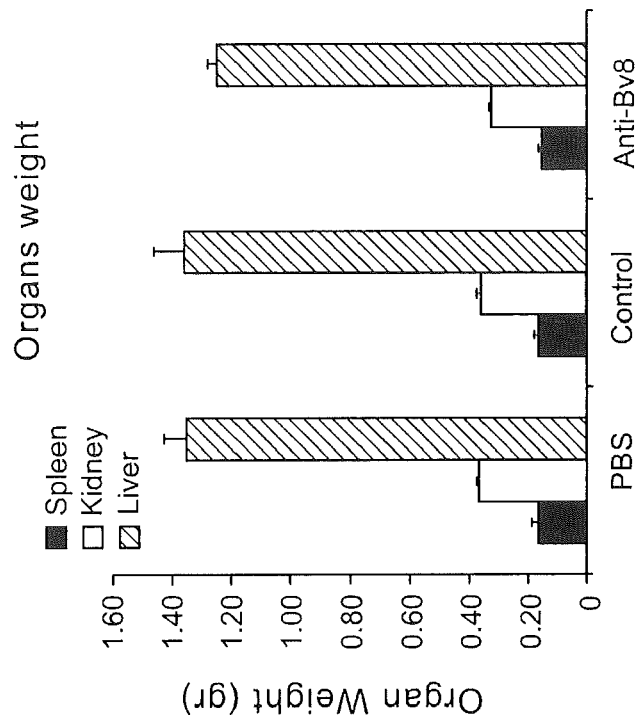
Figure 22A:
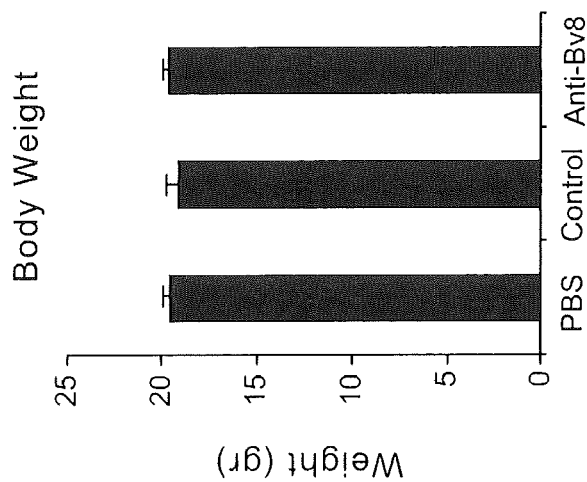
Figure 22C:
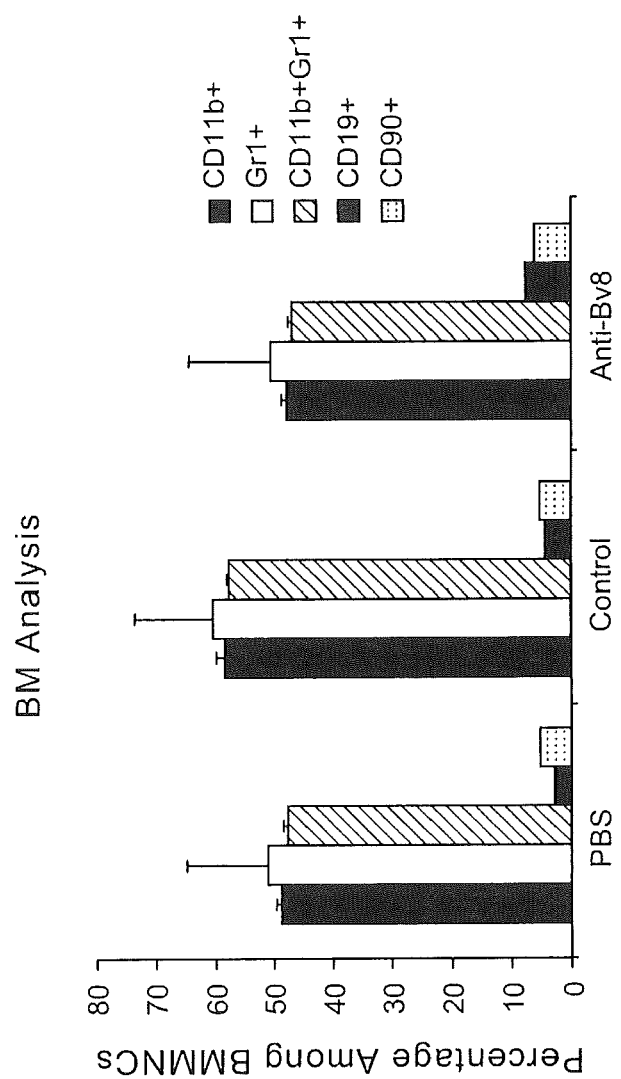
Figure 22D:
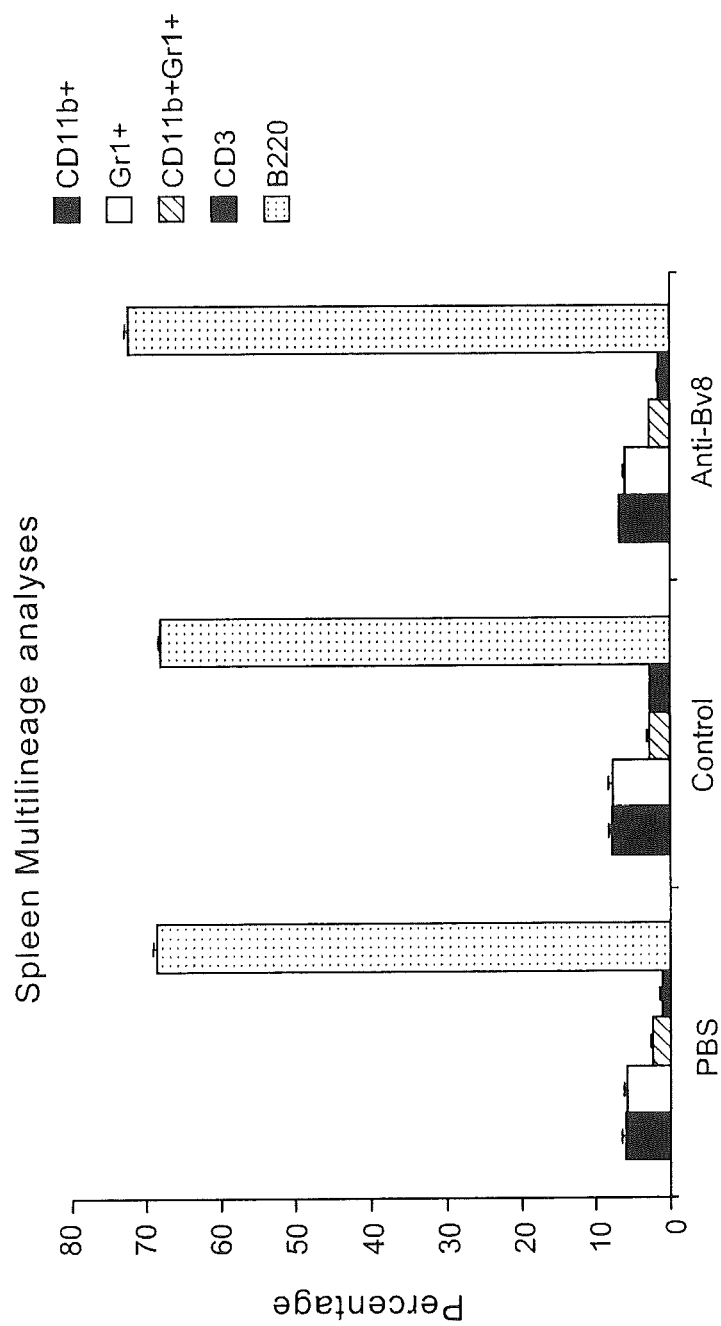
Figure 22E:
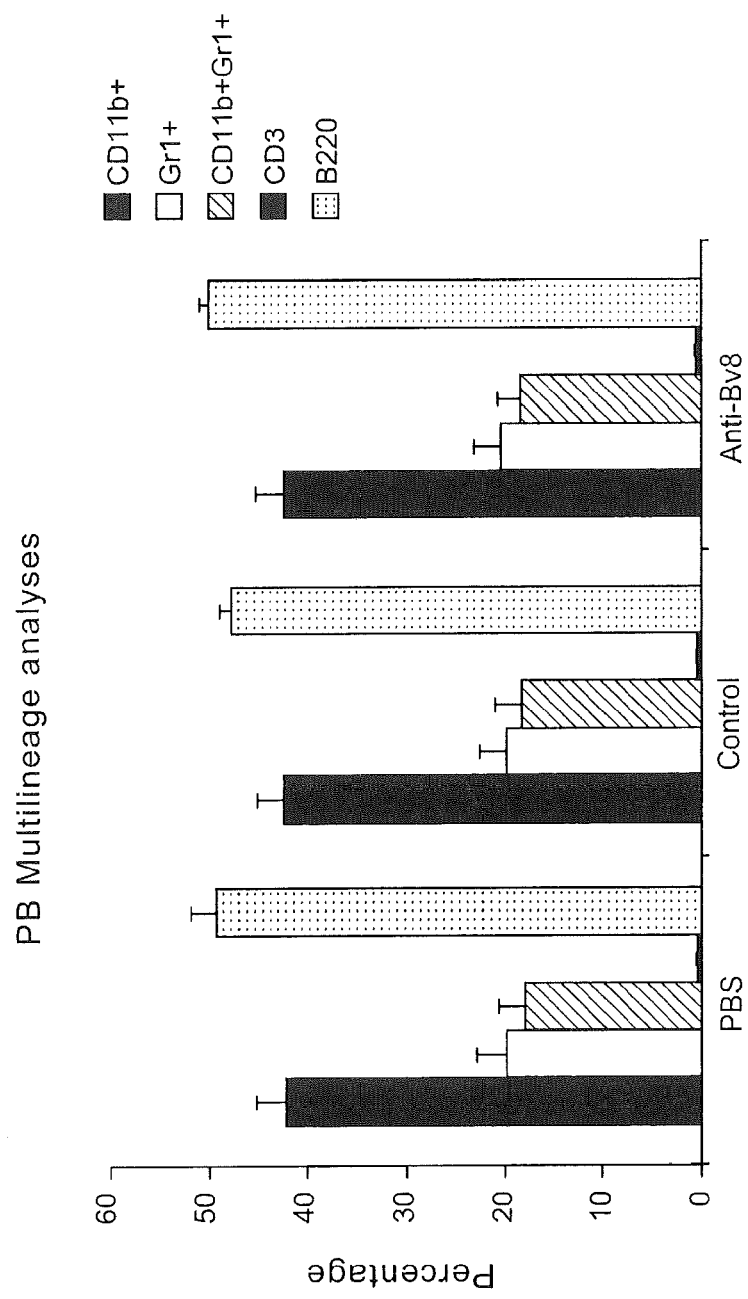
Figure 23A:
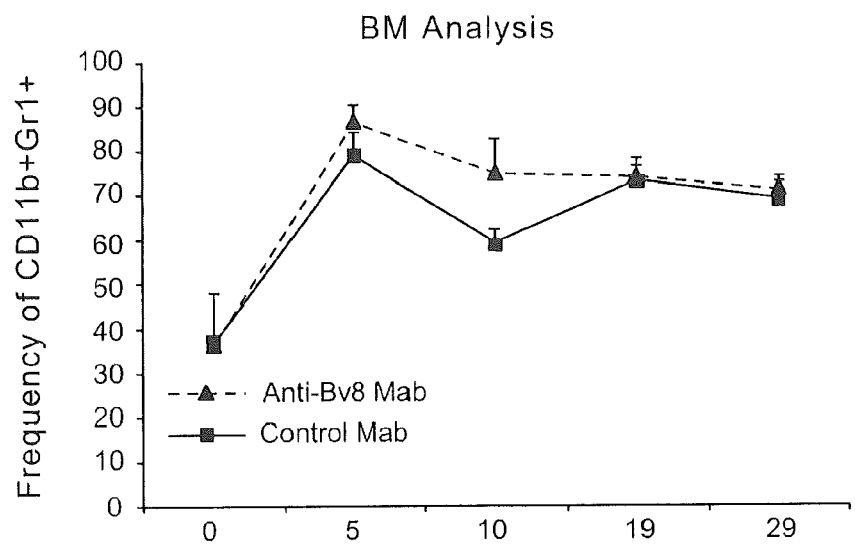
Figure 23B:
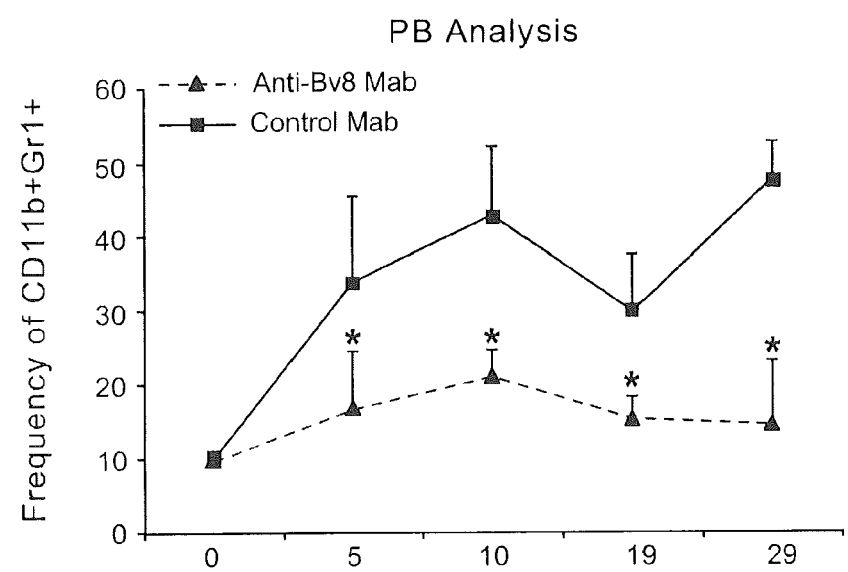
Figure 23C:
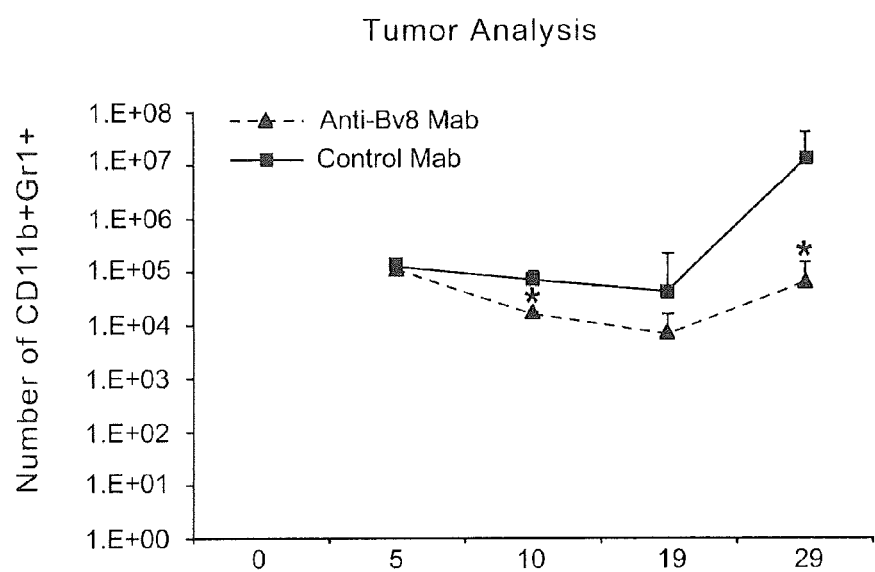
Figure 24A:
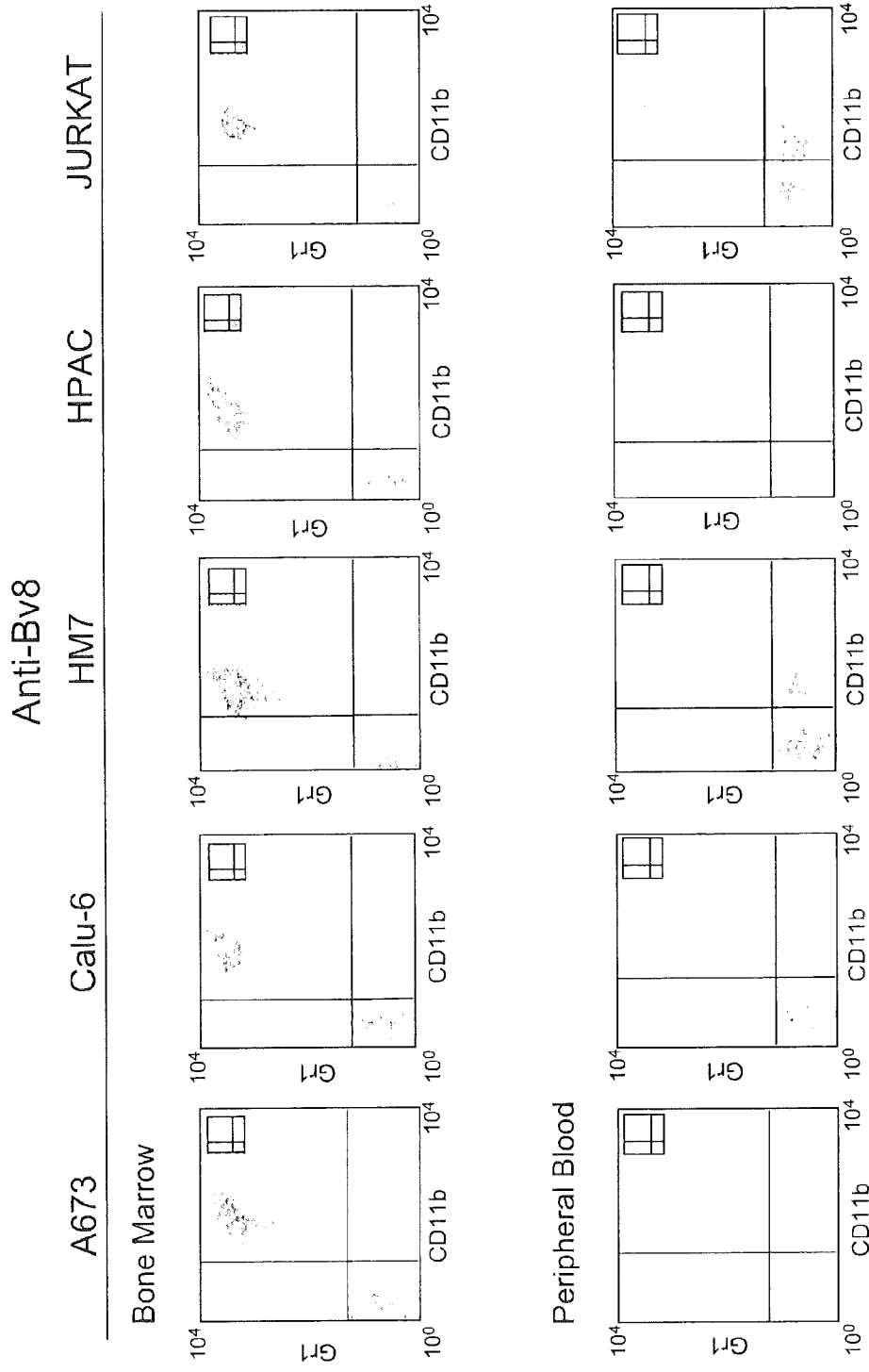
Figure 24B:
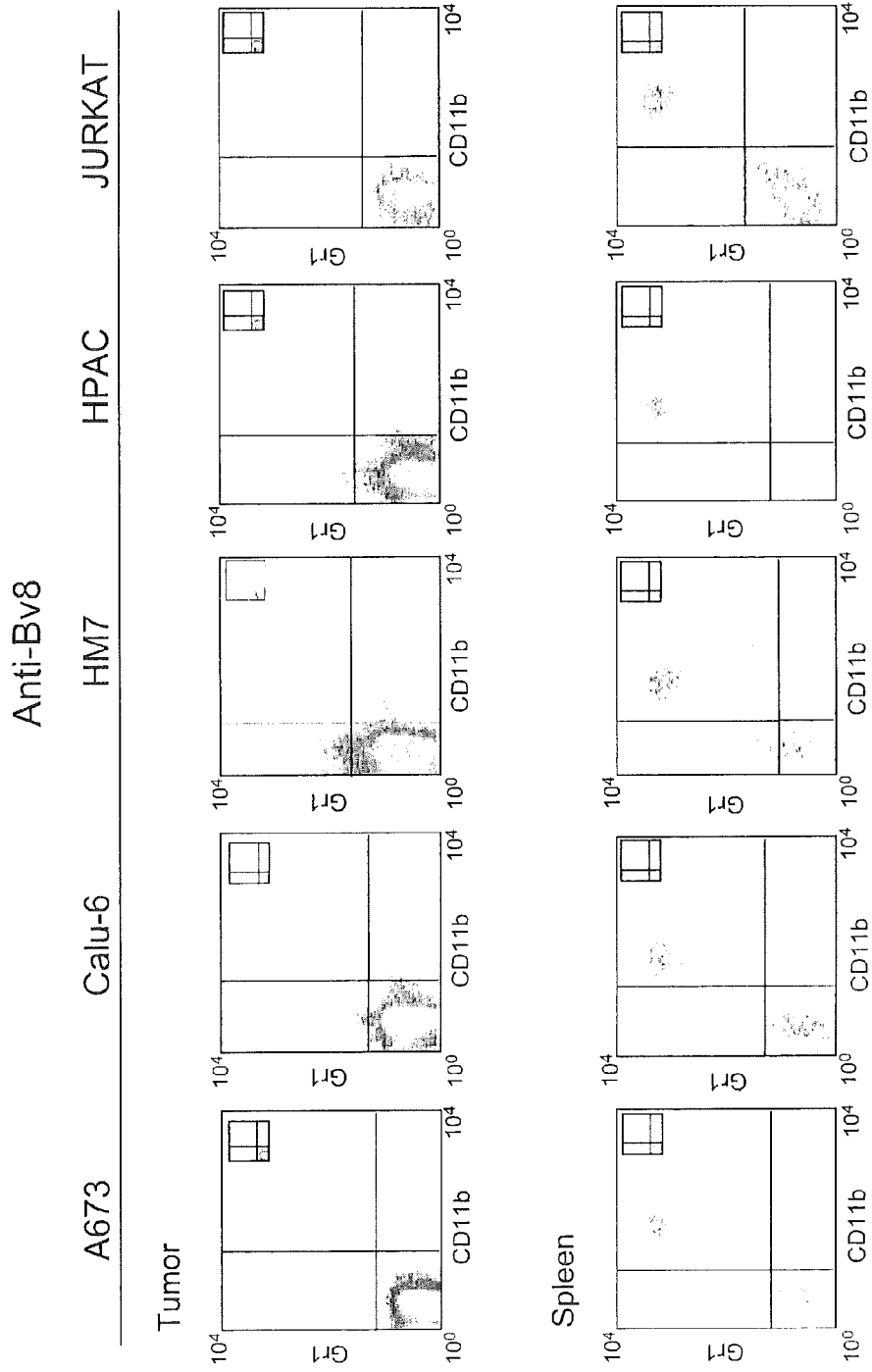
Figure 24C:
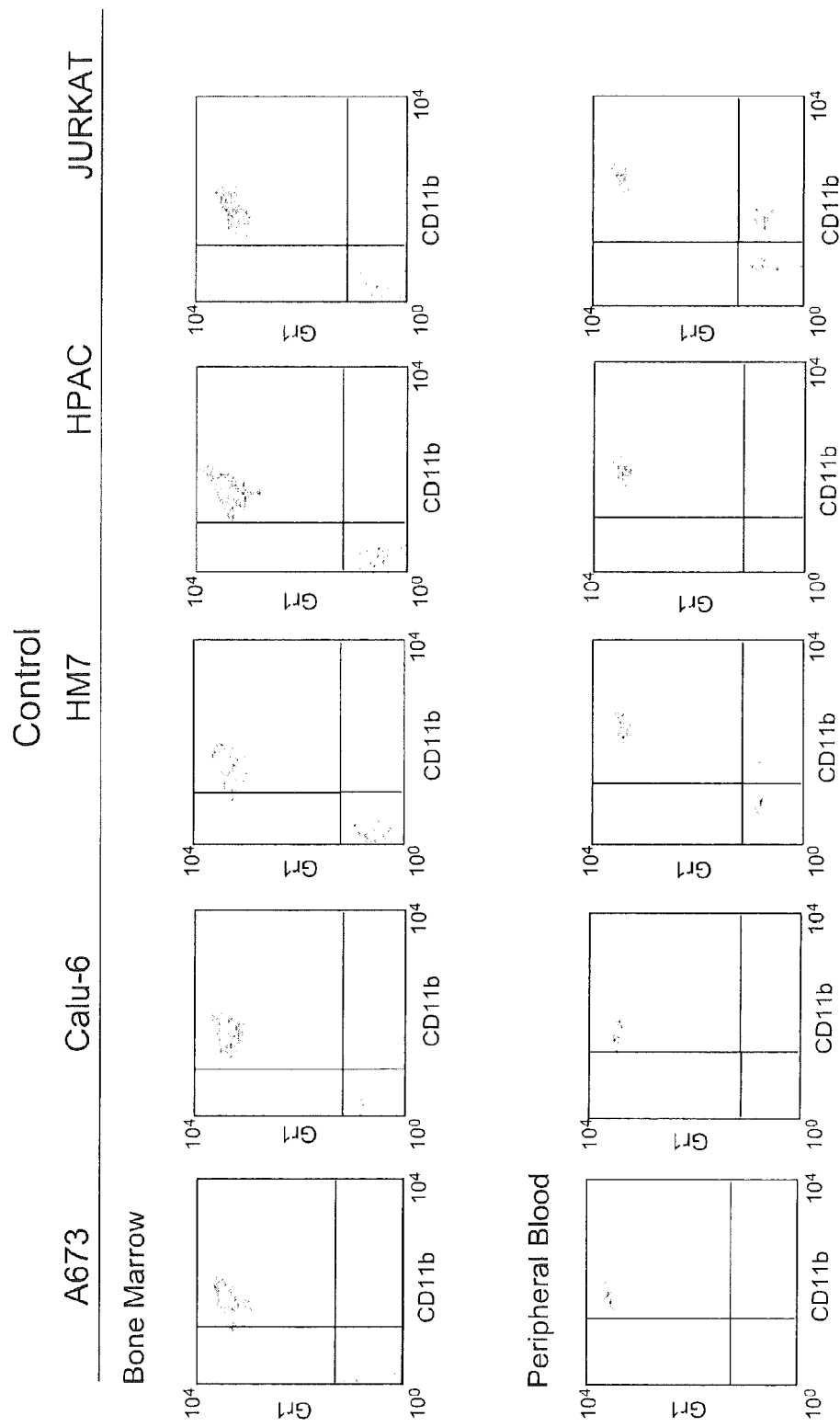
Figure 24D:
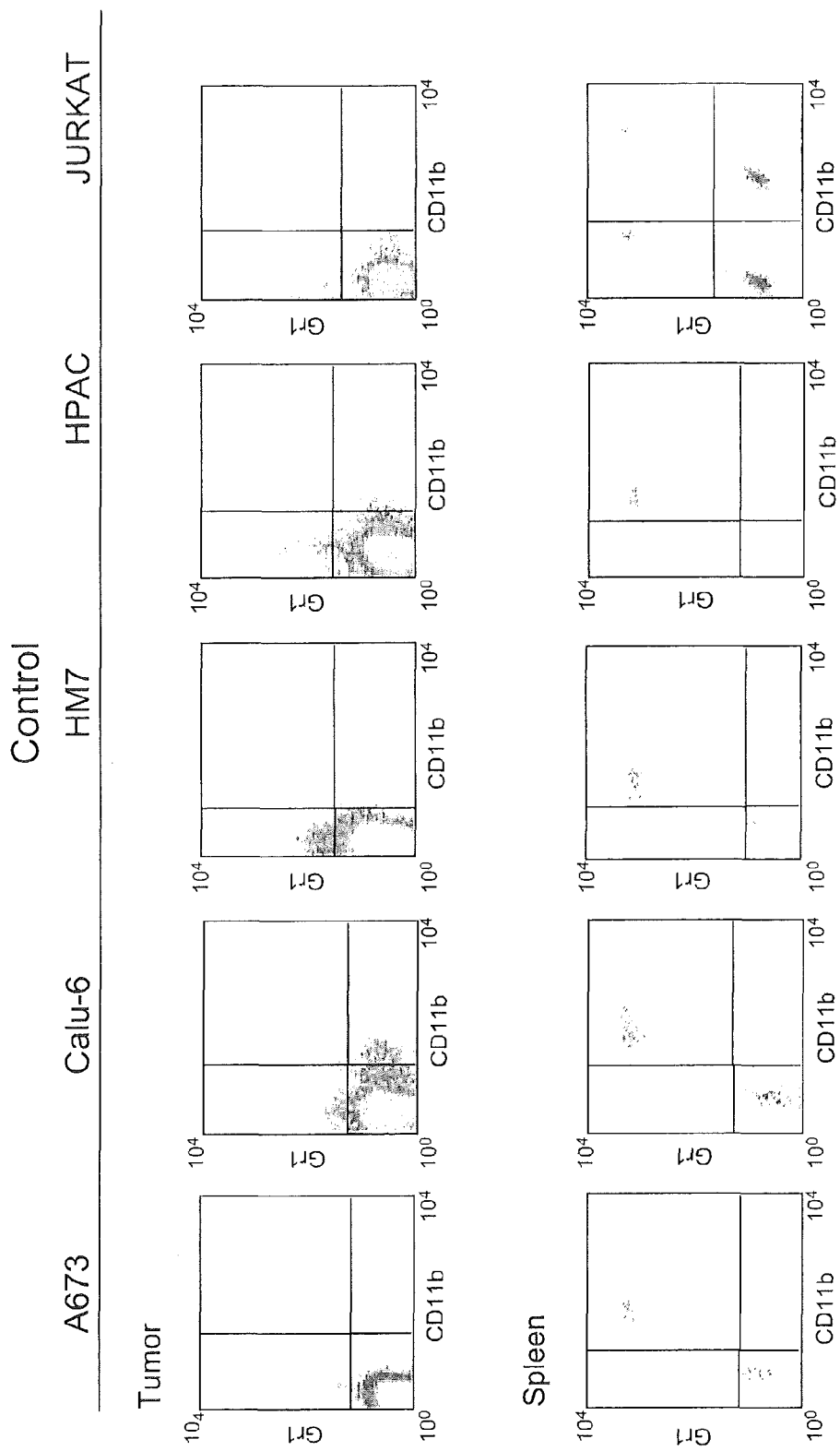
Figure 25A:
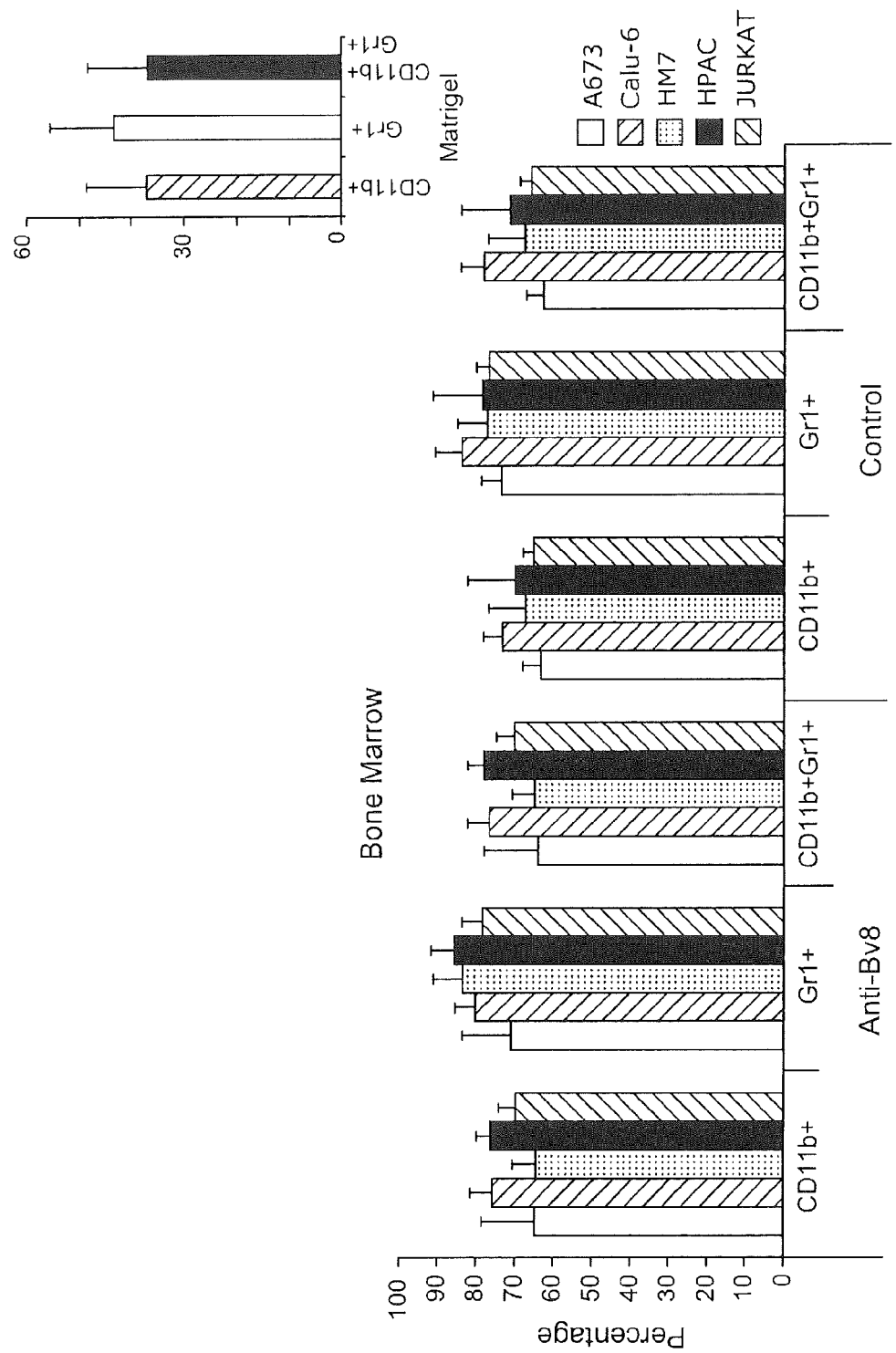
Figure 25B:
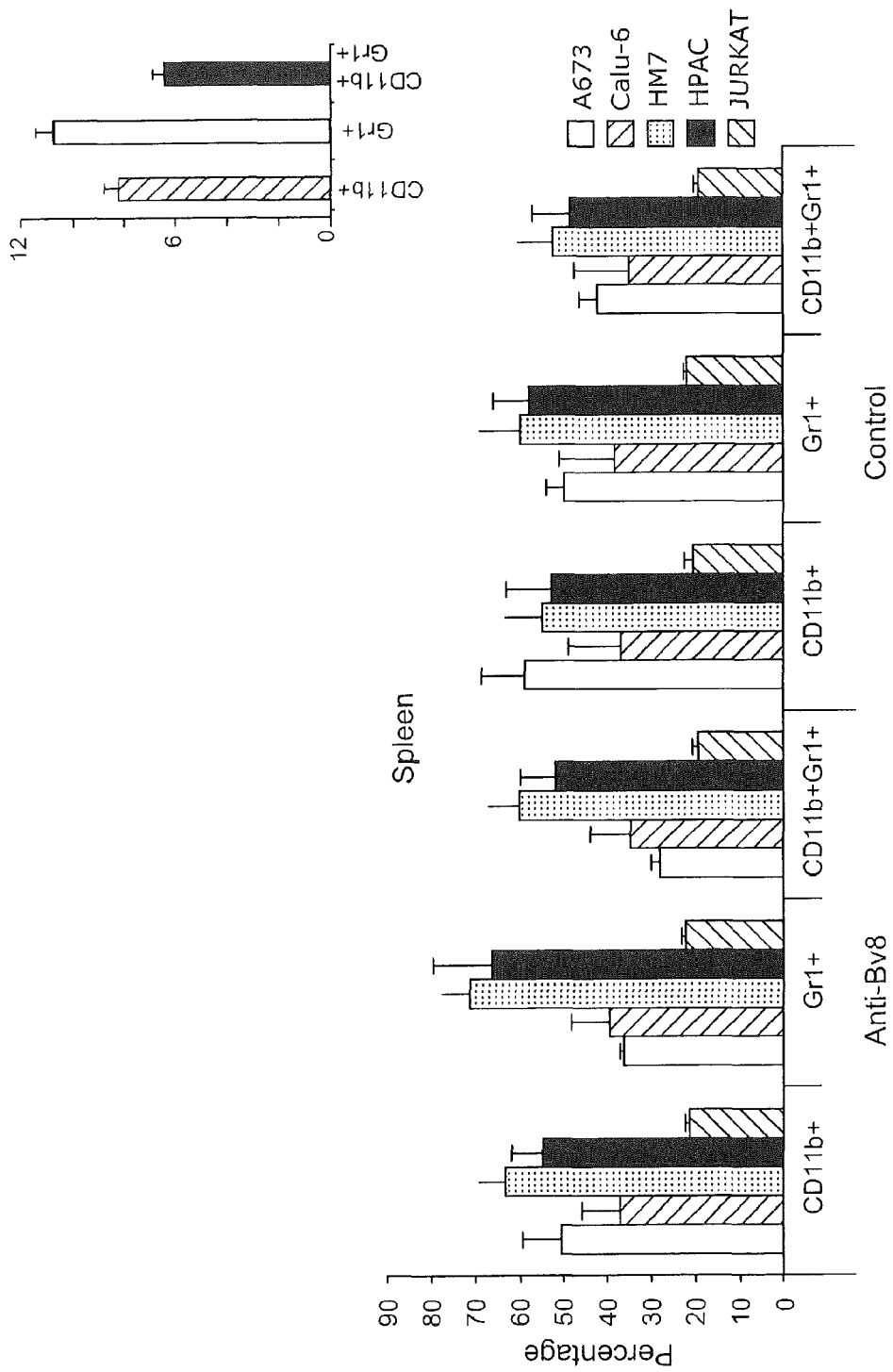
Figure 25C:
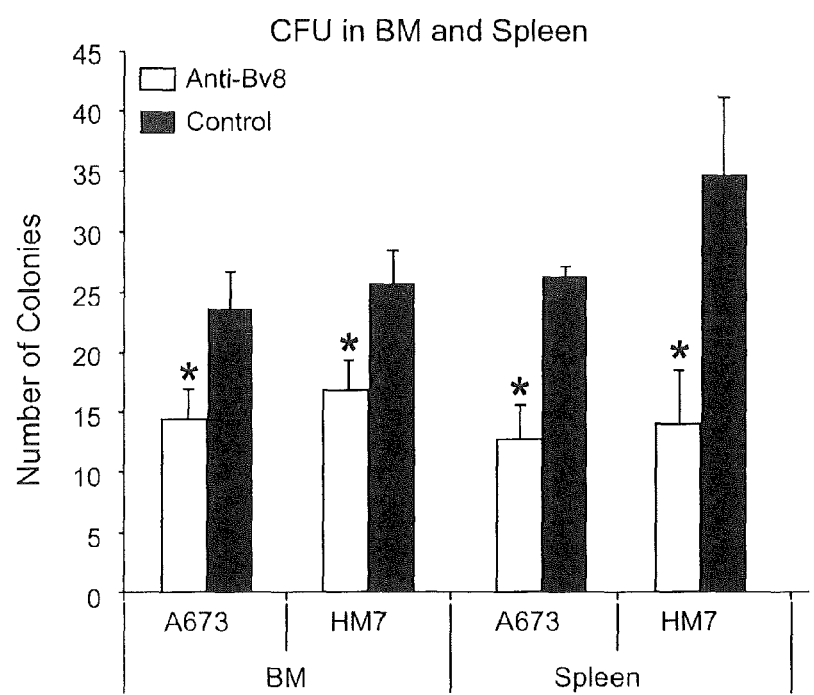
Figure 26A:
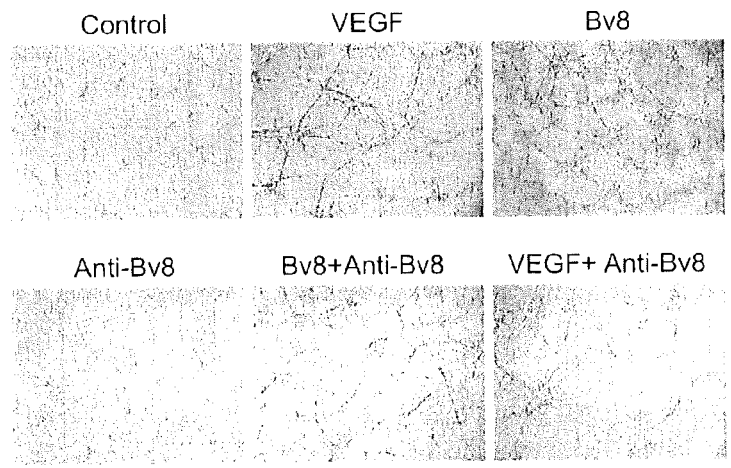
Figure 26B:
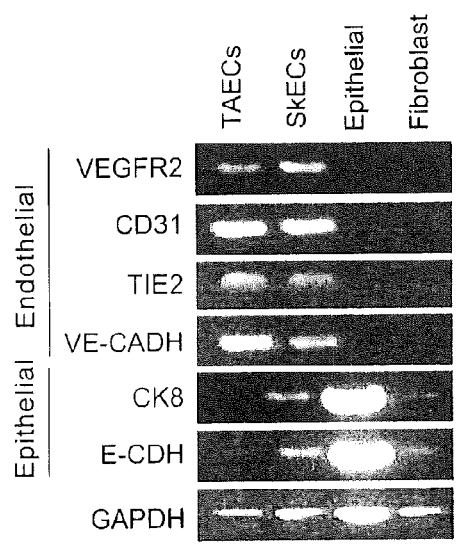
Figure 26C:
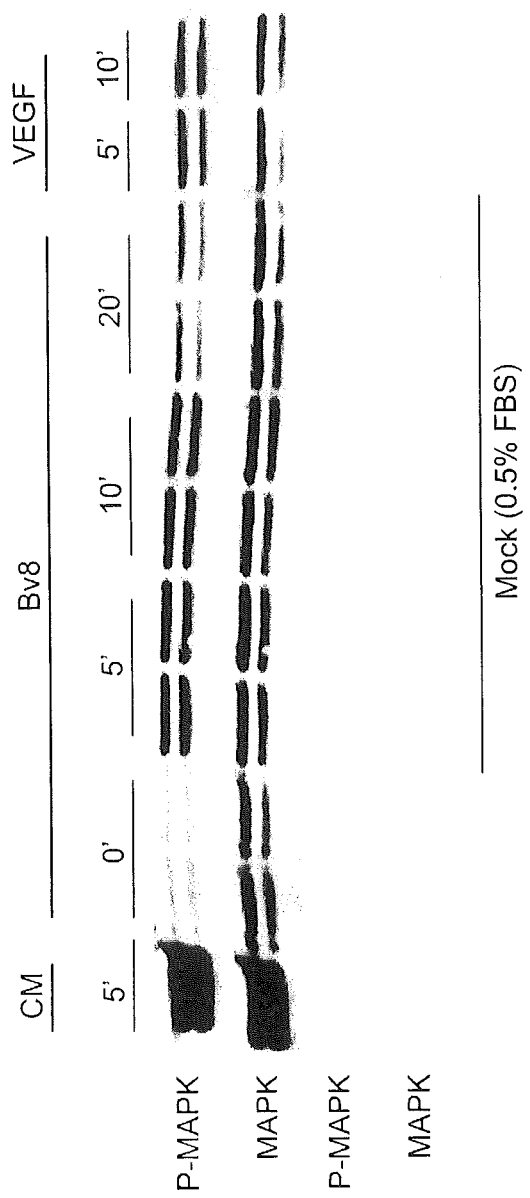
Figure 26D:
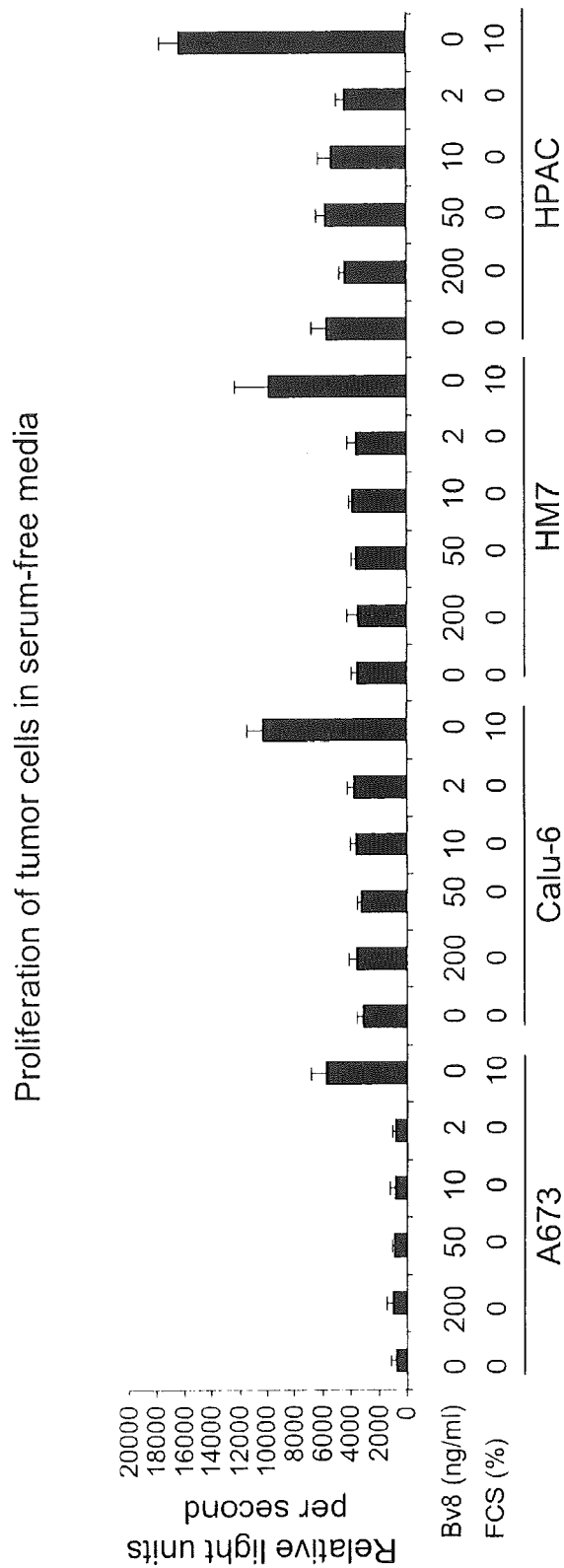
Figure 27A:
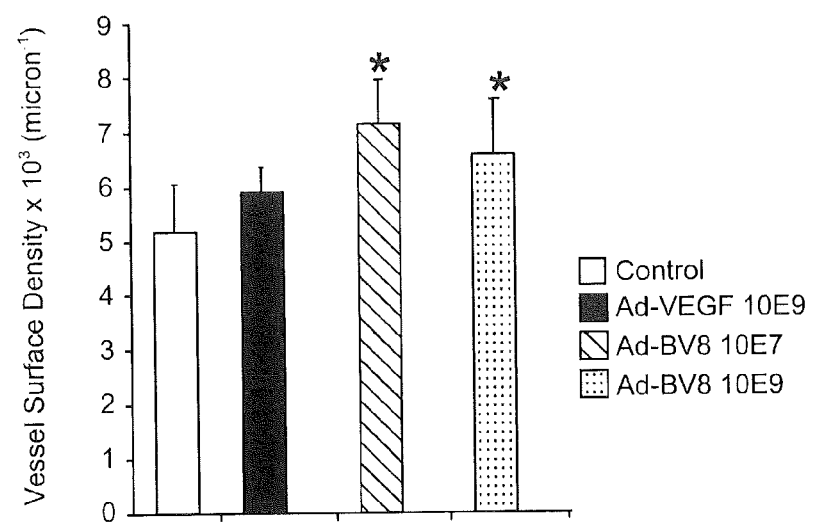
Figure 27B:
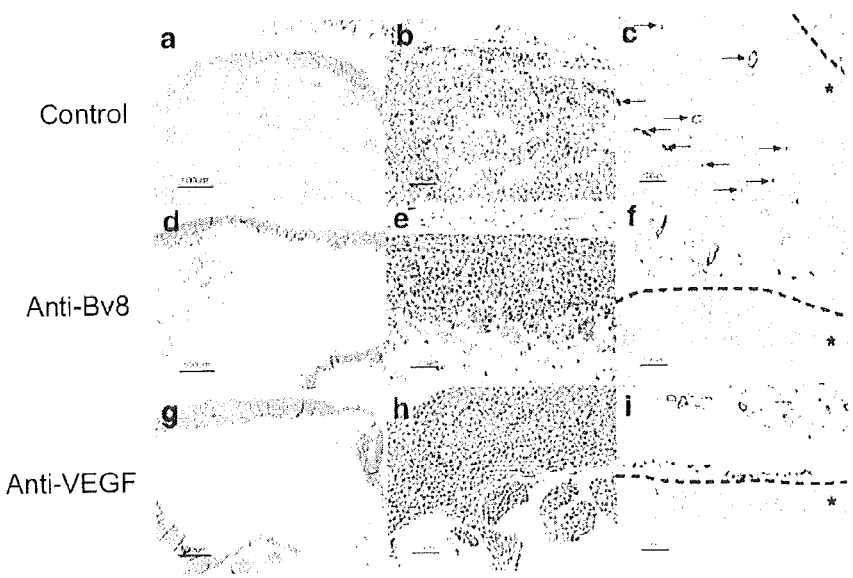
Figure 28:
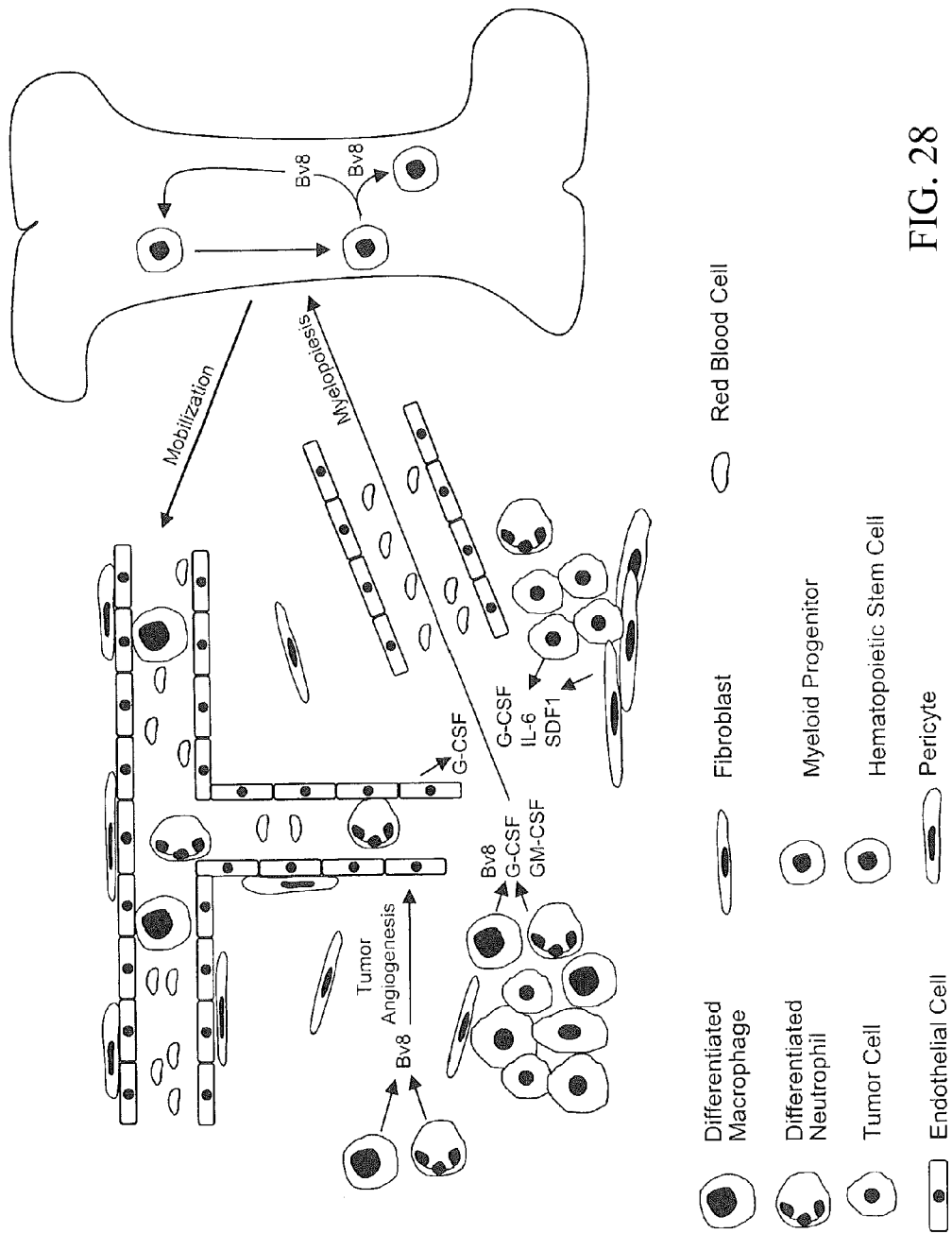

Since even trace amounts of Triton® X-100 were found to be significantly cytotoxic to endothelial cells in proliferation assays, we sought to test the activity of the neutrophil-derived Bv8 protein in an assay that requires shorter stimulation times. We took advantage of PKR1/EG-VEGFR1 stably transfected CHO cells, as described in Materials and Methods. As expected, recombinant human Bv8 (0.2-200 ng/ml) elicited a dose-dependent stimulation (data not shown). As shown in FIG. 17B, column fractions containing immunoreactive Bv8 showed a significant stimulation compared to Triton® X-100 buffer control. However, side fractions devoid of immunoreactive Bv8 showed no stimulatory effect. Also, anti-Bv8 antibodies blocked the stimulation by pooled Bv8-containing fractions. VEGF-A, tested up to 200 ng/ml, did not elicit any response, further confirming the specificity of the effects.

Effect of Bv8 on Neutrophil Migration

We tested the possibility that Bv8 may have chemotactic effects on human neutrophils. As illustrated in FIG. 18, Bv8 induced a significant stimulation of chemotaxis, with a maximal effect ~3-fold above control. Interestingly, the maximal stimulation occurred at a very low Bv8 concentration (~2 pM). A similar pattern was observed in 6 independent donors (FIG. 18). Other chemotactic factors such as, SDF-1α, IL-8 and G-CSF required higher concentrations (20 nM) in order to stimulate neutrophil migration. VEGF and MCP-1 did not show any effect at all concentrations tested (data not shown).

Expression of Bv8 in Various Human Leukemia Cell Lines and Regulation by G-CSF

To determine whether Bv8 is expressed by leukemic cells, we tested a panel of human cell lines. Bv8 expression was undetectable in Jurkat and K562 cell lines (data not shown). However, detectable Bv8 mRNA levels were found in the HL-60, KG-1, Hel 92.1.7 and U937 cell lines. 10 ng/ml G-CSF induced an increase in Bv8 expression (2-3 fold) in several cell lines (Supplemental Table 2). However, no significant induction by GM-CSF was observed in any of the cell lines tested. Neither G-CSF nor GM-CSF affected Bv8 expression in the acute promyelocytic leukemia cell line HL-60.

Discussions

Neutrophils and other myeloid cells are best known for their role in innate immunity, providing the first line of protection against pathogens (Bendelac and Fearon, *Curr Opin Immunol* 9:1-3 (1997). Also, the participation of these cells in a variety of acute and chronic inflammatory processes is well established (O'Shea and Murray, *Immunity* 28:477-487 (2008). Furthermore, the link between inflammatory cells and cancer, which was originally proposed in the $19^{th}$ century, has recently received wide experimental and clinical support (reviewed in Coussens and Werb, *Nature* 420:860-867 (2002); Lin and Karin, *J Clin Invest* 117:1175-1183 (2007)). Secretion of a variety of proinflammatory cytokines and chemokines may directly promote tumor growth and angiogenesis. Furthermore, tumor-infiltrating myeloid cells may facilitate tumor growth by virtue of their ability to down-regulate the immune responses in subtypes of T-cells including $CD4^+$ and $CD8^+$ cells, hence the denomination of myeloid derived suppressor cells (MDSC) for at least a subset of $CD11b^+Gr1^+$ cells (reviewed in Talmadge J E, *Clin Cancer Res* 3:5243-5248 (2007)).

Recent studies have tested the hypothesis that myeloid cells may also play a role in mediating refractoriness to VEGF blocking agents in tumor models (Shojaei et al., *Nature Biotechnology* 25:911-920 (2007)). Anti-VEGF refractory tumors were associated with a significant increase in the frequency of tumor-infiltrating $CD11b^+Gr1^+$ cells, compared to sensitive ones (Shojaei et al., supra). In evaluating the mechanism of VEGF-independent angiogenesis mediated by $CD11b^+Gr1^+$ cells, the orthologue of the secreted protein Bv8 was identified as a critical regulator (Shojaei et al., *Nature* 450:825-831 (2007)). These studies, including the data provided in Example 1, provided evidence that Bv8 is a mediator of myeloid cell mobilization and angiogenesis during tumor development, not only in xenografts (Shojaei et al., *Nature*, 2007, supra), but also in a transgenic mouse model of cancer progression (Shojaei et al., *Proc Natl Acad Sci USA* 105: 2640-2645 (2008)).

The present study aimed at characterizing Bv8 expression in human bone marrow and mature blood cells. Our analysis indicates that the regulation of Bv8 expression in human blood cells by various cytokines is cell-type specific. Similar to the mouse, the highest Bv8 expression was in bone marrow cells and neutrophils, while a lower level was detected in monocytes and lymphocytes. To verify that the Bv8 protein is biologically active, Bv8 was partially purified from human neutrophils and its activity documented in a bioassay. Furthermore, in the present study a novel activity of Bv8 was identified, the ability to promote neutrophil migration at very low concentrations in vitro, suggesting that Bv8, potentially from sources other than neutrophils, may physiologically regulate neutrophil migration. In addition, the present results show that of the two receptors for Bv8, only PKR2/EG-VEGFR2 was expressed in both isolated human neutrophils and G-CSF mobilized cells, suggesting that this is indeed the main receptor implicated in the hematopoietic effects of Bv8.

G-CSF was the main inducer of Bv8 expression in neutrophils and bone marrow cells, although it had no effect on monocytes and lymphocytes. Importantly, Bv8 up-regulation could be demonstrated in vivo as assessed by the increased expression in peripheral blood from G-CSF treated donors. G-CSF can be generated by stromal cells, fibroblasts and endothelial cells within the tumor microenvironment. Up-regulation of Bv8 in human neutrophils and bone marrow cells by GM-CSF was intriguing, since this factor did not elicit such effect in mouse mononuclear cells. Indeed both G-CSF and GM-CSF are known to modulate proliferation, differentiation, survival and maturation of neutrophils and monocytes from bone marrow. Also, both factors can be produced by a variety of non-hematopoietic cells, including fibroblasts, endothelial cells, keratinocytes and tumor cells. Furthermore, several reports suggest that colony stimulating factors may promote malignant growth, at least in experimental systems (Karcher et al., *Int J Cancer* 118:2182-2189 (2006); Morales-Arias et al., *Cancer* 110:1568-1577 (2007); Okazaki et al., *International Immunology* 18:1-9 (2006)). Both IL-10 and SDF-1α significantly up-regulated Bv8 expression in human monocytes. In lymphocytes, IL-10 was the major inducer of Bv8 expression. Interestingly, much evidence supports a role for tumor infiltrating macrophages and lymphocytes in secreting angiogenic factors such as VEGF (Freeman et al., *Cancer Res* 55:4140-4145 (1995); Lewis and Murdoch, *Am J Pathol* 167-627-635 (2005)). Therefore, Bv8 produced by these cell types may contribute to angiogenesis and might have also additional regulatory roles that remain to be defined. Originally described as a cytokine produced by T helper 2 (Th2) cells (Boyman et al., *Curr Opin Immunol* 19:320-326 (2007)), IL-10 has been also implicated in angiogenesis (Silvestre et al., *Circ Res.* 87:448-452 (2000); Sakamoto et al., *Int J Cancer* 118:1909-1914 (2006)).

In conclusion, our studies demonstrated that expression and regulation of Bv8 in human hematopoietic cells are substantially conserved relative to the mouse, providing the basis for further investigation of the pathophysiological role of Bv8 in human tumors and inflammatory disorders and for therapeutic application of Bv8 inhibitors.

All references cited throughout the disclosure are hereby expressly incorporated by reference in their entirety.

While the present invention has been described with reference to what are considered to be the specific embodiments, it is to be understood that the invention is not limited to such embodiments. To the contrary, the invention is intended to cover various modifications and equivalents included within the spirit and scope of the appended claims.

Throughout the present application, including the claims, the term "comprising" is used as an inclusive, open-ended transition phrase, which does not exclude additional, unrecited elements or method steps.

What is claimed is:

1. A method of tumor treatment in a human subject having a tumor refractory to treatment with a vascular endothelial growth factor (VEGF) antagonist, comprising administering to said human subject an effective amount of an anti-Bv8 antibody or an antigen-binding fragment thereof and an effective amount of an anti-VEGF antibody or an antigen-binding fragment thereof.

2. The method of claim 1 wherein the anti-VEGF antibody is bevacizumab.

3. The method of claim 1 wherein the anti-Bv8 antibody or the antigen-binding fragment thereof is chimeric, humanized or human.

4. The method of claim 1 further comprising subjecting said human subject to chemotherapy or radiation therapy.

5. The method of claim 1, wherein the human subject has a tumor refractory to monotherapy with a VEGF antagonist.

* * * * *